(12) United States Patent
Mazur et al.

(10) Patent No.: US 11,638,707 B2
(45) Date of Patent: May 2, 2023

(54) SUBSTITUTED AMINO TRIAZOLES USEFUL AS CHITINASE INHIBITORS

(71) Applicant: Molecure S.A., Warsaw (PL)

(72) Inventors: Marzena Mazur, Lodz (PL); Gleb Andryianau, Warsaw (PL); Lukasz Joachimiak, Lodz (PL); Wojciech Czestkowski, Pabianice (PL); Michal Kowalski, Godziszka (PL); Piotr Niedziejko, Warsaw (PL); Sylwia Olejniczak, Lodz (PL); Krzysztof Matyszewski, Lodz (PL); Robert Koralewski, Lodz (PL); Jacek Olczak, Lodz (PL); Adam Golebiowski, Madison, CT (US); Agnieszka Bartoszewicz, Warsaw (PL)

(73) Assignee: Molecure S.A., Warsaw (PL)

( * ) Notice: Subject to any disclaimer, the term of this patent is extended or adjusted under 35 U.S.C. 154(b) by 0 days.

(21) Appl. No.: 16/929,893

(22) Filed: Jul. 15, 2020

(65) Prior Publication Data

US 2021/0015822 A1 Jan. 21, 2021

Related U.S. Application Data

(60) Provisional application No. 62/874,108, filed on Jul. 15, 2019.

(30) Foreign Application Priority Data

Jul. 15, 2019 (PL) .......................................... 430586

(51) Int. Cl.

| | |
|---|---|
| *C07D 401/14* | (2006.01) |
| *C07D 413/14* | (2006.01) |
| *A61K 31/00* | (2006.01) |
| *A61K 31/5365* | (2006.01) |
| *A61K 31/454* | (2006.01) |
| *A61K 31/4545* | (2006.01) |
| *A61K 31/5355* | (2006.01) |
| *A61K 45/06* | (2006.01) |
| *C07D 498/04* | (2006.01) |

(52) U.S. Cl.
CPC ........ *A61K 31/5365* (2013.01); *A61K 31/454* (2013.01); *A61K 31/4545* (2013.01); *A61K 31/5355* (2013.01); *A61K 45/06* (2013.01); *C07D 401/14* (2013.01); *C07D 413/14* (2013.01); *C07D 498/04* (2013.01)

(58) Field of Classification Search
CPC ............ C07D 401/14; C07D 413/14; A61K 31/5365; A61K 31/454; A61K 31/4545; A61K 31/5355; A61K 45/06

See application file for complete search history.

(56) References Cited

U.S. PATENT DOCUMENTS 9,944,624 B2 * 4/2018 Mazur .................. C07D 413/14

FOREIGN PATENT DOCUMENTS

WO 2017037670 A1 3/2017

OTHER PUBLICATIONS

Silverman, R. "The Organic Chemistry of Drug Design and Drug Action," 2004, Elsevier, pp. 29-32.*
Sklepkiewicz P. et al. "Inhibition of CHIT1 as a novel therapeutic approach in idiopathic pulmonary fibrosis," European Journal of Pharmacology, No. 919, Jan. 25, 2022, pp. 1-13.
Dymek, B. et al., "Dual AMCase/CHIT1 Inhibitor OAT-889 Reverses Pulmonary Inflammation and Airway Remodeling in Two Mice Models of Airway Inflammation," ATS—Washington, May 19-24, 2017, 1 page.
Dymek, B. et al., "The Therapeutic Efficacy of OAT-889 (Dual AMCase/CHIT1 Inhibitor) in Comparison to Montelukast in HDM-induced Model of Chronic Airway Inflammation in Mice," ERS—Milan, Sep. 9-13, 2017, 1 page.
Dymek, B. et al., "OATD-01, a Dual Chitinase Inhibitor, Significantly Ameliorates Pulmonary Fibrosis in the Bleomycin-Induced Mouse Model," ATS—San Diego, USA, May 18-23, 2018, 1 page.
Andryianau, G. et al., "Discovery of OAT-1441—Highly Potent, Selective and Orally Bioavailable Inhibitor of Human Acidic Mammalian Chitinase," 54th International Conference on Medicinal Chemistry—Strasbourg, France, Jul. 4-6, 2018, 1 page.
Lipner, J. et al., "First-in-Human Study of OATD-01, a Dual Chitinase Inhibitor," ERS International Congress 2018—Paris, France, Sep. 15-19, 2018, 1 page.

(Continued)

Primary Examiner — Sikarl A Witherspoon
(74) Attorney, Agent, or Firm — Dana M. Gordon; Laura A. Wzorek; Foley Hoag LLP

(57) ABSTRACT

Disclosed are amino triazole compounds of formula (I). These compounds are inhibitors of acidic mammalian chitinase and chitotriosidase. Also disclosed are methods of using the compounds to treat asthma reactions caused by allergens, as well as acute and chronic inflammatory diseases, autoimmune diseases, dental diseases, neurologic diseases, metabolic diseases, liver diseases, polycystic ovary syndrome, endometriosis, and cancer.

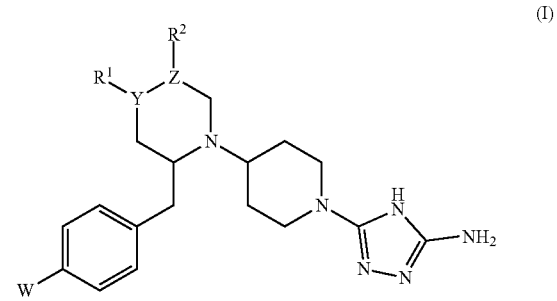

(I)

14 Claims, No Drawings

(56) References Cited

OTHER PUBLICATIONS

Mazur, M. et al., "Development of Dual AMCase and CHIT1 Inhibitor OAT-870 as a Potential Therapeutic for Interstitial Lung Diseases," EFMC—International Symposium on Medicinal Chemistry—Ljubljana, Sep. 2-6, 2018, 1 page.
Niedziejko, P. et al., "Discovery of Selective, Orally Bioavailable Inhibitor of Human Acidic Mammalian Chitinase," EFMC—International Symposium on Medicinal Chemistry—Ljubljana, Sep. 2-6, 2018, 1 page.
Mazur, M. et al., "Development of Potent, in Vivo Active, Acidic Mammalian Chitinase Inhibitors as Potential Therapeutics for Asthma," EFMC—International Symposium on Advances in Synthetic and Medicinal Chemistry—Vienna, Austria, Aug. 27-31, 2017, 1 page.
Borek, B. et al., "OAT-2068—The First Selective Inhibitor of Mouse Chitotriosidase (mCHIT1)," 1st Alpine Winter Conference on Medicinal and Synthetic Chemistry—St. Anton, Austria, Jan. 28-Feb. 1, 2018, 1 page.
Czestkowski, W. et al., "Development of highly active acidic mammalian chitinase (AMCase) inhibitors of zwitterionic character," IX Konwersatorium Chemii Medycznej—Lublin, Sep. 13-15, 2018, 1 page.
Czestkowski, W. et al., "The first Selective Inhibitor of Murine Chitotriosidase" 60 Zjazd Polskiego Towarzystwa Chemicznego—Wroclaw, Sep. 17-21, 2017, 1 page.
Czestkowski, W. et al., "Discovery of OAT-2068—A Potent, Selective, Orally Bioavailable Inhibitor of Mouse Chitotriosidase and its in Vivo Activity in the Bleomycin-Induced Pulmonary Fibrosis Model in Mice," EFMC-ACSMEDI MedChem Frontiers 2019—Krakow, Jun. 10-13, 2019, 1 page.
Sklepkiewicz, P. et al., "Clinical Development of OATD-01: A Novel Chitinase Inhibitor for Treatment of Interstitial Lung Disease," ATS—Dallas, May 17-22, 2019, 1 page.
Gruza, M. et al., "Benzoxazepine Derived OAT-1441 as Selective Orally Bioavailable Inhibitor of Human Acidic Mammalian Chitinase (hAMCase)," RICT 2019—55th International Conference on Medicinal Chemistry—Nantes, France, Jul. 3-5, 2019, 1 page.
Niedziejko, P. et al., "Development of OAT-870—Dual Chit1 and AMCase Inhibitor Effective in HDM-Induced Allergic Airway Inflammation Mouse Model," RICT 2019—55th International Conference on Medicinal Chemistry—Mantes, France, Jul. 3-5, 2019, 1 page.
Kowalski, M. et al., "Discovery of an Advanced Dual Chitinase Inhibitor OAT-870: A new Potential Therapeutic in Therapy of Lung Diseases," ACS—San Diego, CA, Aug. 25-29, 2019, 1 page.
Bartoszewicz, A. et al., "OATD-01, A Dual hAMCase and hCHIT Inhibitor as a Potential Therapeutic Agent for Treatment of Pulmonary Diseases," ACS—San Diego, CA, Aug. 25-29, 2019, 1 page.
Andryianau, G. et al., "Discovery of OAT-1441—Highly Active, Selective and Orally Bioavailable Inhibitor of Human AMCase," ACS—San Diego, CA, Aug. 25-29, 2019, 1 page.
Mazur, M. et al., "OATD-01—Orally Bioavailable, Dual Chitinase Inhibitor as a Potential Therapy for Interstitial Lung Diseases," EFMC—ASMC'19—International Symposium on Advances in Synthetic and Medicinal Chemistry—Athens, Greece, Sep. 1-5, 2019, 1 page.
Sklepkiewicz, P. et al.,Chitotriosidase (CHIT1) as a Novel Therapeutics Target in Idiopathic Pulmonary Fibrosis (IPF), Fibrosis and Tissue Repair: From Molecules and Mechanics to Therapeutic Approaches—Victoria, BC, Canada, Feb. 19-23, 2020, 1 page.
Mlacki, M, et al.,"Therapeutic efficacy of the chitotriosidase inhibitors in STAM model of nonalcoholic steatohepatitis," The Digital International Liver Congress—Aug. 27-29, 2020, 1 page.
Dymek, B. et al., "Chit1 is a Novel Therapeutic Target in IPF: Anti-Fibrotic Efficacy of OATD-01, A Potent and Selective Chitinase Inhibitor, in the Mouse Model of Pulmonary Fibrosis," ERS International Chit1 is a Novel Therapeutic Target in IPF, Congress 2018—Paris, France, Sep. 15-19, 2018, pp. 1-17.
Bartoszewicz, A., "OAT-2068—A Potent, Selective, Orally Bioavailable Inhibitor of Mouse Chitotriosidase and Its Efficacy in the Bleomycin-Induced Pulmonary Fibrosis Model," EFMC-ACSMEDI Med. Chem Frontiers 2019—Kraków, Jun. 10-13, 2019, pp. 1-14.
Mazur, M. et al., "Targeting Acidic Mammalian Chitinase is Effective in Animal Model of Asthma ," J. Med. Chem. 2018, vol. 61, No. 3, pp. 695-710.
Mazur, M. et al., "Development of Dual Chitinases Inhibitors as Potential New Treatment for Respiratory System Diseases," J. Med. Chem. 2019, vol. 62, pp. 7126-7145.
Andryianau, G. et al., "Benzoxazepine-Derived Selective, Orally Bioavailable Inhibitor of Human Acidic Mammalian Chitinase," ACS Med. Chem. Lett. 2020, vol. 11, pp. 1228-1235.
Koralewski, R. et al., "Discovery of OATD-01, a First-in-Class Chitinase Inhibitor as Potential New Therapeutics for Idiopathic Pulmonary Fibrosis," J. Med. Chem. 2020, vol. 63, No. 24, pp. 15527-15540.
International Search Report issued in PCT/EP2020/069974, dated Nov. 6, 2020, pp. 1-4.
Mazur M. et al., "Discovery of Selective, Orally Bioavailable Inhibitor of Mouse Chitotriosidase," Bioorganic & Medicinal Chemistry Letters, vol. 28, No. 3, Feb. 2018, pp. 310-314.
Marzena Mazur et al. "Chitinases and Chitinase-like Proteins as Therapeutic Targets in Inflammatory Diseases, with a Special Focus on Inflammatory Bowel Diseases", International Journal of Molecular Sciences, Jun. 2021, 22, 6966 (17 pages).
Andryianau et al., "Benzoxazepine-Derived Selective, Orally Bioavailable Inhibitor of Human Acidic Mammalian Chitinase," ACS Medicinal Chemistry Letters, 11(6): 1228-1235 (2020).
Andryianau et al., "Discovery of OAT-1441—Highly Active, Selective and Orally Bioavailable Inhibitor of Human AMCase," OncoArendi Therapeutics (2019).
Andryianau et al., "Discovery of OAT-1441—Highly Potent, Selective and Orally Bioavailable Inhibitor of Human Acidic Mammalian Chitinase," OncoArendi Therapeutics (2018).
Bartoszewicz et al., "OATD-01, a dual hAMCase and hCHIT Inhibitor as a Potential Therapeutic Agent for Treatment of Pulmonary Diseases," Onco Arendi Therapeutics (2019).
Bartoszewicz, "OAT-2068—A potent, selective, orally bioavailable inhibitor of mouse chitotriosidase and its efficacy in the bleomycin-induced pulmonary fibrosis model," OncoArendi Therapeutics (2019).
Borek et al., "Development of highly active acidic mammalian chitinase (AMCase) inhibitors of zwitterionic character," OncoArendi Therapeutics, (2018).
Borek et al., "OAT-2068—The first selective inhibitor of mouse chitotriosidase (mCHIT1)," OncoArendi Therapeutics (2018).
Czestkowski et al., "Discovery of OAT-2068—A potent, selective, orally bioavailable inhibitor of mouse chitotriosidase and its in vivo activity in the bleomycin-induced pulmonary fibrosis model in mice," OncoArendi Therapeutics (2019).
Czestkowski et al., "Pierwsky selecktywny inhibitor mysiej chitotriozydazy (mCHIT1)," OncoArendi Therapeutics (2017).
Dymek et al., "Dual AMCase/CHIT1 inhibitor OAT-899 reverses pulmonary inflammation and airway remodeling in two mice models of airway inflammation," OncoArendi Therapeutics (2017).
Dymek et al., "OATD-01, a Dual Chitinase Inhibitor, Significantly Ameliorates Pulmonary Fibrosis in the Bleomycin-Induced Mouse Model," Onco Arendi Therapeutics (2018).
Dymek et al., "The therapeutic efficacy of OAT-889 (Dual AMCase/CHIT1 Inhibitor) in comparison to montelukast in HDM-induced model of chronic airway inflammation in mice," OncoArendi Therapeutics (2017).
Gruza et al., "Benzoxazepine derived OAT-1441 as selective orally bioavailable inhibitor of human acidic mammalian chitinase (hAMCase)," OncoArendi Therapeutics (2019).
Kowalski et al., "Discovery of an advanced dual chitinase inhibitor OAT-870: A new potential therapeutic in therapy of lung diseasds," OncoArendi Therapeutics (2019).
Lipner et al., "Phase 1, first-in human study of OATD-01, a dual chitinase inhibitor," Onco Arendi Therapeutics (2018).

(56) References Cited

OTHER PUBLICATIONS

Mazur et al., "Development of dual AMCase and CHIT1 inhibitor OAT-870 as a potential therapeutic for interstitial lung diseases," Onco Arendi Therapeutics, (2018).

Mazur et al., "Development of dual chitinase inhibitors as potential new treatment for respiratory system diseases," J Med Chem, 62:7126-7145 (2019).

Mazur et al., "Development of potent, in vivo active, acidic mammalian chitinase inhibitors as potential therapeutics for asthma," Onco Arendi Therapeutics (2017).

Mazur et al., "Discovery of selective, orally bioavailable inhibitor of mouse chitotriosidase," Bioorganic & Medicinal Chemistry Letters, 28:310-314 (2018).

Mazur et al., "OATD-01—orally bioavailable, dual chitinase inhibitor as a potential therapy for interstitial lung diseases," Onco Arendi Therapeutics (2019).

Mazur et al., "Targeting acidic mammalian chitinase is effective in animal model of asthma," J Med Chem, 61:695-710 (2018).

Mlacki et al., "Therapeutic efficacy of the chitotriosidase inhibitors in STAM model of nonalcoholic steatohepatitis," Onco Arendi Therapeutics (2020).

Niedziejko et al., "Development of OAT-870—Dual CHIT1 and amcase inhibitor effective in HDM-induced allergic airway inflammation mouse model," Onco Arendi Therapeutics, (2019).

Niedziejko et al., "Discovery of selective, orally bioavailable inhibitor of human acidic mammalian chitnase," Onco Arendi Therapeutics, (2018).

Sklepkiewicz et al., "CHIT1 is a novel therapeutic target in IPF: anti-fibrotic efficacy of OATD-01, a potent and selective chitinase inhibitor, in the mouse model of pulmonary fibrosis," Onco Arendi Therapeutics (2018).

Sklepkiewicz et al., "Chitotriosidase (CHIT1) as a Novel Therapeutic Target in Idiopathic Pulmonary Fibrosis (IPF)," Onco Arendi Therapeutics (2020).

Sklepkiewicz et al., "Clinical Development of OATD-01: a Novel Chitinase Inhibitor for Treatment of Interstitial Lung Diseases," Onco Arendi Therapeutics (2019).

Sklepkiewicz et al., "OATD-01, a dual chitinase inhibitor, significantly ameliorates pulmonary fibrosis in the bleomycin-induced mouse model," Onco Arendi Therapeutics (2018).

* cited by examiner

SUBSTITUTED AMINO TRIAZOLES USEFUL AS CHITINASE INHIBITORS

RELATED APPLICATION

This application claims the benefit of priority to Polish Patent Application number P.430586, filed Jul. 15, 2019, and to U.S. Provisional Patent Application Ser. No. 62/874,108, filed Jul. 15, 2019.

BACKGROUND OF THE INVENTION

The glycosyl hydrolase family 18 in humans consists of two enzymatically active chitinases, CHIT1 and AMCase, and the non-active chitinase-like proteins (CLPs): YKL-40, YKL-39, oviductin and stabilin-interacting protein that lack enzymatic activity due to amino acid substitutions in the active site. Although chitinases and CLPs are evolutionary highly conserved, their physiological role in mammals has not been fully elucidated. In most mammals, e.g., rodents, chitinases confer protection against chitin-containing organisms which are either inhaled or ingested. However, in humans, chitinases and CLPs are thought to have evolved to perform different functions, often associated with inflammatory and fibrotic pathologies (Lee C G et al., Role of chitin and chitinase/chitinase-like proteins in inflammation, tissue remodeling, and injury. Annu Rev Physiol. 73:479-501, 2011).

Chitotriosidase 1 (CHIT1, MW=~52 kDa) is the predominant chitinase detected in humans (Seibold M et al., Chitotriosidase is the primary active chitinase in the human lung and is modulated by genotype and disease. J Allergy Clin Immunol, 122(5): 944-950, 2008). CHIT1 is a circulating enzyme, with both endochitinolytic and transglycosylating activity. Besides its role in chitin recognition and innate immune response, CHIT1 has been implicated in pathogenesis of multiple fibrotic lung diseases including idiopathic pulmonary fibrosis (IPF), scleroderma, sarcoidosis, chronic obstructive pulmonary disease (COPD) and asthma, as well as in other diseases with inflammatory and/or fibrotic phenotype such as non-alcoholic steatohepatitis (NASH), diabetic nephropathy and amyotrophic lateral sclerosis (ALS). CHIT1 is primarily expressed by pathologically activated macrophages including epithelioid and giant cells, Kupffer cells and microglia.

In humans, acidic mammalian chitinase (AMCase; MW=~52 kD) is a secreted enzyme, expressed by epithelial cells and macrophages, typically found in the stomach and the salivary gland. Unique among mammalian enzymes in that it has an acidic pH optimum, the enzyme catalyzes the hydrolysis of chitin (Chou Y et al., Kinetic characterization of recombinant human acidic mammalian chitinase. Biochemistry, 45:4444-4454, 2006). In animals models AMCase was demonstrated to be induced during Th2 inflammation through an IL-13-dependent mechanism and has been implicated in the pathogenesis of asthma, as well as other diseases with Th2 inflammatory phenotype such as eosinophilic esophagitis or allergic ocular pathologies.

Interstitial lung diseases (ILDs) is a group of over 300 lung disorders which affect lung interstitium: the most common are sarcoidosis and idiopathic pulmonary fibrosis (IPF). These diseases, many with unknown etiology, are characterized by the alveolar damage which often leads to a chronic inflammation and fibrosis resulting in diminished lung functions.

Sarcoidosis is a multiorgan systemic disease characterized by a formation of granulomas that can develop in various organs, with most patients developing pulmonary presentation. Spontaneous remission occurs in a majority of cases, but up to one-third of patients develop a chronic, progressive or relapsing disease with a concomitant interstitial fibrosis and decline in lung functions. (Valeyre D et al., Sarcoidosis. 383(9923):1155-67, Lancet, 2014). The clinical studies demonstrated highly elevated (10-30 fold) activity of CHIT1 in the serum of patients with sarcoidosis that correlated with disease severity, progression and clinical prognosis (Bargagli et al., Human chitotriosidase: a sensitive biomarker of sarcoidosis. J Clin Immunol. 33:264-270, 2013).

IPF is a progressive fibroproliferative disorder with no curative therapies with a median survival of only 3-5 years following diagnosis. IPF is a devastating disease characterized by excessive matrix deposition that disrupts the normal architecture of the lung parenchyma and impairs lung functions. The key pathological features of IPF include fibroblastic foci, areas of epithelial cysts associated with the honeycombing appearance of the lung, and mild lymphoplasmacytic interstitial inflammation that is associated with areas of type II cell hyperplasia (Richeldi L et al., Idiopathic pulmonary fibrosis. 389(10082):1941-1952. Lancet, 2017). CHIT1 overexpression was demonstrated in fibrotic ILDs, including IPF (Bargagli E et al., Chitotriosidase activity in patients with interstitial lung diseases. Respir Med. 101(10): 2176-81, 2007). Importantly, CHIT1 was shown to be a potent amplifier of TGFβ1 signaling (Lee C G et al., Chitinase 1 is a biomarker for and a therapeutic target in the scleroderma-associated interstitial lung disease that augments TGF-β1 signaling. J Immunol. 189(5):2635-44, 2012). This study demonstrated that CHIT1 activity was elevated in the BAL of IPF patients compared to controls suggesting that it might be involved in remodeling and tissue damage seen in lungs from IPF patients.

Studies in animal models have demonstrated a functional role of CHIT1 in IPF. In Chit1 knock-out mice, lung fibrosis induced by either bleomycin or over-expression of IL-13 was markedly reduced compared to control animals, in addition to attenuation of IL-13-induced lung inflammation (Lee C G et al., Chitinase 1 is a biomarker for and a therapeutic target in the scleroderma-associated interstitial lung disease that augments TGF-β1 signaling. J Immunol. 189(5):2635-44, 2012). Furthermore, enhanced lung fibrosis was observed in CHIT1 over-expressing transgenic mice after bleomycin administration providing additional evidence implicating CHIT1 in the pathophysiology of pulmonary fibrosis.

Obstructive lung diseases (among them asthma and chronic obstructive lung disease COPD) are chronic inflammatory disorders that involve the small airways and cause airflow limitation. Asthma is characterized by recurrent episodes of reversible airway obstruction and airway hyper responsiveness. Typical clinical manifestations include shortness of breath, wheezing, coughing and chest tightness that can become life threatening or fatal. While existing therapies focus on reducing the symptomatic bronchospasm and pulmonary inflammation, there is a growing recognition of the role of long-term airway remodeling in the accelerated lung deterioration in asthmatics. (Papi A et al. Asthma. 391(10122):783-800, Lancet, 2018). COPD is a disease characterized by a progressive, irreversible limitation of airflow due to emphysema and remodeling of small airways. Currently, no drugs reducing COPD progression are available with smoking cessation the only intervention demonstrated to slow the rate of decline in lung function. (Rabe K et al. Chronic obstructive pulmonary disease. 389(10082): 1931-1940, Lancet, 2017).

Multiple studies have demonstrated that chitinases activity or expression is elevated in patients with asthma and COPD compared to healthy control subjects and the increased levels correlated with reduced lung function (Zhu Z et al., Acidic mammalian chitinase in asthmatic Th2 inflammation and IL-13 pathway activation. 304(5677): 1678-1682, Science, 2004; James A et al., Increased YKL-40 and Chitotriosidase in Asthma and Chronic Obstructive Pulmonary Disease. 193(2):131-422016, Am J Respir Crit Care Med, 2016). Studies in murine models of asthma have demonstrated that AMCase is involved in Th2 inflammation and airway hyperresponsiveness (Zhu Z et al., Acidic mammalian chitinase in asthmatic Th2 inflammation and IL-13 pathway activation. Science 304: 1678-1682, 2004). A highly potent and selective AMCase inhibitor demonstrated significant anti-inflammatory efficacy in HDM-induced allergic airway inflammation in mice with efficacy correlating to a decrease in chitinolytic activity (Mazur M et al., Targeting acidic mammalian chitinase is effective in animal model of asthma. 1(3):695-710, J Med Chem, 2018).

Diseases, disorders, and conditions in which CHIT1 and AMCase have been implicated and chitinases inhibition may confer a therapeutic strategy, are discussed in more detail below.

Substituted amino triazoles that inhibit AMCase and CHIT1 have been described (see U.S. Pat. No. 9,440,953 B2, U.S. Pat. No. 9,944,624 B2, U.S. Pat. No. 10,208,020 B2 and European Patent no. EP3344616; international patent application publications no. WO 2016/099311 A1 and WO 2017/037670 A1; European patent application publication no. EP3233832; Chinese patent application publication no. CN 107428720 A; Mazur, M. et al., Targeting acidic mammalian chitinase is effective in animal model of asthma. *J Med Chem* 2018, 61, 3, 695-710; Mazur, M. et al., Discovery of selective, orally bioavailable inhibitor of mouse chitotriosidase *Bioorg. Med. Chem. Lett.* 2018, 28, 310-314.).

Unfortunately, some inhibitors of AMCase and CHIT1 have been associated with cardiotoxicity, likely stemming from inhibition of the hERG potassium channel. Accordingly, there exists a need to develop compounds for the inhibition of AMCase and CHIT1, which compounds exhibit not only excellent activity and selectivity within the family of chitinases, but also exhibit a favorable cardiac safety profile. AMCase and CHIT1 inhibitors are useful for the treatment of conditions associated with elevated expression of AMCase or CHIT1, such as asthma and allergic responses or COPD and fibroproliferative disorders.

SUMMARY OF THE INVENTION

In one aspect, the invention provides a compound represented by formula (I),

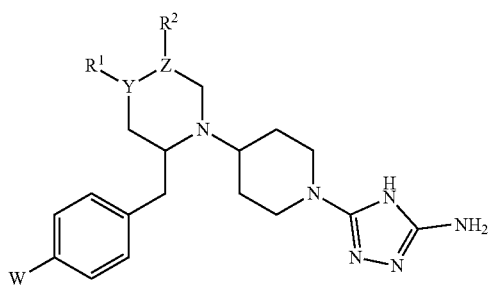

(I)

wherein:

W is halo or —$CF_3$;

Y is a single bond, —CH—, —C(OH)—, —N—, or —O—;
  if Y is a single bond or —O—, then $R^1$ is absent;
  if Y is —C(OH)—, then $R^1$ is ($C_1$-$C_6$)alkyl;
  if Y is —N—, then:
    either Z is —C—, and $R^1$, Y, Z, and $R^2$ taken together represent a 5-membered optionally substituted heteroaryl ring containing two N-heteroatoms as ring members,
    or Z is —CH—, and $R^1$, Y, Z, and $R^2$ taken together represent a 5- or 6-membered optionally substituted heterocyclyl ring containing one N heteroatom and optionally one O heteroatom as ring member(s);

if present, $R^1$ is H or ($C_1$-$C_6$)alkyl;

Z is —C— or —CH— or —C(halo)-;

if Z is —CH—, then $R^2$ is haloalkyl, hydroxyalkyl, (halo)(hydroxy)alkyl, optionally substituted heterocycloalkyl, optionally substituted heteroaryl, —C(O)NH(haloalkyl), —C(O)NH(alkyl substituted by —S(O)$_2$(alkyl)), —C(O)NH(alkyl substituted by —S(O)$_2$NH(alkyl)), —C(O)NH(optionally substituted cycloalkyl), —C(O)(heterocycloalkyl substituted by halo), —C(O)N($R^c$)($R^d$), or alkyl substituted by one or more substituents selected from the group consisting of optionally substituted heteroaryl, optionally substituted heterocycloalkyl, haloalkoxy, alkylthio, cyano, —S(O)(alkyl), —S(O)$_2$(alkyl), —OC(O)N(alkyl)$_2$, and —N($R^a$)C(O)$R^b$;

if Z is —C(halo)-, then $R^2$ is halo, haloalkyl, (halo)(hydroxy)alkyl, optionally substituted heterocycloalkyl, optionally substituted heteroaryl, —C(O)NH(haloalkyl), —C(O)NH(alkyl substituted by —S(O)$_2$(alkyl)), —C(O)NH(alkyl substituted by —S(O)$_2$NH(alkyl)), —C(O)NH(optionally substituted cycloalkyl), —C(O)(heterocycloalkyl substituted by halo), —C(O)N($R^c$)($R^d$), or alkyl substituted by one or more substituents selected from the group consisting of optionally substituted heteroaryl, optionally substituted heterocycloalkyl, haloalkoxy, alkylthio, cyano, —S(O)(alkyl), —S(O)$_2$(alkyl), —OC(O)N(alkyl)$_2$, and —N($R^a$)C(O)$R^b$;

$R^a$ and $R^b$, taken together with the intervening atoms, form an optionally substituted lactam;

$R^c$ and $R^d$, taken together with the intervening atoms, form an optionally substituted heterocycloalkyl ring;

if Y is —C(OH)—, then Z is —CH—, and $R^2$ is H; and any occurrence of optionally substituted heteroaryl, optionally substituted heterocycloalkyl, optionally substituted cycloalkyl, or optionally substituted lactam may be substituted with one or more substituents independently selected from the group consisting of —OH, halo, —$NH_2$, —NH(alkyl), —N(alkyl)$_2$, —CN, —$NO_2$, alkyl, haloalkyl, alkoxy, aryl, heteroaryl, arylalkyl, heteroarylalkyl, cycloalkyl, heterocycloalkyl, —C(O)OH, —C(O)Oalkyl, —C(O)$NH_2$, —C(O)NHalkyl, and —C(O)N(alkyl)$_2$;

or a pharmaceutically acceptable salt, solvate, tautomer, stereoisomer, prodrug, or polymorph thereof.

Also provided herein are pharmaceutical compositions comprising a therapeutically effective amount of a compound of the invention, and a pharmaceutically acceptable carrier.

In certain aspects, the pharmaceutical composition also includes one or more second therapeutic agents selected from the group consisting of steroids, membrane stabilizers, 5LO inhibitors, leukotriene synthesis and receptor inhibitors, inhibitors of IgE isotype switching or IgE synthesis, inhibitors of IgG isotype switching or IgG synthesis, β-agonists, tryptase inhibitors, acetylsalicylic acid, COX inhibitors, methotrexate, anti-TNF drugs, rituxin, PD4 inhibitors, p38 inhibitors, PDE4 inhibitors, and antihistamines.

In another aspect, the invention provides methods for inhibiting acidic mammalian chitinase in a cell or a tissue, comprising contacting the cell or the tissue with at least one compound of the invention, or with a pharmaceutical composition of the invention.

In another aspect, the invention provides methods for inhibiting chitotriosidase 1 (CHIT1) in a cell or a tissue, comprising contacting the cell or the tissue with at least one compound of the invention, or with a pharmaceutical composition of the invention.

Also provided herein are methods for treatment or prevention of a disease, disorder, or condition associated with aberrant expression or activity of acidic mammalian chitinase, comprising administering to a subject in need thereof a therapeutically effective amount of at least one compound of the invention, or a pharmaceutical composition of the invention.

The present invention also provides methods for treatment or prevention of a disease, disorder, or condition associated with aberrant expression or activity of chitotriosidase, comprising administering to a subject in need thereof a therapeutically effective amount of at least one compound of the invention, or a pharmaceutical composition of the invention.

Also provided herein are methods for treatment or prevention of a disease, disorder, or condition selected from the group consisting of allergic diseases, acute and chronic inflammatory diseases, autoimmune diseases, dental diseases, neurologic diseases, metabolic diseases, liver diseases, kidney diseases, skin diseases, polycystic ovary syndrome, endometriosis, fibrotic disorders, storage diseases, and cancer, comprising administering to a subject in need thereof a therapeutically effective amount of at least one compound of the invention, or a pharmaceutical composition of the invention.

The invention further provides methods for inhibiting chitotriosidase and/or acidic mammalian chitinase in a cell or a tissue, comprising contacting a cell or a tissue with at least one compound of the invention, or with a pharmaceutical composition of the invention.

DETAILED DESCRIPTION

The present invention is based on the unexpected discovery that chemical modification of amino triazole 4-amino piperidine small molecule compounds with a heterocyclic ring (e.g., a substituted morpholine or piperazine) increases the rigidity of the molecule, thus fixing its molecular geometry. This geometrical rigidity beneficially changes numerous molecular properties, and yields unexpected inhibitory efficacy toward acidic mammalian chitinase.

The amino triazole compounds according to the invention are thus useful in the treatment of disorders associated with upregulated and dysregulated AMCase activity, such as asthma and allergic reactions, as well as those disorders associated with upregulated and dysregulated CHIT1 activity. Furthermore, the compounds of the invention exhibit a favorable cardiac safety profile as evidenced by their limited activity toward hERG potassium channel inhibition.

Definitions

The articles "a" and "an" are used herein to refer to one or to more than one (i.e., to at least one) of the grammatical object of the article. By way of example, "an element" means one element or more than one element.

The terms "group" and "radical" are used interchangeably herein and denote a portion of a molecule in question which is bound to the rest of the molecule by a covalent bond (or bonds, as results from the previous paragraph).

The terms used herein may be preceded and/or followed by a single dash "—", or a double dash "=", to indicate the bond order of the bond between the named substituent and its parent moiety; a single dash indicates a single bond and a double dash indicates a double bond. In the absence of a single or double dash, it is understood that a single bond is formed between the substituent and its parent moiety; further, substituents are intended to be read "from left to right," unless a dash indicates otherwise. For example, ($C_1$-$C_6$)-alkoxycarbonyloxy and —OC(O)($C_1$-$C_6$)alkyl indicate the same functionality; similarly, arylalkyl and -alkylaryl indicate the same functionality.

The term "single bond" as used herein, denotes a single covalent bond between two atoms, such as C—C, C—H, or C—O.

The term "alkyl" as used herein is a term of art and refers to saturated aliphatic groups, including straight-chain alkyl groups and branched-chain alkyl groups. The subscripts following C indicate the number (or range of numbers) of carbon atoms in the straight-chain or branched-chain alkyl. In certain embodiments, a straight-chain or branched-chain alkyl has about 30 or fewer carbon atoms in its backbone (e.g., $C_1$-$C_{30}$ for straight chain, $C_3$-$C_{30}$ for branched chain), and alternatively, about 20 or fewer, 10 or fewer, or 6 or fewer carbon atoms. Preferably, the alkyl group is ($C_1$-$C_6$) alkyl. Representative examples of ($C_1$-$C_6$)alkyl include, but are not limited to, methyl, ethyl, n-propyl, isopropyl, n-butyl, sec-butyl, isobutyl, tert-butyl, n-pentyl, isopentyl, neopentyl, and n-hexyl. Examples of ($C_1$-$C_3$)alkyl include methyl, ethyl, n-propyl, and isopropyl. Alkyl may represent a group, as already defined, or a portion of a larger moiety, such as ($C_1$-$C_3$)alkoxy($C_1$-$C_3$)alkyl. A ($C_1$-$C_3$)alkoxy($C_1$-$C_3$)alkyl is bound to the rest of the molecule through the ($C_1$-$C_3$)alkyl moiety.

The term "cycloalkyl" means mono- or bicyclic or bridged saturated or partially saturated carbocyclic rings, each having from 3 to 12 carbon atoms. Certain cycloalkyls have from 3-8, or from 3-6 carbon atoms in their ring structure. Certain cycloalkyls have from 5-12 carbon atoms in their ring structure, and may have 6-10 carbons in the ring structure. Preferably, cycloalkyl is ($C_3$-$C_7$)cycloalkyl, which represents a monocyclic saturated carbocyclic ring, having from 3 to 7 carbon atoms. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems include bridged monocyclic rings and fused bicyclic rings. Bridged monocyclic rings contain a monocyclic cycloalkyl ring where two non-adjacent carbon atoms of the monocyclic ring are linked by an alkylene bridge of between one and three additional carbon atoms (i.e., a bridging group of the form —($CH_2$)$_w$—, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. The bridged or fused bicyclic cycloalkyl is attached to the parent molecular moiety through any carbon atom contained within the monocyclic cycloalkyl ring. Cycloalkyl groups are optionally substituted. In certain embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted.

The term "cycloalkylalkyl" as used herein refers to an alkyl group substituted with one or more cycloalkyl groups. An example of cycloalkylalkyl is cyclohexylmethyl group.

The terms "heterocyclyl" and "heterocycloalkyl" as used herein refers to a radical of a nonaromatic ring system, including, but not limited to, monocyclic, bicyclic, and tricyclic rings, which can be completely saturated or which can contain one or more units of unsaturation, for the avoidance of doubt, the degree of unsaturation does not result in an aromatic ring system, and having 3 to 14, or 3 to 12 atoms including at least one heteroatom, such as nitrogen, oxygen, or sulfur. More preferred heterocycloalkyl groups have from 5-10 ring members where from 1-4 of the ring members are hetero atoms selected from the group consisting of O, N, and S, the remaining ring atoms being C. For purposes of exemplification, which should not be construed as limiting the scope of this invention, the following are examples of heterocycloalkyl: aziridinyl, azirinyl, oxiranyl, thiiranyl, thiirenyl, dioxiranyl, diazirinyl, diazepanyl, 1,3-dioxanyl, 1,3-dioxolanyl, 1,3-dithiolanyl, 1,3-dithianyl, imidazolidinyl, isothiazolinyl, isothiazolidinyl, isoxazolinyl, isoxazolidinyl, azetyl, oxetanyl, oxetyl, thietanyl, thietyl, diazetidinyl, dioxetanyl, dioxetenyl, dithietanyl, dithietyl, dioxalanyl, oxazolyl, thiazolyl, triazinyl, isothiazolyl, isoxazolyl, azepines, azetidinyl, morpholinyl, oxadiazolinyl, oxadiazolidinyl, oxazolinyl, oxazolidinyl, oxopiperidinyl, oxopyrrolidinyl, piperazinyl, piperidinyl, pyranyl, pyrazolinyl, pyrazolidinyl, pyrrolinyl, pyrrolidinyl, quinuclidinyl, thiomorpholinyl, tetrahydropyranyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. A heterocycloalkyl group is optionally substituted by one or more substituents as described below.

As used herein, the terms "heterocyclylene" and "heterocycloalkylene" refers to a bivalent heterocyclyl (heterocycloalkyl) group, i.e., a cyclic alkylene group, having from 3-10 members and from 1-4 hetero atoms selected from S, O, and N. An example is piperidine-2,3-dicarboxylic acid, i.e., in that compound, the piperidine ring is a heterocyclylene group.

The term "heteroatom" is art-recognized, and includes an atom of any element other than carbon or hydrogen. Illustrative heteroatoms include boron, nitrogen, oxygen, phosphorus, sulfur and selenium, and alternatively oxygen, nitrogen or sulfur.

The term "heterocycloalkylalkyl" as used herein refers to an alkyl group substituted with one or more heterocycloalkyl (i.e., heterocyclyl) groups.

The term "alkenyl" as used herein means a straight or branched chain hydrocarbon radical containing from 2 to 10 carbons and containing at least one carbon-carbon double bond formed by the removal of two hydrogens. Preferably, alkenyl contains from 2 to 6 carbons. Representative examples of alkenyl include, but are not limited to, ethenyl, 2-propenyl, 2-methyl-2-propenyl, 3-butenyl, 4-pentenyl, and 5-hexenyl. The unsaturated bond(s) of the alkenyl group can be located anywhere in the moiety and can have either the (Z) or the (E) configuration about the double bond(s). The molecules differing only in their configuration about the double bond are called geometrical isomers.

The term "alkynyl" as used herein means a straight or branched chain hydrocarbon radical containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "alkylene" is art-recognized, and as used herein pertains to a diradical obtained by removing two hydrogen atoms of an alkyl group, as defined above. In one embodiment an alkylene refers to a disubstituted alkane, i.e., an alkane substituted at two positions with substituents such as halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, fluoroalkyl (such as trifluromethyl), cyano, or the like. That is, in one embodiment, a "substituted alkyl" is an "alkylene".

The term "amino" is a term of art and as used herein refers to both unsubstituted and substituted amines, e.g., a moiety that may be represented by one of the general formulas:

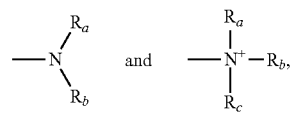

wherein $R_a$, $R_b$, and $R_c$ each independently represent a hydrogen, an alkyl, an alkenyl, —$(CH_2)_x$—$R_d$, or $R_a$ and $R_b$, taken together with the N atom to which they are attached complete a heterocycle having from 4 to 8 atoms in the ring structure; R represents an aryl, a cycloalkyl, a cycloalkenyl, a heterocyclyl or a polycyclyl; and x is zero or an integer in the range of 1 to 8. In certain embodiments, only one of $R_a$ or $R_b$ may be a carbonyl, e.g., $R_a$, $R_b$, and the nitrogen together do not form an imide. In other embodiments, $R_a$ and $R_b$ (and optionally $R_c$) each independently represent a hydrogen, an alkyl, an alkenyl, or —$(CH_2)_x$—$R_d$. In certain embodiments, the term "amino" refers to —$NH_2$.

The term "amido", as used herein, means —NHC(=O)—, wherein the amido group is bound to the parent molecular moiety through the nitrogen. Examples of amido include alkylamido such as $CH_3C(=O)N(H)$— and $CH_3CH_2C(=O)N(H)$—.

The term "acyl" is a term of art and as used herein refers to any group or radical of the form RCO— where R is any organic group, e.g., alkyl, aryl, heteroaryl, aralkyl, and heteroaralkyl. Representative acyl groups include acetyl, benzoyl, and malonyl.

The term "aminoalkyl" as used herein refers to an alkyl group substituted with one or more one amino groups. In one embodiment, the term "aminoalkyl" refers to an aminomethyl group.

The term "aminoacyl" is a term of art and as used herein refers to an acyl group substituted with one or more amino groups.

The term "aminothionyl" as used herein refers to an analog of an aminoacyl in which the O of RC(O)— has been replaced by sulfur, hence is of the form RC(S)—.

The term "azide" or "azido", as used herein, means an —$N_3$ group.

The term "carbonyl" as used herein refers to —C(=O)—.

The term "thiocarbonyl" as used herein refers to —C(=S)—.

The term "alkylthio" as used herein refers to alkyl-S—. Representative examples of ($C_1$-$C_6$)alkylthio include methylthio, ethylthio, n-propylthio, and tert-butylthio. Representative examples of ($C_1$-$C_3$)alkylthio include methylthio, ethylthio, and n-propylthio.

The term "mercaptoalkyl" as used herein refers to an alkyl group substituted by an —SH moiety. Representative examples of ($C_1$-$C_6$)mercaptoalkyl include mercaptomethyl, mercaptoethyl, and mercapto-n-propyl.

The term "carboxy", as used herein, means a —$CO_2H$ group. This group can form a portion of another substituent, such as carboxymethyl, i.e., $HO_2C$—$CH_2$—.

The term "aryl" is a term of art and as used herein refers to include monocyclic, bicyclic, and polycyclic aromatic hydrocarbon groups, for example, benzene, naphthalene, 1,2,3,4-tetrahydronaphthalene, indene, 2,3-dihydroindene, and pyrene. The aromatic ring may be substituted at one or more ring positions with one or more substituents, such as halogen, azide, alkyl, aralkyl, alkenyl, alkynyl, cycloalkyl, cycloalkylalkyl, (cycloalkyl)alkoxyl, hydroxyl, alkoxyl, amino, nitro, sulfhydryl, imino, amido, phosphonate, phosphinate, carbonyl, carboxyl, silyl, ether, alkylthio, sulfonyl, aminosulfonyl, sulfonamido, ketone, aldehyde, ester, heterocyclyl, heterocyclylalkyl, aromatic or heteroaromatic moieties, aminoalkyl, haloalkyl, fluoroalkyl (such as trifluoromethyl), haloalkoxyl, cyano, or the like. The term "aryl" also includes polycyclic ring systems having two or more cyclic rings in which two or more carbons are common to two adjoining rings (the rings are "fused rings") wherein at least one of the rings is an aromatic hydrocarbon, e.g., the other cyclic rings may be cycloalkyls, cycloalkenyls, cycloalkynyls, aryls, heteroaryls, and/or heterocycloalkyls. Representative examples of the polcyclic aryl ring systems include, but are not limited to, azulenyl, naphthyl, dihydroinden-1-yl, dihydroinden-2-yl, dihydroinden-3-yl, dihydroinden-4-yl, 2,3-dihydroindol-4-yl, 2,3-dihydroindol-5-yl, 2,3-dihydroindol-6-yl, 2,3-dihydroindol-7-yl, inden-1-yl, inden-2-yl, inden-3-yl, inden-4-yl, dihydronaphthalen-2-yl, dihydronaphthalen-3-yl, dihydronaphthalen-4-yl, dihydronaphthalen-1-yl, 5,6,7,8-tetrahydronaphthalen-1-yl, 5,6,7,8-tetrahydronaphthalen-2-yl, 2,3-dihydrobenzofuran-4-yl, 2,3-dihydrobenzofuran-5-yl, 2,3-dihydrobenzofuran-6-yl, 2,3-dihydrobenzofuran-7-yl, benzo[d][1,3]dioxol-4-yl, benzo[d][1,3]dioxol-5-yl, 2H-chromen-2-on-5-yl, 2H-chromen-2-on-6-yl, 2H-chromen-2-on-7-yl, 2H-chromen-2-on-8-yl, isoindoline-1,3-dion-4-yl, isoindoline-1,3-dion-5-yl, inden-1-on-4-yl, inden-1-on-5-yl, inden-1-on-6-yl, inden-1-on-6-yl, 2,3-dihydrobenzo[b][1,4]dioxan-5-yl, 2,3-dihydrobenzo[b][1,4]dioxan-6-yl, 2H-benzo[b][1,4]oxazin3(4H)-on-5-yl, 2H-benzo[b][1,4]oxazin3(4H)-on-6-yl, 2H-benzo[b][1,4]oxazin3(4H)-on-7-yl, 2H-benzo[b][1,4]oxazin3(4H)-on-8-yl, benzo[d]oxazin-2(3H)-on-5-yl, benzo[d]oxazin-2(3H)-on-6-yl, benzo[d]oxazin-2(3H)-on-7-yl, benzo[d]oxazin-2(3H)-on-8-yl, quinazolin-4(3H)-on-5-yl, quinazolin-4(3H)-on-6-yl, quinazolin-4(3H)-on-7-yl, quinazolin-4(3H)-on-8-yl, quinoxalin-2(1H)-on-5-yl, quinoxalin-2(1H)-on-6-yl, quinoxalin-2(1H)-on-7-yl, quinoxalin-2(1H)-on-8-yl, benzo[d]thiazol-2(3H)-on-4-yl, benzo[d]thiazol-2(3H)-on-5-yl, benzo[d]thiazol-2(3H)-on-6-yl, and, benzo[d]thiazol-2(3H)-on-7-yl. In certain embodiments, the bicyclic aryl is (i) naphthyl, or (ii) a phenyl ring fused to either a 5 or 6 membered monocyclic cycloalkyl, a 5 or 6 membered monocyclic cycloalkenyl, or a 5 or 6 membered monocyclic heterocyclyl, wherein the fused cycloalkyl, cycloalkenyl, and heterocyclyl groups are optionally substituted. In certain embodiments, the term "aryl" refers to $C_6$-$C_{10}$aryl. In certain embodiments, the term "aryl" refers to a phenyl group or a naphthyl group.

The term "heteroaryl" is a term of art and as used herein refers to a monocyclic or bicyclic aromatic group having 3 to 14, 5 to 14, 3 to 12, or 3 to 10 total atoms including one or more heteroatoms such as nitrogen, oxygen, or sulfur in the ring structure. More preferred heteroaryl groups have from 5-10 ring members where from 1-4 of the ring members are heteroatoms selected from the group consisting of O, N, and S. Exemplary heteroaryl groups include, for example, azaindolyl, benzo(b)thienyl, benzimidazolyl, benzofuranyl, benzoxazolyl, benzothiazolyl, benzothiadiazolyl, benzotriazolyl, benzoxadiazolyl, furanyl, imidazolyl, imidazopyridinyl, indolyl, indolinyl, indazolyl, isoindolinyl, isoxazolyl, isothiazolyl, isoquinolinyl, oxadiazolyl, oxazolyl, purinyl, pyranyl, pyrazinyl, pyrazolyl, pyridinyl, pyrimidinyl, pyrrolyl, pyrrolo[2,3-d]pyrimidinyl, pyrazolo[3,4-d]pyrimidinyl, quinolinyl, quinazolinyl, triazolyl, thiazolyl, thiophenyl, tetrahydroindolyl, tetrazolyl, thiadiazolyl, thienyl, thiomorpholinyl, triazolyl or tropanyl, and the like. Any heteroaryl can be optionally substituted at one or more ring positions with one or more substituents such as halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, fluoroalkyl (such as trifluromethyl), cyano, or the like. The term "heteroaryl" also includes polycyclic ring systems having two or more cyclic rings in which two or more carbons are common to two adjoining rings (the rings are "fused rings") wherein at least one of the rings is an aromatic group having one or more heteroatoms in the ring structure, e.g., the other cyclic rings may be cycloalkyls, cycloalkenyls, cycloalkynyls, aryls, heteroaryls, and/or heterocyclyls. Representative examples of bicyclic heteroaryl include, but are not limited to, benzimidazolyl, benzofuranyl, benzothienyl, benzoxadiazolyl, benzoxathiadiazolyl, benzothiazolyl, cinnolinyl, 5,6-dihydroquinolin-2-yl, 5,6-dihydroisoquinolin-1-yl, furopyridinyl, indazolyl, indolyl, isoquinolinyl, naphthyridinyl, quinolinyl, purinyl, 5,6,7,8-tetrahydroquinolin-2-yl, 5,6,7,8-tetrahydroquinolin-3-yl, 5,6,7,8-tetrahydroquinolin-4-yl, 5,6,7,8-tetrahydroisoquinolin-1-yl, thienopyridinyl, 4,5,6,7-tetrahydrobenzo[c][1,2,5]oxadiazolyl, and 6,7-dihydrobenzo[c][1,2,5]oxadiazol-4(5H)-onyl. Any heteroaryl or bicyclic heteroaryl can be optionally substituted as detailed below.

The term "aralkyl", "arylalkyl", or "aryl($C_1$-$C_6$)alkyl" is a term of art and as used herein refers to an alkyl group, for example a $C_1$-$C_6$ alkyl group, substituted with an aryl group, wherein the moiety is appended to the parent molecule through the alkyl group. An example of aralkyl is the benzyl group, i.e., the phenyl-methyl-group.

The term "arylene" is art-recognized, and as used herein pertains to a diradical obtained by removing two hydrogen atoms of an aryl group, as defined above. An exemplary arylene group is 1,4-phenylene.

The term "heteroaralkyl", "heteroarylalkyl", or "heteroaryl($C_1$-$C_6$)alkyl" is a term of art and as used herein refers to an alkyl group, for example a $C_1$-$C_6$ alkyl group, substituted with a heteroaryl group, appended to the parent molecular moiety through the alkyl group.

The term "alkoxy" or "alkoxyl" as used herein means an alkyl group, as defined herein, appended to the parent molecular moiety through an oxygen atom. Preferably, the alkoxy group is $(C_1-C_6)$alkoxy. Representative examples include, but are not limited to, methoxy, ethoxy, propoxy, 2-propoxy, butoxy, tert-butoxy, pentyloxy, and hexyloxy. Representative examples of $(C_1-C_3)$alkoxy include methoxy, ethoxy, and propoxy.

The term "alkoxycarbonyl" means an alkoxy group, as defined herein, appended to the parent molecular moiety through a carbonyl group, represented by —C(=O)—, as defined herein. Representative examples of alkoxycarbonyl include, but are not limited to, methoxycarbonyl, ethoxycarbonyl, and tert-butoxycarbonyl. Alkoxycarbonyl can form a portion of another moiety, e.g., methoxycarbonylmethyl.

The term "alkylcarbonyl", as used herein, means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "arylcarbonyl", as used herein, means an aryl group, as defined herein, appended to the parent molecular moiety through a carbonyl group, as defined herein. Representative examples of arylcarbonyl include, but are not limited to, benzoyl and (2-pyridinyl)carbonyl.

The term "alkylcarbonyloxy" and "arylcarbonyloxy", as used herein, means an alkylcarbonyl or arylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy. Representative examples of arylcarbonyloxy include, but are not limited to phenylcarbonyloxy.

The term "alkenoxy" or "alkenoxyl" means an alkenyl group, as defined herein, appended to the parent molecular moiety through an oxygen atom. Representative examples of alkenoxyl include, but are not limited to, 2-propen-1-oxyl (i.e., $CH_2=CH-CH_2-O-$) and vinyloxy (i.e., $CH_2=CH-O-$).

The term "aryloxy" as used herein means an aryl group, as defined herein, appended to the parent molecular moiety through an oxygen atom.

The term "heteroaryloxy" as used herein means a heteroaryl group, as defined herein, appended to the parent molecular moiety through an oxygen atom.

The terms "cyano" and "nitrile" is a term of art and as used herein refers to —CN.

The term "nitro", as used herein, means —$NO_2$.

The term "halo" or "halogen" is a term of art and as used herein refers to —F, —Cl, —Br, or —I.

The term "haloalkyl" as used herein refers to an alkyl group, as defined herein, wherein one or more or all of the hydrogens are replaced with halogen atoms. The term "haloalkoxyl" refers to an alkoxy group, as defined herein, wherein one or more or all of the hydrogens are replaced with halogen atoms. An exemplary $(C_1-C_6)$haloalkyl group is trifluoromethyl.

The term "hydroxy" is a term of art and as used herein refers to —OH.

The term "hydroxyalkyl", as used herein, means at least one hydroxy group, as defined herein, is appended to the parent molecular moiety through an alkyl group, as defined herein. Representative examples of $(C_1-C_6)$hydroxyalkyl include, but are not limited to, hydroxymethyl, 2-hydroxyethyl, 3-hydroxypropyl, and 2,3-dihydroxypentyl.

The term "sulfonyl", as used herein, refers to the group —$S(O)_2$— that may form a portion of larger moieties, such as methanesulfonyl or p-toluenesulfonyl.

The term "silyl", as used herein, includes hydrocarbyl derivatives of the silyl ($H_3Si$—) group (i.e., (hydrocarbyl)$_3$Si—), wherein a hydrocarbon radicals are univalent groups formed by removing a hydrogen atom from a hydrocarbon, e.g., ethyl, phenyl. The hydrocarbon radicals can be combinations of differing groups which can be varied in order to provide a number of silyl groups, such as trimethylsilyl (TMS), tert-butyldiphenylsilyl (TBDPS), tert-butyldimethylsilyl (TBS/TBDMS), triisopropylsilyl (TIPS), and [2-(trimethylsilyl)ethoxy]methyl (SEM).

The term "silyloxy", as used herein, means a silyl group, as defined herein, is appended to the parent molecule through an oxygen atom.

Certain compounds contained in compositions of the present invention may exist in particular geometric or stereoisomeric forms. In addition, compounds of the present invention may also be optically active. The present invention contemplates all such compounds, including cis- and trans-isomers, (R)- and (S)-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

The term "racemic mixture" refers to a mixture containing equal proportions of the first enantiomer of the molecule and of the second enantiomer of this molecule, wherein the second enantiomer is the mirror image of the first one.

The term "scalemic mixture" refers to any non-racemic mixture of stereoisomers of the molecule.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Organic compounds frequently occur in more than one crystalline form, that can differ in their physical and biological properties, such as melting point, stability, solubility, bioavailability. Such crystalline forms are termed polymorphs. All polymorphs of the inventive compounds of formula (I) and of their salts are intended to be within the scope of this invention.

Since many chemical elements can occur as isotopes, their abundance in the molecule of the inventive compound of formula (I) may be identical as in the nature or altered. Some isotopes exhibit different spectral or biological properties, and this phenomenon may be used for analysis of distribution and metabolism of drugs in the body of the recipient. All forms of the compounds of formula (I), both having a natural or unnatural abundance of isotopes of any of their constituent elements are intended to be within the scope of this invention.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, fragmentation, decomposition, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, halogen, azide, alkyl, aralkyl, alkenyl, alkynyl, cycloalkyl, cycloalkylalkyl, (cycloalkyl)alkoxyl, hydroxyl, alkoxyl, amino, nitro, sulfhydryl, imino, amido, phosphonate, phosphinate, carbonyl, carboxyl, silyl, ether, alkylthio, sulfonyl, aminosulfonyl, sulfonamido, ketone, aldehyde, ester, heterocycloalkyl, heterocycloalkylalkyl, (heterocycloalkyl)alkoxyl, aromatic or heteroaromatic moieties, aminoalkyl, haloalkyl, fluoroalkyl (such as trifluoromethyl), haloalkoxyl, cyano, or other substitutents described above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group", as used herein, means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, 2$^{nd}$ ed.; Wiley: New York, 1991). Protected forms of the inventive compounds are included within the scope of this invention.

A "saturated" or "fully saturated" compound means that the referenced chemical structure does not contain any multiple carbon-carbon bonds. For example, a saturated cycloalkyl group as defined herein includes cyclohexyl, cyclopropyl, and the like.

An "unsaturated" or "partially saturated" compound means that the referenced chemical structure may contain one or more multiple carbon-carbon bonds, but is not aromatic. For example, a unsaturated cycloalkyl group as defined herein includes cyclohexenyl, cyclopentenyl, cyclohexadienyl, and the like.

For purposes of the invention, the chemical elements are identified in accordance with the Periodic Chart of the Elements, IUPAC version, The Merck Index, Twelfth Edition, 1996, inside cover.

Other chemistry terms herein are used according to conventional usage in the art, as exemplified by The McGraw-Hill Dictionary of Chemical Terms (ed. Parker, S., 1985), McGraw-Hill, San Francisco). Unless otherwise defined, all technical and scientific terms used herein have the same meaning as commonly understood by one of ordinary skill in the art to which this invention pertains.

It will be apparent to one skilled in the art that the compounds of this disclosure may exist in tautomeric forms. For example, the following structures illustrate some tautomeric forms of the triazole group.

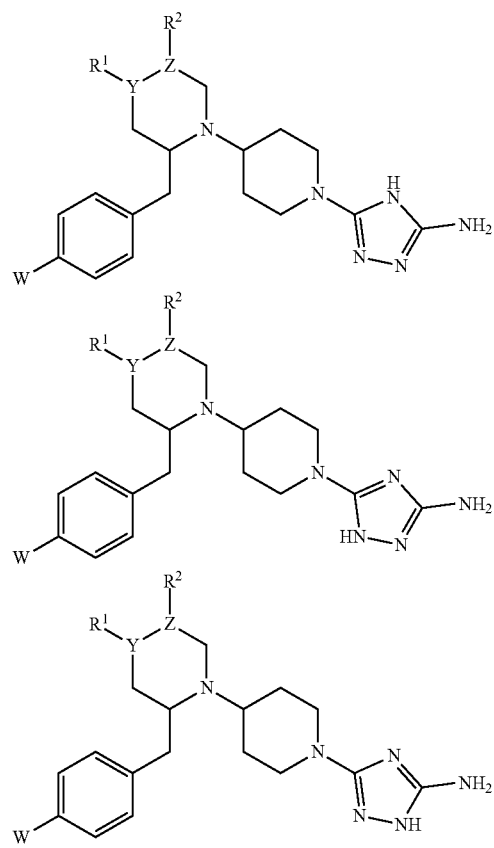

In this specification only one tautomeric form is depicted for each compound, but all such tautomeric forms of the compounds are within the scope of the disclosure.

Unless otherwise stated, structures depicted herein include all stereochemical configurations consistent with the depicted structure. For example, (i) a structure with a single stereocenter encompasses both the R and S configurations at the stereocenter and mixtures thereof, including racemic mixtures, and (ii) in a structure with two or more stereocenters, any wedged and dashed bonds show relative stereochemistry unless otherwise noted, such that the structure encompasses the individual enantiomers of the depicted compound and mixtures thereof, including racemic mixtures. Therefore, single stereochemical isomers as well as enantiomeric and diastereomeric mixtures of the present compounds are within the scope of the disclosure. Both the R and the S stereochemical isomers, as well as all mixtures thereof, are included within the scope of the disclosure. Similarly, indications of stereochemistry in chemical structures with two or more chiral centers convey relative stereochemistry unless otherwise defined.

If a stereocenter (e.g., an asymmetric carbon, nitrogen, or sulfur atom) is depicted in a structural formula without specifying its configuration, then the structural formula in question represents any stereoisomer at this stereocenter or a mixture of any such stereoisomers in any proportion thereof.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically acceptable salt" as used herein includes salts derived from inorganic or organic acids including, for example, hydrochloric, hydrobromic, sulfuric, nitric, perchloric, phosphoric, formic, acetic, lactic, maleic, fumaric, succinic, tartaric, glycolic, salicylic, citric, methanesulfonic, benzenesulfonic, benzoic, malonic, trifluoroacetic, trichloroacetic, naphthalene-2-sulfonic, and other acids. Pharmaceutically acceptable salt forms can include forms wherein the ratio of molecules comprising the salt is not 1:1. For example, the salt may comprise more than one inorganic or organic acid molecule per molecule of base, such as two hydrochloric acid molecules per molecule of compound of Formula I. As another example, the salt may comprise less than one inorganic or organic acid molecule per molecule of base, such as two molecules of compound of Formula I per molecule of tartaric acid.

As used herein, a protic solvent is a solvent that has a hydrogen atom bound to an oxygen (as in a hydroxyl group) or a nitrogen (as in an amine group). In general terms, any solvent that contains labile $H^+$ is called a protic solvent. The molecules of such solvents readily donate protons ($H^+$) to reagents. In contrast, an aprotic solvent is a solvent that does not have a hydrogen atom bound to an oxygen (as in a hydroxyl group) or a nitrogen (as in an amine group), and it cannot donate hydrogen.

As used herein, a polar protic solvent is a protic solvent that will dissolve many salts. In general, these solvents have high dielectric constants and high polarity. Non-limiting examples of polar protic solvents include acetic acid, ammonia, ethanol, formic acid, isopropanol, methanol, n-butanol, nitromethane, n-propanol, t-butanol, and water.

As used herein, a polar aprotic solvent is a solvent that will dissolve many salts, but lacks an acidic hydrogen; these solvents generally have intermediate to high dielectric constants and polarity. Non-limiting examples of polar aprotic solvents include acetone, acetonitrile, dichloromethane (DCM), dimethyl sulfoxide (DMSO), ethyl acetate, hexamethylphosphoric triamide (HMPT), N,N-dimethylformamide (DMF), and tetrahydrofuran (THF).

As used herein, a nonpolar aprotic solvent is a solvent that will dissolve many salts, but lacks an acidic hydrogen; these solvents generally have low dielectric constants and polarity. Non-limiting examples of nonpolar aprotic solvents include benzene, chloroform, cyclohexane, diethyl ether, hexane, pentane, and toluene.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, the mode of administration, the bioavailability of the particular compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

"Modulating" or "modulate" refers to the treating, prevention, suppression, enhancement or induction of a function, condition or disorder.

The term "treating" includes prophylactic and/or therapeutic treatments. The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof). In certain embodiments, the methods of the invention are for therapeutically treating.

As used herein, "subject" refers to a warm blooded animal such as a mammal, preferably a human, or a human child, which is afflicted with, or has the potential to be afflicted with one or more diseases and disorders described herein.

"$EC_{50}$" refers to a dosage, concentration or amount of a particular test compound that elicits a dose-dependent response at 50% of maximal expression of a particular response that is induced, provoked or potentiated by the particular test compound.

"$IC_{50}$" refers to an amount, concentration or dosage of a particular test compound that achieves a 50% inhibition of a maximal response in an assay that measures such response.

Compounds of the Invention

In one aspect, the invention provides a compound represented by formula (I),

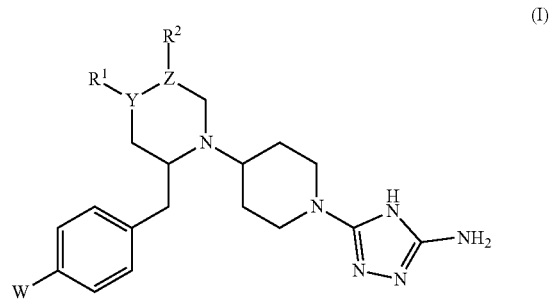

(I)

wherein:

W is halo or —$CF_3$;

Y is a single bond, —CH—, —C(OH)—, —N—, or —O—;
  if Y is a single bond or —O—, then $R^1$ is absent;
  if Y is —C(OH)—, then $R^1$ is ($C_1$-$C_6$)alkyl;
  if Y is —N—, then:
    either Z is —C—, and $R^1$, Y, Z, and $R^2$ taken together represent a 5-membered optionally substituted heteroaryl ring containing two N-heteroatoms as ring members,
    or Z is —CH—, and $R^1$, Y, Z, and $R^2$ taken together represent a 5- or 6-membered optionally substituted heterocyclyl ring containing one N heteroatom and optionally one O heteroatom as ring member(s);
if present, $R^1$ is H or ($C_1$-$C_6$)alkyl;
Z is —C— or —CH— or —C(halo)-;

if Z is —CH—, then $R^2$ is haloalkyl, hydroxyalkyl, (halo)(hydroxy)alkyl, optionally substituted heterocycloalkyl, optionally substituted heteroaryl, —C(O)NH(haloalkyl), —C(O)NH(alkyl substituted by —S(O)$_2$(alkyl)), —C(O)NH(alkyl substituted by —S(O)$_2$NH(alkyl)), —C(O)NH(optionally substituted cycloalkyl), —C(O)(heterocycloalkyl substituted by halo), —C(O)N($R^c$)($R^d$), or alkyl substituted by one or more substituents selected from the group consisting of optionally substituted heteroaryl, optionally substituted heterocycloalkyl, haloalkoxy, alkylthio, cyano, —S(O)(alkyl), —S(O)$_2$(alkyl), —OC(O)N(alkyl)$_2$, and —N($R^a$)C(O)$R^b$;

if Z is —C(halo)-, then $R^2$ is halo, haloalkyl, (halo)(hydroxy)alkyl, optionally substituted heterocycloalkyl, optionally substituted heteroaryl, —C(O)NH(haloalkyl), —C(O)NH(alkyl substituted by —S(O)$_2$(alkyl)), —C(O)NH(alkyl substituted by —S(O)$_2$NH(alkyl)), —C(O)NH(optionally substituted cycloalkyl), —C(O)(heterocycloalkyl substituted by halo), —C(O)N($R^c$)($R^d$), or alkyl substituted by one or more substituents selected from the group consisting of optionally substituted heteroaryl, optionally substituted heterocycloalkyl, haloalkoxy, alkylthio, cyano, —S(O)(alkyl), —S(O)$_2$(alkyl), —OC(O)N(alkyl)$_2$, and —N($R^a$)C(O)$R^b$;

$R^a$ and $R^b$, taken together with the intervening atoms, form an optionally substituted lactam;

$R^c$ and $R^d$, taken together with the intervening atoms, form an optionally substituted heterocycloalkyl ring;

if Y is —C(OH)—, then Z is —CH—, and $R^2$ is H; and any occurrence of optionally substituted heteroaryl, optionally substituted heterocycloalkyl, optionally substituted cycloalkyl, or optionally substituted lactam may be substituted with one or more substituents independently selected from the group consisting of —OH, halo, —NH$_2$, —NH(alkyl), —N(alkyl)$_2$, —CN, —NO$_2$, alkyl, haloalkyl, alkoxy, aryl, heteroaryl, arylalkyl, heteroarylalkyl, cycloalkyl, heterocycloalkyl, —C(O)OH, —C(O)Oalkyl, —C(O)NH$_2$, —C(O)NHalkyl, and —C(O)N(alkyl)$_2$;

or a pharmaceutically acceptable salt, solvate, tautomer, stereoisomer, prodrug, or polymorph thereof.

In certain embodiments, the compound is represented by formula (I), wherein:

W is halo;

Y is a single bond, —CH—, —C(OH)—, or —O—;
  if Y is a single bond or —O—, then $R^1$ is absent; and
  if Y is —C(OH)—, then $R^1$ is (C$_1$-C$_6$)alkyl;

if present, $R^1$ is H or (C$_1$-C$_6$)alkyl;

Z is —CH— or —C(halo)-;

if Z is —CH—, then $R^2$ is haloalkyl, (halo)(hydroxy)alkyl, optionally substituted heterocycloalkyl, optionally substituted heteroaryl, —C(O)NH(haloalkyl), —C(O)NH(alkyl substituted by —S(O)$_2$(alkyl)), —C(O)NH(alkyl substituted by —S(O)$_2$NH(alkyl)), —C(O)NH(optionally substituted cycloalkyl), —C(O)(heterocycloalkyl substituted by halo), —C(O)N($R^c$)($R^d$), or alkyl substituted by one or more substituents selected from the group consisting of optionally substituted heteroaryl, optionally substituted heterocycloalkyl, haloalkoxy, alkylthio, cyano, —S(O)(alkyl), —S(O)$_2$(alkyl), —OC(O)N(alkyl)$_2$, and —N($R^a$)C(O)$R^b$;

if Z is —C(halo)-, then $R^2$ is halo, haloalkyl, (halo)(hydroxy)alkyl, optionally substituted heterocycloalkyl, optionally substituted heteroaryl, —C(O)NH(haloalkyl), —C(O)NH(alkyl substituted by —S(O)$_2$(alkyl)), —C(O)NH(alkyl substituted by —S(O)$_2$NH(alkyl)), —C(O)NH(optionally substituted cycloalkyl), —C(O)(heterocycloalkyl substituted by halo), —C(O)N($R^c$)($R^d$), or alkyl substituted by one or more substituents selected from the group consisting of optionally substituted heteroaryl, optionally substituted heterocycloalkyl, haloalkoxy, alkylthio, cyano, —S(O)(alkyl), —S(O)$_2$(alkyl), —OC(O)N(alkyl)$_2$, and —N($R^a$)C(O)$R^b$;

$R^a$ and $R^b$, taken together with the intervening atoms, form an optionally substituted lactam;

$R^c$ and $R^d$, taken together with the intervening atoms, form an optionally substituted heterocycloalkyl ring;

if Y is —C(OH)—, then Z is —CH—, and $R^2$ is H; and any occurrence of optionally substituted heteroaryl, optionally substituted heterocycloalkyl, optionally substituted cycloalkyl, or optionally substituted lactam may be substituted with one or more substituents independently selected from the group consisting of —OH, halo, —NH$_2$, —NH(alkyl), —N(alkyl)$_2$, —CN, —NO$_2$, alkyl, haloalkyl, alkoxy, aryl, heteroaryl, arylalkyl, heteroarylalkyl, cycloalkyl, heterocycloalkyl, —C(O)OH, —C(O)Oalkyl, —C(O)NH$_2$, —C(O)NHalkyl, and —C(O)N(alkyl)$_2$;

or a pharmaceutically acceptable salt, solvate, tautomer, stereoisomer, or polymorph thereof.

In certain embodiments, W is halo.
In certain embodiments, W is fluoro, chloro, or bromo.
In certain embodiments, W is chloro or bromo.
In certain embodiments, W is chloro.
In certain embodiments, Y is a single bond, —CH—, —C(OH)—, or —O—.
In certain embodiments, Y is a single bond, —O—, or —CH—.
In certain embodiments, Y is a single bond.
In certain embodiments, Y is —O—.
In certain embodiments, Y is —CH—.
In certain embodiments, Y is —N—.
In certain embodiments, if Z is —CH—, then $R^2$ is haloalkyl, (halo)(hydroxy)alkyl, optionally substituted heterocycloalkyl, optionally substituted heteroaryl, —C(O)NH(haloalkyl), —C(O)NH(alkyl substituted by —S(O)$_2$(alkyl)), —C(O)NH(alkyl substituted by —S(O)$_2$NH(alkyl)), —C(O)NH(optionally substituted cycloalkyl), —C(O)(heterocycloalkyl substituted by halo), —C(O)N($R^c$)($R^d$), or alkyl substituted by one or more substituents selected from the group consisting of optionally substituted heteroaryl, optionally substituted heterocycloalkyl, haloalkoxy, alkylthio, cyano, —S(O)(alkyl), —S(O)$_2$(alkyl), —OC(O)N(alkyl)$_2$, and —N($R^a$)C(O)$R^b$.

In certain embodiments, Z is —CH—.

In certain embodiments, $R^2$ is optionally substituted heterocycloalkyl, optionally substituted heteroaryl, —C(O)NH(alkyl substituted by —S(O)$_2$(alkyl)), —C(O)NH(alkyl substituted by —S(O)$_2$NH(alkyl)), —C(O)NH(optionally substituted cycloalkyl), or alkyl substituted by one or more substituents selected from the group consisting of alkylthio, —S(O)(alkyl), —S(O)$_2$(alkyl), and —OC(O)N(alkyl)$_2$.

In certain embodiments, R$^2$ is optionally substituted heteroaryl.

In certain embodiments, R$^2$ is —C(O)NH(optionally substituted cycloalkyl), e.g., —C(O)NH(optionally substituted cyclopropyl).

In certain embodiments, R$^2$ is alkyl substituted by one or more substituents selected from the group consisting of —S(O)(alkyl), —S(O)$_2$(alkyl), and —OC(O)N(alkyl)$_2$.

In certain embodiments, R$^2$ is haloalkyl, (halo)(hydroxy)alkyl, —C(O)NH(haloalkyl), —C(O)(heterocycloalkyl substituted by halo), or alkyl substituted by one or more substituents selected from the group consisting of optionally substituted heteroaryl, optionally substituted heterocycloalkyl, haloalkoxy, and cyano.

In certain embodiments, R$^2$ is haloalkyl, —C(O)NH(haloalkyl), or —C(O)(heterocycloalkyl substituted by halo).

In certain embodiments, R$^2$ is alkyl substituted by one or more substituents selected from the group consisting of optionally substituted heteroaryl, optionally substituted heterocycloalkyl, haloalkoxy, and cyano.

In certain embodiments, R$^2$ is haloalkyl. For example, R$^2$ may be fluoroalkyl, or perfluoroalkyl.

In certain embodiments, Z is —C(halo)-. In certain such embodiments, R$^2$ is halo. For example, in some embodiments, Z is —C(F)— and R$^2$ is F.

In certain embodiments, Y is —C(OH)—, Z is —CH—, and R$^2$ is H. In certain such embodiments, R$^1$ is methyl.

In certain embodiments, the compound is represented by formula (Ia):

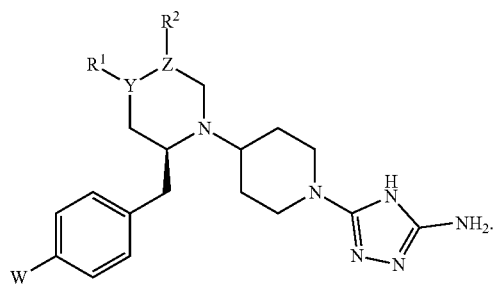

(Ia)

In certain embodiments, the compound is represented by formula (Ib):

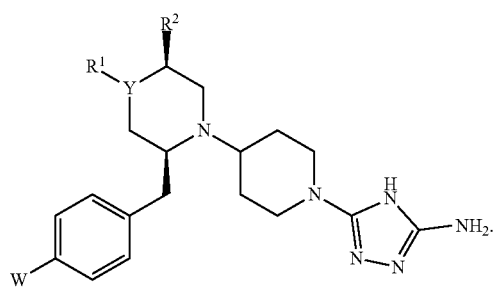

(Ib)

In certain embodiments, the invention relates to a compound of any one of the following structural formulas:

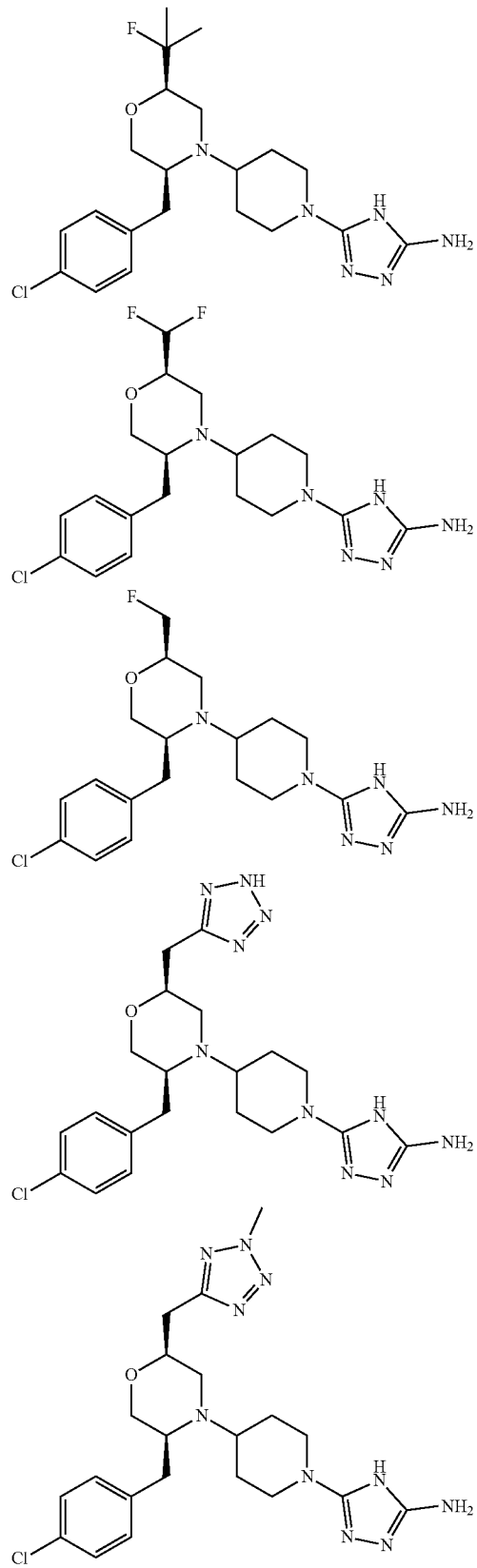

-continued
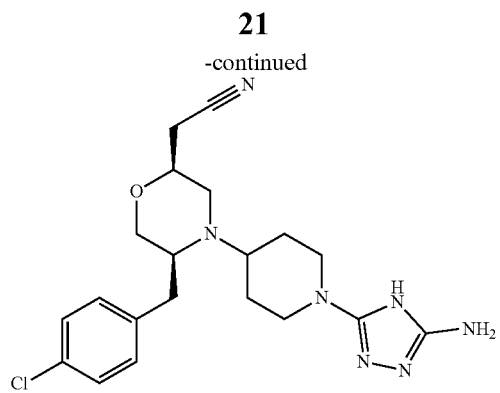
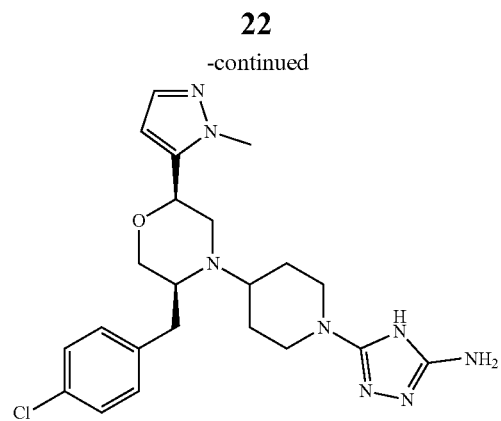
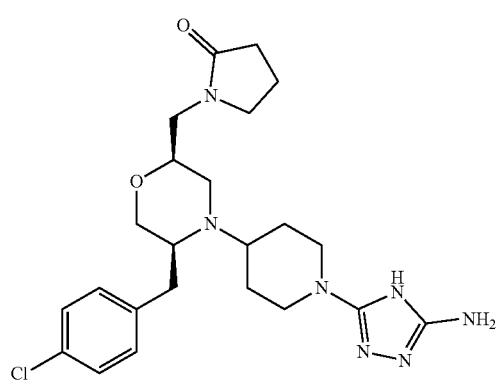
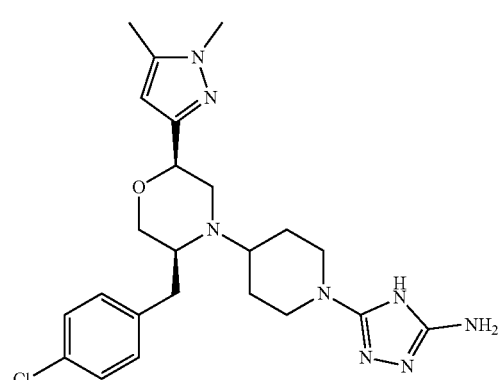
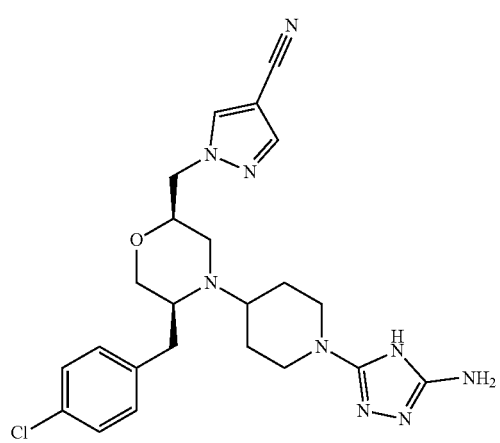
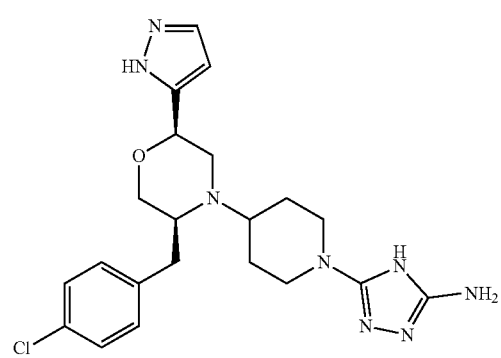
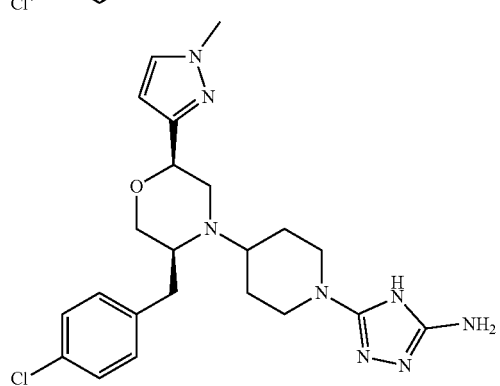
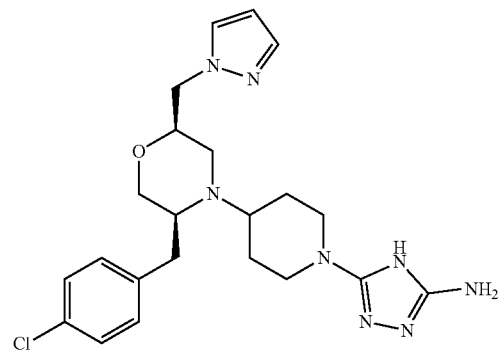

-continued
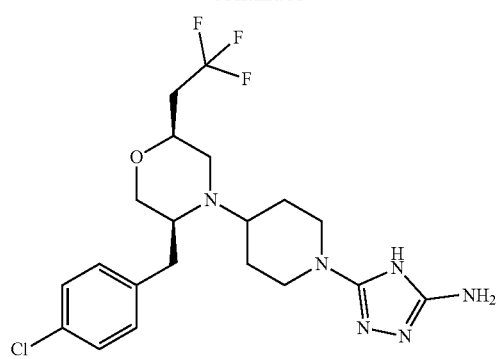
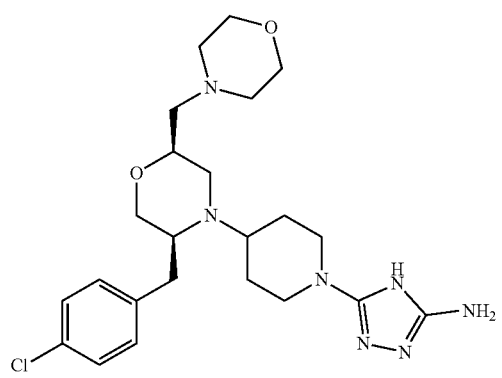
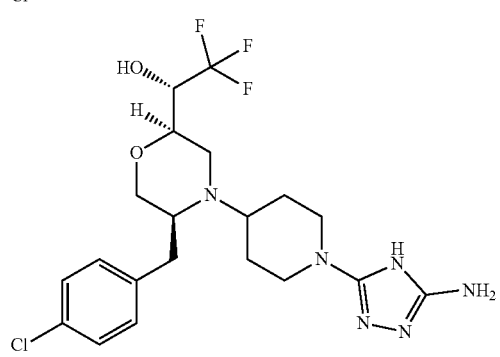
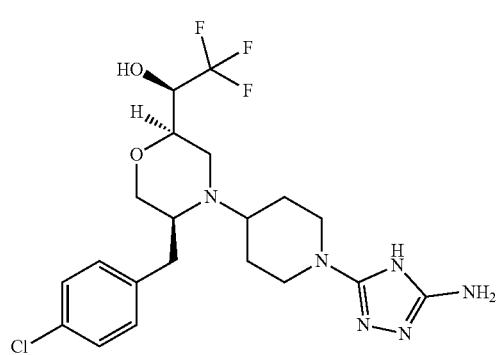
-continued
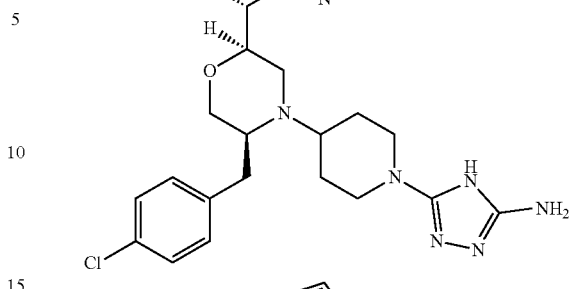
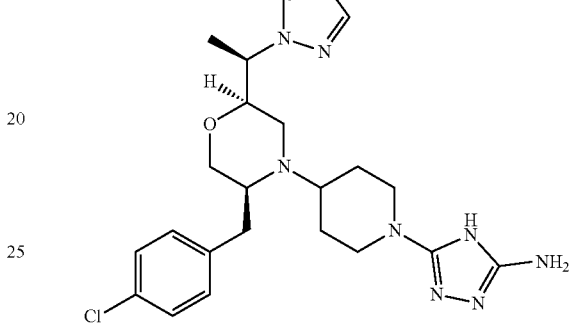
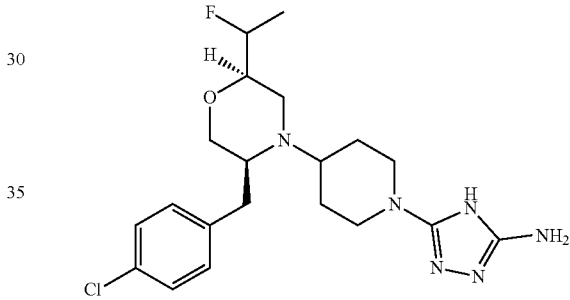
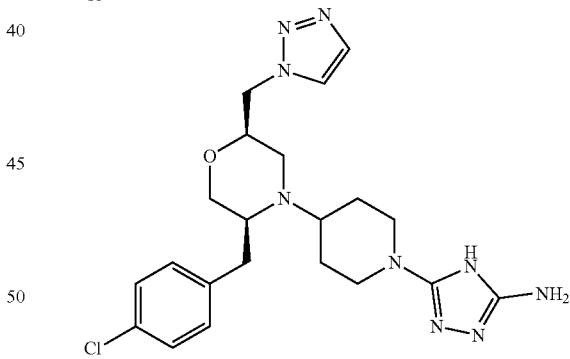
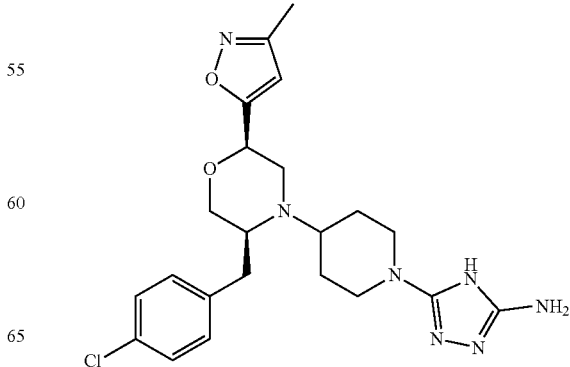

25
-continued
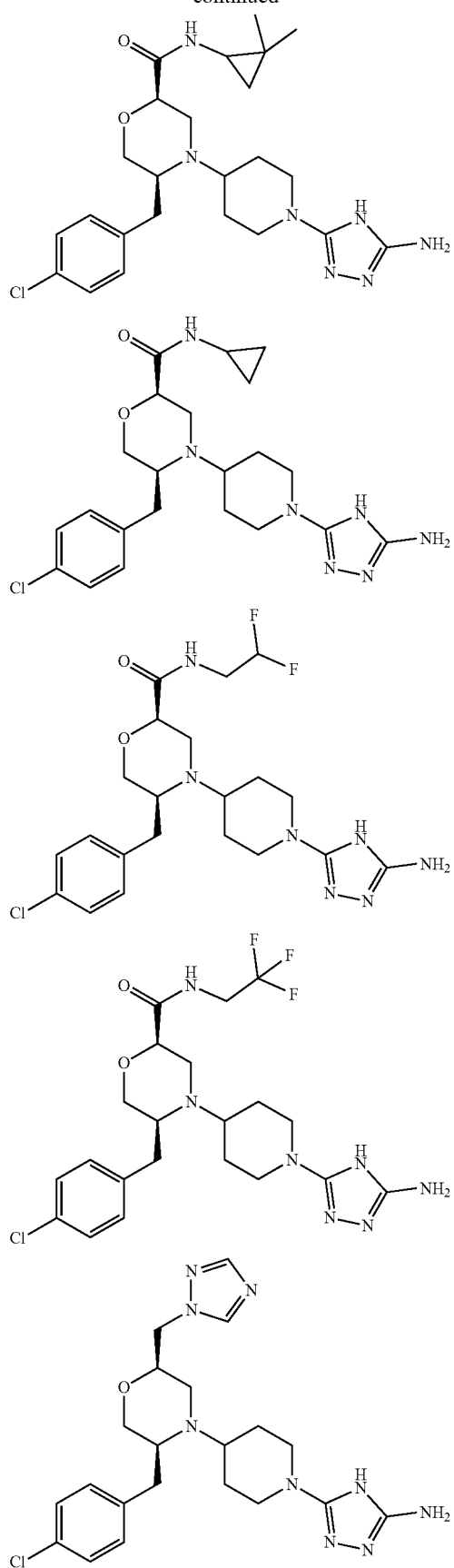
26
-continued
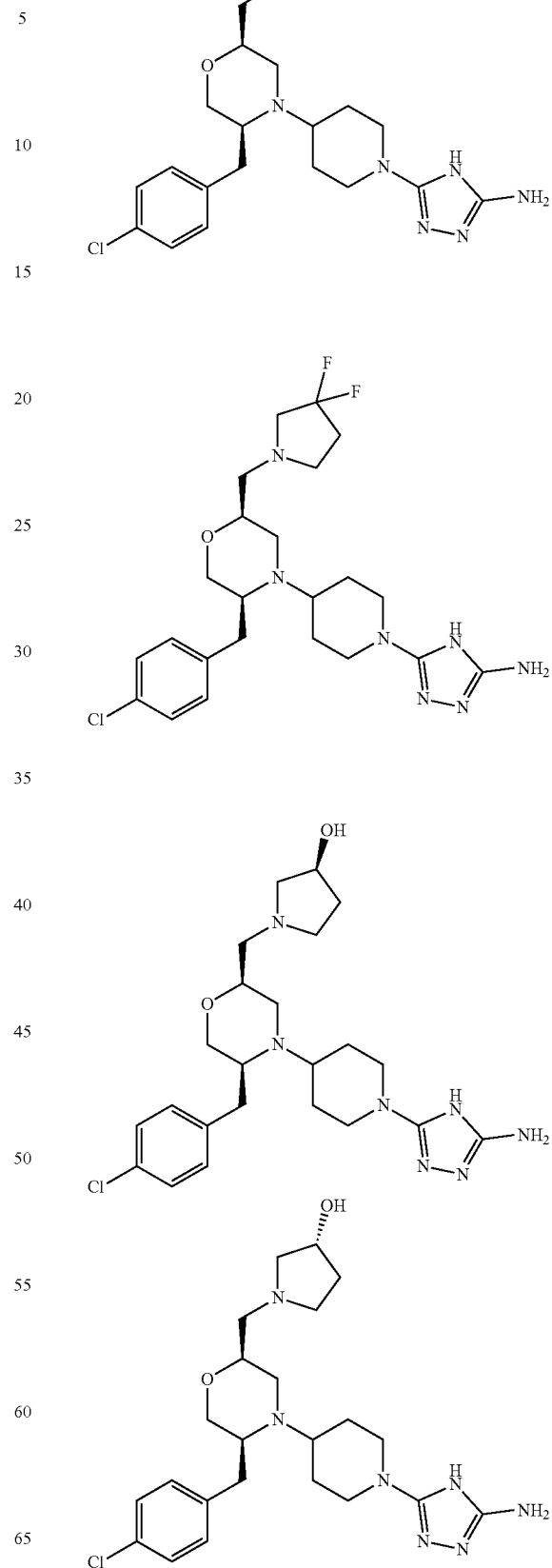

27
-continued
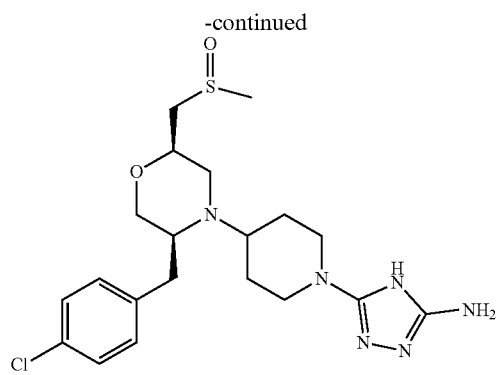
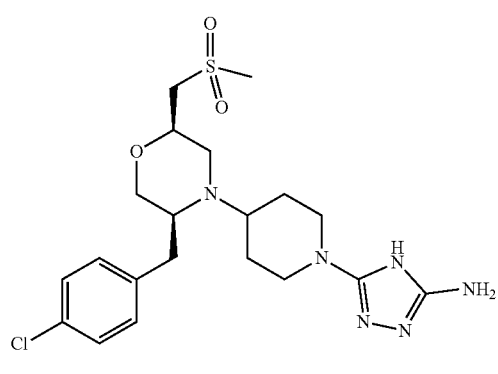
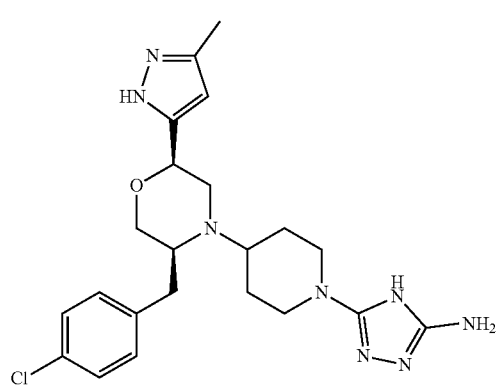
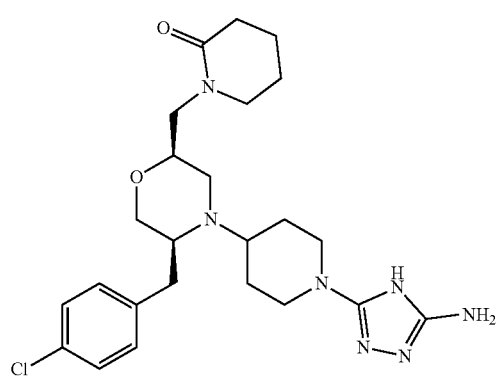
28
-continued
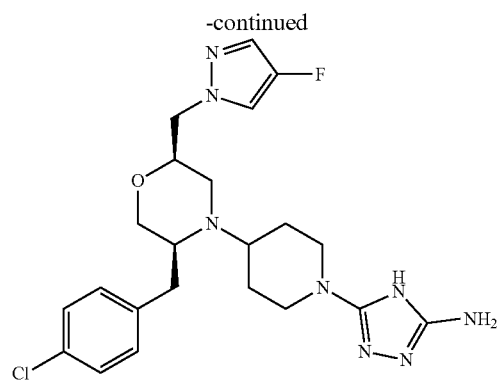
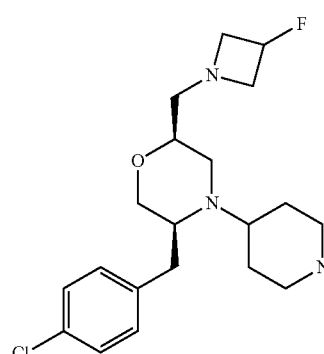
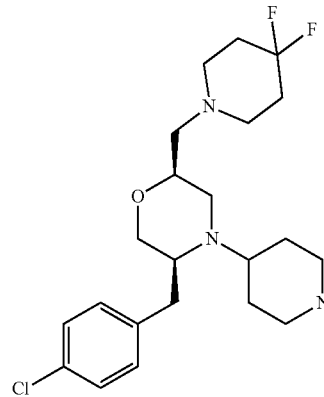
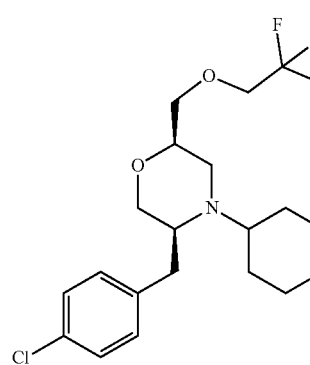

29
-continued
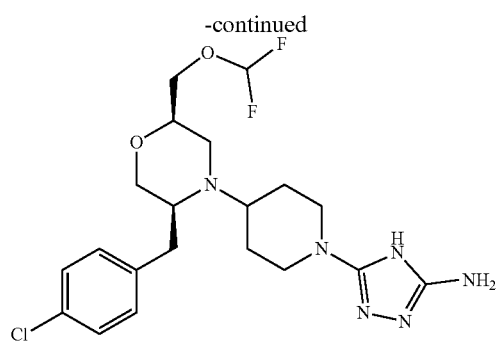
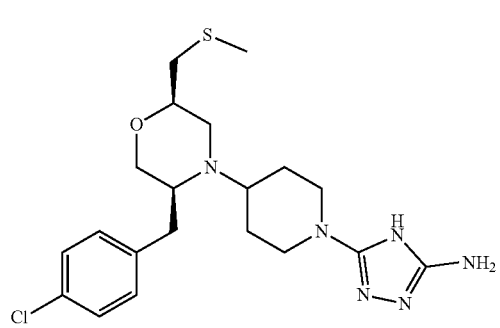
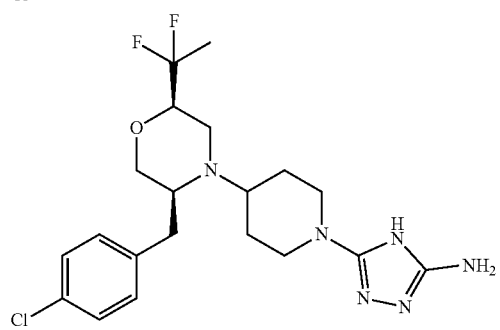
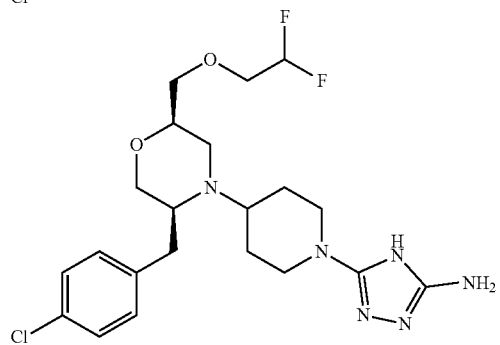
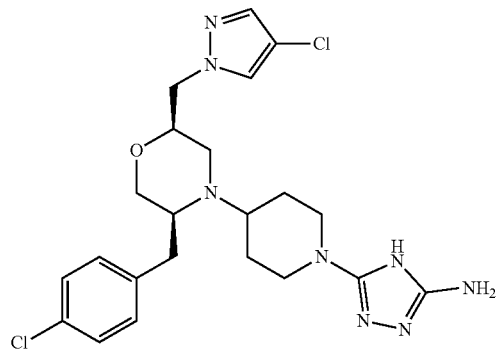
30
-continued
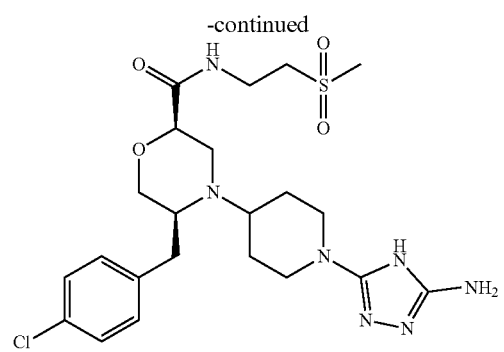
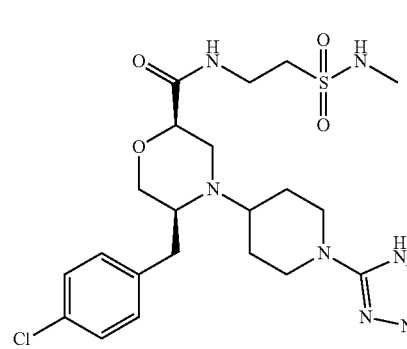
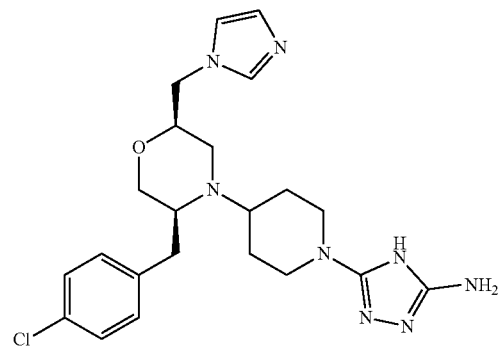
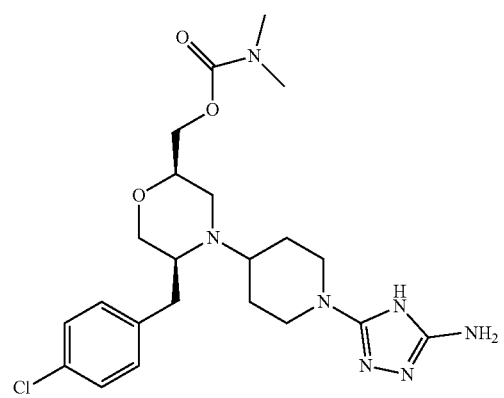

31
-continued
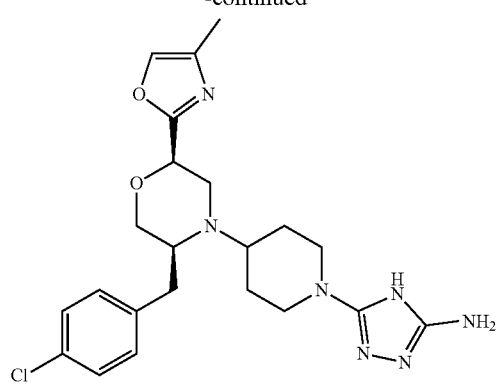
32
-continued
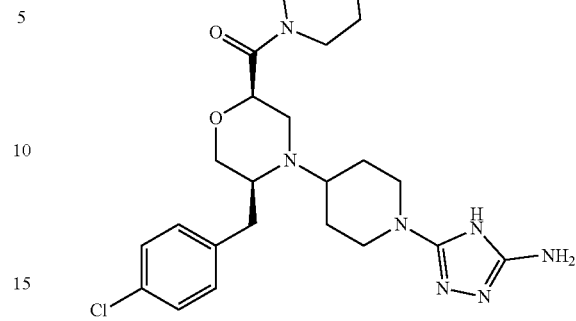
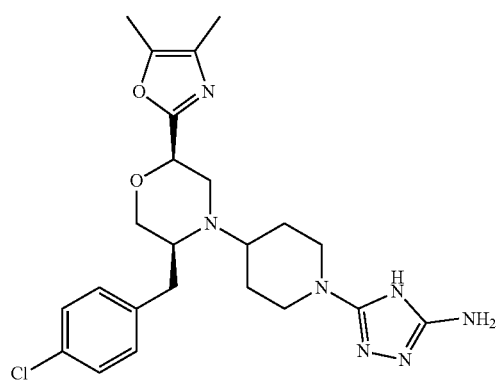
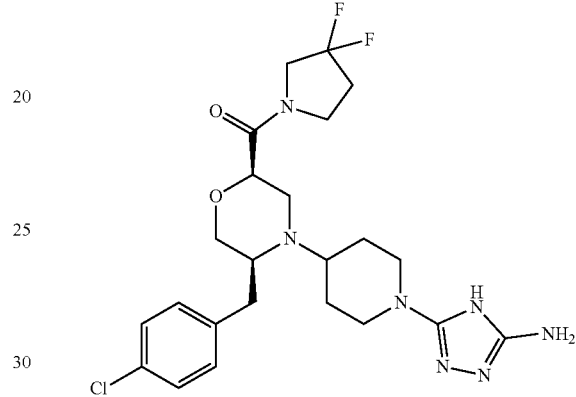
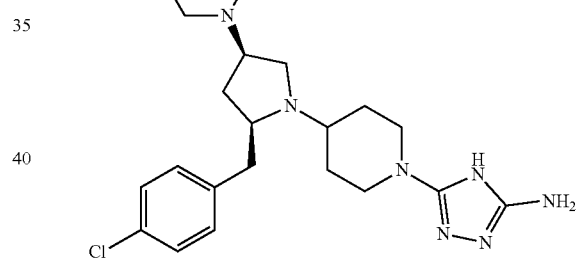
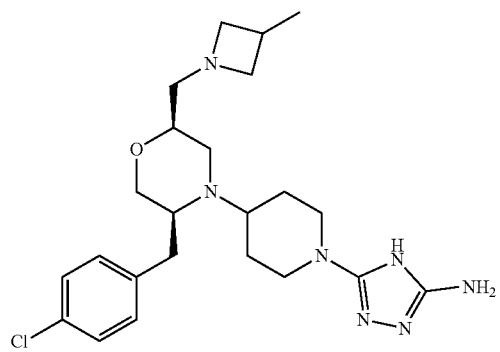
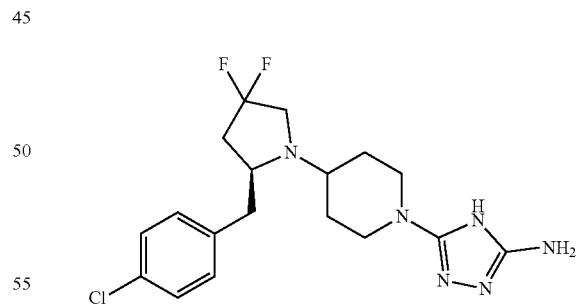
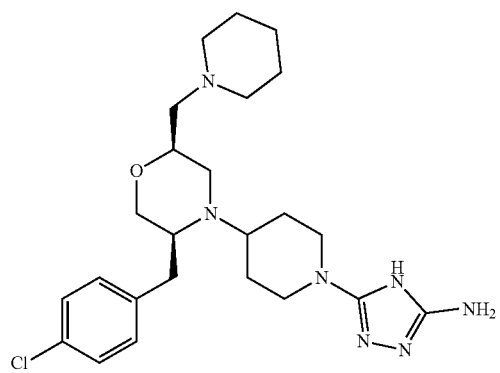
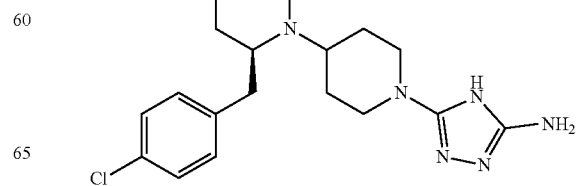

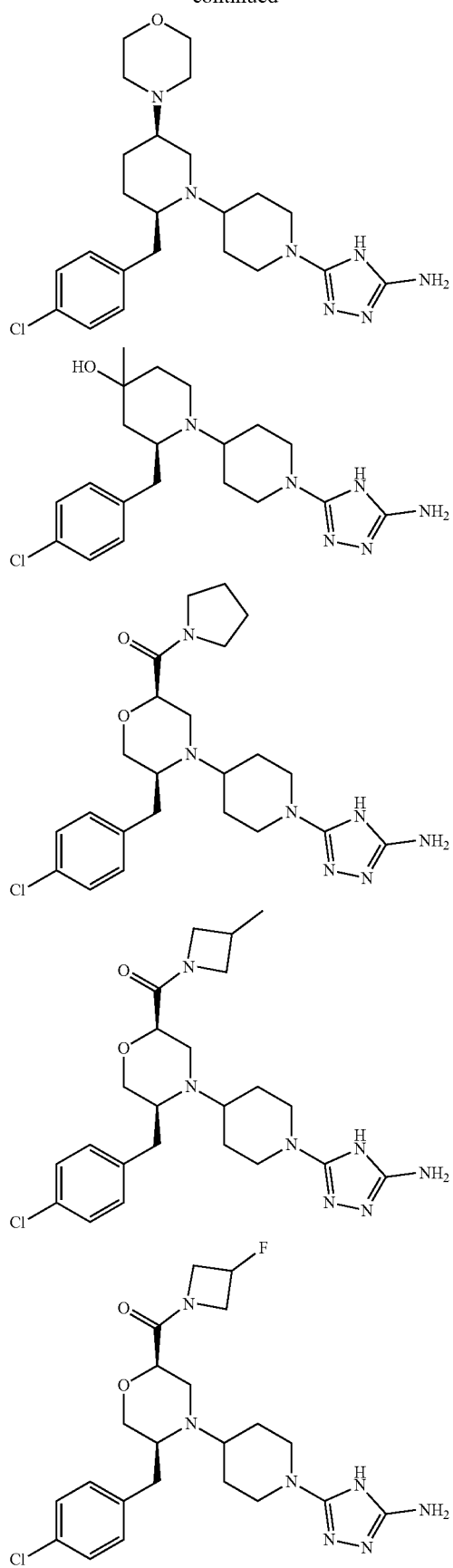
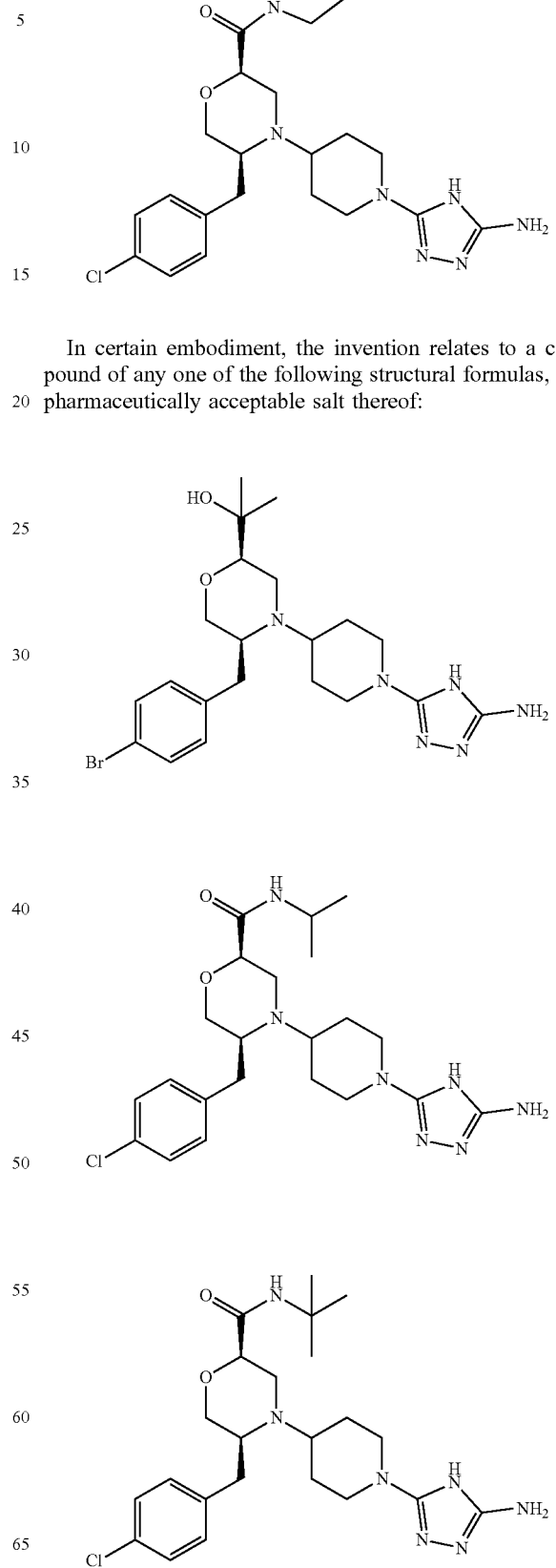
In certain embodiment, the invention relates to a compound of any one of the following structural formulas, or a pharmaceutically acceptable salt thereof:

35
-continued
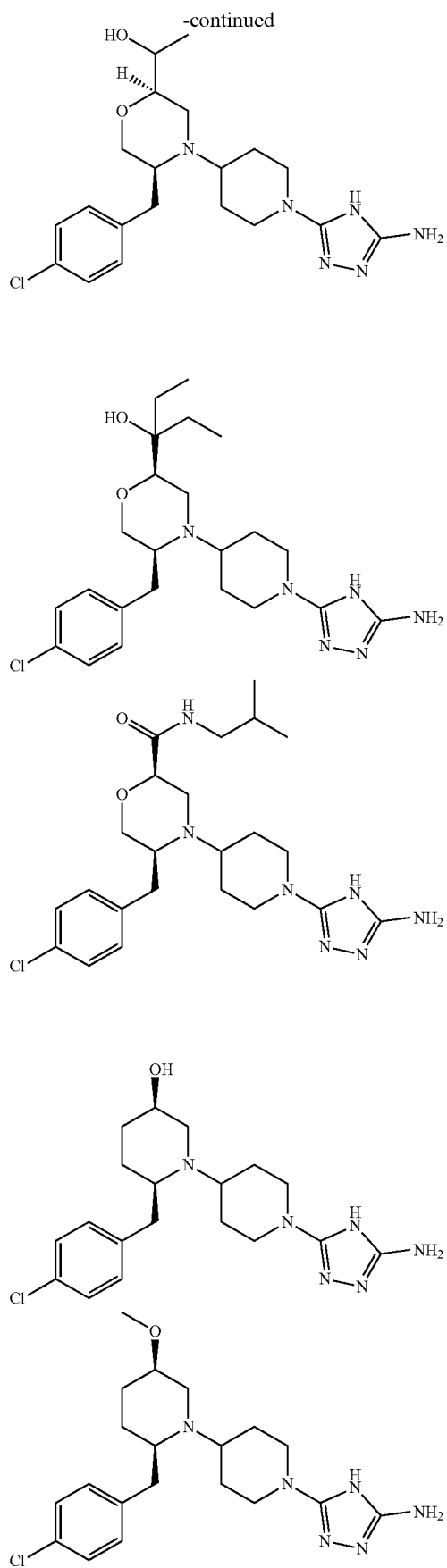
36
-continued
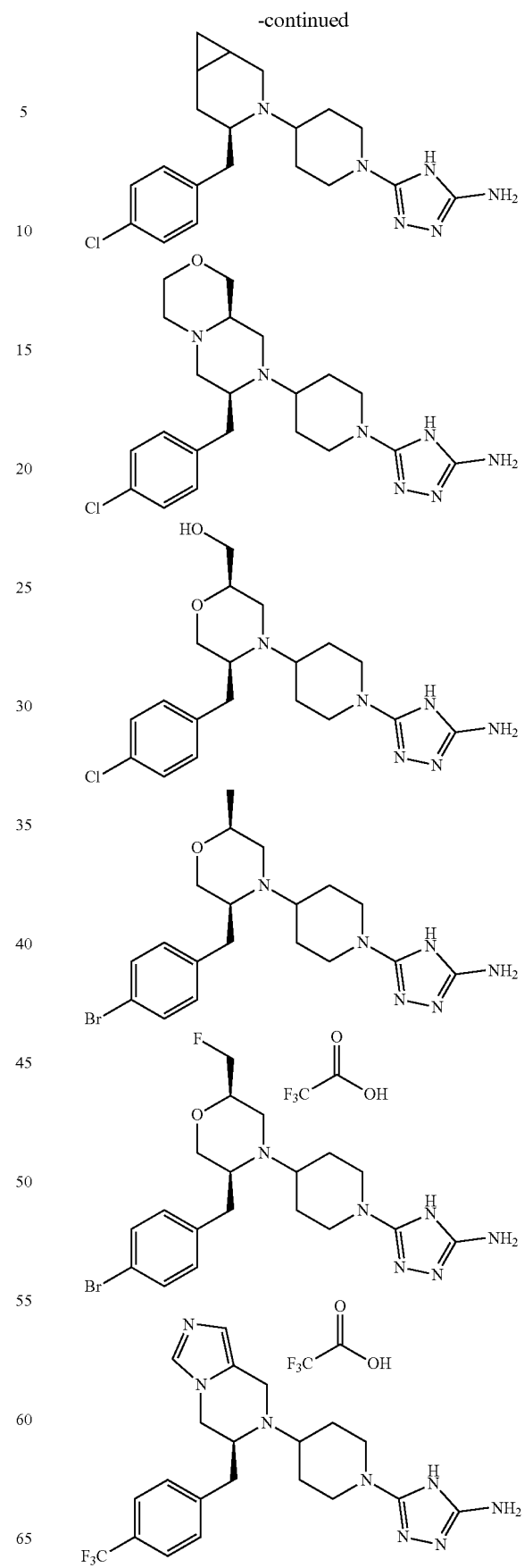

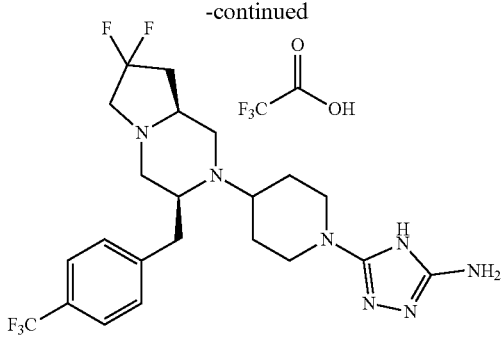

The salts, hydrates, and solvates of the compounds of the invention are preferably pharmaceutically acceptable salts, hydrates, and solvates. The solvates may contain a stoichiometric or non-stoichiometric amount of one or more solvents, such as water, ethanol, or ethyl acetate, in addition to the molecule of the compound of the invention. The solvates formed with water are called hydrates.

The compounds described herein are useful in treating inflammatory diseases, such as esophageal eosinophilic inflammation, keratoconjunctivitis, seasonal allergic conjunctivitis, dry eye syndrome, or chronic rhinosinusitis with or without nasal polyps. The compounds can be used in treating diseases caused by infectious agents, such as fungi, worms and parasites. The compounds can be used in treating chronic obstructive pulmonary disease (COPD) or autoimmune diseases including but not restricted to inflammatory bowel disease or rheumatoid arthritis.

Pharmaceutical Compositions of the Invention

Another aspect of the invention provides a pharmaceutical composition comprising a therapeutically effective amount of a compound of the invention (e.g., a compound of formula (I)), and a pharmaceutically acceptable carrier.

The exact nature of the carrier, or, for example excipient or diluent, will depend upon the desired use for the composition, and may be suitable or acceptable for veterinary use and/or suitable or acceptable for human use. The composition may optionally include one or more additional compounds, including one or more additional therapeutic agents.

Compounds of the invention can be combined with other therapeutic agents. The compound of the invention and other therapeutic agent may be administered simultaneously or sequentially. When the other therapeutic agents are administered simultaneously, they can be administered in the same or separate formulations, but they are administered substantially at the same time. The other therapeutic agents are administered sequentially with one another and with compound of the invention, when the administration of the other therapeutic agents and the compound of the invention is temporally separated. The separation in time between the administration of these compounds may be a matter of minutes or it may be longer.

Examples of other therapeutic agents that may be administered with the compounds of the invention include steroids, membrane stabilizers, 5LO inhibitors, leukotriene synthesis and receptor inhibitors, inhibitors of IgE isotype switching or IgE synthesis, inhibitors of IgG isotype switching or IgG synthesis, β-agonists, tryptase inhibitors, aspirin, COX inhibitors, methotrexate, anti-TNF drugs, rituxin, PD4 inhibitors, p38 inhibitors, PDE4 inhibitors, and antihistamines.

Thus, another aspect of the invention provides a pharmaceutical composition comprising a therapeutically effective amount of a compound of the invention and a second therapeutic agent selected from the group consisting of steroids, membrane stabilizers, 5LO inhibitors, leukotriene synthesis and receptor inhibitors, inhibitors of IgE isotype switching or IgE synthesis, inhibitors of IgG isotype switching or IgG synthesis, β-agonists, tryptase inhibitors, acetylsalicylic acid, COX inhibitors, methotrexate, anti-TNF drugs, rituxin and other B-cell targeting agents, TNF-targeting agents, PD4 inhibitors, p38 inhibitors, PDE4 inhibitors, and antihistamines.

As stated above, an "effective amount" refers to any amount that is sufficient to achieve a desired biological effect. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial unwanted toxicity and yet is effective to treat the particular subject. The effective amount for any particular application can vary depending on such factors as the disease or condition being treated, the particular compound of the invention being administered, the size of the subject, or the severity of the disease or condition. One of ordinary skill in the art can empirically determine the effective amount of a particular compound of the invention and/or other therapeutic agent without necessitating undue experimentation. It is preferred generally that a maximum dose be used, that is, the highest safe dose according to some medical judgment. Multiple doses per day may be contemplated to achieve appropriate systemic levels of compounds. Appropriate systemic levels can be determined by, for example, measurement of the patient's peak or sustained plasma level of the drug. "Dose" and "dosage" are used interchangeably herein.

Generally, daily oral doses of active compounds will be, for human subjects, from about 0.0001 milligrams/kg per day, 0.001 milligrams/kg per day, or 0.01 milligrams/kg per day to about 100 milligrams/kg per day or 1000 milligrams/kg per day. It is expected that oral doses in the range of 0.5 to 50 milligrams/kg, in one or several administrations per day, will yield the desired results. Dosage may be adjusted appropriately to achieve desired drug levels sufficient to achieve or maintain a desired therapeutic effect, local or systemic, depending upon the mode of administration. For example, it is expected that intravenous administration would be from one order to several orders of magnitude lower dose per day. In the event that the response in a subject is insufficient at such doses, even higher doses (or effective higher doses by a different, more localized delivery route) may be employed to the extent that patient tolerance permits. Multiple doses per day are contemplated to achieve appropriate systemic levels of compounds. The compounds may be administered once per week, several times per week (e.g., every other day), once per day or multiple times per day, depending upon, among other things, the mode of administration, the specific indication being treated and the judgment of the prescribing physician.

In one embodiment, intravenous administration of a compound of the invention may typically be from 0.1 mg/kg/day to 20 mg/kg/day.

Determination of an effective dosage of a compound for a particular use and mode of administration is well within the capabilities of those skilled in the art. Effective dosages may be estimated initially from in vitro activity and metabolism assays. For example, an initial dosage of compound for use in animals may be formulated to achieve a circulating blood or serum concentration of the metabolite active compound that is at or above an $IC_{50}$ of the particular compound as measured in as in vitro assay. Calculating dosages to achieve such circulating blood or serum concentrations taking into account the bioavailability of the particular compound via the desired route of administration is well within the capabilities of skilled artisans. Initial dosages of compound can also be estimated from in vivo data, such as animal models. For any compound described herein the therapeutically effective amount can be initially determined from animal models. A therapeutically effective dose can also be determined from human data for compounds of the invention which have been tested in humans and for compounds which are known to exhibit similar pharmacological activities, such as other related active agents. Higher doses may be required for parenteral administration. The applied dose can be adjusted based on the relative bioavailability and potency of the administered compound. Adjusting the dose to achieve maximal efficacy based on the methods described above and other methods as are well-known in the art is well within the capabilities of the ordinarily skilled artisan.

The formulations of the invention can be administered in pharmaceutically acceptable solutions, which may routinely contain pharmaceutically acceptable concentrations of salt, buffering agents, preservatives, compatible carriers, adjuvants, and optionally other therapeutic ingredients.

Pharmaceutical compositions comprising the compound of the invention may be manufactured by means of conventional mixing, dissolving, granulating, dragee-making levigating, emulsifying, encapsulating, entrapping or lyophilization processes. The compositions may be formulated in conventional manner using one or more physiologically acceptable carriers, diluents, excipients or auxiliaries which facilitate processing of the compounds into preparations which can be used pharmaceutically.

For use in therapy, an effective amount of the compound of the invention can be administered to a subject by any mode that delivers the compound of the invention to the desired surface. Administering the pharmaceutical composition of the present invention may be accomplished by any means known to the skilled artisan. Routes of administration include but are not limited to oral, buccal, nasal, rectal, vaginal, ocular, topical, intravenous, intramuscular, intraperitoneal, subcutaneous, transdermal, intrathecal, direct injection (for example, into an abscess), mucosal, inhalation, and insufflation.

For oral administration, the compounds (i.e., compounds of the invention, and other therapeutic agents) can be formulated readily by combining the active compound(s) with pharmaceutically acceptable carriers well known in the art. Such carriers enable the compounds of the invention to be formulated as tablets, pills, dragees, lozenges, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, binding agents, fillers, lubricants, disintegrants, and wetting agents. Suitable fillers include sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers, e.g., EDTA for neutralizing internal acid conditions or may be administered without any carriers.

Also specifically contemplated are oral dosage forms of the above component or components. The component or components may be chemically modified so that oral delivery of the derivative is efficacious. Generally, the chemical modification contemplated is the attachment of at least one moiety to the component molecule itself, where said moiety permits (a) inhibition of acid hydrolysis; and (b) uptake into the blood stream from the stomach or intestine. Also desired is the increase in overall stability of the component or components and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. Abuchowski and Davis, "Soluble Polymer-Enzyme Adducts", In: Enzymes as Drugs, Hocenberg and Roberts, eds., Wiley-Interscience, New York, N.Y., pp. 367-383 (1981); Newmark et al., *J Appl Biochem* 4:185-9 (1982). Other polymers that could be used are poly-1,3-dioxolane and poly-1,3,6-tioxocane. Preferred for pharmaceutical usage, as indicated above, are polyethylene glycol moieties.

For the component (or derivative) the location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the compound of the invention (or derivative) or by release of the biologically active material beyond the stomach environment, such as in the intestine.

To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic (e.g., powder); for liquid forms, a soft gelatin shell may be used. The shell material of cachets could be thick starch or other edible paper. For pills, lozenges, molded tablets or tablet triturates, moist massing techniques can be used.

The therapeutic can be included in the formulation as fine multi-particulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the compound of the invention (or derivative) may be formulated (such as by liposome or microsphere encapsulation) and then further contained within an edible product, such as a refrigerated beverage containing colorants and flavoring agents.

One may dilute or increase the volume of the therapeutic with an inert material. These diluents could include carbohydrates, especially mannitol, α-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to forma hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment a surfactant might be added as a wetting agent. Surfactants may include anionic detergents such as sodium lauryl sulfate, dioctyl sodium sulfosuccinate and dioctyl sodium sulfonate. Cationic detergents which can be used and can include benzalkonium chloride and benzethonium chloride. Potential non-ionic detergents that could be included in the formulation as surfactants include lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the compound of the invention or derivative either alone or as a mixture in different ratios.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

Microspheres formulated for oral administration may also be used. Such microspheres have been well defined in the art. All formulations for oral administration should be in dosages suitable for such administration.

Liquid preparations for oral administration may take the form of, for example, elixirs, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl-p-hydroxybenzoates or sorbic acid). The preparations may also contain buffer salts, preservatives, flavoring, coloring and sweetening agents as appropriate.

The pharmaceutical compositions may, if desired, be presented in a pack or dispenser device which may contain one or more unit dosage forms containing the compound(s). The pack may, for example, comprise metal or plastic foil, such as a blister pack. The pack or dispenser device may be accompanied by instructions for administration.

For buccal administration, the compositions may take the form of tablets or lozenges formulated in conventional manner.

For topical administration, the compound may be formulated as solutions, gels, ointments, creams, suspensions, etc. as are well-known in the art. Systemic formulations include those designed for administration by injection, e.g., subcutaneous, intravenous, intramuscular, intrathecal or intraperitoneal injection, as well as those designed for transdermal, transmucosal oral or pulmonary administration.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

Also contemplated herein is pulmonary delivery of the compounds of the invention (or derivatives thereof). The compound of the invention (or derivative) is delivered to the lungs of a mammal while inhaling and traverses across the lung epithelial lining to the blood stream. Other reports of inhaled molecules include Adjei et al., *Pharm Res* 7:565-569 (1990); Adjei et al., *Int J Pharmaceutics* 63:135-144 (1990) (leuprolide acetate); Braquet et al., *J Cardiovasc Pharmacol* 13(suppl. 5):143-146 (1989) (endothelin-1); Hubbard et al., *Annal Int Med* 3:206-212 (1989) (al-antitrypsin); Smith et al., 1989, *J Clin Invest* 84:1145-1146 (a-1-proteinase); Oswein et al., 1990, "Aerosolization of Proteins", Proceedings of Symposium on Respiratory Drug Delivery II, Keystone, Colo., March, (recombinant human growth hormone); Debs et al., 1988, *J Immunol* 140:3482-3488 (interferon-gamma and tumor necrosis factor alpha) and Platz et al., U.S. Pat. No. 5,284,656 (granulocyte colony stimulating factor). A method and composition for pulmonary delivery of drugs for systemic effect is described in U.S. Pat. No. 5,451,569, issued Sep. 19, 1995 to Wong et al.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art.

Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, N.C.; the Spinhaler powder inhaler, manufactured by Fisons Corp., Bedford, Mass.; and the Respimat Soft Mist Inhaler, manufactured by Boehringer Ingelheim, Germany. Other hand-driven or human-powered inhaler devices are also applicable.

All such devices require the use of formulations suitable for the dispensing of compound of the invention (or derivative). Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated. Chemically modified compound of the invention may also be prepared in different formulations depending on the type of chemical modification or the type of device employed.

Formulations suitable for use with a nebulizer, either jet, ultrasonic, or soft mist type, will typically comprise compound of the invention (or derivative) dissolved in water at a concentration of about 0.1 to 25 mg of biologically active compound of the invention per mL of solution. The formulation may also include a buffer and a simple sugar (e.g., for compound of the invention stabilization and regulation of osmotic pressure). The nebulizer formulation may also contain a surfactant, to reduce or prevent surface induced aggregation of the compound of the invention caused by atomization of the solution in forming the aerosol.

Formulations for use with a metered-dose inhaler device will generally comprise a finely divided powder containing the compound of the invention (or derivative) suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing compound of the invention (or derivative) and may also include a bulking agent, such as lactose, sorbitol, sucrose, or mannitol in amounts which facilitate dispersal of the powder from the device, e.g., 50 to 90% by weight of the formulation. The compound of the invention (or derivative) should advantageously be prepared in particulate form with an average particle size of less than 10 micrometers (μm), most preferably 0.5 to 5 μm, for most effective delivery to the deep lung.

Nasal delivery of a pharmaceutical composition of the present invention is also contemplated. Nasal delivery allows the passage of a pharmaceutical composition of the present invention to the blood stream directly after administering the therapeutic product to the nose, without the necessity for deposition of the product in the lung. Formulations for nasal delivery include those with dextran or cyclodextran.

For nasal administration, a useful device is a small, hard bottle to which a metered dose sprayer is attached. In one embodiment, the metered dose is delivered by drawing the pharmaceutical composition of the present invention solution into a chamber of defined volume, which chamber has an aperture dimensioned to aerosolize and aerosol formulation by forming a spray when a liquid in the chamber is compressed. The chamber is compressed to administer the pharmaceutical composition of the present invention. In a specific embodiment, the chamber is a piston arrangement. Such devices are commercially available.

Alternatively, a plastic squeeze bottle with an aperture or opening dimensioned to aerosolize an aerosol formulation by forming a spray when squeezed is used. The opening is usually found in the top of the bottle, and the top is generally tapered to partially fit in the nasal passages for efficient administration of the aerosol formulation. Preferably, the nasal inhaler will provide a metered amount of the aerosol formulation, for administration of a measured dose of the drug.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as sterile suspensions, solutions, or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethylcellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, buffer, dextrose solution, before use. To this end, the active compound may be dried by any art-known technique, such as lyophilization, and reconstituted prior to use.

The compounds may also be formulated in rectal or vaginal compositions such as suppositories or retention enemas, e.g., containing conventional suppository bases such as cocoa butter or other glycerides.

For transmucosal administration, penetrants appropriate to the barrier to be permeated are used in the formulation. Such penetrants are known in the art.

For ocular administration, the compound(s) may be formulated as a solution, emulsion, suspension, etc. suitable for administration to the eye. A variety of vehicles suitable for administering compounds to the eye are known in the art.

In addition to the formulations described above, for prolonged delivery, the compounds may also be formulated as a depot preparation for administration by, for example, implantation or intramuscular injection. Such long acting formulations may be formulated with suitable polymeric or hydrophobic materials (for example as an emulsion in an acceptable oil) or ion exchange resins, or as sparingly soluble derivatives, for example, as a sparingly soluble salt. Alternatively, transdermal delivery systems manufactured as an adhesive disc or patch which slowly releases the compound for percutaneous absorption may be used. To this end, permeation enhancers may be used to facilitate transdermal penetration of the compound.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer R, *Science* 249:1527-33 (1990), which is incorporated herein by reference.

The compounds of the invention and optionally other therapeutics may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulfuric, nitric, phosphoric, maleic, acetic, salicylic, p-toluenesulfonic, tartaric, citric, methanesulfonic, formic, malonic, succinic, naphthalene-2-sulfonic, and benzenesulfonic. Also, such salts can be prepared as alkaline metal or alkaline earth salts, such as sodium, potassium or calcium salts of the carboxylic acid group. Typically, such salts are more soluble in aqueous solutions than the corresponding free acids and bases, but salts having lower solubility than the corresponding free acids and bases may also be formed.

The compounds may alternatively be formulated in the pharmaceutical composition per se, or in the form of a hydrate, solvate, or N-oxide.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

Pharmaceutical compositions of the invention contain an effective amount of a compound of the invention and optionally therapeutic agents included in a pharmaceutically acceptable carrier. The term "pharmaceutically acceptable carrier" means one or more compatible solid or liquid filler, diluents or encapsulating substances which are suitable for administration to a human or other vertebrate animal. The term "carrier" denotes an organic or inorganic ingredient, natural or synthetic, with which the active ingredient is combined to facilitate the application. The components of the pharmaceutical compositions also are capable of being commingled with the compounds of the present invention, and with each other, in a manner such that there is no interaction which would substantially impair the desired pharmaceutical efficiency.

The therapeutic agent(s), including specifically but not limited to the compound of the invention, may be provided in particles. Particles as used herein means nanoparticles or microparticles (or in some instances larger particles) which can consist in whole or in part of the compound of the invention or the other therapeutic agent(s) as described herein. The particles may contain the therapeutic agent(s) in a core surrounded by a coating, including, but not limited to, an enteric coating. The therapeutic agent(s) also may be dispersed throughout the particles. The therapeutic agent(s) also may be adsorbed into the particles. The particles may be of any order release kinetics, including zero-order release, first-order release, second-order release, delayed release, sustained release, immediate release, and any combination thereof, etc. The particle may include, in addition to the therapeutic agent(s), any of those materials routinely used in the art of pharmacy and medicine, including, but not limited to, erodible, nonerodible, biodegradable, or nonbiodegradable material or combinations thereof. The particles may be microcapsules which contain the compound of the invention in a solution or in a semi-solid state. The particles may be of virtually any shape.

Both non-biodegradable and biodegradable polymeric materials can be used in the manufacture of particles for delivering the therapeutic agent(s). Such polymers may be natural or synthetic polymers. The polymer is selected based on the period of time over which release is desired. Bioadhesive polymers of particular interest include bioerodible hydrogels described in Sawhney H S et al. (1993) *Macromolecules* 26:581-7, the teachings of which are incorporated herein. These include polyhyaluronic acids, casein, gelatin, glutin, polyanhydrides, polyacrylic acid, alginate, chitosan, poly(methyl methacrylates), poly(ethyl methacrylates), poly (butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

The therapeutic agent(s) may be contained in controlled release systems. The term "controlled release" is intended to refer to any drug-containing formulation in which the manner and profile of drug release from the formulation are controlled. This refers to immediate as well as non-immediate release formulations, with non-immediate release formulations including but not limited to sustained release and delayed release formulations. The term "sustained release" (also referred to as "extended release") is used in its conventional sense to refer to a drug formulation that provides for gradual release of a drug over an extended period of time, and that preferably, although not necessarily, results in substantially constant blood levels of a drug over an extended time period. The term "delayed release" is used in its conventional sense to refer to a drug formulation in which there is a time delay between administration of the formulation and the release of the drug there from. "Delayed release" may or may not involve gradual release of drug over an extended period of time, and thus may or may not be "sustained release."

Use of a long-term sustained release implant may be particularly suitable for treatment of chronic conditions.

"Long-term" release, as used herein, means that the implant is constructed and arranged to deliver therapeutic levels of the active ingredient for at least 7 days, and preferably 30-60 days. Long-term sustained release implants are well-known to those of ordinary skill in the art and include some of the release systems described above.

It will be understood by one of ordinary skill in the relevant arts that other suitable modifications and adaptations to the compositions and methods described herein are readily apparent from the description of the invention contained herein in view of information known to the ordinarily skilled artisan, and may be made without departing from the scope of the invention or any embodiment thereof.

Methods and Uses

As shown herein, the compounds of the invention are useful for inhibiting the enzymatic and biological activity of Acidic Mammalian Chitinase ("AMCase") and chitotriosidase 1 ("CHIT1").

Accordingly, the invention provides methods for inhibiting acidic mammalian chitinase in a cell or a tissue, comprising contacting a cell or a tissue with at least one compound according to the invention, or with a pharmaceutical composition according to the invention.

Similarly, the invention provides methods for inhibiting chitotriosidase 1 in a cell or a tissue, comprising contacting a cell or a tissue with at least one compound according to the invention, or with a pharmaceutical composition according to the invention.

In other aspects, the invention provides methods for the treatment or prevention of a disease, disorder, or condition associated with aberrant expression or activity of acidic mammalian chitinase, comprising administering to a subject in need thereof a therapeutically effective amount of at least one compound according to the invention, or with a pharmaceutical composition according to the invention.

Similarly, the invention provides methods for the treatment or prevention of a disease, disorder, or condition associated with aberrant expression or activity of chitotriosidase 1, comprising administering to a subject in need thereof a therapeutically effective amount of at least one compound according to the invention, or with a pharmaceutical composition according to the invention.

In certain embodiments, the diseases, disorders, or conditions associated with aberrant expression or activity of acidic mammalian chitinase include allergic diseases, acute and chronic inflammatory diseases, autoimmune diseases, dental diseases, neurologic diseases, metabolic diseases, liver diseases, polycystic ovary syndrome, endometriosis, and cancer.

In further embodiments, the diseases, disorders, or conditions associated with aberrant expression or activity of chitotriosidase 1 include asthma or fibrotic disorders such as idiopathic pulmonary fibrosis (IPF). In other embodiments, such diseases and disorders include fibrotic interstitial lung diseases such as IPF or chronic obstructive pulmonary disease (COPD).

Moreover, the invention provides methods of treating diseases caused by infectious agents, such as fungi, worms, and parasites, the method comprising administering to a subject in need of such treatment an effective amount of one or more compounds of the invention.

In one embodiment, the invention provides methods of treating allergies, comprising administering to a subject in need of such treatment an effective amount of one or more compounds of the invention. In certain embodiments, such allergies are caused by any of a variety of antigens including biological sources such as dust mites, mold, cockroaches and other insects, dander from pets or other mammals, pollens, spores, mold, other fungal sources, and other plant antigens, or non-biological sources such as chemicals (e.g., isocyanates).

In other embodiments, the invention provides a method of screening for therapeutic agents useful for treating asthma in a mammal, comprising: (a) contacting an acidic mammalian chitinase protein with a compound (e.g., a compound of the invention) and a substrate of said chitinase; and (b) determining if the compound inhibits the activity of the chitinase; wherein if the compound inhibits the activity of the chitinase, then the compound is a therapeutic agent useful for treating asthma.

In other aspects, the invention provides methods for monitoring the efficacy of a treatment for asthma, comprising (a) administering a compound of the invention to a mammal, and (b) monitoring the expression of acidic mammalian chitinase in the mammal after administration of the compound, wherein a decrease in the expression of acidic mammalian chitinase indicates that the compound is useful in treating asthma, allergic diseases such as hay fever, allergic rhinitis, atopic dermatitis or other Th-2 mediated or associated diseases.

In other embodiments, the invention provides a method of screening for therapeutic agents useful for treating asthma in a mammal, comprising: (a) contacting a chitotriosidase 1 protein with a compound (e.g., a compound of the invention) and a substrate of said protein; and (b) determining if the compound inhibits the activity of the chitotriosidase 1; wherein if the compound inhibits the activity of the chitotriosidase 1, then the compound is a therapeutic agent useful for treating asthma.

In other aspects, the invention provides methods for monitoring the efficacy of a treatment for asthma and other allergic diseases, comprising (a) administering a compound of the invention to a mammal, and (b) monitoring the expression of inflammatory mediators such as IL-13, IL-5, IL-4, eotaxin, or IgE or inflammatory cells such as eosinophils, neutrophils, or lymphocytes in bronchoalveolar washings, sputum, or tissues obtained from the mammal after administration of the compound; wherein a decrease in expression indicates that the compound is useful in treating asthma or allergic diseases such as hay fever, allergic rhinitis, atopic dermatitis or other Th-2 mediated or associated diseases.

In another aspect, the invention provides methods for assessing the efficacy of an agent for treating asthma in a subject, comprising the steps of a) detecting in a subject sample collected at a first point in time the expression level of acidic mammalian chitinase protein;

b) repeating step a) at one or more subsequent points in time after administration of the agent; and c) comparing expression level of acidic mammalian chitinase protein detected in step a) with the expression level(s) detected in step b), wherein a higher expression level of acidic mammalian chitinase protein at the first point in time relative to at least one subsequent point in time indicates that the agent is efficacious in treating asthma.

In certain embodiments, an agent identified by such a method is efficacious in treating asthma, hay fever, allergic rhinitis, atopic dermatitis, allergic reactions, or a disorder associated with Th-2.

Alternatively, the efficacy of an agent for treating asthma or an allergic reaction can be assessed via measuring the expression level of an inflammatory mediator such as IL-13, IL-5, IL-4, eotaxin, IgE, or measuring the amount of inflammatory cells such as eosinophils, neutrophils, or lymphocytes in bronchoalveolar washings, sputum, or tissues obtained from a mammal. In certain such embodiments, the expression level can be measured prior to and after administration of an agent. When the expression level of the inflammatory mediator or the level of inflammatory cells decreases after administration of an agent, such an agent is efficacious in treating asthma, hay fever, allergic rhinitis, atopic dermatitis, allergic reactions, or a disorder associated with Th-2.

Another aspect of the invention provides methods of identifying an agent for treating asthma, comprising:

a) contacting a sample comprising acidic mammalian chitinase protein with the agent; and b) determining the ability of the agent to inhibit activity of acidic mammalian chitinase protein, wherein decreased activity of acidic mammalian chitinase protein identifies an agent for treating asthma.

In certain embodiments, the activity of acidic mammalian chitinase protein is assessed by fluorescence assay using a reagent that is hydrolyzed by acidic mammalian chitinase protein. In certain embodiments, the reagent is 4-methylumbelliferyl B-D-N,N'-diacetylchitobioside hydrate.

In certain embodiments, the invention provides a method for inhibiting chitotriosidase and acidic mammalian chitinase in a cell or a tissue, comprising contacting a cell or a tissue with at least one compound of the invention.

Therapeutic Applications

The inventive compounds are useful for inhibiting the enzymatic and biological activity of Acidic Mammalian Chitinase (AMCase) and chitotriosidase 1 (CHIT1). AMCase has been shown to be induced in animal models of asthma and in humans that have died from asthma, while inhibition of AMCase with anti-sera to AMCase or by allosamidin (Zhu et al. Science 304:1678-1682, 2004) or desmethylallosamidin (Matsumoto et al., Biochemical and Biophysical Research Communications 390:103-108, 2009) reduces inflammation in mice. Furthermore, these studies clearly established a link between IL-13 and the induction of AMCase, and that allergic inflammation was dependent on AMCase enzymatic activity. Overexpression of CHIT1 has been linked to fibrotic interstitial lung disease, including idiopathic pulmonary fibrosis and chronic obstructive pulmonary disease (COPD).

More specifically, the invention provides methods for inhibiting AMCase in a cell, comprising contacting a cell with at least one compound according to the present invention, or a composition thereof as described herein.

In some embodiments, the invention provides methods for treatment or prevention of a disease or condition associated with expression or activity of AMCase in a subject in need thereof. For instance, the disease, disorder, or condition is selected from the group consisting of allergic diseases, acute and chronic inflammatory diseases, autoimmune diseases, dental diseases, neurologic diseases, metabolic diseases, liver diseases, polycystic ovary syndrome, endometriosis, and cancer.

According to certain embodiments, the compounds of the invention are useful for treating allergic diseases, such as asthma, allergic rhinitis, seasonal allergic rhinitis, chronic rhinosinusitis with or without nasal polyps, conjunctivitis, keratoconjunctivitis, seasonal allergic conjunctivitis, dry eye syndrome, eosinophilic esophagitis, celiac disease, food allergies, irritable bowel syndrome, irritable bowel disease, atopic eczema, atopic dermatitis, allergic contact dermatitis, eosinophilic otitis media, eosinophilic pneumonia, and IgG4 mediated disease.

In certain embodiments, the reaction caused by an allergen is allergic rhinitis or atopic dermatitis.

In certain embodiments, the reaction caused by an allergen is characterized by the occurrence of one or more symptoms, which can include red eyes, itchiness, runny nose, eczema, impaired hearing, hives, an asthma attack, increased mucus production in the lungs, coughing, wheezing, and shortness of breath.

Exemplary acute and chronic inflammatory disorders that can be treated using the compounds of the invention include fungal diseases, parasitic infection, celiac disease, microscopic colitis, chronic obstructive pulmonary disease (COPD), idiopathic pulmonary fibrosis, interstitial lung diseases, Cystic Fibrosis (CF), Hermansky-Pudlak and Alzheimer's disease (AD).

In certain embodiments, the disease or condition treated by the methods of the invention is an autoimmune disorder selected from the group consisting of inflammatory bowel disease, ulcerative colitis (UC), Crohn's disease (CD), rheumatoid arthritis (RA), osteoarthritis, psoriasis, scleroderma, multiple sclerosis (MS), Sjögren's syndrome, atherosclerosis, and sarcoidosis.

Compounds in accordance with the present invention are also useful for treating dental diseases such as periodontitis.

The compounds of the invention are also useful for treating metabolic diseases such as insulin-dependent diabetes mellitus (IDDM) and non-insulin-dependent diabetes mellitus (NIDDM).

In certain embodiments, the invention provides methods of treating a liver disease selected from group consisting of non-alcoholic fatty liver disease, non-alcoholic steatohepatitis, hepatitis-C virus-induced fibrosis and cirrhosis, and alcoholic fibrosis.

In some embodiments, the methods of the invention are used in the treatment of cancer, wherein the cancer is selected from the group consisting of glioblastoma, breast cancer, colon cancer, primary and metastatic lung cancer, mesothelioma, osteosarcoma, malignant melanoma, ovarian cancer, cervical cancer, prostate cancer, liver cancer, gastric cancer, metastatic renal cancer, leukemia, and lymphoma.

In certain embodiments, the disease or condition treated by the methods of the invention is a kidney disease selected from the group consisting of nephropathy (e.g., diabetic nephropathy), focal segmental glomerulosclerosis, tubulointerstitial fibrosis, postransplant fibrosis, and retroperitoneal fibrosis (Ormond's disease).

In certain embodiments, the disease or condition treated by the methods of the invention is a storage disease selected from the group consisting of Gaucher disease, Fabry disease, lysosomal storage disorders, Niemann-Pick disease, nephropatic cysteinosis, and X-linked globotiaosylceramidosis.

In some embodiments, the subject receiving treatment is a mammal. For instance, the methods and uses described herein are suitable for medical use in humans. Alternatively, the methods and uses are also suitable in a veterinary context, wherein the invention may be administered to warm-blooded animals, birds and reptiles. Warm-blooded animals include, for example, all non-human primates (e.g., chimpanzee and ape), ruminants (e.g., cow, sheep and goat), porcines (e.g., pig), equines (e.g., horse, mule and donkey), camelines (e.g., camel and dromedary), canines (e.g., dog), felines (e.g., cat), leporine (e.g., rabbit), murines (e.g., mouse and rat) cavines (e.g., guinea pig), gerbiline (e.g., gerbil), cricetine (e.g., hamster), mustelines (e.g., ferret and weasel) and chinchilines (e.g., chinchilla). Birds include animals of the avian class, for example, all phasianines (e.g., chicken and quail), anserines (e.g., goose), anatines (e.g., ducks), meleagridines (e.g., turkey), daruduelines (e.g., canary), psittacines (e.g., parrot, macaw, parakeet and lovebird), cacatuines (e.g., cockatoo) and columbines (e.g., pigeon and turtle dove).

In certain embodiments, the invention is preferably administered to domesticated companion animals and to productive and breeding animals.

In certain embodiments, the method of the invention further comprises administering a second therapeutic agent. Exemplary second therapeutic agents include steroids, membrane stabilizers, 5LO inhibitors, leukotriene synthesis and receptor inhibitors, inhibitors of IgE isotype switching or IgE synthesis, inhibitors of IgG isotype switching or IgG synthesis, β-agonists, tryptase inhibitors, acetylsalicylic acid, COX inhibitors, methotrexate, anti-TNF drugs, rituxin and other B-cell targeting agents, THF-targeting agents, PD4 inhibitors, p38 inhibitors, PDE4 inhibitors, and antihistamines.

Asthma

As described above, AMCase protein has been shown to be induced in the lungs of animal models of asthma and in humans that have died from asthma (Zhu et al. Science 304:1678-1682, 2004, Matsumoto et al., Biochemical and Biophysical Research Communications 390:103-108, 2009, Sutherland et al. Chemistry and Biology 18:569-579, 2011). Further, these investigators also demonstrated that inhibition of AMCase with anti-sera to AMCase, or by inhibitors of AMCase enzymatic activity, reduces inflammation and airway hyper-responsiveness in mice. These studies also clearly established a link between the well described Th-2 interleukin IL-13, and the induction of AMCase protein expression. These studies also demonstrated that IL-13 mediated allergic inflammation can be reduced or eliminated by inhibiting the enzymatic activity of AMCase establishing proof that allergic inflammation is partially or wholly dependent on AMCase enzymatic activity. In one embodiment of the invention, compounds that inhibit enzymatic activity of AMCase or biologic activity of AMCase can be administered to subjects with asthma and or asthmatic symptoms to inhibit related inflammation and alleviate disease symptoms.

Rhinitis

In another embodiment, compounds of the invention can be administered to subjects with allergic rhinitis, seasonal allergic rhinitis, or chronic rhinosinusitis to treat the disease since these syndromes are linked to IL-13 (Akdis et al., J. Allergy and Clinical Immunology 131:1479-1490, 2013) and AMCase is known to be produced by epithelial cells from chronic rhinosinusitis with nasal polyps (Ramanathan et al., Am. J. Rhinol. 20: 330-335, 2006, Lalaker et al., Am. J. Rhinol. Allergy 23(1):8-14, 2009, Gu et al. J. Otolaryngol. Head Neck Surg. 40(1):64-69, 2011).

Ocular Diseases

AMCase has been clearly demonstrated as an inflammatory mediator in conjunctivitis, keratoconjunctivitis, seasonal allergic conjunctivitis, and dry eye syndrome (Bucolo et al., Frontiers in Pharmacology 2(43):1-4, 2011; Musumeci et al., Cornea 28(6):667-672, 2009.) In addition, inhibition of AMCase in an animal model of inflammatory eye diseases has been shown to alleviate inflammation (Bucolo et al. Pharmacol Res. 3:247-252, 2008). Chitinase proteins have also been shown to be increased in eye tissue of patients with macular degeneration (Rakic et al., Invest. Ophthalmol. Vis. Sci. 44(4)1740-1746, 2003). Therefore an aspect of this invention is to treat inflammatory and other eye diseases using a preparation of one or more of the compounds described herein.

Other Allergic Diseases

Eosinophilic Otitis Media is known to involve the AMCase inducing cytokine IL-13 (Ohta et al., Allergology International 63:171-180, 2014) and that AMCase mediates aspects of IL-13 inflammation and pathology. Atopic eczema is another allergic disease where clinical severity has been correlated with levels of IL-13 in lesional skin (Szegedi et al., J. Eur. Acad. Dermatol. Venereol., epub 2015).

Allergic contact dermatitis also involves IL-13 which is also proposed as a complementary test for the disease (Martins and Reis, J. Eur. Acad. Dermatol. Venereol., 27(3): 390-393, 2013).

Given that these conditions are all associated with IL-13, a potent stimulant for AMCase upregulation and that inhibition of AMCase has been shown to reduce IL-13 mediated inflammation, treatment of subjects with one or more compounds described herein is expected to lead to improvement in these diseases.

Esophageal Eosinophilic Inflammation (EoE)

EoE is a condition mediated by Th-2 inflammation including the presence of eosinophils, CD8+ lymphocytes, FcepsilonRI, mast cells, collagen deposition, and eotaxin-3 (CCL26) mRNA. EoE is associated with other allergic disease where the antigens are often food but also pollen. Existing treatments have low efficacy (attempt to eliminate antigen exposure) and side effects (topical steroids followed by oral steroids then mechanical dilatation). In a mouse model of EoE, AMCase levels are increased in esophageal tissue. Importantly, the AMCase inhibitor allosamidin inhibits eosinophilic inflammation including number of eosinophils, esophageal remodeling, and eotaxin-1 protein (Cho et al., Int. Immunopharmacol. 18(1):35-42, 2014). Treatment of subjects with EoE by one or more compounds described herein is expected to reduce or cure disease symptoms.

Celiac Disease, Food Allergy, Irritable Bowel Syndrome, Inflammatory Bowel Disease A form of Celiac disease is often associated with EoE and also has hallmarks of allergic disease including elevated tissue eosinophils (Mehta and Furuta, Immunol. Allergy Clin. North Am. 35(3):413-437, 2015). Celiac disease has also been defined as an autoimmune disorder distinct from wheat allergy and has some overlap with irritable bowel syndrome (Elli et al., World J. Gastroenterology 21(27): 8221-8226, 2015). Mehta and Furuta also include inflammatory bowel diseases as involving eosinophils in the disease pathogenesis. Therefore, because AMCase is constitutively expressed in the gastrointestinal tract (Boot et al., J. Histochem. Cytochem. 53:1283-1292, 2005) and there is at least partial involvement of allergic inflammation in these diseases, inhibition of AMCase in subjects with these or similar diseases can be treated by the AMCase inhibitors described.

Autoimmune Diseases

For autoimmune diseases including Inflammatory Bowel Disease (IBD), Rheumatoid Arthritis (RA), Multiple Sclerosis (MS) and Insulin-Dependent Diabetes Mellitus (IDDM) or type I diabetes there is evidence of up regulation of AMCase and other proteins in the 18 glycosyl hydrolase family. There is also evidence that these proteins can activate autoimmunity (Sekine et al., Ann. Rheum. Dis., 60(1) 49-54, 2001, Tsuruha et al., J. Rheumatol., 29(7):1459-1466, 2002, Du et al., Rheumatol. Int., 26(1):35-41, 2005)

Inflammatory Bowel Disease (Ulcerative Colitis and Crohn's Disease)

Chitinases have been shown to play a role in the pathogenesis of inflammatory bowel disease (IBD) and models of IBD. There is a growing body of evidence that IBD symptoms can be modified by altering the gut biome (Strober et al., J. Clin. Invest. 117:514-521, 2007, Zatorski and Fichna, 1:15-16, 2014). It has also been established that pathogenic strains of bacteria bind to colonic epithelial cells via bacterial chitin binding protein and chitinase-like molecules (Kawanda et al., Lab. Invest. 88:883-895, 2008) particularly in Crohn's disease (Chassing et al., Gastroenterology 140: 1720-1728, 2011). Pathogenic strains of bacteria in CD invade the intestinal mucosa via binding to epithelial cells and studies in a mouse model of IBD showed enhanced colitis when the mice were infected with bacteria with enhanced binding capability to colonic epithelial cells via chitinase proteins (Low et al. Gastroenterology 145(3):602-612, 2013). Treatment of mammals with intestinal inflammation (UC, CD, irritable bowel disease, microscopic colitis, and or other intestinal diseases) with a preparation of one or more compounds of this invention can be used to treat disease and disease symptoms.

Rheumatoid Arthritis (RA) and Osteoarthritis (OA)

Chitinase-like proteins are over expressed in articular chondrocytes and synovial fibroblasts and serum from RA and OA patients (Hakala et al., J. Biol. Chem., 268(34): 25803-25810, 1993, Hu et al., J. Biol. Chem., 271(32): 19415-19420, 1996, Volck et al., Scand. J. Rheumatol. 28(3):171-179, 1999, Connor et al., Osteoarthritis Cartilage 8(2):87-95, 2000). Serum concentrations of chitinase-like proteins correlates with joint inflammation and destruction in RA and OA (Kzyshkowska et al., Biomarker Insights 2:128-146, 2007). IL-6, a prominent cytokine and target for treatment of RA is known to up-regulate expression of at least one of the chitinase-like proteins (Johansen et al. Can. Epidemiol. Biomarkers Prev. 15(2)194-202, 2006). Furthermore the chitinase proteins have been shown to induce Th1 immune response in RA leukocytes and stimulates growth of synovial cells (Kzyshkowska et al., Biomarker Insights 2:128-146, 2007) and thus can augment and perpetuate chronic inflammation in RA Multiple Sclerosis (MS)

Chitinase proteins are elevated in central spinal fluid in patients with relapsing remitting MS and neuromyelitis optica. These chitinases increased inflammatory mediator release and stimulated migration of inflammatory cells across an in vitro blood brain barrier (Correale and Fiol, Mult. Scler. 17(5):521-31, 2011). Compounds described herein can be used to treat multiple sclerosis and related neurologic diseases.

Diabetes Mellitus

In patients with proliferative diabetic retinopathy, there is increased IL-13 in the vitreous compared to the healthy individuals and especially elevated levels in areas that have developed fibrovascular membranes and contributes to retinopathy (Yoshida et al., Br. J. Ophthalmol., 99(5):629-634, 2014). Application of compounds of this invention inhibits AMCase, a downstream mediator of IL-13 effects and can be expected to interfere with diabetic retinopathy. In type II diabetes, also known as non-insulin-dependent diabetes mellitus (NIDDM), plasma concentration of chitinase-like molecules is associated with insulin resistance (Rathcke et al., Inflamm. Res., 55(2):53-59, 2006) and children at risk for diabetes demonstrate increased levels of chitinase proteins vs. normal children (Kyrgios et al., Metabolism 61(4)562-568, 2012). It can reasonably be expected that treatment of subjects with diabetes or pre-diabetes with one or more compounds of this invention can treat or prevent diabetes.

Sjögren's Syndrome (SS)

Chitinase expression is increased in SS patients and levels correlate with disease severity (Greenwell-Wild et al., Arthritis Rheum. 63(10):3103-3115, 2011) indicating that subjects with this syndrome can be treated by compounds herein.

Atherosclerosis

Chitinases and associated family proteins are indicators of activated macrophages in atherosclerotic plaque and enzyme level is increased up to 55 fold in atherosclerotic plaque (Boot et al., J. Biol. Chem., 273(40):25680-25685, 1998, Artieda et al., Arterioscler. Thromb. Vasc. Biol., 23(9):1645-1652, 2003) and causes vascular smooth muscle cell migration. With chitinases involved in the pathogenesis of atherosclerosis, inhibitors of chitinases described in this invention can reasonably be predicted to treat, prevent or resolve atherosclerosis in affected subjects.

Sarcoidosis

Chitinases are also elevated in the serum of patients with sarcoidosis (Grosso et al., Scand. J. Clin. Lab. Invest., 64(1):57-62, 2004) and are produced in sarcoid granuloma in the lung (Johansen et al., Resp. Med. 99(4):396-402, 2005). Chitinase inhibitors described herein can be used to treat subjects with sarcoidosis.

Liver Diseases

Increased chitinase is synthesized in Kupffer cells of non-alcoholic fatty liver steatohepatitis (NASH) patients and stimulates activation of hepatic stellate cells suggesting a role of chitinase proteins in progression of liver fibrosis (Malaguarnera et al., Gut 55(9):1313-1320, 2006, Malaguarnera et al., Am. J. Gastroenterol., 10(9):2060-2069, 2006). Chitinase family proteins are also associated with hepatitis C virus (HCV) induced fibrosis and cirrhosis and in alcoholic and non-alcoholic liver fibrosis (Shakel et al., Hepatology 38(3):577-588, 2003, Tran et al., Eur. J. Gastroenterol. Hepatol. 12(9):989-993, 2000). Also alcoholic steatohepatitis; non-alcoholic steatohepatitis and non-alcoholic fatty-acid liver disease, which occur on a background of metabolic and cardiovascular disease; virally induced hepatic fibrosis; and primary biliary cirrhosis, which has an autoimmune basis are associated with chronic inflammation and fibrosis, and as a result, the compounds described in this invention can be used to treat various liver diseases.

Kidney Diseases

Inflammation and fibrosis are accompanying many kidney diseases such as nephropathy, including diabetic nephropathy, focal segmental glomerulosclerosis, tubulointerstitial fibrosis, postranseplant fibrosis, as well as retroperitoneal fibrosis/Ormond's disease. Compounds described herein may be used to treat subjects with these disorders to alleviate symptoms and reduce exacerbations and disease progression.

Skin Diseases

Increased fibrosis is associated with dermal injury and chronic inflammation accompanying formation of excessive or hypertrophic scars, keloids, autoimmune diseases such as scleroderma, systemic lupus erythematosus (SLE). The compounds described in this invention are reasonably expected to be effective in preventing or treatment of these diseases.

Chronic Obstructive Pulmonary Disease (COPD)

Proteins of the chitinase family are increased by exposure to cigarette smoke and are present at very high levels in patients with COPD (Nikota et al., Resp. Res., 12:39-50, 2011; Letuve et al., Am. J. Pathol., 176:638-649, 2010) and chitinases stimulate release of other pro-inflammatory mediators that mediate lung tissue destruction. Genetic association has also been made between lung function and chitinase expression (Aminuddin et al., Hum. Genet. 131 (7):1105-1114, 2012). Compounds described herein may be used to treat subjects with COPD to alleviate symptoms and reduce exacerbations and disease progression.

Interstitial Lung Diseases, Scleroderma and Hermansky-Pudlak Syndrome

Idiopathic pulmonary fibrosis (IPF) and other interstitial lung diseases are associated with increased chitinases in lung tissue and plasma, and augments TGFbeta pro-fibrotic activity (Cho et al., Allergy Asthma Immunol. Res. 7(1):14-21, 2015; Lee et al. J Immunol. 189(5):2635-44, 2012) and chitinase proteins contribute to injury (Zhou et al. J Clin Invest. 125(8):3178-3192, 2015; Zhou et al., Sci. Transl. Med., 6(240): 240ra76, 2014) such that inhibitors of chitinases can reasonably be expected to treat subjects with lung fibrotic changes.

Cystic Fibrosis (CF)

Chitinase-like proteins are elevated in CF and correlate with disease severity (Hector et al., Plos One, 6(9):e24399-24405, 2011). Therefore treatment of CF patients with one or more compounds of this invention can be expected to improve symptoms and disease severity or progression.

Alzheimer's Disease (AD)

In Alzheimer's disease, chitinase family mRNA and proteins are highly elevated in brain of patients and these proteins are also associated with pathogenic alternatively activated microglial cells in mouse AD models (Colton et al. J. Neuroimflamm. 3:27-38 2006). Chitinase expression was also elevated in ischemic cerebrovascular dementia (CvD) (DiRosa et al., Eur. J. Neurosci., 23(10)2648-2656, 2006) Treatment of subjects with AD or CvD by one or more compounds described herein is expected to reduce disease pathology and progression.

Polycystic Ovary Syndrome (POCS) and Endometriosis

Polycystic ovary syndrome (PCOS) is a low-grade chronic inflammatory state with significantly increased serum chitinase activity (Alanbay et al. Arch Gynecol Obstet. 2012; 286:1065; Aydogdu et al. Exp Clin Endocrinol Diabetes. 2012; 120:261). Chitinase activity in plasma of patients with endometriosis is also significantly increased (Alanbay et al. Gynecol Endocrinol. 2012; 28:220). Treatment of subjects with POCS or endometriosis by one or more compounds described herein is expected to reduce disease pathology and progression.

Other Diseases and Applications

Because chitin is needed for growth of most fungi and insects and chitin remodeling is needed during growth of these organisms which includes chitinase activity to degrade chitin as well as chitin synthesis, inhibitors of chitinase activity and thus the ability of these organisms to remodel, shed ectoskeleton etc., the compounds described in this invention can also have use in medical, agricultural, food processing and production, or other applications where chitinase inhibition would result in reduced survival of chitin containing organisms. These include but are not limited to fungal diseases of mammals such as aspergillosis, cryptococcosis and plant diseases caused by fungal infection or insect damage, tropical diseases including but not limited to malaria and other parasitic diseases. In fact, chitinase activity is increased in malaria (Barone et al., Clin. Chim. Acta. 331(1-2):79-85, 2003) and thus inhibition of chitinase may be useful in inactivating or otherwise rendering the parasite ineffectual.

Lysosomal Storage Diseases

Chitinases are strongly upregulated in Gaucher disease (Bussink et al. Int Rev Cytol. 2006; 252:71-128). Thus inhibition of chitinases with compounds described herein is expected to reduce progression of storage diseases such as Gaucher disease, Fabry disease, lysosomal storage disorders, Niemann-Pick disease, nephropatic cysteinosis, X-linked globotiaosylceramidosis.

Cancer

Chitinase and chitinase-like proteins are over expressed in many cancers including brain tumors such as glioblastoma (Francescone et al. J Biol Chem 2011; 286:15332-43; Ku et al. Int J Cancer 2011; 128:1316-26) or astrocytoma (Zhang et al. Cancer. 2010; 116:2688), breast cancer (Johansen et al. Breast Cancer Res Treat 2003; 80:15-21), colon cancer (Nutt et al., 2005, Pelloski et al., 2005; Fijneman et al. Clin Cancer Res. 2012; 18:2613; Chen et al. Am J Pathol. 2011; 179: 1494), primary and metastatic lung cancer (Wang et al. Tumour Biol 2015; 36:901-7; Johansen et al. Lung Cancer 2004; 46:333-40), mesothelioma (Corradi et al. Anticancer Res. 2013 December; 33(12):5517), osteosarcoma, malignant melanoma (Ma et al. Cancer Res 2015; 75:487-96), ovarian cancer (Hogdall et al. BMC Cancer 2009; 9:8; Dupont et al. J Clin Oncol. 2004; 22:3330), cervical cancer (Ngernyuang et al. Int J Biochem Cell Biol 2014; 51:45-52.), prostate cancer (Jeet et al. Endocr Relat Cancer. 2014; 21:723), liver cancer (Pan et al. J Cancer Res Clin Oncol 2013; 139:1043-54), gastric cancer (Li et al. Chin Med J 2012; 125:1777), metastatic renal cancer (Zhangg et al. Tumour Biol 2014; 35:12131-7), hematologic malignancies such as leukemia or lymphoma (Mactier et al. J Proteome Res. 2011; 10:1030; Marchesi et al. Vet Pathol. 2006; 43:773-6; Marchesi et al. J Vet Med A Physiol Pathol Clin Med. 2003; 50:103) and other types of cancers with inflammatory background (Quershi et al. Genes Cancer. 2011; 2:74; Eurich et al. World J Gastroenterol. 2009; 15:5249; Roslind and Johansen, Methods of Mol Biol. 2009; 511: 159). In fact, higher plasma levels indicate poor prognosis and increased metastatic potential for several cancers (Johansen et al., Cancer Epidemiol. Biomarkers Prev., 15(2): 194-202, 2006). Inhibition of chitinase and chitinase-like protein biological function with one or more compounds described in this invention is anticipated to have therapeutic utility in subjects with cancer.

EXAMPLES

The present invention is further illustrated by the following examples, which in no way should be construed as limiting the scope of the claimed invention.

Materials and Methods of Preparation and Characterization

The compounds of the present disclosure may be prepared by use of known chemical reactions and procedures. Representative methods for synthesizing compounds of the disclosure are presented below. It is understood that the nature of the substituents required for the desired target compound often determines the preferred method of synthesis. All variable groups of these methods are as described in the generic description if they are not specifically defined below. Substituents carry the same meaning as defined above, unless otherwise noted.

If not specified otherwise, proportions of liquid components of a liquid mixture are expressed by volume ratios (e.g., 1:2) of these components. If not specified otherwise, content of a solute in a buffer solution is expressed as the weight (in grams) of the solute contained in 100 mL of the solution.

Reaction yields are expressed as percentage by weight of the desired product related to the weight theoretically obtainable. Purities of chemicals are expressed as percentage by weight (%).

Those having skill in the art will recognize that the starting materials and reaction conditions may be varied, the sequence of the reactions altered, and additional steps employed to produce compounds encompassed by the present disclosure, as demonstrated by the following examples. Many general references providing commonly known chemical synthetic schemes and conditions useful for synthesizing the disclosed compounds are available (see, e.g., Smith and March, *March's Advanced Organic Chemistry: Reactions, Mechanisms, and Structure*, Fifth Edition, Wiley-Interscience, 2001; or Vogel, *A Textbook of Practical Organic Chemistry, Including Qualitative Organic Analysis*, Fourth Edition, New York: Longman, 1978).

The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the disclosure.

In some cases, protection of certain reactive functionalities may be necessary to achieve some of the above transformations. In general, the need for such protecting groups as well as the conditions necessary to attach and remove such groups will be apparent to those skilled in the art of organic synthesis. An authoritative account describing the many alternatives to the trained practitioner are J. F. W. McOmie, "*Protective Groups in Organic Chemistry*," Plenum Press, London and New York 1973, in T. W. Greene and P. G. M. Wuts, "*Protective Groups in Organic Synthesis*," Third edition, Wiley, New York 1999, in "*The Peptides*;" Volume 3 (editors: E. Gross and J. Meienhofer), Academic Press, London and New York 1981, in "*Methoden der organischen Chemie*," Houben-Weyl, 4th edition, Vol. 15/1, Georg Thieme Verlag, Stuttgart 1974, in H.-D. Jakubke and H. Jescheit, "*Aminosauren, Peptide, Proteine*," Verlag Chemie, Weinheim, Deerfield Beach, and Basel 1982, and/or in Jochen Lehmann, "*Chemie der Kohlenhydrate: Monosaccharide und Derivate*," Georg Thieme Verlag, Stuttgart 1974. The protecting groups may be removed at a convenient subsequent stage using methods known from the art. The disclosures of all articles and references mentioned in this application, including patents, are incorporated herein by reference in their entirety.

Starting materials can be obtained from commercial sources or prepared by well-established literature methods known to those skilled in the art.

All solvents, substrates and reagents that were commercially available were used without further purification. TLC analysis was performed using pre-coated glass plates (0.2±0.03 mm thickness, GF-254, particle size 0.01-0.04 mm) from Fluorochem Ltd, UK. Column chromatography was performed using high-purity grade silica gel (pore size 60 Å, 220-440 mesh particle size, 35-75 μm particle size) from Fluka.

$^1$H NMR spectra were recorded on Agilent Mercury 400 MHz spectrometer and Bruker Avance 500, 600, and 700 MHz spectrometers (DRX400, DXR500, DXR600, and DXR700, respectively).

All spectra were recorded in appropriate deuterated solvents ($CDCl_3$, DMSO-$d_6$, $D_2O$, $CD_3OD$, etc.) that were commercially available.

Resonances are given in parts per million relative to tetramethylsilane internal standard. Data are reported as follows: chemical shift (δ), multiplicity (s=singlet, d=doublet, t=triplet, m=multiplet, bs=broad singlet), coupling constants (J in Hz) and integration.

ESI-MS spectra were obtained on a Waters Alliance 2695 separation module with a PDA 1996 UV detector and Waters Micromass ZQ 2000 mass detector equipped with Kinetex 2.1/50 mm, 2.6 μm C18 column eluted with 0.3 mL/min flow of 3-100% gradient (over 6 min) of acetonitrile in water, and a Shimadzu Prominence LC-20AD separation module with a SPD-M20A PDA detector and Shimadzu LCMS-2020 mass detector equipped with Luna, C18, 2 um, 100 A, 150×3 mm column eluted with 0.5 mL/min flow of 15-90% gradient (over 13 min) of acetonitrile in water, and LC-MS data were recorded on Shimadzu Prominence LC-30AD separation module (with a SPD-M20A PDA detector and Shimadzu LCMS-2020 mass detector) equipped with Kinetex, C18, 1.7 μm, 100 A, 30×2.1 mm column eluted with 1 mL/min flow of 10-90% gradient (over 3 min) of acetonitrile in water, both with 0.4% of formic acid (v/v). Alternatively, HPLC-ESI-MS spectra were recorded on a Shimadzu Prominence LC-20AD separation module with a SPD-M20A DAD detector and Shimadzu LCMS-2020 mass detector equipped with Luna® 3 μm Phenyl-Hexyl column (ø=3 mm; l=100 mm) eluted with 0.5 mL/min flow of 10-90% gradient (over 6 min) of MeCN in water (+0.1% of formic acid).

Human AMCase Activity Assay

An enzymatic assay with recombinant human AMCase was used in order to establish inhibitory activity of the compounds (Boot et al., 2001, *JBC:* 276). The assay was run in the 96-well plate format, each reaction in the total volume of 100 μL. 4-Methylumbelliferyl B-D-N,N'-diacetylchitobioside hydrate was used as a substrate for the enzyme. Upon hydrolysis by AMCase, the substrate releases 4-methylumbelliferyl (4MU) that, when ionized in basic pH, emits fluorescence at 460 nm.

Briefly, 40 μL of a substrate was added to each well, followed by 10 μL of compound dilution and 50 μL of hAMCase recombinant enzyme solution. The reaction was carried out in citrate buffer, pH 5.2, in the dark, at 37° C. for 60 minutes with shaking. After that time the reaction was stopped by adding 195 μL of Stop Buffer (pH 10.5) to each well. The fluorescence of the reaction product was measured in Tecan Spark multimode plate reader at an excitation wavelength of 355 nm. The $IC_{50}$ values were calculated using GraphPad Prism.

Human CHIT1 Activity Assay

An enzymatic assay with recombinant human CHIT1 was used in order to establish inhibitory activity of the compounds (Boot et al., 2001, *JBC:* 276). The assay was run in the 96-well plate format, each reaction in the total volume of 100 μL. 4-methylumbelliferyl β-D-N,N',N"'-triacetylchitotriose was used as a substrate for the enzyme. Upon hydrolysis by CHIT1, the substrate releases 4-methylumbelliferyl (4MU) that, when ionized in basic pH, emits fluorescence at 460 nm.

Briefly, 40 μL of a substrate was added to each well, followed by 10 μL of compound dilution and 50 μL of CHIT1 recombinant enzyme solution. The reaction was carried out in citrate buffer, pH 5.2, in the dark, at 37° C. for 60 minutes with shaking. After that time the reaction was stopped by adding 195 μL of Stop Solution (pH 10.5) to each well. The fluorescence of the reaction product was measured in Tecan Spark multimode plate reader at an excitation wavelength of 355 nm. The $IC_{50}$ values were calculated using GraphPad Prism.

Human ERG Channel Binding Assay

Fluorescence polarization assay based on the principle of fluorescence polarization where a red-shifted fluorescent tracer is displaced from the hERG channel by compounds that bind to the channel was used to establish the binding of the compounds to hERG channel. (Piper D R et al., 2008, *Assay Drug Dev Technol:* 6). Briefly, the compounds in serial dilutions were incubated with a membrane fraction containing hERG channel protein and a high-affinity red fluorescent hERG channel ligand in black 384-well plate. The reaction was incubated for 4 h at room temperature followed by the measurement of the fluorescence polarization using Tecan Spark multimode plate reader at excitation wavelength of 535 nm and emission wavelength 590 nm. The $IC_{50}$ values were calculated using GraphPad Prism.

The compounds disclosed in Table 1 have the $IC_{50}$ values towards human AMCase and CHIT1 generally ranging from about 0.001 μM to about 100 μM. Their ranges of activity have been assigned as follows:

A: <0.1 μM;
B: 0.1-1 μM;
C: 1-10 μM;
D: 10-100 μM; and
E: >100 μM.

The compounds disclosed in Table 1 have the $IC_{50}$ towards hERG values generally ranging from about 0.09 μM to about 100 μM. Their ranges of activity have been assigned as follows:

A: >100 μM;
B: 25-100 μM;
C: 10-25 μM;
D: 1-10 μM; and
E: <1 μM.

TABLE 1

| Ex. # | Structure | hCHIT1, $IC_{50}$ | hAMCase, $IC_{50}$ | hERG, $IC_{50}$ |
| --- | --- | --- | --- | --- |
| 1. | 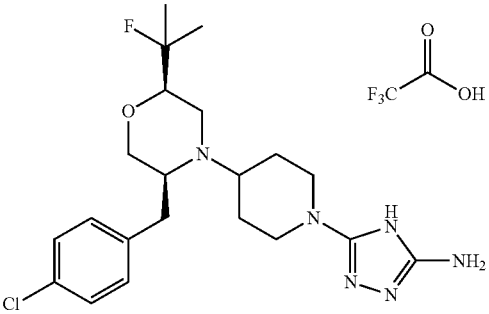 [SMILES: CC(C)(F)[C@H]1CN(C2CCN(c3nnc(N)[nH]3)CC2)[C@@H](Cc2ccc(Cl)cc2)CO1 ; O=C(O)C(F)(F)F] | A | A | B |
| 2. | 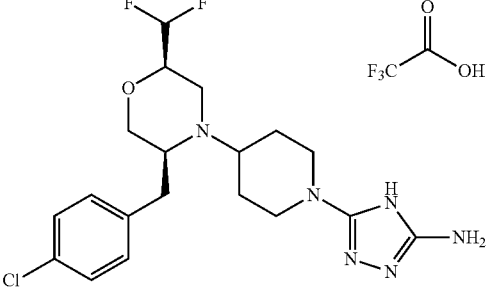 | A | A | A |
| 3. | 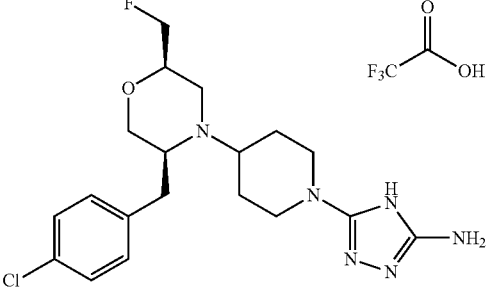 | A | A | A |

TABLE 1-continued
| Ex. # | Structure | hCHIT1, IC$_{50}$ | hAMCase, IC$_{50}$ | hERG, IC$_{50}$ |
|---|---|---|---|---|
| 4. | 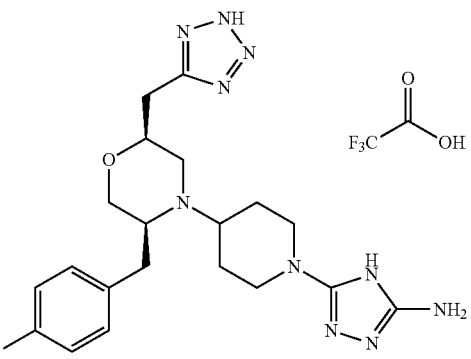 | A | A | A |
| 5. | 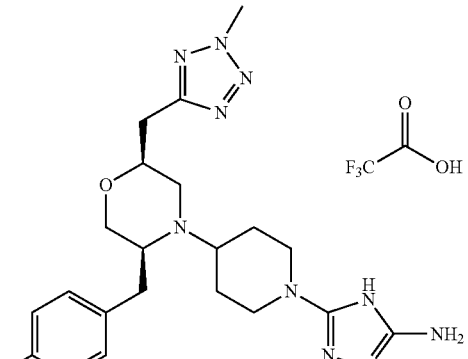 | A | A | B |
| 6. | 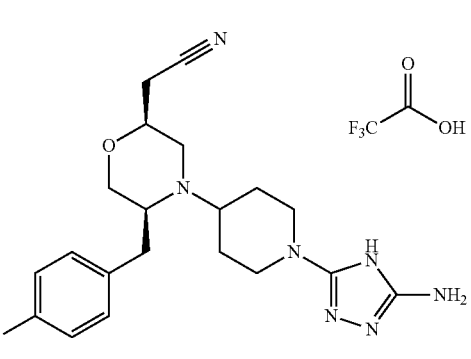 | A | A | A |
| 7. | 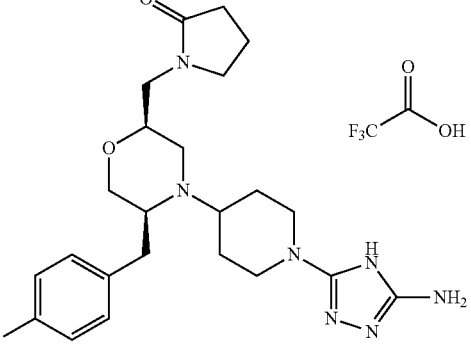 | A | A | A |

TABLE 1-continued

| Ex. # | Structure | hCHIT1, IC$_{50}$ | hAMCase, IC$_{50}$ | hERG, IC$_{50}$ |
|---|---|---|---|---|
| 8. | 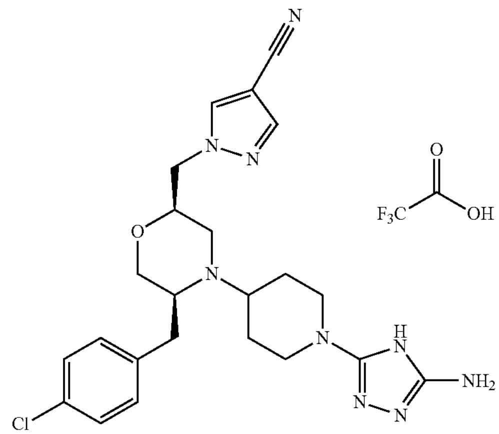 [SMILES: N#Cc1cnn(C[C@H]2CN(C3CCN(c4nnc(N)[nH]4)CC3)[C@@H](Cc3ccc(Cl)cc3)CO2)c1 ; O=C(O)C(F)(F)F] | A | A | B |
| 9. | 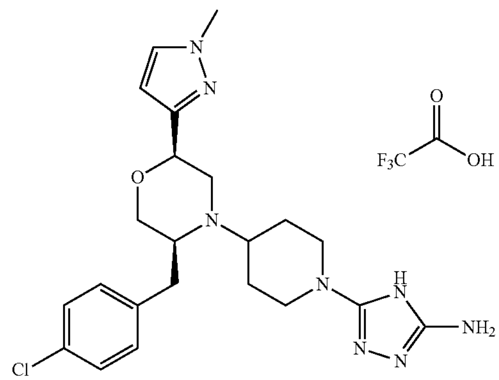 [SMILES: Cn1ccc([C@H]2CN(C3CCN(c4nnc(N)[nH]4)CC3)[C@@H](Cc3ccc(Cl)cc3)CO2)n1 ; O=C(O)C(F)(F)F] | A | A | A |
| 10. | 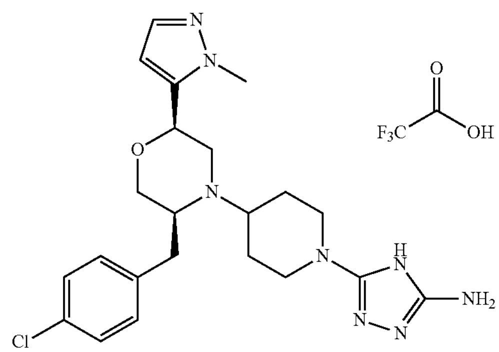 [SMILES: Cn1nccc1[C@H]1CN(C2CCN(c3nnc(N)[nH]3)CC2)[C@@H](Cc2ccc(Cl)cc2)CO1 ; O=C(O)C(F)(F)F] | A | A | A |
| 11. | 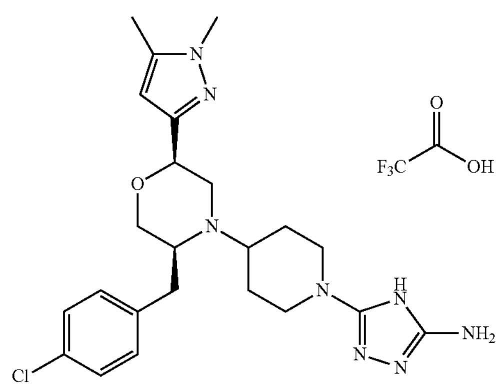 [SMILES: Cc1cc([C@H]2CN(C3CCN(c4nnc(N)[nH]4)CC3)[C@@H](Cc3ccc(Cl)cc3)CO2)nn1C ; O=C(O)C(F)(F)F] | A | A | A |

TABLE 1-continued
| Ex. # | Structure | hCHIT1, IC$_{50}$ | hAMCase, IC$_{50}$ | hERG, IC$_{50}$ |
|---|---|---|---|---|
| 12. | 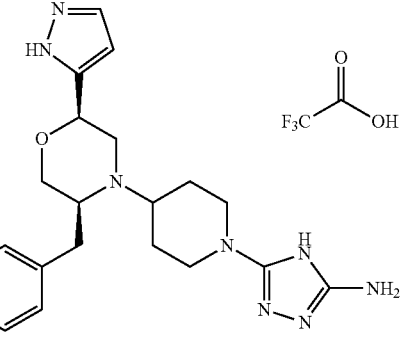 | A | A | A |
| 13. | 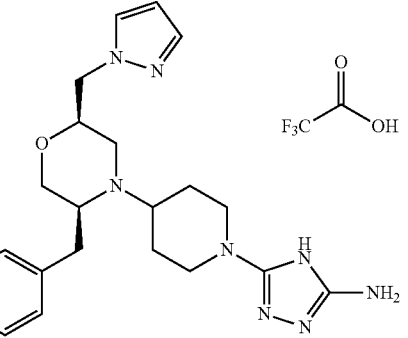 | A | A | A |
| 14. | 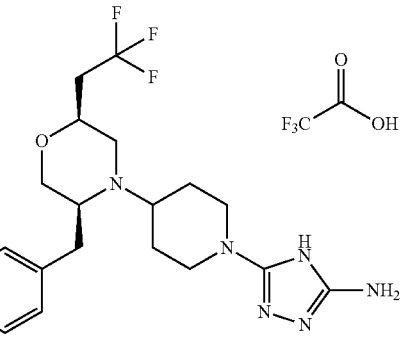 | A | A | A |
| 15. | 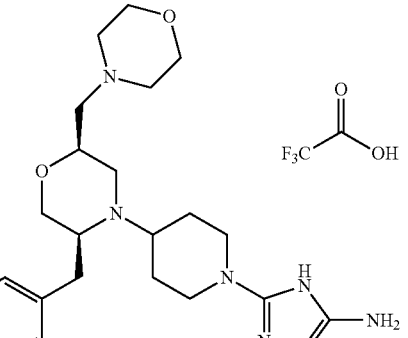 | A | A | A |

TABLE 1-continued
| Ex. # | Structure | hCHIT1, IC$_{50}$ | hAMCase, IC$_{50}$ | hERG, IC$_{50}$ |
|---|---|---|---|---|
| 16. | 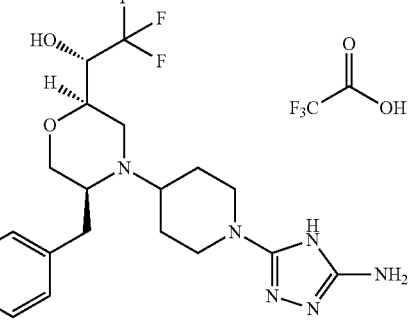 | A | A | A |
| 17. | 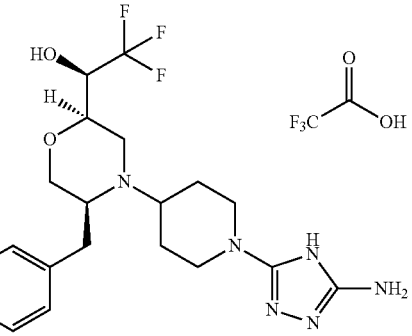 | A | A | B |
| 18. | 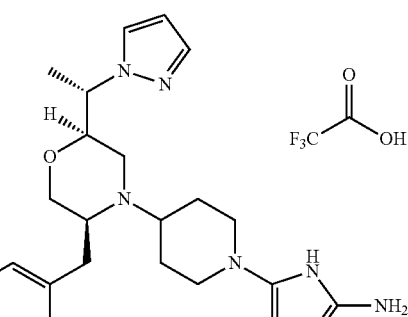 | A | A | B |
| 19. | 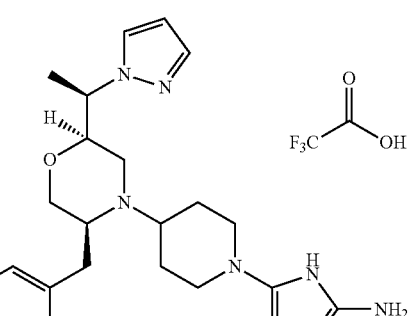 | A | A | B |

TABLE 1-continued
| Ex. # | Structure | hCHIT1, IC$_{50}$ | hAMCase, IC$_{50}$ | hERG, IC$_{50}$ |
|---|---|---|---|---|
| 20. | 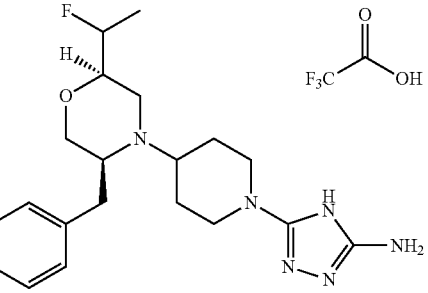<br>single enantiomer with relative stereochemistry depicted | A | A | A |
| 21. | 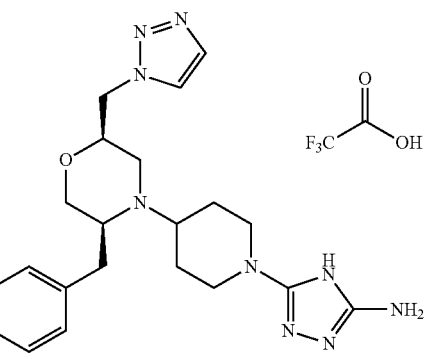 | A | A | B |
| 22. | 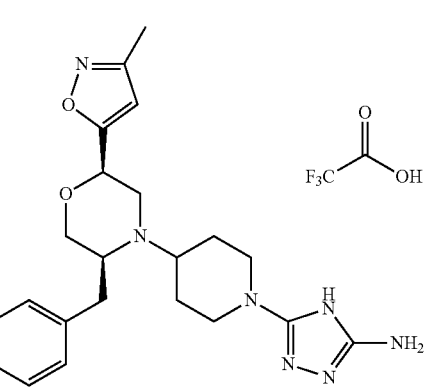 | A | A | A |
| 23. | 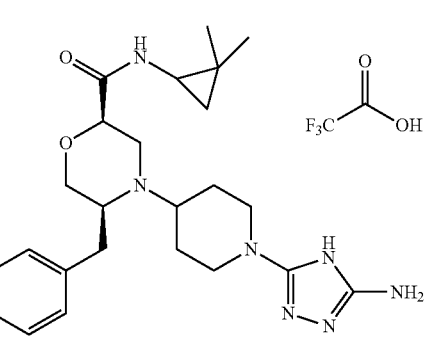 | A | A | A |

TABLE 1-continued
| Ex. # | Structure | hCHIT1, IC$_{50}$ | hAMCase, IC$_{50}$ | hERG, IC$_{50}$ |
|---|---|---|---|---|
| 24. | 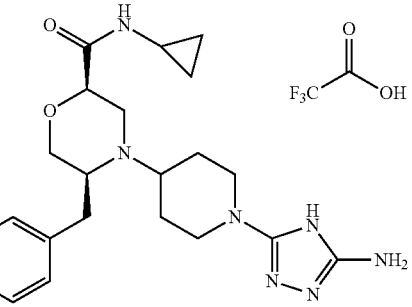 | A | A | A |
| 25. | 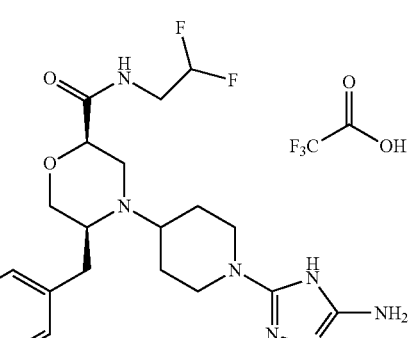 | A | A | A |
| 26. | 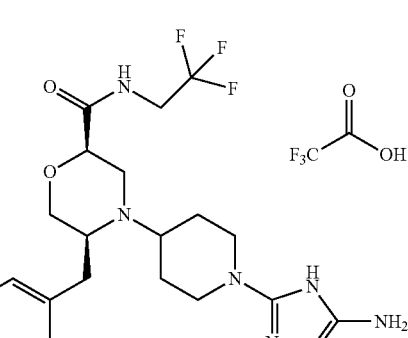 | B | A | A |
| 27. | 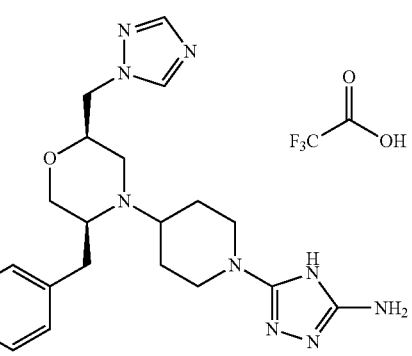 | A | A | A |

TABLE 1-continued
| Ex. # | Structure | hCHIT1, IC$_{50}$ | hAMCase, IC$_{50}$ | hERG, IC$_{50}$ |
|---|---|---|---|---|
| 28. | 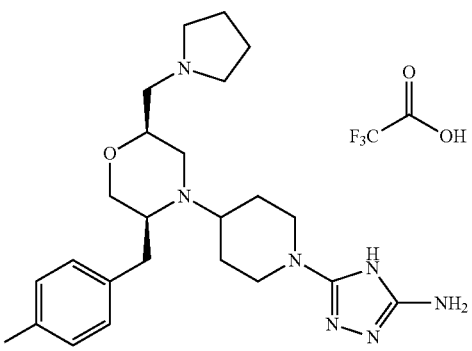 | A | A | A |
| 29. | 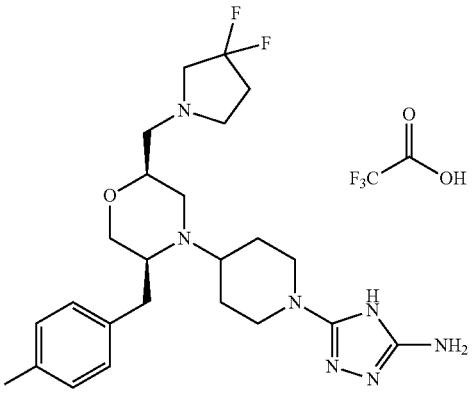 | A | A | A |
| 30. | 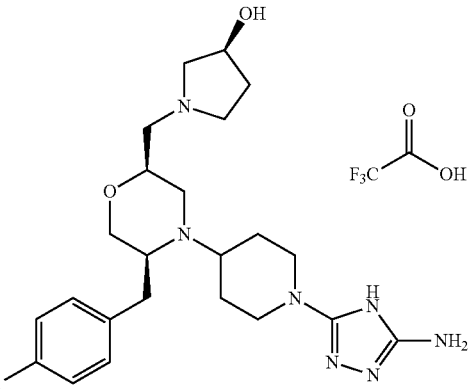 | B | A | A |
| 31. | 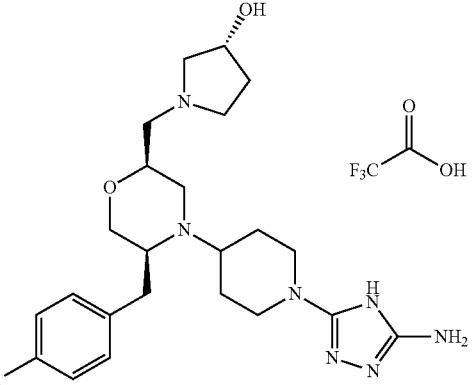 | B | A | A |

TABLE 1-continued
| Ex. # | Structure | hCHIT1, IC$_{50}$ | hAMCase, IC$_{50}$ | hERG, IC$_{50}$ |
|---|---|---|---|---|
| 32. | 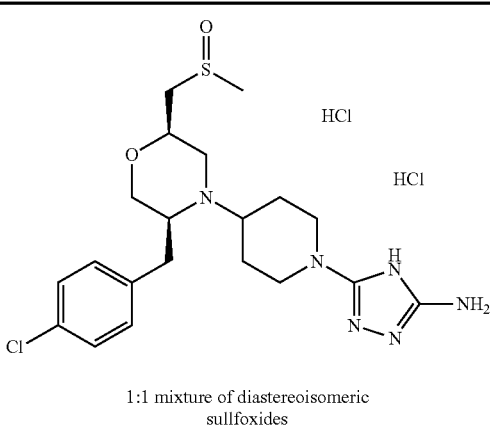<br>1:1 mixture of diastereoisomeric sulfoxides | A | A | A |
| 33. | 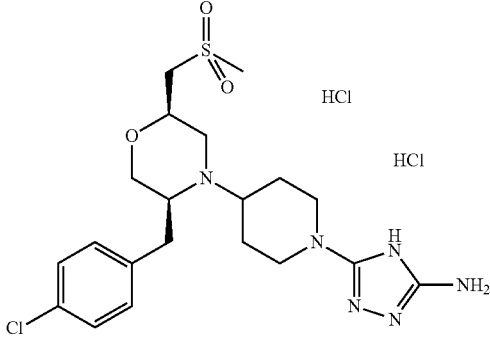 [SMILES: CS(=O)(=O)C[C@H]1CN(C2CCN(c3nnc(N)[nH]3)CC2)[C@@H](Cc2ccc(Cl)cc2)CO1 ; Cl ; Cl] | A | A | A |
| 34. | 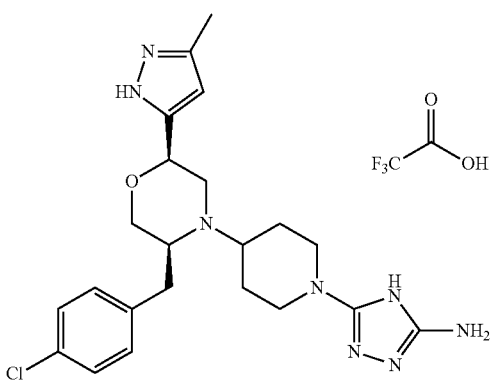 [SMILES: Cc1cc([C@H]2CN(C3CCN(c4nnc(N)[nH]4)CC3)[C@@H](Cc3ccc(Cl)cc3)CO2)[nH]n1 ; O=C(O)C(F)(F)F] | A | A | B |
| 35. | 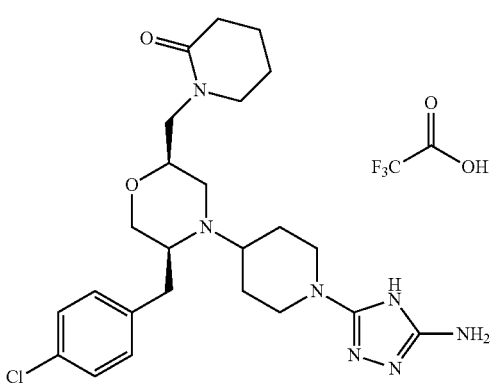 [SMILES: Nc1nnc(N2CCC(N3C[C@H](CN4CCCCC4=O)OC[C@@H]3Cc3ccc(Cl)cc3)CC2)[nH]1 ; O=C(O)C(F)(F)F] | A | A | B |

TABLE 1-continued
| Ex. # | Structure | hCHIT1, IC$_{50}$ | hAMCase, IC$_{50}$ | hERG, IC$_{50}$ |
|---|---|---|---|---|
| 36. | 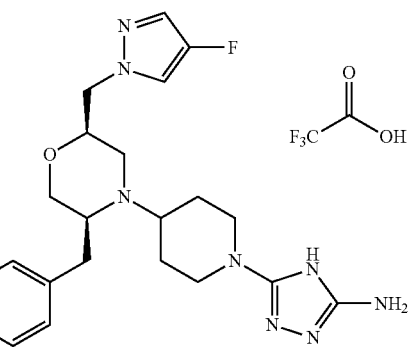 | A | A | C |
| 37. | 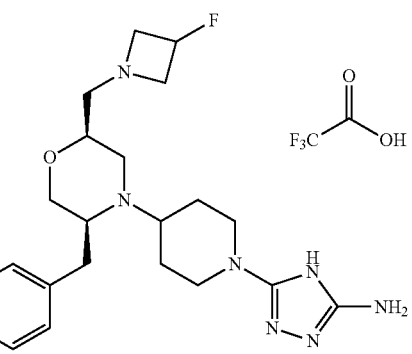 | A | A | B |
| 38. | 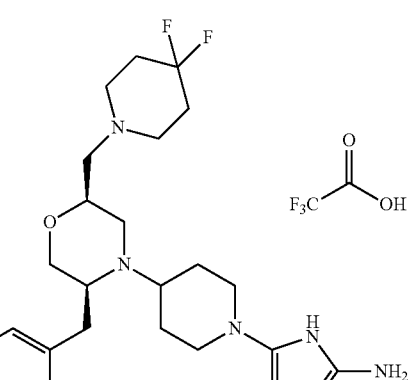 | A | A | C |
| 39. | 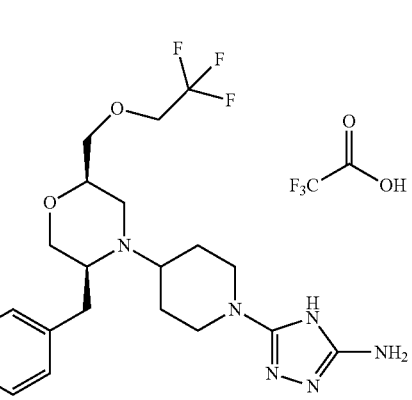 | A | A | D |

| Ex. # | Structure | hCHIT1, IC$_{50}$ | hAMCase, IC$_{50}$ | hERG, IC$_{50}$ |
|---|---|---|---|---|
| 40. | 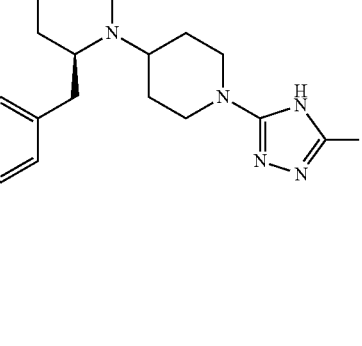 | A | A | C |
| 41. | 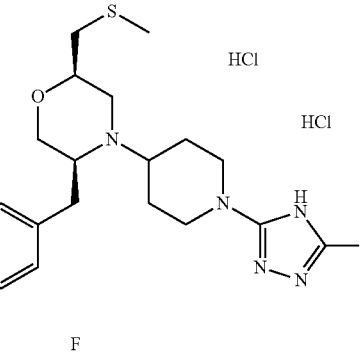 | A | A | B |
| 42. | 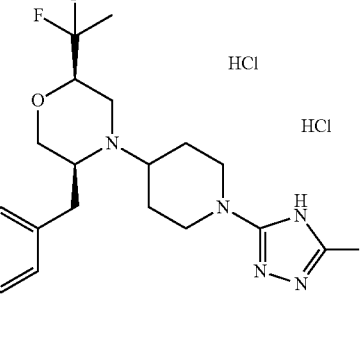 | A | A | B |
| 43. | 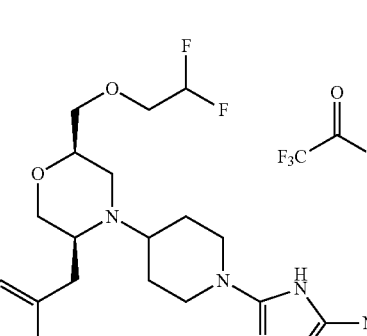 | A | A | D |

TABLE 1-continued

| Ex. # | Structure | hCHIT1, IC$_{50}$ | hAMCase, IC$_{50}$ | hERG, IC$_{50}$ |
|---|---|---|---|---|
| 44. | 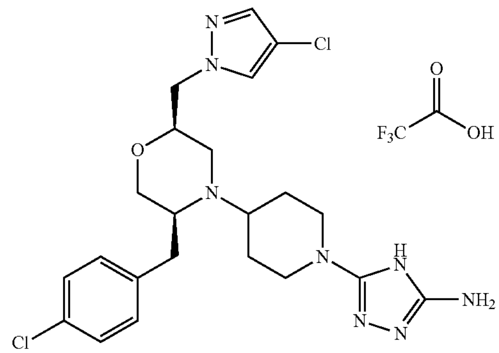 [SMILES: Nc1nnc(N2CCC(N3C[C@H](Cn4cc(F)cn4)OC[C@@H]3Cc3ccc(Cl)cc3)CC2)[nH]1 ; O=C(O)C(F)(F)F] | A | A | D |
| 45. | 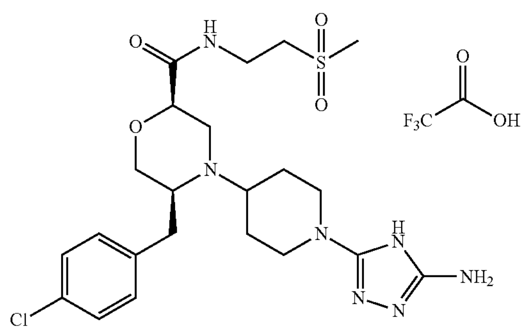 [SMILES: CS(=O)(=O)CCNC(=O)[C@H]1CN(C2CCN(c3nnc(N)[nH]3)CC2)[C@@H](Cc2ccc(Cl)cc2)CO1 ; O=C(O)C(F)(F)F] | A | A | A |
| 46. | 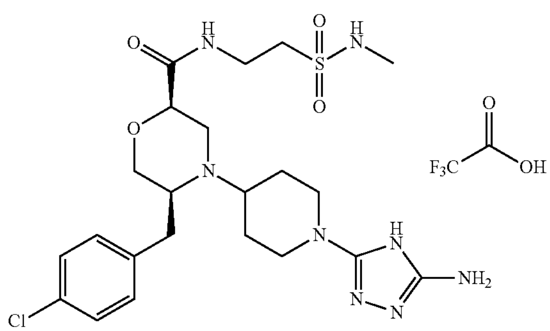 [SMILES: CNS(=O)(=O)CCNC(=O)[C@H]1CN(C2CCN(c3nnc(N)[nH]3)CC2)[C@@H](Cc2ccc(Cl)cc2)CO1 ; O=C(O)C(F)(F)F] | A | A | A |
| 47. | 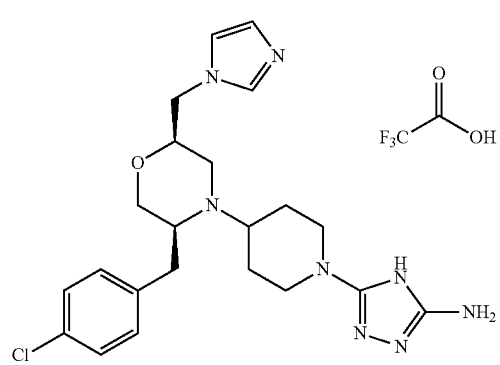 [SMILES: Nc1nnc(N2CCC(N3C[C@H](Cn4ccnc4)OC[C@@H]3Cc3ccc(Cl)cc3)CC2)[nH]1 ; O=C(O)C(F)(F)F] | A | A | C |

TABLE 1-continued
| Ex. # | Structure | hCHIT1, IC$_{50}$ | hAMCase, IC$_{50}$ | hERG, IC$_{50}$ |
|---|---|---|---|---|
| 48. | 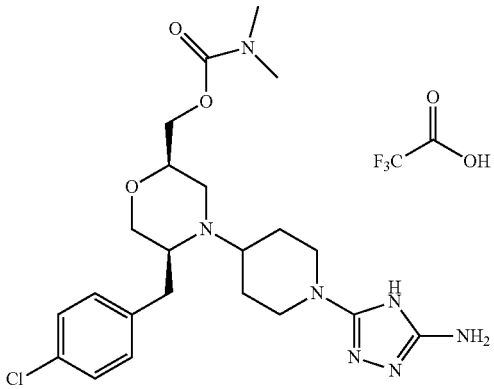 [SMILES: CN(C)C(=O)OC[C@H]1CN(C2CCN(c3nnc(N)[nH]3)CC2)[C@@H](Cc2ccc(Cl)cc2)CO1 ; O=C(O)C(F)(F)F] | A | A | B |
| 49. | 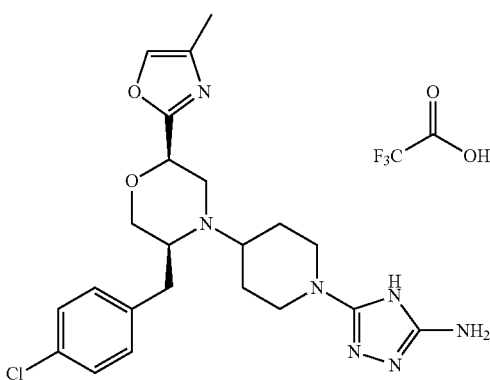 [SMILES: Cc1coc([C@H]2CN(C3CCN(c4nnc(N)[nH]4)CC3)[C@@H](Cc3ccc(Cl)cc3)CO2)n1 ; O=C(O)C(F)(F)F] | A | A | C |
| 50. | 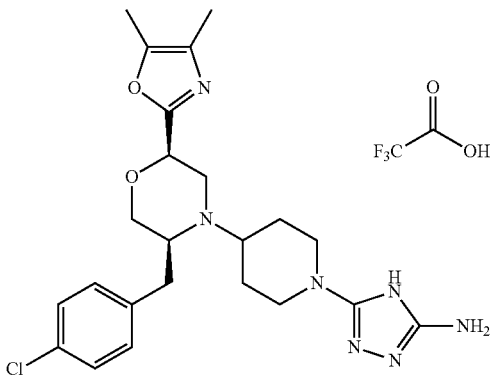 [SMILES: Cc1nc([C@H]2CN(C3CCN(c4nnc(N)[nH]4)CC3)[C@@H](Cc3ccc(Cl)cc3)CO2)oc1C ; O=C(O)C(F)(F)F]<br>single enantiomer with relative stereochemistry depicted | A | A | D |
| 51. | 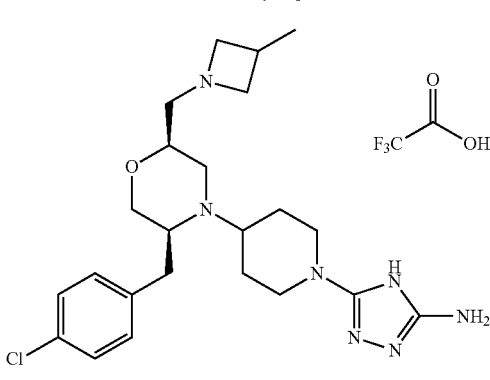 | B | A | B |

TABLE 1-continued
| Ex. # | Structure | hCHIT1, IC$_{50}$ | hAMCase, IC$_{50}$ | hERG, IC$_{50}$ |
|---|---|---|---|---|
| 52. | 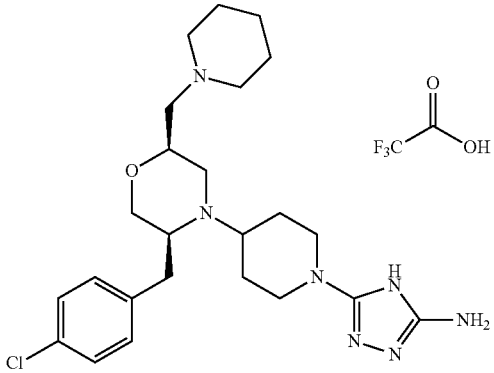 [SMILES: Nc1nnc(N2CCC(N3C[C@H](CN4CCCCC4)OC[C@@H]3Cc3ccc(Cl)cc3)CC2)[nH]1 ; O=C(O)C(F)(F)F] | B | A | B |
| 53. | 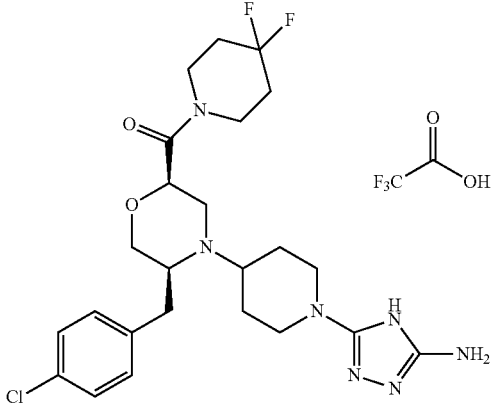 [SMILES: Nc1nnc(N2CCC(N3C[C@H](C(=O)N4CCC(F)(F)CC4)OC[C@@H]3Cc3ccc(Cl)cc3)CC2)[nH]1 ; O=C(O)C(F)(F)F] | B | A | B |
| 54. | 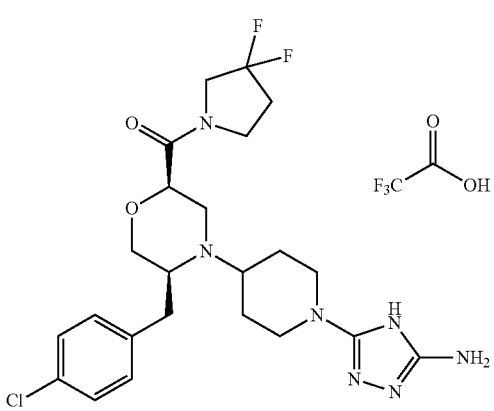 [SMILES: Nc1nnc(N2CCC(N3C[C@H](C(=O)N4CCC(F)(F)C4)OC[C@@H]3Cc3ccc(Cl)cc3)CC2)[nH]1 ; O=C(O)C(F)(F)F] | B | A | A |
| 55. | 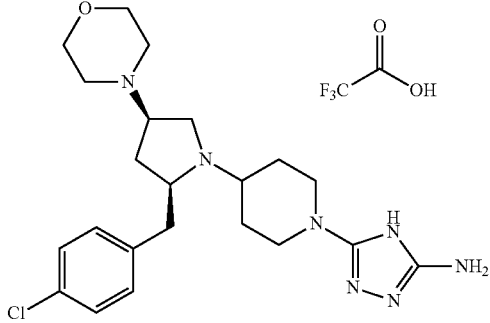 [SMILES: Nc1nnc(N2CCC(N3C[C@H](N4CCOCC4)C[C@@H]3Cc3ccc(Cl)cc3)CC2)[nH]1 ; O=C(O)C(F)(F)F] | A | A | B |

TABLE 1-continued
| Ex. # | Structure | hCHIT1, IC$_{50}$ | hAMCase, IC$_{50}$ | hERG, IC$_{50}$ |
|---|---|---|---|---|
| 56. | 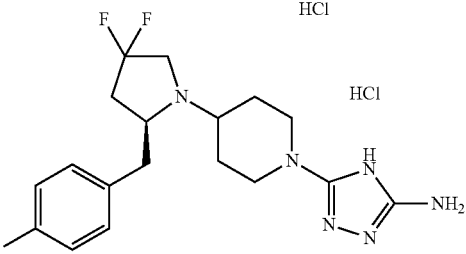 | A | B | B |
| 57. | 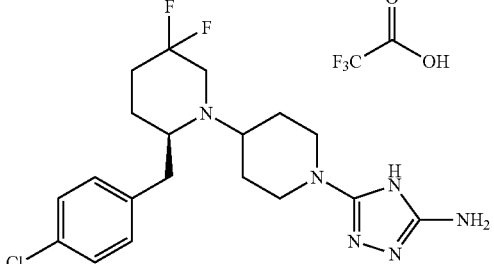 | A | A | A |
| 58. | 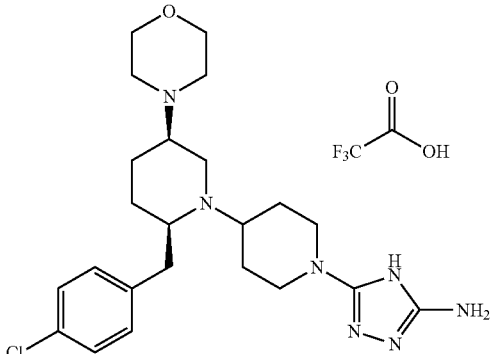 | B | A | C |
| 59. | 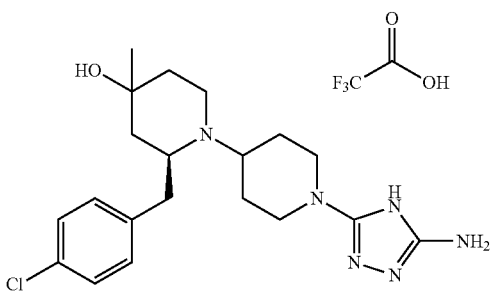 [SMILES: CC1(O)CCN(C2CCN(c3nnc(N)[nH]3)CC2)[C@@H](Cc2ccc(Cl)cc2)C1 ; O=C(O)C(F)(F)F] | C | A | B |
| 60. | 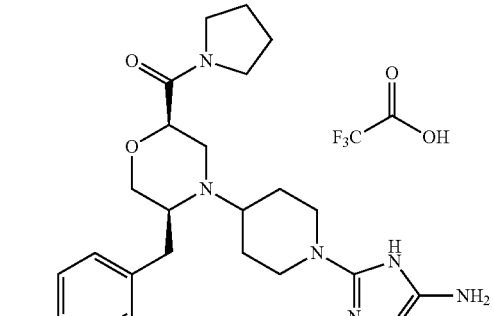 | B | A | A |

| Ex. # | Structure | hCHIT1, IC$_{50}$ | hAMCase, IC$_{50}$ | hERG, IC$_{50}$ |
|---|---|---|---|---|
| 61. | 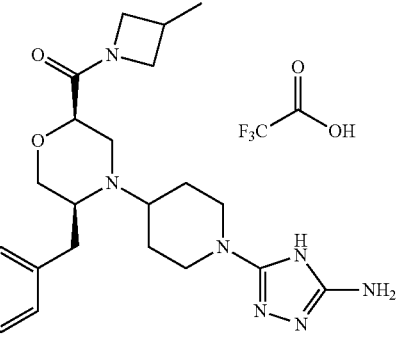 | A | A | A |
| 62. | 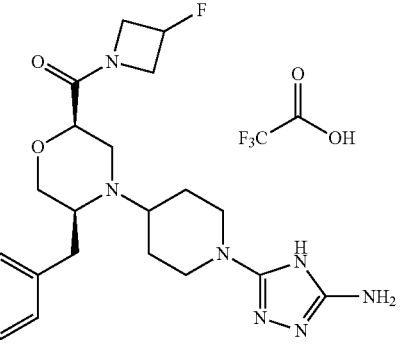 | A | A | A |
| 63. | 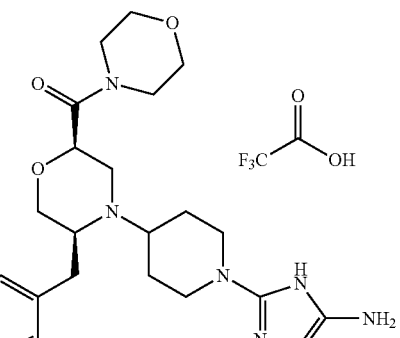 | B | A | A |
| 64. | 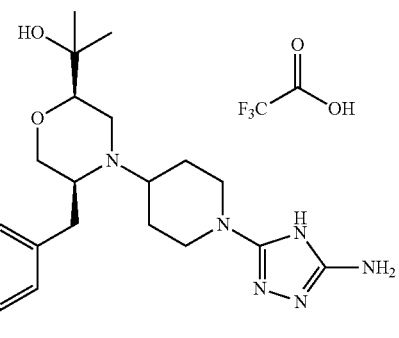 | A | A | A |

TABLE 1-continued
| Ex. # | Structure | hCHIT1, IC$_{50}$ | hAMCase, IC$_{50}$ | hERG, IC$_{50}$ |
|---|---|---|---|---|
| 65. | 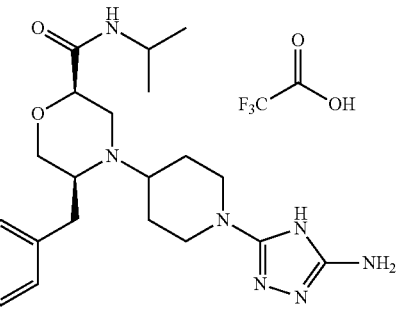 | B | A | A |
| 66. | 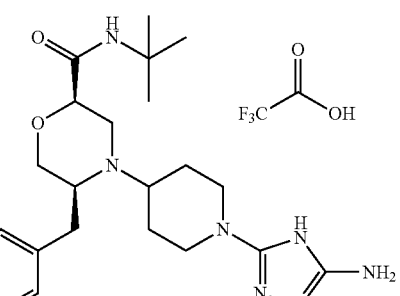 | B | A | A |
| 67. | 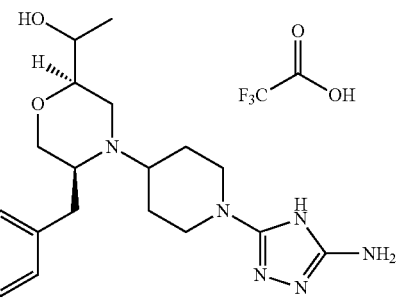<br>single enantiomer with relative stereochemistry depicted | A | A | A |
| 68. | 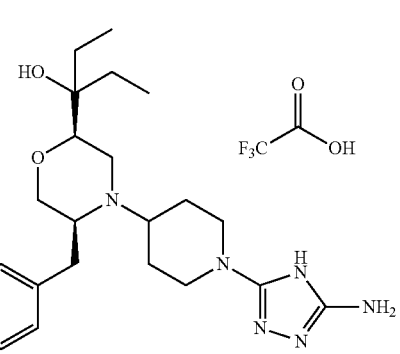 | A | A | B |

TABLE 1-continued
| Ex. # | Structure | hCHIT1, IC$_{50}$ | hAMCase, IC$_{50}$ | hERG, IC$_{50}$ |
|---|---|---|---|---|
| 69. | 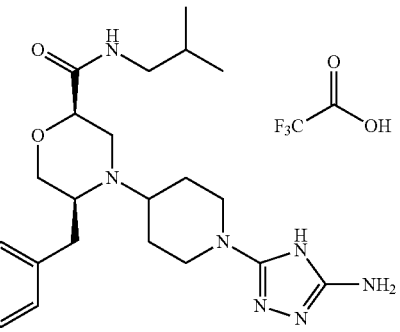 | A | A | B |
| 70. | 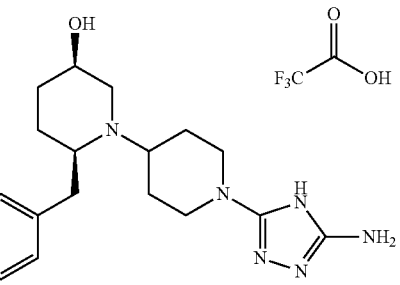 | A | A | B |
| 71. | 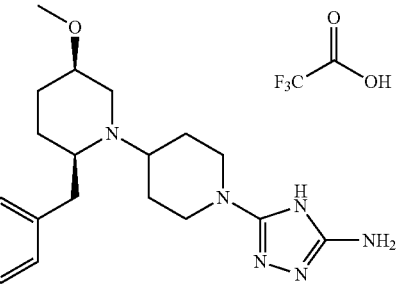 | B | A | B |
| 72. | 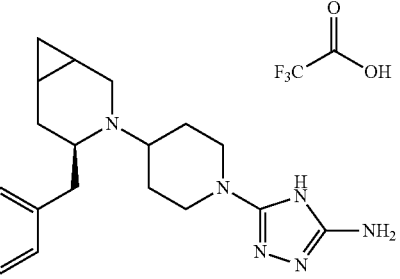<br>racemic | B | A | D |
| 73. | 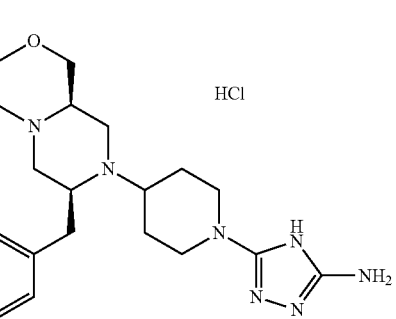 | B | A | D |

TABLE 1-continued
| Ex. # | Structure | hCHIT1, IC$_{50}$ | hAMCase, IC$_{50}$ | hERG, IC$_{50}$ |
|---|---|---|---|---|
| 74. | 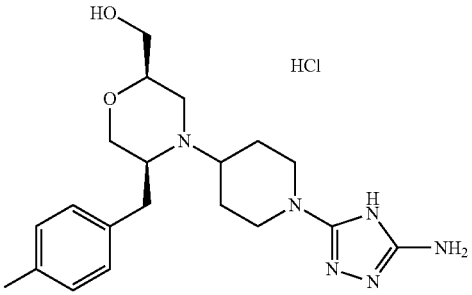 | A | A | B |
| 75. | 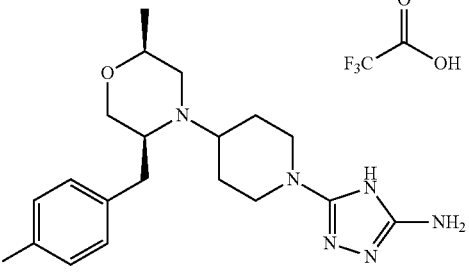 | A | A | D |
| 76. | 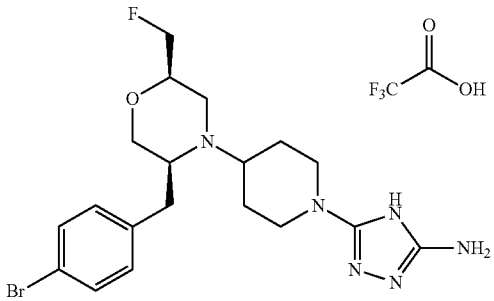 [SMILES: Nc1nnc(N2CCC(N3C[C@H](CF)OC[C@@H]3Cc3ccc(Br)cc3)CC2)[nH]1 ; O=C(O)C(F)(F)F] | A | A | A |
| 77. | 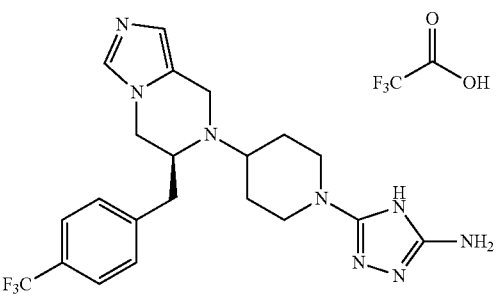 [SMILES: Nc1nnc(N2CCC(N3Cc4cncn4C[C@@H]3Cc3ccc(C(F)(F)F)cc3)CC2)[nH]1 ; O=C(O)C(F)(F)F] | C | C | C |
| 78. | 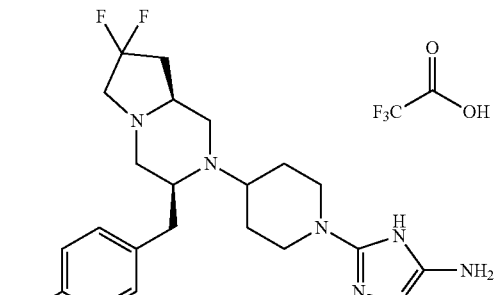 | A | A | C |

The compounds of the invention exhibit excellent activity and selectivity toward Acidic Mammalian Chitinase ("AMCase") and chitotriosidase 1 ("CHIT1") within the family of chitinases. The compounds of the invention are also characterized by a favorable cardiac safety profile related to hERG potassium channel inhibition. The limited activity of these compounds towards hERG (IC$_{50}$>25 µM), as shown in Table 1, provides an advantage over existing AMCase and CHIT1 inhibitors that are shown in Table 2.

TABLE 2

| Comparative Example | Structure | hERG IC$_{50}$ |
|---|---|---|
| C1. | 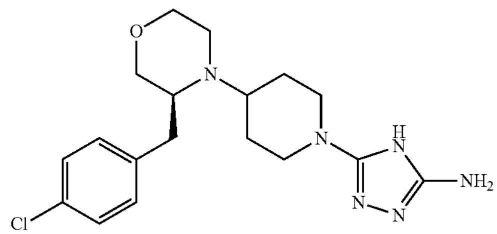 [SMILES: Nc1nnc(N2CCC(N3CCOC[C@@H]3Cc3ccc(Cl)cc3)CC2)[nH]1] | C |
| C2. | 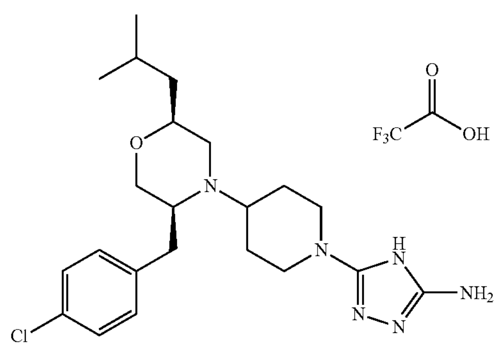 [SMILES: CC(C)C[C@H]1CN(C2CCN(c3nnc(N)[nH]3)CC2)[C@@H](Cc2ccc(Cl)cc2)CO1 ; O=C(O)C(F)(F)F] | D |
| C3. | 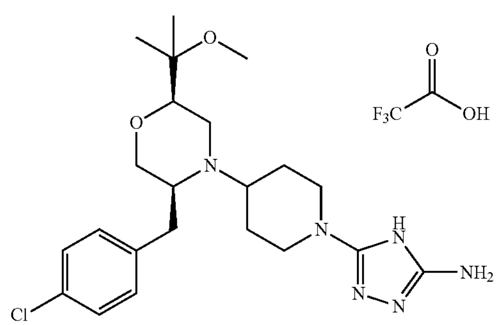 [SMILES: COC(C)(C)[C@H]1CN(C2CCN(c3nnc(N)[nH]3)CC2)[C@@H](Cc2ccc(Cl)cc2)CO1 ; O=C(O)C(F)(F)F] | C |
| C4. | 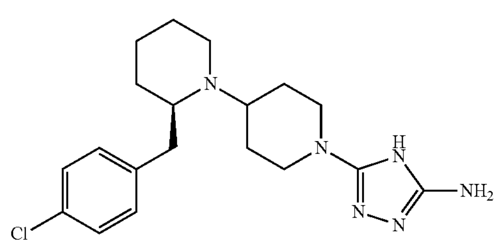 [SMILES: Nc1nnc(N2CCC(N3CCCC[C@@H]3Cc3ccc(Cl)cc3)CC2)[nH]1] | D |

TABLE 2-continued
| Comparative Example | Structure | hERG IC$_{50}$ |
|---|---|---|
| C5. | 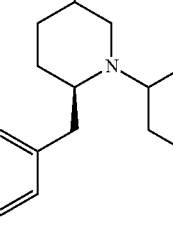 | D |
| C6. | 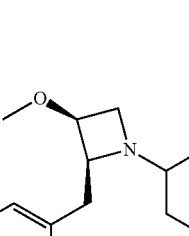 | E |
| C7. | 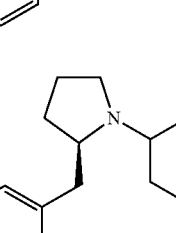 | D |
| C8. | 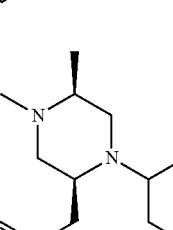 | D |
| C9. | 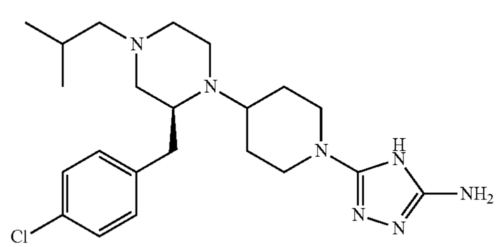 [SMILES: CC(C)CN1CCN(C2CCN(c3nnc(N)[nH]3)CC2)[C@@H](Cc2ccc(Cl)cc2)C1] | D |

TABLE 2-continued

| Comparative Example | Structure | hERG IC$_{50}$ |
|---|---|---|
| C10. | 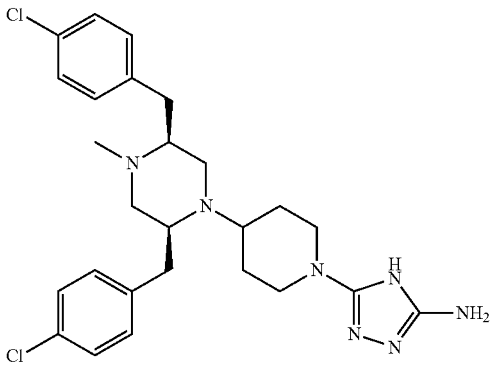 [SMILES: CN1C[C@H](Cc2ccc(Cl)cc2)N(C2CCN(c3nnc(N)[nH]3)CC2)C[C@@H]1Cc1ccc(Cl)cc1] | E |
| C11. | 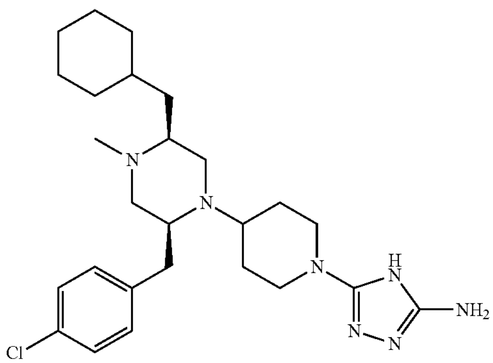 [SMILES: CN1C[C@H](Cc2ccc(Cl)cc2)N(C2CCN(c3nnc(N)[nH]3)CC2)C[C@@H]1CC1CCCCC1] | E |
| C12. | 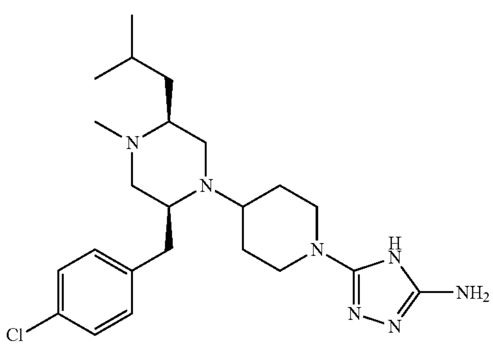 [SMILES: CC(C)C[C@H]1CN(C2CCN(c3nnc(N)[nH]3)CC2)[C@@H](Cc2ccc(Cl)cc2)CN1C] | E |
| C13. | 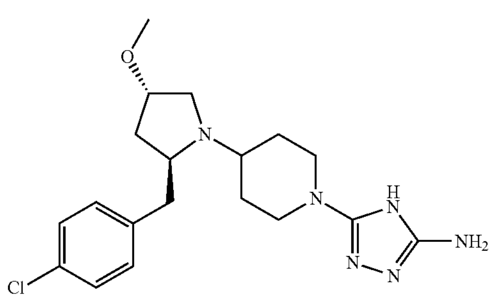 [SMILES: CO[C@H]1C[C@H](Cc2ccc(Cl)cc2)N(C2CCN(c3nnc(N)[nH]3)CC2)C1] | C |

TABLE 2-continued
| Comparative Example | Structure | hERG IC$_{50}$ |
|---|---|---|
| C14. | 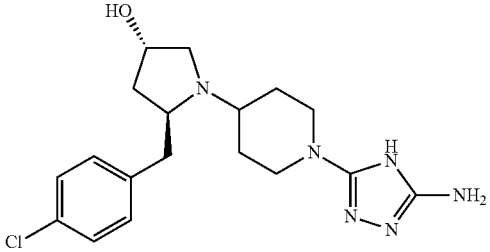 [SMILES: Nc1nnc(N2CCC(N3C[C@@H](O)C[C@@H]3Cc3ccc(Cl)cc3)CC2)[nH]1] | C |
| C15. | 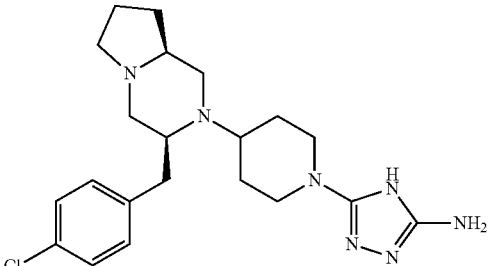 | D |
| C16. | 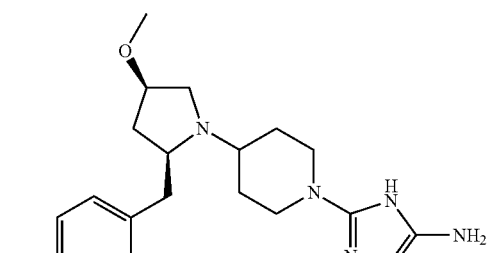 | C |
| C17. | 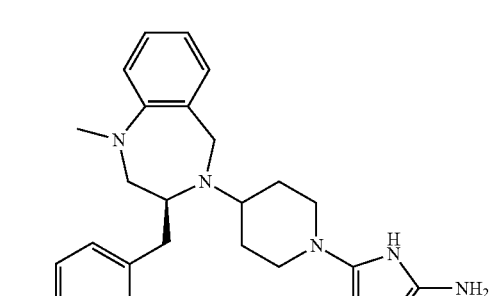 | D |
| C18. | 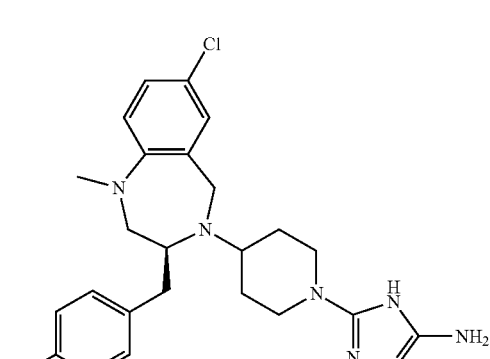 | E |

TABLE 2-continued

| Comparative Example | Structure | hERG IC$_{50}$ |
|---|---|---|
| C19. | (structure) | C |
| C20. | (structure) | D |
| C21. | (structure) | D |

General Synthetic Procedures
General Procedure Ia
Reduction of α-Amino Acid to the Corresponding Amino Alcohol.

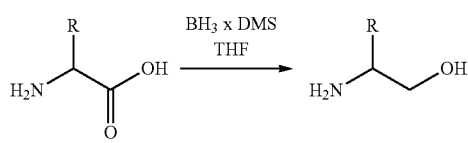

To a suspension of amino acid in anhydrous tetrahydrofuran (THF) (3 mL/mmol) borane-dimethylsulfide complex (BH$_3$×DMS; 3 equivalents) is added dropwise at 0° C. (Caution: foaming!) The cooling bath is removed and reaction mixture is refluxed overnight, after which time TLC control indicates completion of the reaction. The mixture is cooled to room temperature and 6 M HCl (8 equivalents with respect to the starting material) is carefully added (Caution: foaming!) and the mixture is again refluxed for 1.5 hours. The mixture is cooled to room temperature and pH is brought up to 10 by addition of suitable amount of 4 M NaOH. Product is extracted several times with ethyl acetate (AcOEt), extracts are combined, dried over MgSO$_4$, filtered and concentrated in vacuo. The crude product is triturated with ethyl ether (Et$_2$O) and filtered off.

General Procedure Ib
Reduction of Morpholin-3-One to Morpholine or Amide to Amine.

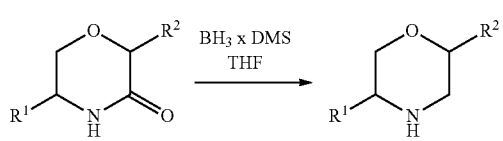

To the solution of either morpholin-3-one or 2-piperazinone or amide in THF (3 mL/mmol) borane-dimethylsulfide complex (BH₃×DMS; 3 equivalents) is added and the reaction mixture is refluxed for 3 hours, after which time the TLC or LC-MS control indicates complete consumption of the starting material. Reaction mixture is cooled to room temperature and 2 M HCl is cautiously added (6 equivalents with respect to the starting material). The resulting reaction mixture is refluxed for 2 hours and cooled back to room temperature. The pH of the solution is then adjusted to strongly alkaline (~10) by a dropwise addition of 6 M NaOH. The organic layer is separated and the aqueous layer is additionally extracted with diethyl ether. Combined organic extracts are then dried over MgSO₄, filtered and the solvents are evaporated. Crude product, in most cases, is sufficiently pure to be used in the next step without any additional purification.

General Procedure II
Cyclization of α-Haloamide to Morpholin-3-One.

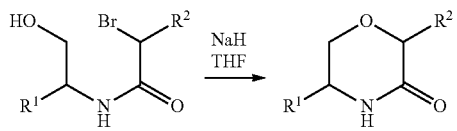

To the solution of the α-haloamide (i.e., α-chloro- or α-bromoamide) in THF (10 mL/mmol) 3 equivalents of sodium hydride (NaH) is added in one portion (cooling the solution prior to the addition of NaH may be advisable when working on larger scale) and the reaction mixture is allowed to stir at room temperature for 2 hours. The excess of NaH is then carefully quenched by dropwise addition of brine and then additional volume of brine (equal to the initial volume of THF) is added causing phases separation. The organic layer is separated and the aqueous layer is additionally extracted with diethyl ether. Combined organic extracts are then dried over MgSO₄, filtered and the solvents are evaporated. Crude product, in most cases, is sufficiently pure to be used in the next step without any additional purification.

General Procedure III
Amino-Selective Acylation of Amino Alcohol with α-Bromoacid with the Use of an Amide-Forming Reagent.

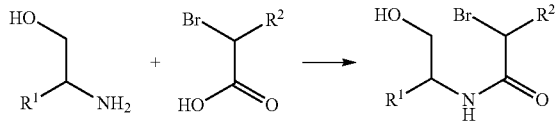

To the solution of α-bromoacid in dichloromethane (7 mL/mmol) diisopropylethylamine (DIPEA, 1 equivalent with respect to the starting α-bromoacid), coupling reagent (1 equivalent; typically TBTU or HATU, but other commonly used coupling reagents may be used as well) and amino alcohol (1 equivalent) are added sequentially and the reaction mixture is stirred for 1.5 hours at room temperature. After this time TLC control shows complete consumption of the starting materials and the reaction mixture is transferred to the separatory funnel and washed sequentially with 1 M HCl, 1 M NaOH, and brine. The organic phase is dried over MgSO₄, filtered and evaporated to give the crude product which is further purified by crystallization or silica-gel chromatography.

General Procedure IVa
Removal of the Tert-Butoxycarbonyl (Boc-) Group from Amine with HCl.

The N-Boc protected amine is treated with a 4 M solution of HCl (5 mL/mmol of starting material) in an appropriate organic solvent (e.g., AcOEt, 1,4-dioxane, MeOH, DCM) for the time necessary for complete consumption of the starting material (typically 30 minutes-2 hours). The volatiles are then removed in vacuo providing de-protected amine in the form of its hydrochloride salt. Crude product is usually sufficiently pure to be used in the following step, but additional trituration with diethyl ether may help to remove any colored impurities.

General Procedure IVb
Removal of the Tert-Butoxycarbonyl (Boc-) Group from Amine with TFA.

The N-Boc protected amine is treated with solution of TFA (6 equivalents) in DCM for the time necessary for complete consumption of the starting material (typically 30 minutes-2 hours). The volatiles are then removed in vacuo providing de-protected amine in the form of its TFA salt. Crude product is usually sufficiently pure to be used in the following step.

General Procedure Va
Installation of the 2,5-Diamino-1,2,4-Triazole Ring on the Secondary Amine.

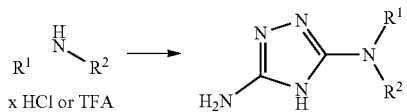

The hydrochloride/TFA salt of the secondary amine, anhydrous K₂CO₃ (2 equivalents) and S,S'-dimethyl-N-cyano-dithioiminocarbonate (1.2 equivalent) are added to acetonitrile (2 mL/mmol of the starting material) and the resulting suspension is refluxed for 1-7 hours (monitoring by TLC or LC-MS). Hydrazine monohydrate (3-5 equivalents) is then added and the reaction is refluxed further for another 2-5 hours. When analysis indicates completion of the reaction, the mixture is cooled to room temperature and solids are filtered off. The filtrate is concentrated in vacuo and the crude product is purified either by crystallization from appropriate solvent or by silica-gel or reversed-phase (C18) chromatography.

General Procedure Vb
Reductive Amination of the Cyclic Ketone and Installation of the 2,5-Diamino-1,2,4-Triazole Ring on the Secondary Amine.

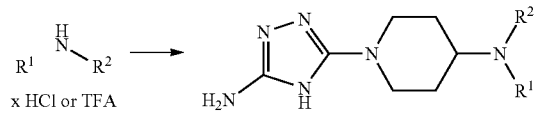

Cyclic secondary amine is dissolved in 1,2-dichloroethane (DCE, 0.65 mL/mmol) and appropriate ketone (1.5-2 equivalents with respect to the cyclic amine) and triethylamine (Et₃N) (2 equivalents with respect to the cyclic amine) are added and the mixture is stirred for 4 hours. Sodium triacetoxyborohydride (NaBH(OAc)₃, 2.5 equivalents) is then added in one portion and the thick mixture is stirred overnight at room temperature. After this time a 5% aqueous solution of sodium bicarbonate (NaHCO₃) is added (twice the volume of the DCE used) and the biphasic mixture is stirred for 30 minutes. The layers are separated and the aqueous layer is additionally extracted with dichloromethane. Combined organic extracts are dried over MgSO$_4$, filtered and the solvents are evaporated providing crude product which typically needs further purification by silica-gel chromatography. Then, obtained product is dissolved in acetonitrile (2 mL/mmol of the starting material) and to the resulting suspension hydrazine monohydrate (3-5 equivalents) is added and the reaction is refluxed for another 2-5 hours. When analysis indicates completion of the reaction, the mixture is cooled to room temperature and solids are filtered off. The filtrate is concentrated in vacuo and the crude product is purified either by crystallization from appropriate solvent or by silica-gel or reversed-phase (C18) chromatography.

General Procedure VI
Addition of Grignard Reagent to Carbonyl Group.

An appropriate Grignard reagent (3 equivalents) is added dropwise to a solution of carbonyl compound in Et$_2$O or THF (6 mL/mmol) at −40° C. After this reaction is allowed to warm up to rt. The reaction progress is monitored by TLC and LC-MS analysis of small aliquots of the crude reaction mixture. When analyses indicates completion of the reaction, the mixture is poured into saturated solution of NH$_4$Cl. Organic phase is separated, and the aqueous phase is extracted with AcOEt. Combined organic phases are dried over MgSO$_4$, filtered and concentrated in vacuo. Crude product is purified by silica-gel chromatography or flash chromatography or reversed-phase (C18) chromatography.

General Procedure VII
Fluorination of Alcohols and Carbonyl Compounds

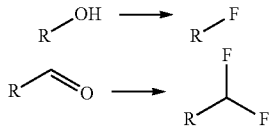

To a cooled to −20° C. or −70° C. solution of alcohol or aldehyde in dry THF or DCM (6 mL/mmol) DAST (2-2.5 equivalents) is added dropwise and the reaction is allowed to warm to room temperature and stirring is continued overnight. The reaction is poured into 5% NaHCO$_3$ and the resulting mixture is stirred for 15 minutes. Organic phase is separated and an aqueous one is extracted with DCM, washed with brine, dried over MgSO$_4$, filtered and concentrated in vacuo. Crude product is purified by silica-gel chromatography or flash chromatography or reversed-phase (C18) chromatography.

General Procedure VIII
Substitution of Mesylate with Appropriate Amine.

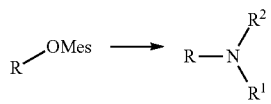

The solution of mesylate, amine (2 equivalents) and K$_2$CO$_3$ (3 equivalents) in acetonitrile is heated at 100° C. in a sealed vial overnight. Then solid is removed by filtration and the filtrate is concentrated in vacuo. Crude product is purified by silica-gel chromatography or flash chromatography.

General Procedure IX
Reductive Amination of the Cyclic Ketone with Secondary Cyclic Amine.

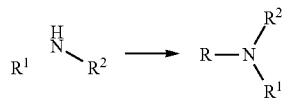

Cyclic secondary amine is dissolved in 1,2-dichloroethane (DCE, 0.65 mL/mmol) or DCM (5 mL/mmol) and appropriate ketone (1.5-2 equivalents with respect to the cyclic amine) and glacial acetic acid (AcOH) (2 equivalents with respect to the cyclic amine) or Et$_3$N (6 equivalents with respect to the cyclic amine) are added and the mixture is stirred for 4 hours. Sodium triacetoxyborohydride (NaBH(OAc)$_3$, 2 equivalents) is then added in one portion and the thick mixture is stirred overnight at room temperature. After this time a 5% aqueous solution of sodium bicarbonate (NaHCO$_3$) is added (twice the volume of the DCE used) and the biphasic mixture is stirred for 30 minutes. The layers are separated and the aqueous layer is additionally extracted with dichloromethane. Combined organic extracts are dried over MgSO$_4$, filtered and the solvents are evaporated providing crude product which typically needed further purification by silica-gel chromatography.

General Procedure X
Mesylation of Appropriate Hydroxyl Group.

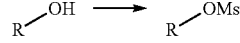

To a cooled to 0° C. solution of alcohol, triethylamine (Et$_3$N, 1.6 equivalent) in DCM (20 mL/mmol) a solution of methanesulfonic anhydride (1.5 equivalent) in DCM (6 mL/mmol) is added dropwise and the mixture is stirred at room temperature for 30 minutes. After this time the reaction is washed with 1 M K$_2$CO$_3$, brine, dried over MgSO$_4$, filtered and the solvents are evaporated. Crude product, in most cases, is sufficiently pure to be used in the next step without any additional purification.

General Procedure XI
Reaction of Mesylated Compound or Methyl Iodide with Appropriate Amine or Amide or Alcohol.

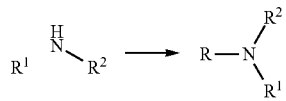

To a solution of amine (1 equivalent) or amide (2 equivalents) or alcohol (3 equivalents) in THF (1.5 mL/mmol) NaH (60% in oil; 3 equivalents) is added slowly and the mixture is stirred for 15 minutes and then solution of mesylate (1 equivalent) in THF (1.5 mL/mmol) or methyl iodide (2 equivalents) is added dropwise and the resulting mixture is refluxed overnight (for mesylate) or stirred at room temperature overnight (for methyl iodide). The reaction progress is monitored by LC-MS analysis of small aliquots of the crude reaction mixture. When analyses indicates completion of the reaction, the mixture is poured into water and product is extracted with AcOEt. Combined organic phases are dried over MgSO$_4$, filtered and concentrated in vacuo. Crude product, in most cases, is sufficiently pure to be used in the next step without any additional purification.

General Procedure XII

Activation of Carboxylic Group by Mixed Anhydride Followed by Formation of an Amide.

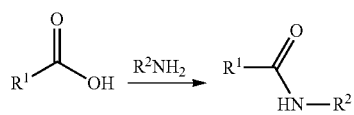

Carboxylic acid is dissolved in dichloromethane (DCM) (3-8 mL/mmol depending on the solubility) and N-methylmorpholine (1.2 equivalent) is added. The solution is cooled to −15° C. and alkyl (typically methyl, ethyl or isobutyl) chloroformate (1.2 equivalent) is added and the mixture is stirred for additional 10 minutes after which the appropriate amine (neat, 1.2 equivalent) is added. The reaction mixture is allowed to warm to room temperature and is typically stirred overnight, though in the cases of reactive amines the coupling is usually completed within minutes. The crude product is isolated by washing of organic phase (DCM) subsequentially with 1 M HCl, 1 M NaOH, and brine. The organic phase is dried over $MgSO_4$, filtered and evaporated to give the crude product which is further purified by crystallization or silica-gel chromatography.

Exemplary Synthetic Procedures

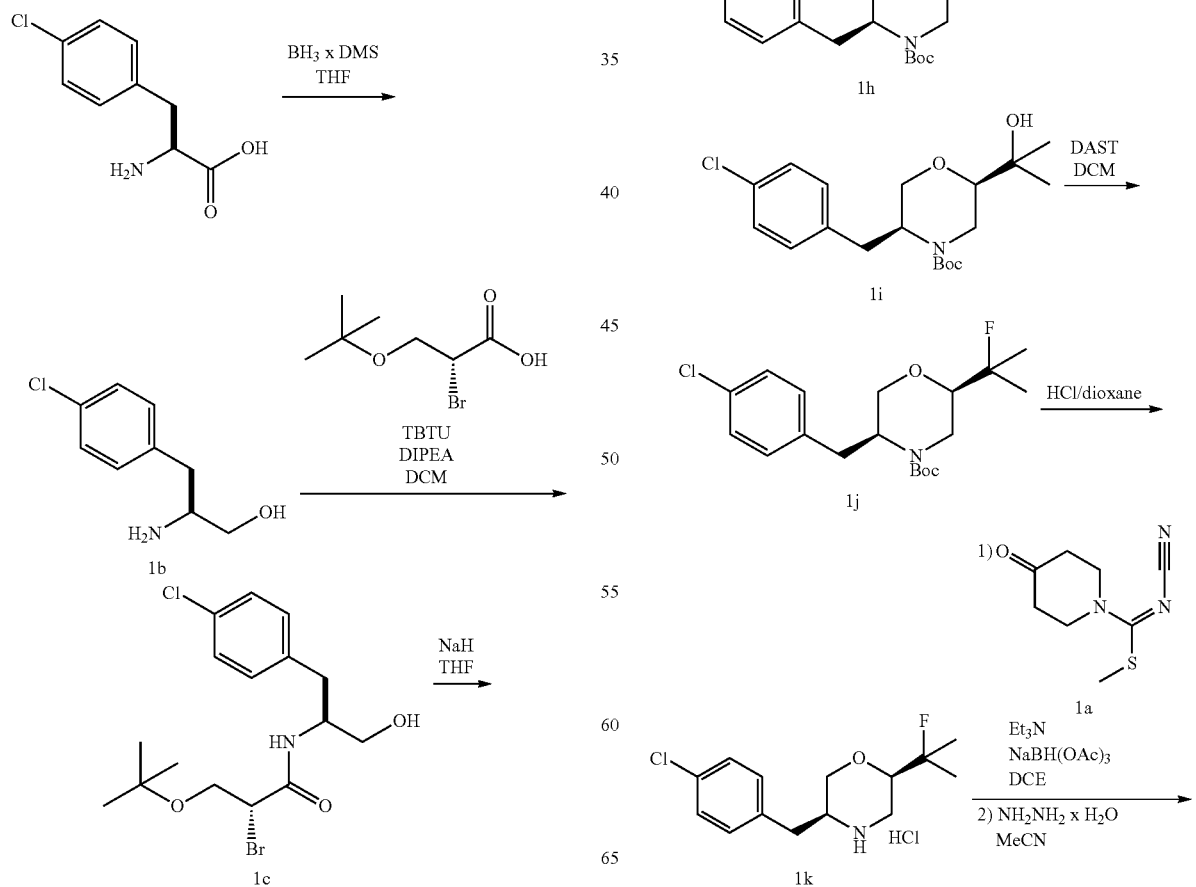
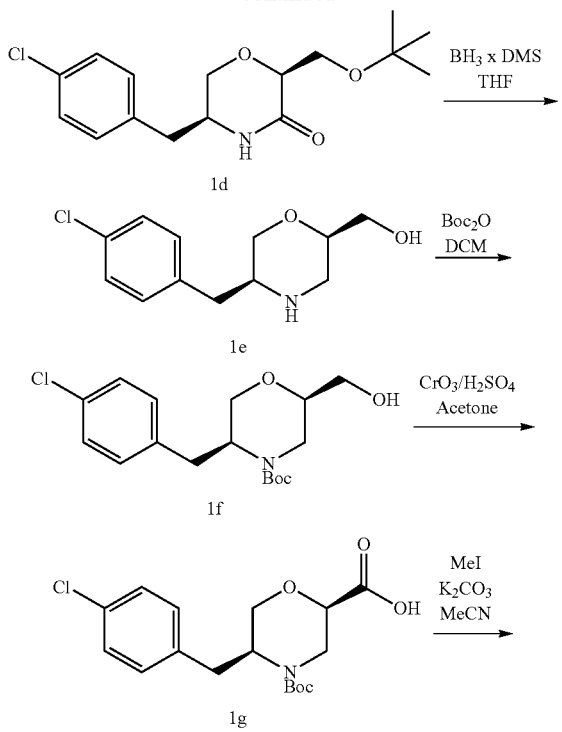
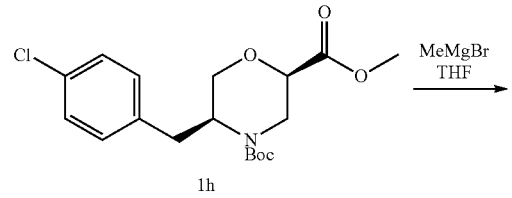
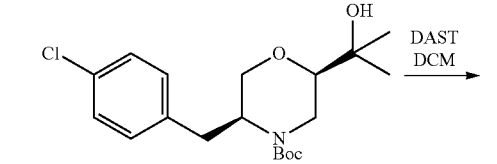
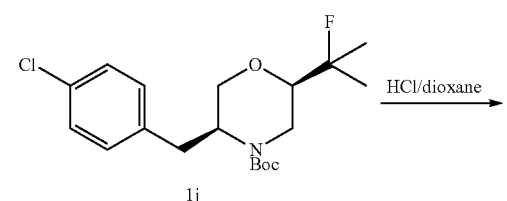
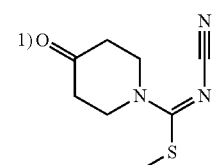
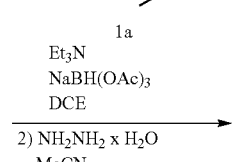

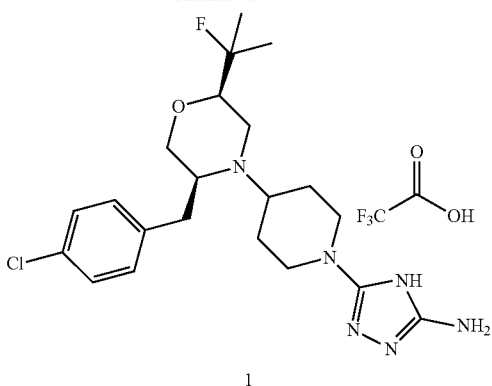

1

Synthesis of Example 1

Example 1

Synthesis of 5-(4-((2R,5S)-5-(4-chlorobenzyl)-2-(2-fluoropropan-2-yl)morpholino)piperidin-1-yl)-4H-1,2,4-triazol-3-amine 2,2,2-trifluoroacetate (1)

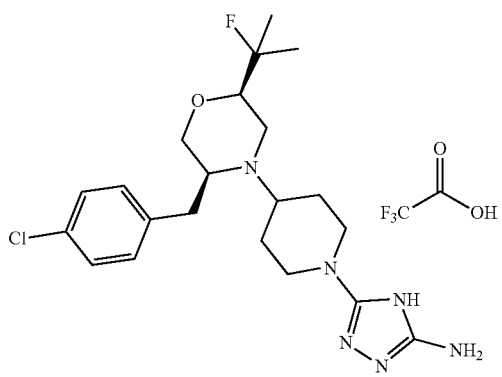

1

Step 1

Synthesis of (E)-methyl N-cyano-4-oxopiperidine-1-carbimidothioate (1a)

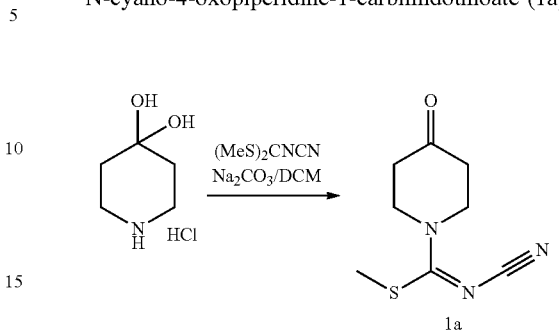

4,4-Dihydroxypiperidine hydrochloride (6.7 g; 43.6 mmol) and (MeS)$_2$CNCN (5.1 g; 34.8 mmol) were dissolved in a mixture of 15% Na$_2$CO$_3$/DCM (45 mL/45 mL) and stirred at room temperature overnight. The reaction progress was monitored by TLC and LC-MS. After analytical control indicated completion of the reaction, phases were separated and the aqueous one was extracted with DCM. Combined organic phases were washed with 1 M HCl, water and then filtered through short pad of silica which was additionally washed with the mixture of DCM/iPrOH (20/1 v/v; 105 mL). The solution was concentrated and compound 1a was obtained in 42% yield (2.86 g; 14.51 mmol).

ESI-MS m/z for C$_8$H$_{12}$N$_3$OS found 198.1 (M+H)$^+$.

Step 2

Synthesis of (2S)-2-amino-3-(4-chlorophenyl)propan-1-ol (1b)

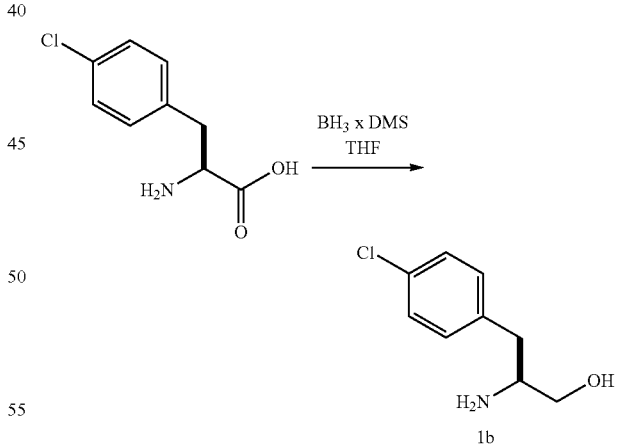

The title compound (1b) was obtained from optically pure L-p-chlorophenylalanine ((2S)-2-amino-3-(4-chlorophenyl)propanoic acid) (10.67 g; 53.45 mmol) according to the General Procedure 1a in 87% yield (8.61 g; 46.50 mmol).

ESI-MS m/z for C$_9$H$_{12}$ClNO found 185.7/187.7 (M+H)$^+$; $^1$H NMR (500 MHz, CDCl$_3$) δ 7.28 (d, J=8.3 Hz, 2H), 7.11 (d, J=8.3 Hz, 2H), 3.62 (dd, J=10.6, 3.8 Hz, 1H), 3.37 (dd, J=10.5, 6.9 Hz, 1H), 3.11-3.07 (brs, 1H), 2.76 (dd, J=13.6, 5.4 Hz, 1H), 2.50 (dd, J=13.6, 8.6 Hz, 1H).

Step 3

Synthesis of (R)-2-bromo-3-(tert-butoxy)-N—((S)-1-(4-chlorophenyl)-3-hydroxypropan-2-yl)propanamide (1c)

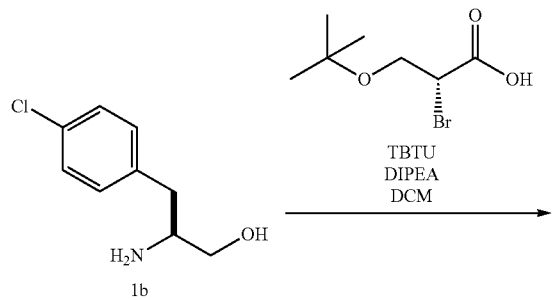

(2S)-2-amino-3-(4-chlorophenyl)propan-1-ol (1b) (1.89 g; 10.2 mmol) was coupled with (2R)-2-bromo-3-tert-butoxypropanoic acid according to the General Procedure III using TBTU as an amide bond forming reagent. Title compound 1c was obtained in 70% yield (2.96 g; 7.14 mmol).

ESI-MS m/z for $C_{16}H_{23}BrClNO_3Na$ found 414.3/416.3 (M+Na)$^+$.

Step 4

Synthesis of (2S,5S)-2-(tert-butoxymethyl)-5-(4-chlorobenzyl)morpholin-3-one (1d)

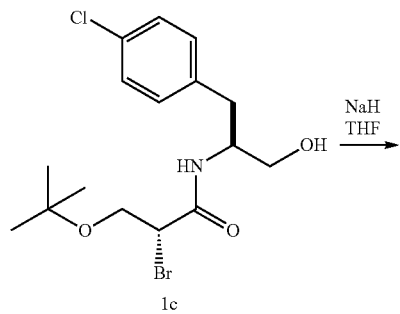

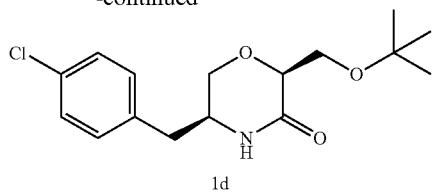

The title compound (1d) was obtained from 1c (1.2 g, 3.05 mmol) according to the General Procedure II in 89% yield (0.85 g; 2.71 mmol).

ESI-MS m/z for $C_{16}H_{22}ClNO_3Na$ found 334.1/336.1 (M+Na)$^+$.

Step 5

Synthesis of ((2R,5S)-5-(4-chlorobenzyl)morpholin-2-yl)methanol (1e)

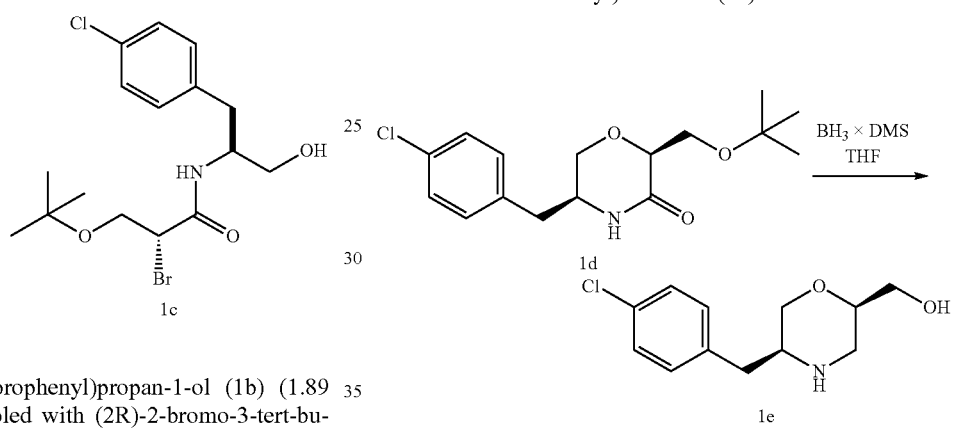

The title compound (1e) was obtained from 1d (0.85 g; 2.71 mmol) according to the General Procedure Ib in 74% yield (0.48 g; 2.01 mmol).

ESI-MS m/z for $C_{12}H_{17}ClNO_2$ found 242.2/244.2 (M+H)$^+$.

Step 6

Synthesis of tert-butyl (2R,5S)-5-(4-chlorobenzyl)-2-(hydroxymethyl)morpholine-4-carboxylate (1f)

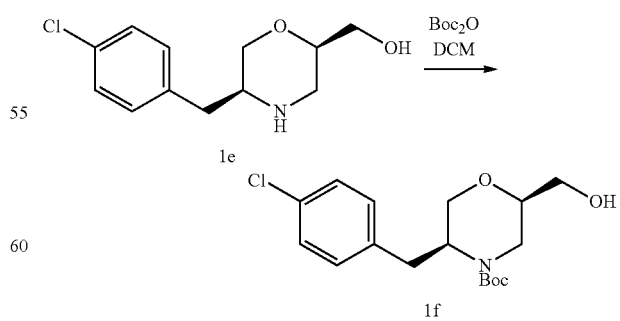

To a solution of amino alcohol 1e (2.87 g, 11.9 mmol) in dichloromethane (110 mL), di-tert-butyl dicarbonate (Boc$_2$O) (2.46 g, 11.3 mmol) was added and the reaction mixture was stirred at room temperature for 2 hours, after which time TLC showed almost complete consumption of the starting material. Volatiles were removed in vacuo and the residue was purified by column chromatography (hexane/AcOEt 1:1 v/v) giving if as colorless oil in 77% yield (3.14 g; 9.16 mmol).

ESI-MS m/z for $C_{12}H_{17}ClNO_2$ found 242.1/246.1 (M+H-Boc)$^+$.

Step 7

Synthesis of (2R,5S)-4-(tert-butoxycarbonyl)-5-(4-chlorobenzyl)morpholine-2-carboxylic acid (1g)

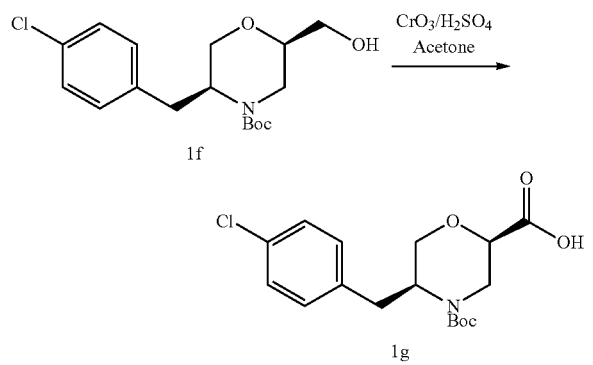

To a cooled to 0° C. solution of alcohol if (1.8 g, 5.26 mmol) in acetone (40 mL), Jones reagent (12 mL, 2.6 M) was added dropwise. The reaction mixture was stirred at 0° C. for 1 hour, and then isopropanol (iPrOH) (5 mL) was added. After 10 minutes ethyl acetate (150 mL) was added and the mixture was filtered through a pad of Celite. The filtrate was washed with brine, dried over $MgSO_4$ and evaporated affording the title compound 1g as white foam in 91% yield (1.7 g; 4.79 mmol).

ESI-MS m/z for $C_{17}H_{22}ClNO_5Na$ found 378.3/380.3 (M+Na)$^+$, 256.1/258.1 (M+H-Boc)$^+$.

Step 8

Synthesis of (2R,5S)-4-tert-butyl 2-methyl 5-(4-chlorobenzyl)morpholine-2,4-dicarboxylate (1h)

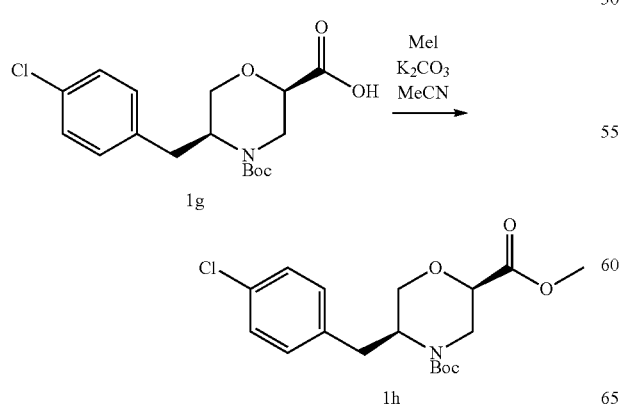

To a solution of Boc-protected amino acid 1g (1 g, 2.81 mmol) in acetonitrile, potassium carbonate (0.77 g, 5.62 mmol) and methyl iodide (MeI) (0.26 mL, 4.21 mmol) were added at room temperature. After reaction was completed as indicated by TLC, the reaction mixture was filtered and the solvent was evaporated. The residue was dissolved in ethyl acetate, washed with brine and dried over $MgSO_4$. The solvent was evaporated in vacuo to give the product 1h in 38% yield (0.4 g; 1.08 mmol) as a yellow oil sufficiently pure to be used in the next step.

ESI-MS m/z for $C_{18}H_{24}ClNO_5Na$ found 393.1/395.1 (M+Na)$^+$.

Step 9

Synthesis of (2R,5S)-tert-butyl 5-(4-chlorobenzyl)-2-(2-hydroxypropan-2-yl)morpholine-4-carboxylate (1i)

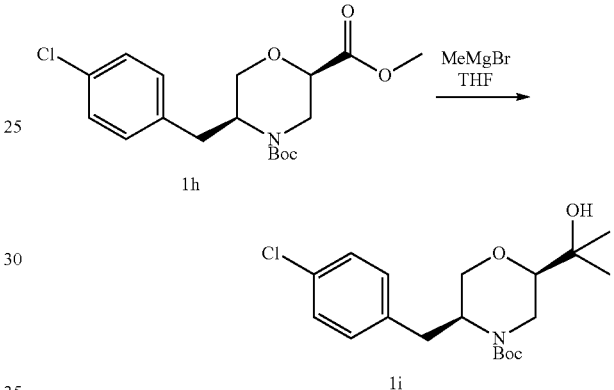

The title compound (1i) was obtained from 1h (0.40 g; 1.08 mmol) according to the General Procedure VI in 99% yield (0.40 g; 1.07 mmol).

ESI-MS $C_{19}H_{28}ClNO_4Na$ found 393.2/395.2 (M+Na)$^+$, 270.0/272.0 (M+H-Boc)$^+$.

Step 10

Synthesis of (2R,5S)-tert-butyl 5-(4-chlorobenzyl)-2-(2-fluoropropan-2-yl)morpholine-4-carboxylate (1j)

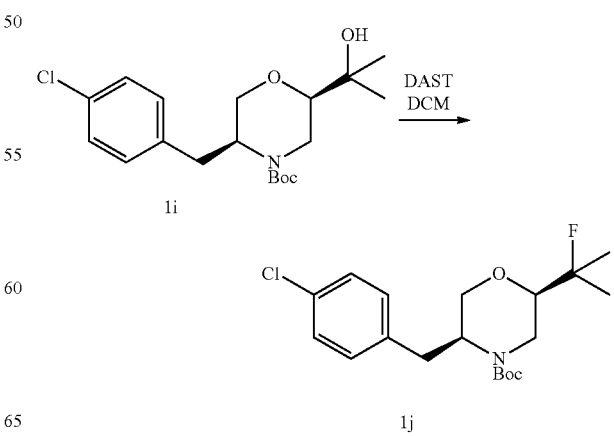

The title compound (1j) was obtained from 1h (0.25 g; 0.68 mmol) according to the General Procedure VII in 44% yield (0.11 g; 0.30 mmol).

ESI-MS C$_{19}$H$_{28}$ClFNO$_3$ found 372.2/374.2 (M+H)$^+$; $^1$H NMR (700 MHz, DMSO-d$_6$) δ 7.32-7.27 (m, 2H), 7.21-7.18 (m, 2H), 4.05-3.98 (m, 1H), 3.80-3.75 (m, 1H), 3.56-3.50 (m, 1H), 3.35-3.28 (m, 1H), 2.98-2.92 (m, 2H), 2.77-2.70 (m, 1H), 2.55-2.52 (m, 1H), 1.38-1.30 (m, 6H), 1.14-1.04 (m, 9H).

Step 11

Synthesis of (2R,5S)-5-(4-chlorobenzyl)-2-(2-fluoropropan-2-yl)morpholine hydrochloride (1k)

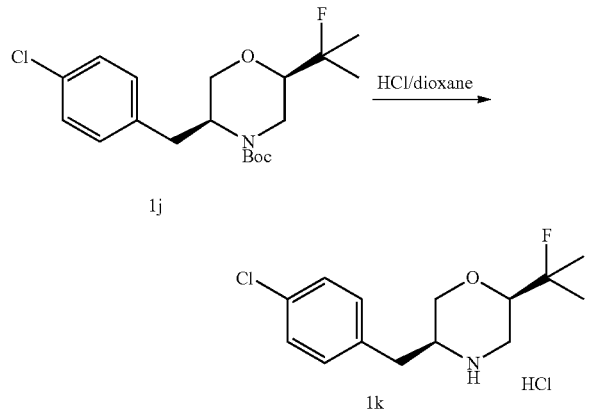

The title compound (1k) was obtained as a hydrochloride salt from 1j (0.11 g; 0.30 mmol) according to the General Procedure IVa in 99% yield (92 mg; 0.30 mmol).

ESI-MS C$_{14}$H$_{20}$ClFNO found 272.2/274.2 (M+H)$^+$.

Step 12

Synthesis of 5-(4-((2R,5S)-5-(4-chlorobenzyl)-2-(2-fluoropropan-2-yl)morpholino)piperidin-1-yl)-4H-1,2,4-triazol-3-amine 2,2,2-trifluoroacetate (1)

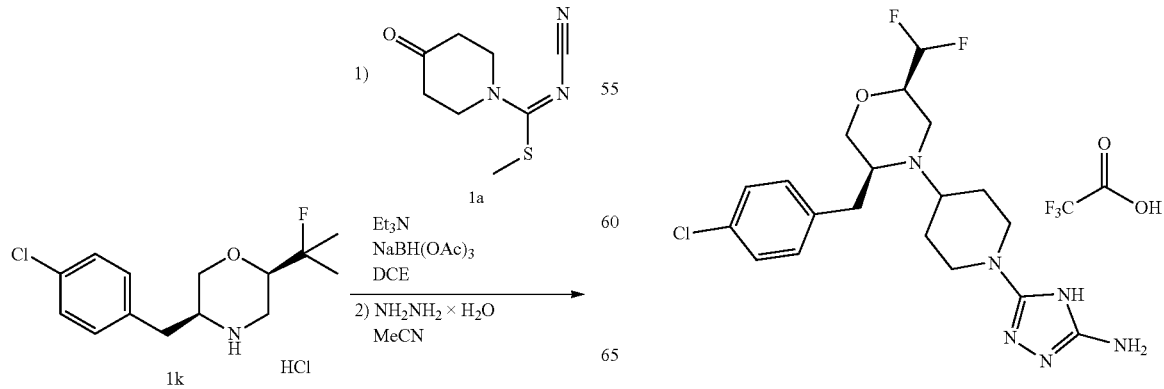

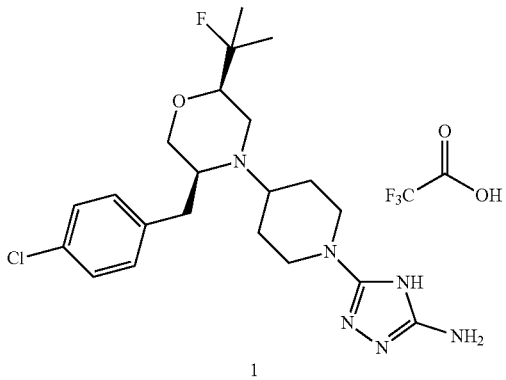

The title compound (1) was obtained as a TFA salt from 1k (92 mg; 0.30 mmol) according to the General Procedure Vb in 63% yield (103 mg; 0.19 mmol).

ESI-MS m/z for C$_{21}$H$_{31}$ClFN$_6$O found 437.0/439.0 (M+H)$^+$; $^1$H NMR (700 MHz, DMSO-d$_6$+D$_2$O, 348 K) δ 7.42-7.35 (m, 2H), 7.33-7.26 (m, 2H), 3.91-3.85 (m, 2H), 3.78-3.65 (m, 4H), 3.64-3.58 (m, 1H), 3.41-3.35 (m, 1H), 3.24-3.16 (m, 1H), 3.14-3.03 (m, 2H), 2.98-2.87 (m, 2H), 2.24 (d, J=12.3 Hz, 1H), 2.15 (d, J=12.1 Hz, 1H), 1.71-1.61 (m, 2H), 1.41 (d, J=6.0 Hz, 3H), 1.38 (d, J=6.0 Hz, 3H); $^{19}$F NMR (235 MHz, DMSO d$_6$) δ −78.91 (s), −152.03 (s).

Example 2

Synthesis of 5-(4-((2R,5S)-5-(4-chlorobenzyl)-2-(difluoromethyl)morpholino)piperidin-1-yl)-4H-1,2,4-triazol-3-amine 2,2,2-trifluoroacetate (2)

Step 1

Synthesis of (2R,5S)-tert-butyl 5-(4-chlorobenzyl)-2-formylmorpholine-4-carboxylate (2a)

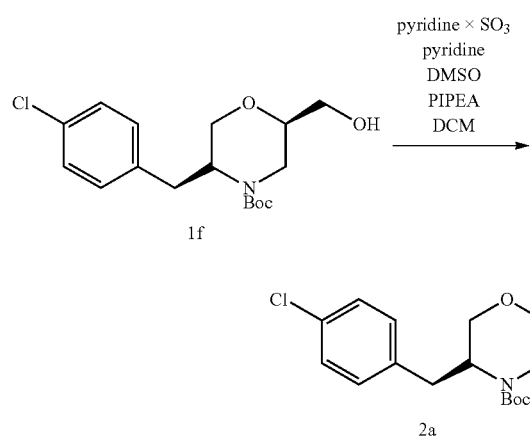

To a sulfur trioxide-pyridine complex (93 mg; 0.59 mmol), pyridine (46 mg; 0.59 mmol) and DMSO (0.11 mL; 1.45 mmol) were added. Resulting suspension was stirred for 15 minutes and, then DCM (4 mL) was added. The reaction was cooled to 0° C. and a solution of an amino alcohol if (0.1 g; 0.29 mmol) in DIPEA (177 μL; 1 mmol) and DMSO (0.11 mL; 1.45 mmol) was added. The reaction was stirred at 0° C. for 2 hours and after this time it was allowed to warm up to room temperature. The reaction progress was monitored by TLC and LC-MS analyses of small aliquots of the crude reaction mixture. When analyses indicated completion of the reaction, water (10 mL) was added. The organic phase was separated, washed with brine, dried over MgSO$_4$, filtered and concentrated in vacuo. After evaporation of solvent, crude product 2a (97 mg; 0.29 mmol) was obtained in 99% yield.

ESI-MS m/z for $C_{17}H_{23}ClNO_4$ found 340.1/342.1 (M+H)$^+$.

Step 2

Synthesis of (2R,5S)-tert-butyl 5-(4-chlorobenzyl)-2-(difluoromethyl)morpholine-4-carboxylate (2b)

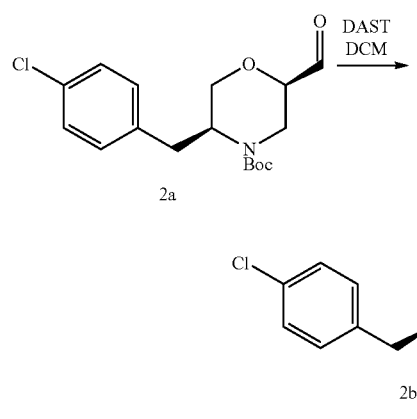

The title compound (2b) was obtained from 2a (97 mg; 0.29 mmol) according to the General Procedure VII in 45% yield (47 mg; 0.13 mmol).

ESI-MS $C_{17}H_{23}ClF_2NO_3$ found 362.2/364.2 (M+H)$^+$;

Step 3

Synthesis of (2R,5S)-5-(4-chlorobenzyl)-2-(difluoromethyl)morpholine hydrochloride (2c)

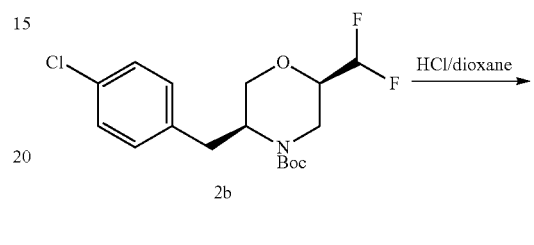

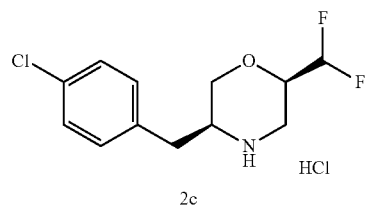

The title compound (2c) was obtained as a hydrochloride salt from 2b (47 mg; 0.13 mmol) according to the General Procedure IVa in 99% yield (39 mg; 0.13 mmol).

ESI-MS $C_{12}H_{15}ClF_2NO$ found 262.2/264.2 (M+H)$^+$.

Step 4

Synthesis of 5-(4-((2R,5S)-5-(4-chlorobenzyl)-2-(difluoromethyl)morpholino)piperidin-1-yl)-4H-1,2,4-triazol-3-amine 2,2,2-trifluoroacetate (2)

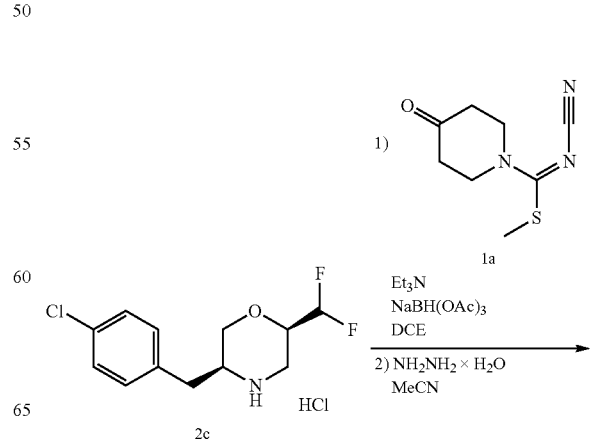

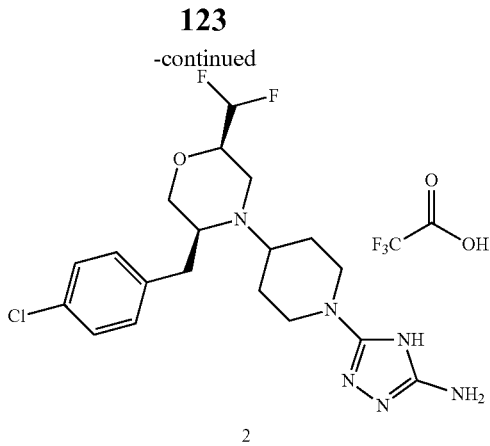

The title compound (2) was obtained as a TFA salt from 2c (39 mg; 0.13 mmol) according to the General Procedure Vb in 52% yield (36 mg; 0.067 mmol).

ESI-MS m/z for $C_{19}H_{26}ClF_2N_6O$ found 427.0/429.0 (M+H)$^+$; $^1$H NMR (700 MHz, DMSO-$d_6$+$D_2O$, 348 K) δ 7.39-7.34 (m, 2H), 7.30-7.24 (m, 2H), 6.18-5.96 (m, 1H), 4.07-3.94 (m, 1H), 3.86-3.77 (m, 2H), 3.72-3.61 (m, 2H), 3.56-3.54 (m, 1H), 3.44-3.39 (m, 1H), 3.30-3.25 (m, 1H), 3.18-3.10 (m, 1H), 3.08-3.02 (m, 2H), 3.01-2.88 (m, 2H), 2.17-2.00 (m, 2H), 1.65-1.47 (m, 2H); $^{19}$F NMR (235 MHz, DMSO-$d_6$) δ−73.96 (s), −128.01−−132.65 (m).

Example 3

Synthesis of 5-(4-((2R,5S)-5-(4-chlorobenzyl)-2-(fluoromethyl)morpholino)piperidin-1-yl)-4H-1,2,4-triazol-3-amine 2,2,2-trifluoroacetate (3)

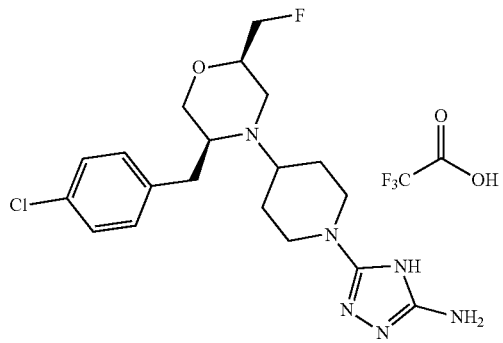

Step 1

Synthesis of (2R,5S)-tert-butyl 5-(4-chlorobenzyl)-2-(fluoromethyl)morpholine-4-carboxylate (3a)

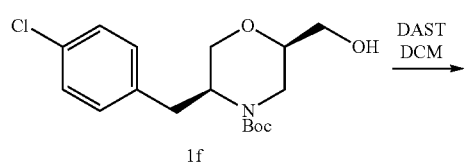

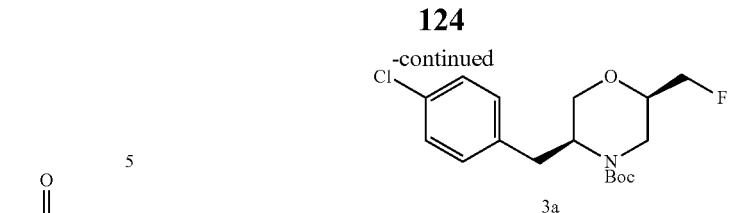

The title compound (3a) was obtained from 1f (160 mg; 0.46 mmol) according to the General Procedure VII in 60% yield (95 mg; 0.28 mmol).

ESI-MS $C_{12}H_{16}ClFNO$ found 243.9/245.9 (M+H-Boc)$^+$; $^1$H NMR (700 MHz, DMSO-$d_6$+$D_2O$, 348 K) δ 7.31-7.24 (m, 2H), 7.23-7.12 (m, 2H), 4.54-4.48 (m, 1H), 4.46-4.40 (m, 1H), 4.08-4.02 (m, 1H), 3.79-3.68 (m, 2H), 3.63-3.57 (m, 1H), 3.54-3.50 (m, 1H), 3.01-2.90 (m, 2H), 2.84-2.79 (m, 1H), 1.31-1.13 (m, 9H).

Step 2

Synthesis of (2R,5S)-5-(4-chlorobenzyl)-2-(fluoromethyl)morpholine hydrochloride (3b)

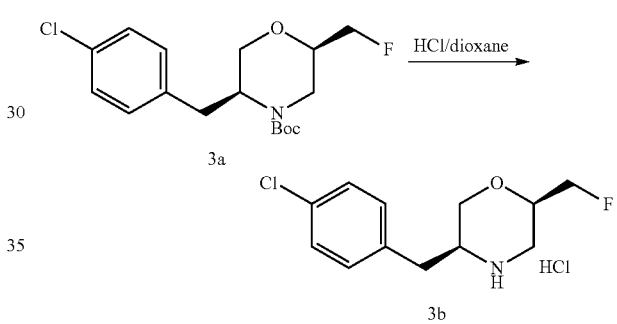

The title compound (3b) was obtained as a hydrochloride salt from 3a (0.55 g; 1.59 mmol) according to the General Procedure IVa in 99% yield (439 mg; 1.57 mmol).

ESI-MS $C_{12}H_{16}ClFNO$ found 243.9/245.9 (M+H)$^+$.

Step 3

Synthesis of 5-(4-((2R,5S)-5-(4-chlorobenzyl)-2-(fluoromethyl)morpholino)piperidin-1-yl)-4H-1,2,4-triazol-3-amine 2,2,2-trifluoroacetate (3)

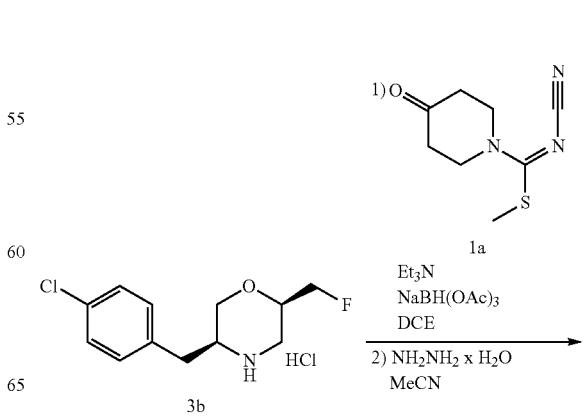

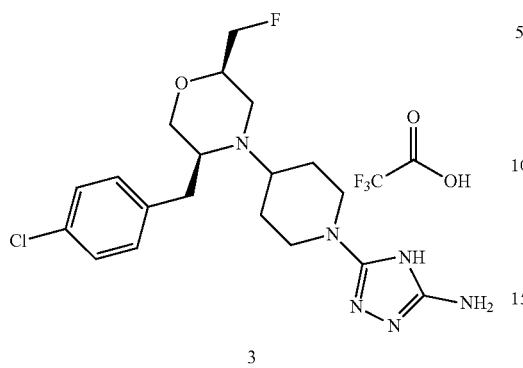

3

The title compound (3) was obtained as a TFA salt from 3b (439 mg; 1.57 mmol) according to the General Procedure Vb in 49% yield (0.4 g; 0.77 mmol).

ESI-MS m/z for $C_{19}H_{27}ClFN_6O$ found 409.0/411.0 (M+H)$^+$; $^1$H NMR (700 MHz, DMSO-$d_6$+$D_2O$, 348 K) δ 7.31-7.25 (m, 2H), 7.24-7.17 (m, 2H), 4.48-4.43 (m, 1H), 4.41-4.36 (m, 1H), 3.74-3.64 (m, 3H), 3.54-3.53 (m, 2H), 3.45-3.40 (m, 1H), 2.96-2.92 (m, 1H), 2.88-2.83 (m, 1H), 2.78-2.71 (m, 3H), 2.68-2.62 (m, 1H), 2.56-2.53 (m, 1H), 1.87-1.80 (m, 2H), 1.41-1.29 (m, 2H).

Example 4

Synthesis of 5-(4-((2S,5S)-2-((2H-tetrazol-5-yl)methyl)-5-(4-chlorobenzyl)morpholino)-piperidin-1-yl)-4H-1,2,4-triazol-3-amine 2,2,2-trifluoroacetate (4)

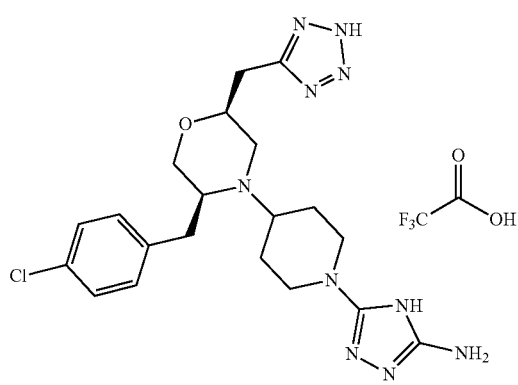

4

Step 1

Synthesis of (2R,5S)-tert-butyl 5-(4-chlorobenzyl)-2-(((methylsulfonyl)oxy)methyl)morpholine-4-carboxylate (4a)

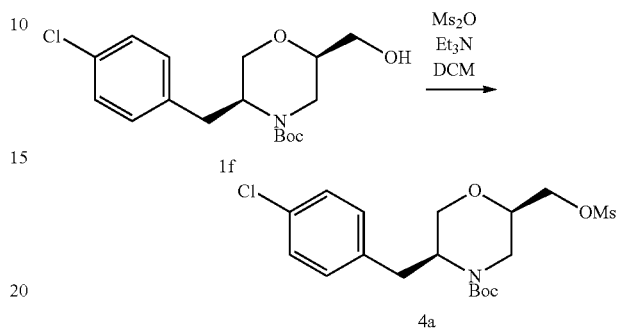

The title compound (4a) was obtained from 1f (2 g; 5.85 mmol) according to the General Procedure X in 98% yield (2.4 g; 5.73 mmol).

ESI-MS $C_{18}H_{27}ClNO_6S$ found 420.1/422.1 (M+H)$^+$.

Step 2

Synthesis of (2S,5S)-tert-butyl 5-(4-chlorobenzyl)-2-(cyanomethyl)morpholine-4-carboxylate (4b)

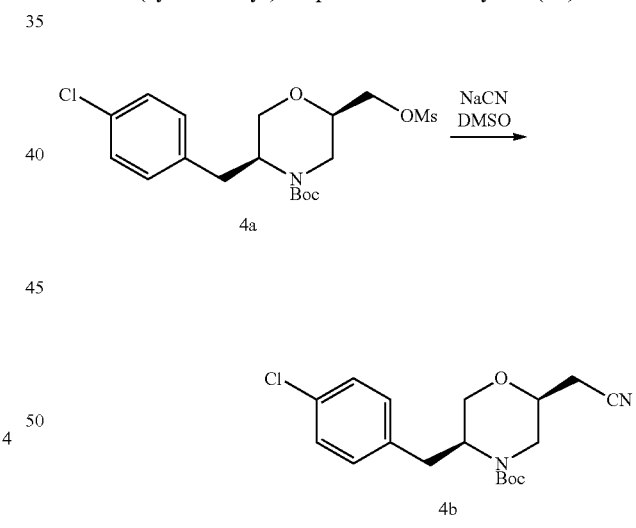

To a solution of 4a (416 mg; 0.99 mmol) in DMSO (3.3 mL) NaCN (145 mg; 2.97 mmol) was added and the mixture was heated at 85° C. overnight. The reaction progress was monitored by LC-MS. After analytical control indicated completion of the reaction, the reaction mixture was taken into AcOEt/water and organic layer was washed with water (3×), brine, dried over MgSO$_4$, filtered and concentrated in vacuo. After evaporation of solvent, crude product 4b (300 mg; 0.86 mmol) was obtained in 87% yield.

ESI-MS m/z for $C_{13}H_{16}ClN_2O$ found 251.1/253.1 (M+H-Boc)$^+$.

Step 3

Synthesis of (2S,5S)-tert-butyl 2-((2H-tetrazol-5-yl)methyl)-5-(4-chlorobenzyl)morpholine-4-carboxylate (4c)

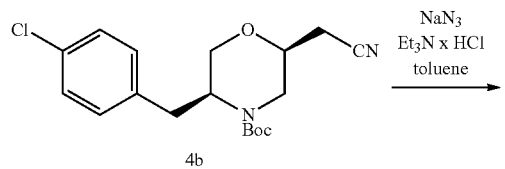

The solution of 4b (300 mg; 0.86 mmol), NaN$_3$ (67 mg; 1.03 mmol), Et$_3$N hydrochloride (0.14 mL; 1.03 mmol) in toluene (0.4 mL) was heated at 100° C. under argon atmosphere overnight. The reaction progress was monitored by LC-MS. After analytical control indicated completion of the reaction, toluene was evaporated and the residue was transferred into AcOEt/water. Then water layer was acidified and product was extracted with AcOEt, dried over MgSO$_4$, filtered and concentrated in vacuo. After evaporation of solvent, crude product 4c (180 mg; 0.46 mmol) was obtained in 53% yield.

ESI-MS m/z for $C_{18}H_{25}ClN_5O_3$ found 394.1/396.1 (M+H)$^+$.

Step 4

Synthesis of (2S,5S)-2-((2H-tetrazol-5-yl)methyl)-5-(4-chlorobenzyl)morpholine hydrochloride (4d)

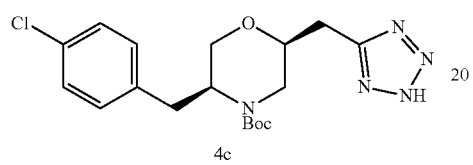

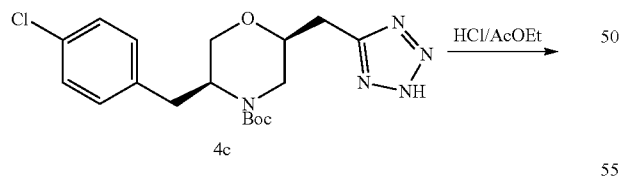

The title compound (4d) was obtained as a hydrochloride salt from 4c (0.17 g; 0.43 mmol) according to the General Procedure IVa in 99% yield (142 mg; 0.43 mmol).

ESI-MS $C_{13}H_{17}ClN_5O$ found 294.1/296.1 (M+H)$^+$.

Step 5

Synthesis of 5-(4-((2S,5S)-2-((2H-tetrazol-5-yl)methyl)-5-(4-chlorobenzyl)morpholino)piperidin-1-yl)-4H-1,2,4-triazol-3-amine 2,2,2-trifluoroacetate (4)

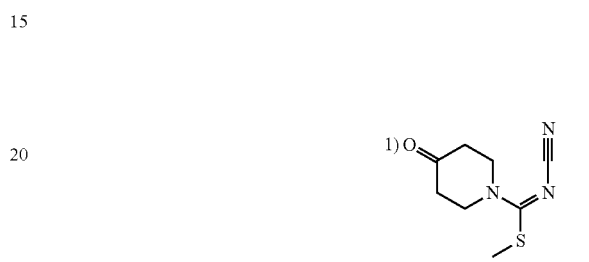

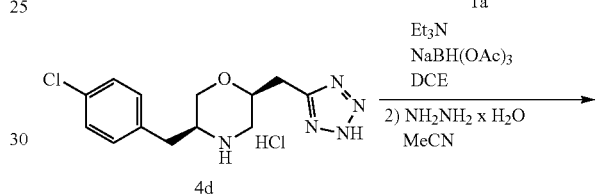

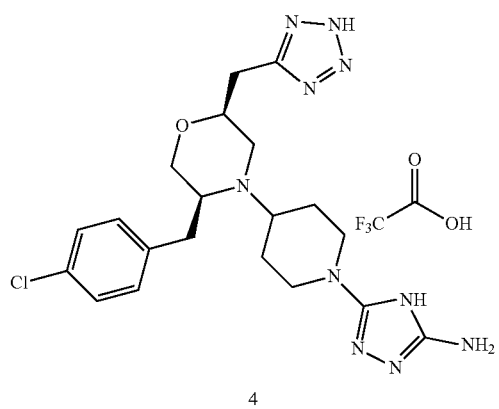

The title compound (4) was obtained as a TFA salt from 4d (142 mg; 0.43 mmol) according to the General Procedure Vb in 9% yield (21 mg; 0.037 mmol).

ESI-MS m/z for $C_{20}H_{28}ClN_{10}O$ found 459.0/461.0 (M+H)$^+$; $^1$H NMR (700 MHz, DMSO-d$_6$+D$_2$O, 348 K) δ 7.41-7.31 (m, 2H), 7.26-7.18 (m, 2H), 4.19-4.08 (m, 1H), 3.91-3.81 (m, 2H), 3.70-3.64 (m, 2H), 3.59-3.54 (m, 3H), 3.31-3.17 (m, 3H), 3.06-3.00 (m, 2H), 2.97-2.85 (m, 2H), 2.22-2.10 (m, 2H), 1.72-1.51 (m, 2H).

Example 5

Synthesis of 5-(4-((2S,5S)-5-(4-chlorobenzyl)-2-((2-methyl-2H-tetrazol-5-yl)methyl)-morpholino)piperidin-1-yl)-4H-1,2,4-triazol-3-amine 2,2,2-trifluoroacetate (5)

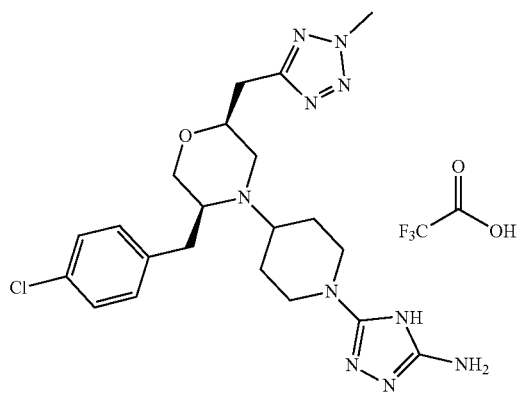

Step 1

Synthesis of (2S,5S)-tert-butyl 5-(4-chlorobenzyl)-2-((2-methyl-2H-tetrazol-5-yl)methyl)-morpholine-4-carboxylate (5a)

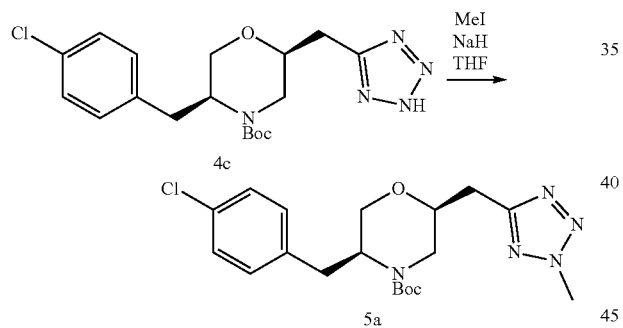

The title compound (5a) was obtained from 4c (133 mg; 0.34 mmol) according to the General Procedure XI in 99% yield (138 mg; 0.34 mmol).
ESI-MS $C_{19}H_{27}ClN_5O_3$ found 408.2/410.2 (M+H)$^+$.

Step 2

Synthesis of (2S,5S)-5-(4-chlorobenzyl)-2-((2-methyl-2H-tetrazol-5-yl)methyl)morpholine hydrochloride (5b)

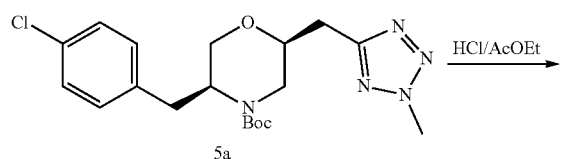

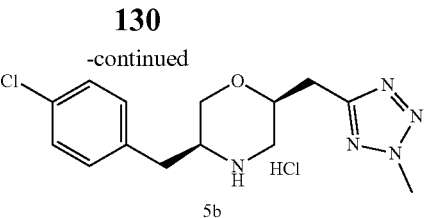

The title compound (5b) was obtained as a hydrochloride salt from 5a (138 mg; 0.34 mmol) according to the General Procedure IVa in 99% yield (117 mg; 0.34 mmol).
ESI-MS $C_{14}H_{19}ClN_5O$ found 308.1/310.1 (M+H)$^+$.

Step 3

Synthesis of 5-(4-((2S,5S)-5-(4-chlorobenzyl)-2-((2-methyl-2H-tetrazol-5-yl)methyl)-morpholino)piperidin-1-yl)-4H-1,2,4-triazol-3-amine 2,2,2-trifluoroacetate (5)

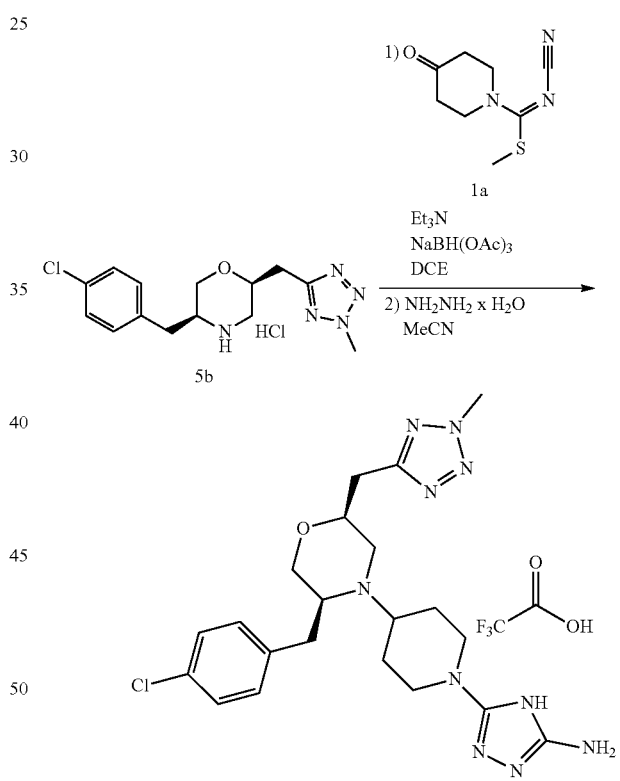

The title compound (5) was obtained as a TFA salt from 5b (117 mg; 0.34 mmol) according to the General Procedure Vb in 13% yield (25 mg; 0.043 mmol).

ESI-MS m/z for $C_{21}H_{30}ClN_{10}O$ found 473.2/475.2 (M+H)$^+$; $^1$H NMR (700 MHz, DMSO-$d_6$+$D_2O$) δ 7.40-7.35 (m, 2H), 7.27-7.23 (m, 2H), 4.30 (s, 3H), 4.24-4.08 (m, 1H), 3.88-3.84 (m, 2H), 3.77-3.73 (m, 2H), 3.69-3.57 (m, 2H), 3.54-3.47 (m, 1H), 3.34-3.26 (m, 1H), 3.22-3.15 (m, 2H), 3.13-3.07 (m, 2H), 3.00-2.87 (m, 2H), 2.25-2.17 (m, 2H), 1.65-1.56 (m, 2H).

Example 6

Synthesis of 2-((2S,5S)-4-(1-(5-amino-4H-1,2,4-triazol-3-yl)piperidin-4-yl)-5-(4-chlorobenzyl)-morpholin-2-yl)acetonitrile 2,2,2-trifluoroacetate (6)

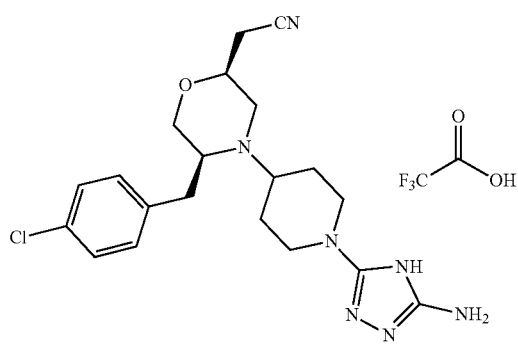

Step 1

Synthesis of 2-((2S,5S)-5-(4-chlorobenzyl)morpholin-2-yl)acetonitrile hydrochloride (6a)

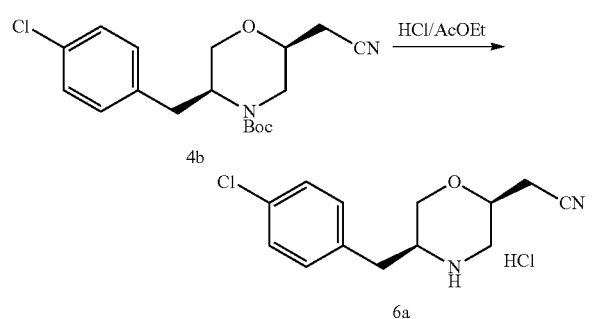

The title compound (6a) was obtained as a hydrochloride salt from 4b (99 mg; 0.28 mmol) according to the General Procedure IVa in 99% yield (80 mg; 0.28 mmol).
ESI-MS $C_{13}H_{16}ClN_2O$ found 251.1/253.1 (M+H)$^+$.

Step 2

Synthesis of 2-((2S,5S)-4-(1-(5-amino-4H-1,2,4-triazol-3-yl)piperidin-4-yl)-5-(4-chlorobenzyl)morpholin-2-yl)acetonitrile 2,2,2-trifluoroacetate (6)

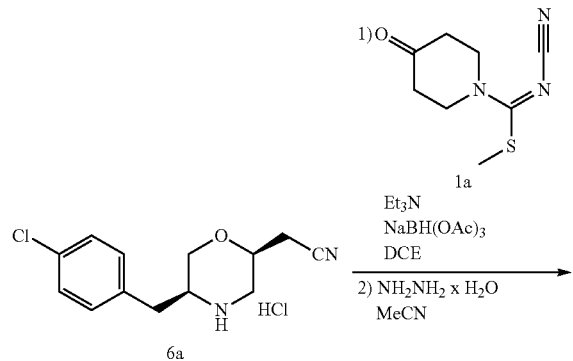

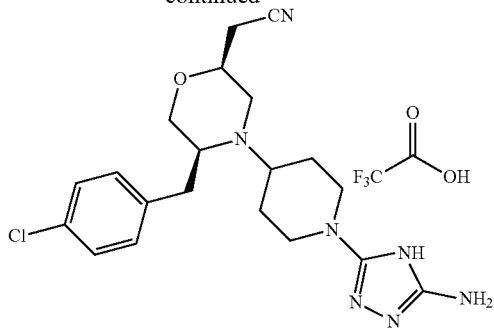

The title compound (6) was obtained as a TFA salt from 6a (80 mg; 0.28 mmol) according to the General Procedure Vb in 10% yield (15 mg; 0.028 mmol).
ESI-MS m/z for $C_{20}H_{27}ClN_7O$ found 416.0/418.0 (M+H)$^+$; $^1$H NMR (700 MHz, DMSO-$d_6$+$D_2O$, 348 K) δ 7.41-7.36 (m, 2H), 7.31-7.27 (m, 2H), 4.00-3.95 (m, 1H), 3.88-3.81 (m, 2H), 3.72-3.67 (m, 1H), 3.66-3.57 (m, 2H), 3.44-3.35 (m, 2H), 3.16-3.01 (m, 3H), 2.97-2.89 (m, 3H), 2.86-2.79 (m, 1H), 2.18-2.09 (m, 2H), 1.65-1.52 (m, 2H).

Example 7

Synthesis of 1-(((2R,5S)-4-(1-(5-amino-4H-1,2,4-triazol-3-yl)piperidin-4-yl)-5-(4-chlorobenzyl)-morpholin-2-yl)methyl)pyrrolidin-2-one 2,2,2-trifluoroacetate (7)

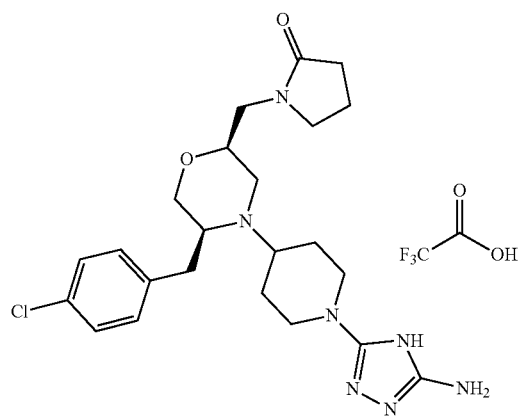

Step 1

Synthesis of ((2R,5S)-5-(4-chlorobenzyl)morpholin-2-yl)methylmethanesulfonate hydrochloride (7a)

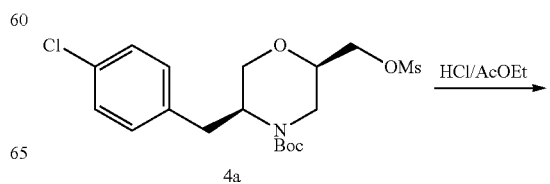

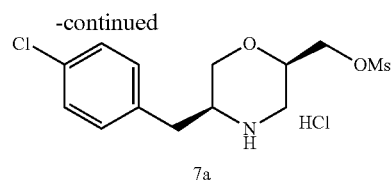

The title compound (7a) was obtained as a hydrochloride salt from 4a (235 mg; 0.56 mmol) according to the General Procedure IVa in 99% yield (200 mg; 0.56 mmol).
ESI-MS $C_{13}H_{19}ClNO_4S$ found 320.1/322.1 (M+H)+.

Step 2

Synthesis of 1-(((2R,5S)-5-(4-chlorobenzyl)morpholin-2-yl)methyl)pyrrolidin-2-one (7b)

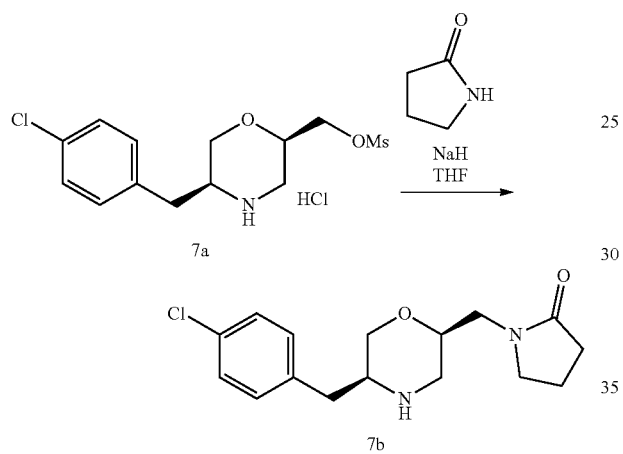

The title compound (7b) was obtained from 7a (200 mg; 0.56 mmol) according to the General Procedure XI in 99% yield (171 mg; 0.55 mmol).
ESI-MS $C_{16}H_{22}ClN_2O_2$ found 309.1/311.1 (M+H)+.

Step 3

Synthesis of 1-(((2R,5S)-4-(1-(5-amino-4H-1,2,4-triazol-3-yl)piperidin-4-yl)-5-(4-chlorobenzyl)-morpholin-2-yl)methyl)pyrrolidin-2-one 2,2,2-trifluoroacetate (7)

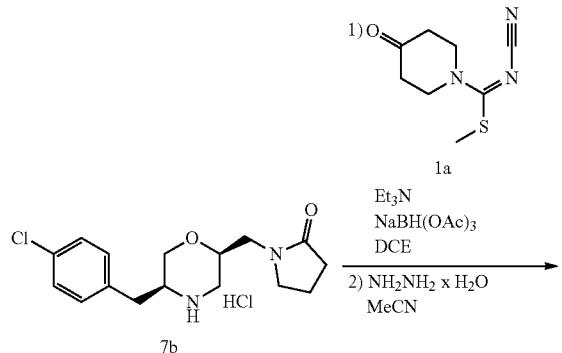

The title compound (7) was obtained as a TFA salt from 7b (147 mg; 0.48 mmol) according to the General Procedure Vb in 21% yield (61 mg; 0.10 mmol).

ESI-MS m/z for $C_{23}H_{33}ClN_7O_2$ found 474.0/476.0 (M+H)+; 1H NMR (700 MHz, DMSO-$d_6$+$D_2O$, 348 K) δ 7.41-7.36 (m, 2H), 7.33-7.27 (m, 2H), 3.94-3.84 (m, 3H), 3.71-3.58 (m, 4H), 3.52-3.46 (m, 3H), 3.39-3.33 (m, 2H), 3.12-3.08 (m, 2H), 3.07-3.00 (m, 1H), 2.96-2.88 (m, 2H), 2.31-2.21 (m, 2H), 2.18-2.10 (m, 2H), 2.01-1.95 (m, 2H), 1.69-1.57 (m, 2H).

Example 8

Synthesis of 1-(((2R,5S)-4-(1-(5-amino-4H-1,2,4-triazol-3-yl)piperidin-4-yl)-5-(4-chlorobenzyl)-morpholin-2-yl)methyl)-1H-pyrazole-4-carbonitrile 2,2,2-trifluoroacetate (8)

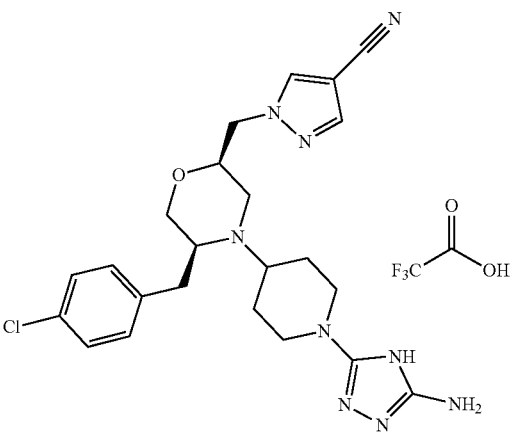

Step 1

Synthesis of (2R,5S)-tert-butyl 5-(4-chlorobenzyl)-2-((4-cyano-1H-pyrazol-1-yl)methyl)-morpholine-4-carboxylate (8a)

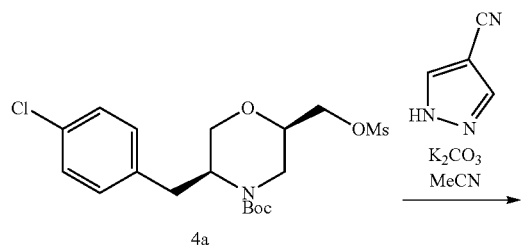

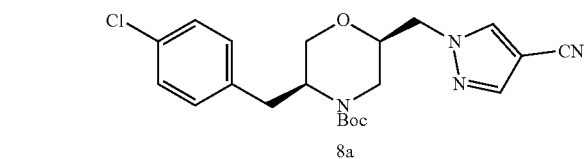

The title compound (8a) was obtained from 4a (150 mg; 0.35 mmol) according to the General Procedure VII in 97% yield (140 mg; 0.34 mmol).

ESI-MS $C_{21}H_{26}ClN_4O_3$ found 417.1/419.1 (M+H); $^1$H NMR (700 MHz, DMSO-$d_6$+$D_2O$, 348 K) δ 8.46-8.41 (m, 1H), 8.02-7.98 (m, 1H), 7.31-7.26 (m, 2H), 7.18-7.14 (m, 2H), 4.39-4.30 (m, 2H), 4.11-4.00 (m, 1H), 3.81-3.66 (m, 3H), 3.51-3.46 (m, 1H), 2.95-2.83 (m, 2H), 2.80-2.70 (m, 1H), 1.23-1.11 (m, 9H).

Step 2

Synthesis of 1-(((2R,5S)-5-(4-chlorobenzyl)morpholin-2-yl)methyl)-1H-pyrazole-4-carbonitrile hydrochloride (8b)

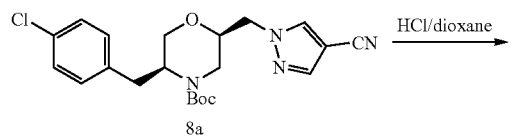

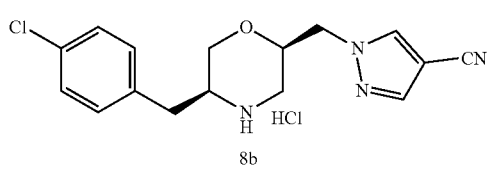

The title compound (8b) was obtained as a hydrochloride salt from 8a (140 mg; 0.34 mmol) according to the General Procedure IVa in 99% yield (120 mg; 0.34 mmol).

ESI-MS $C_{16}H_{18}ClN_4O$ found 317.1/319.1 (M+H)$^+$.

Step 3

Synthesis of 1-(((2R,5S)-4-(1-(5-amino-4H-1,2,4-triazol-3-yl)piperidin-4-yl)-5-(4-chlorobenzyl)-morpholin-2-yl)methyl)-1H-pyrazole-4-carbonitrile 2,2,2-trifluoroacetate (8)

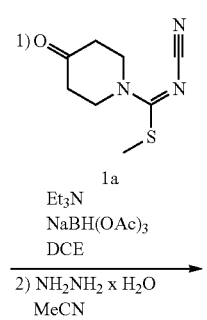

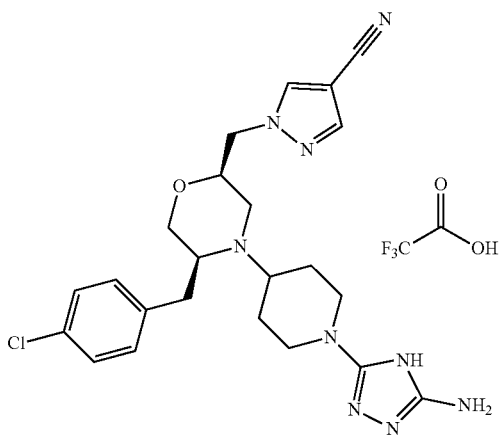

The title compound (8) was obtained as a TFA salt from 8b (120 mg; 0.34 mmol) according to the General Procedure Vb in 17% yield (35 mg; 0.059 mmol).

ESI-MS m/z for $C_{23}H_{29}ClN_9O$ found 482.2/484.2 (M+H)$^+$; $^1$H NMR (700 MHz, DMSO-$d_6$+$D_2O$, 348 K) δ 8.47-8.36 (m, 1H), 8.07-7.99 (m, 1H), 7.40-7.32 (m, 2H), 7.27-7.16 (m, 2H), 4.50-4.36 (m, 2H), 4.16-4.06 (m, 1H), 3.88-3.80 (m, 2H), 3.70-3.62 (m, 2H), 3.61-3.57 (m, 2H), 3.52-3.47 (m, 1H), 3.15-3.06 (m, 1H), 3.04-2.98 (m, 1H), 2.97-2.88 (m, 3H), 2.19-2.10 (m, 2H), 1.69-1.52 (m, 2H).

Examples 9 and 10

Synthesis of 5-(4-((2R,5S)-5-(4-chlorobenzyl)-2-(1-methyl-1H-pyrazol-3-yl)morpholino)-piperidin-1-yl)-4H-1,2,4-triazol-3-amine 2,2,2-trifluoroacetate (9) and 5-(4-((2R,5S)-5-(4-chlorobenzyl)-2-(1-methyl-1H-pyrazol-5-yl)morpholino)piperidin-1-yl)-4H-1,2,4-triazol-3-amine 2,2,2-trifluoroacetate (10)

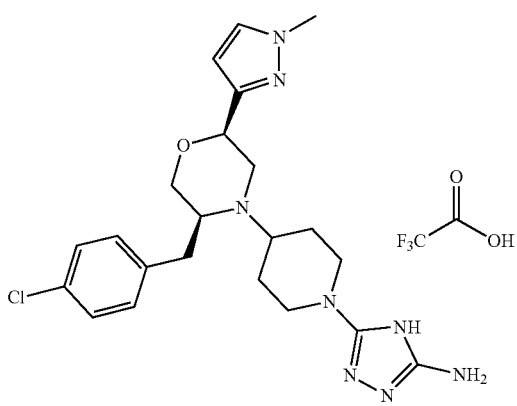

Step 1

Synthesis of (2R,5S)-tert-butyl 5-(4-chlorobenzyl)-2-(methoxy(methyl)carbamoyl)morpholine-4-carboxylate (9a)

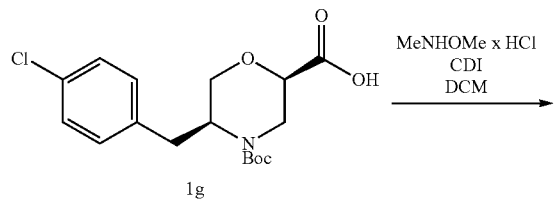

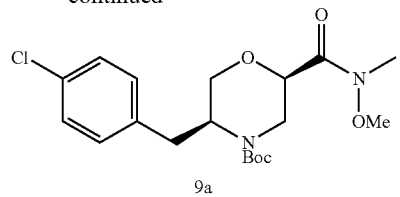

To the solution of 1g (0.5 g; 1.4 mmol) in DCM (6 mL) CDI (0.25 g; 1.5 mmol) was added in small portions. The reaction mixture was stirred at room temperature for 30 minutes, followed by addition of N,O-dimethylhydroxylamine hydrochloride (0.15 g; 1.5 mmol) in one portion and the reaction mixture was stirred at room temperature overnight. The reaction progress was monitored by TLC and LC-MS. When analyses indicated completion of the reaction, the reaction was washed sequentially with 1 M HCl, 1 M NaOH, and brine. The organic phase was dried over MgSO$_4$, filtered and concentrated in vacuo and the crude product was purified by column chromatography (hexane/AcOEt; 5:1 to 2:1 v/v). Compound 9a was obtained as a white crystal in 67% yield (0.37 g; 0.94 mmol).

ESI-MS m/z for $C_{14}H_{20}ClN_2O_3$ found 298.9/300.9 (M+H-Boc)$^+$; $^1$H NMR (700 MHz, DMSO-d$_6$+D$_2$O, 348 K) δ 7.33-7.25 (m, 2H), 7.25-7.15 (m, 2H), 4.26-4.21 (m, 1H), 4.13-4.04 (m, 1H), 3.91-3.83 (m, 1H), 3.78-3.74 (m, 1H), 3.69 (s, 3H), 3.62-3.57 (m, 1H), 3.18-3.10 (m, 4H), 3.01-2.91 (m, 1H), 2.88-2.81 (m, 1H), 1.21 (s, 9H).

Step 2

Synthesis of (2R,5S)-tert-butyl 5-(4-chlorobenzyl)-2-propioloylmorpholine-4-carboxylate (9b)

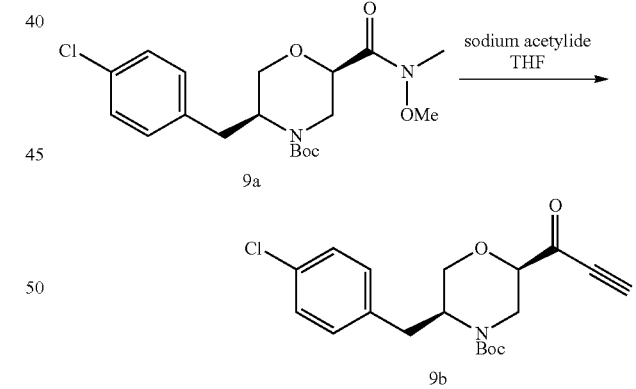

To the solution of 9a (0.35 g; 0.87 mmol) in dry THF (2 mL) at 5° C., sodium acetylide (18% slurry in xylene; 0.25 g; 5.26 mmol) was added dropwise. The reaction mixture was stirred at room temperature for 4 hours. The reaction progress was monitored by TLC and LC-MS. When analyses indicated completion of the reaction, water was added and the product was extracted with AcOEt. Combined organic solutions were washed with brine and dried over MgSO$_4$, filtered and concentrated in vacuo and the crude product was purified by column chromatography (hexane/AcOEt; 2:1 v/v). Compound 9b was obtained in 16% yield (50 mg; 0.14 mmol).

ESI-MS m/z for $C_{19}H_{22}ClNO_4Na$ found 385.9/387.9 (M+Na)$^+$; $^1$H NMR (700 MHz, DMSO-d$_6$+D$_2$O, 348 K) δ 7.31-7.24 (m, 2H), 7.24-7.17 (m, 2H), 4.14-4.07 (m, 3H), 3.82 (d, J=11.0 Hz, 1H), 3.62 (dd, J=11.7, 3.4 Hz, 1H), 3.13-3.02 (m, 1H), 2.93 (dd, J=13.7, 9.4 Hz, 1H), 2.82 (dd, J=13.7, 6.1 Hz, 1H), 2.53-2.52 (m, 1H), 1.21 (s, 9H).

Step 3

Synthesis of (2R,5S)-tert-butyl 5-(4-chlorobenzyl)-2-(1-methyl-1H-pyrazol-3-yl)morpholine-4-carboxylate (9c) and (2R,5S)-tert-butyl 5-(4-chlorobenzyl)-2-(1-methyl-1H-pyrazol-5-yl)-morpholine-4-carboxylate (9c')

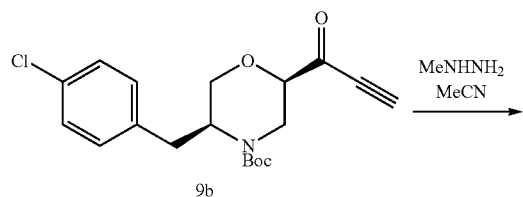

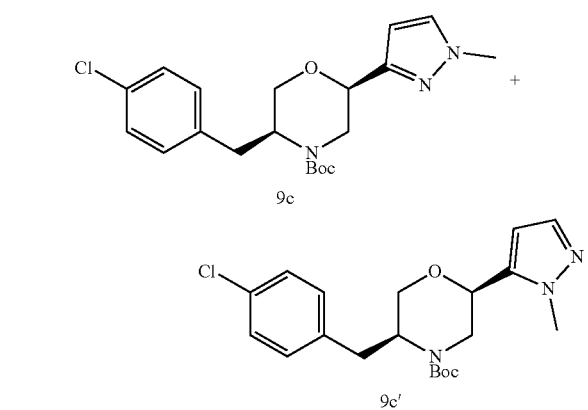

The solution of 9b (50 mg; 0.14 mmol) and methylhydrazine (14 μL; 0.27 mmol) in acetonitrile (0.2 mL) was stirred at room temperature for 2 hours. The reaction progress was monitored by LC-MS. When analysis indicated completion of the reaction, the reaction was concentrated in vacuo and the crude products mixture was used to the next step without additional purification. Compounds 9c and 9c' were obtained as a mixture of two regioisomers in 99% yield (for both regioisomers; 54 mg; 0.14 mmol).

ESI-MS m/z for $C_{20}H_{27}ClN_3O_3Na$ found 392.0/394.0 (M+H)$^+$; $^1$H NMR (700 MHz, DMSO-d$_6$+D$_2$O, 348 K) δ 7.57* (d, J=2.2 Hz, 1H), 7.37 (d, J=1.9 Hz, 0.25H), 7.31-7.26* (m, 2.5H), 7.25-7.19* (m, 2.5H), 6.36 (d, J=1.9 Hz, 0.25H), 6.29* (d, J=2.2 Hz, 1H), 4.55 (dd, J=11.2, 3.1 Hz, 0.25H), 4.35* (dd, J=11.2, 3.1 Hz, 1H), 4.17-4.06* (m, 1.25H), 3.82 (s, 0.75H), 3.80* (s, 3H), 3.79-3.77* (m, 1.25H), 3.76-3.73* (m, 1.25H), 3.68-3.61* (m, 1.25H), 3.34-3.29 (m, 0.25H), 3.27-3.16* (m, 1.25H), 3.07-2.97* (m, 1.25H), 2.93-2.84* (m, 1.25H), 1.28-1.17* (m, 11.25H) *signals for main regioisomer.

Step 4

Synthesis of (2R,5S)-5-(4-chlorobenzyl)-2-(1-methyl-1H-pyrazol-3-yl)morpholine hydrochloride (9d) and (2R,5S)-5-(4-chlorobenzyl)-2-(1-methyl-1H-pyrazol-5-yl)morpholine hydrochloride (9d')

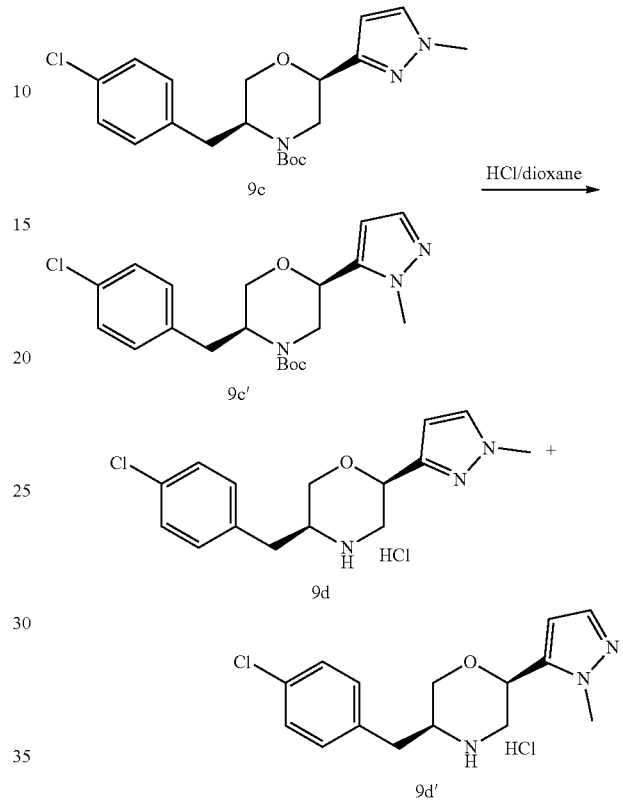

The title compounds (9d and 9d') were obtained as a mixture of hydrochloride salts from mixture of regioisomers 9c and 9c' (54 mg; 0.14 mmol) according to the General Procedure IVa in 99% yield (46 mg; 0.14 mmol).

ESI-MS $C_{15}H_{19}ClN_3O$ found 291.9/293.3 (M+H)$^+$.

Step 5

Synthesis of 5-(4-((2R,5S)-5-(4-chlorobenzyl)-2-(1-methyl-1H-pyrazol-3-yl)morpholino)-piperidin-1-yl)-4H-1,2,4-triazol-3-amine 2,2,2-trifluoroacetate (9) and 5-(4-((2R,5S)-5-(4-chlorobenzyl)-2-(1-methyl-1H-pyrazol-5-yl)morpholino)piperidin-1-yl)-4H-1,2,4-triazol-3-amine 2,2,2-trifluoroacetate (10)

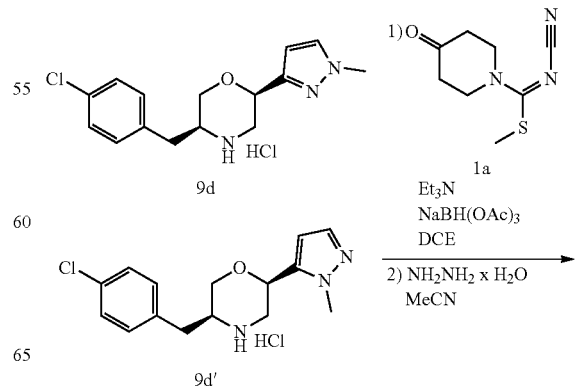

141
-continued

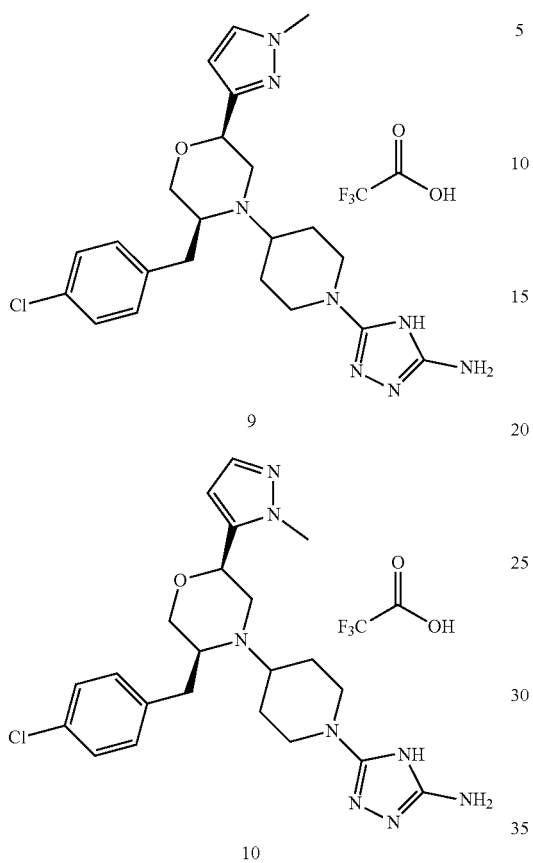

The title compounds (9 and 10) were obtained as a TFA salts from mixture of regioisomers 9d and 9d' (46 mg; 0.14 mmol) according to the General Procedure Vb. Compound 9 was obtained in 8% yield (6 mg; 0.011 mmol) and compound 10 was obtained in 30% yield (24 mg; 0.042 mmol).

For compound 9: ESI-MS m/z for $C_{22}H_{30}ClN_8O$ found 457.1/459.1 (M+H)+; 1H NMR (700 MHz, DMSO-$d_6$+$D_2O$, 348 K) δ 7.40 (d, J=1.9 Hz, 1H), 7.38-7.35 (m, 2H), 7.31-7.28 (m, 2H), 6.43 (d, J=1.9 Hz, 1H), 4.95-4.84 (m, 1H), 3.87-3.81 (m, 7H), 3.70-3.65 (m, 1H), 3.63-3.58 (m, 1H), 3.42-3.38 (m, 1H), 3.16-3.07 (m, 2H), 2.95-2.86 (m, 3H), 2.16-2.09 (m, 2H), 1.66-1.56 (m, 2H).

For compound 10: ESI-MS m/z for $C_{22}H_{30}ClN_8O$ found 457.1/459.1 (M+H)+; 1H NMR (700 MHz, DMSO-$d_6$+$D_2O$, 348 K) δ 7.64 (d, J=2.2 Hz, 1H), 7.41-7.36 (m, 2H), 7.36-7.31 (m, 2H), 6.38 (d, J=2.2 Hz, 1H), 4.88-4.77 (m, 1H), 3.91-3.86 (m, 2H), 3.85-3.82 (m, 4H), 3.78-3.74 (m, 1H), 3.71-3.65 (m, 2H), 3.56-3.53 (m, 1H), 3.51-3.49 (m, 1H), 3.25-3.19 (m, 1H), 3.19-3.13 (m, 1H), 2.96-2.88 (m, 2H), 2.22-2.14 (m, 2H), 1.72-1.62 (m, 2H).

142

Example 11

Synthesis of 5-(4-((2R,5S)-5-(4-chlorobenzyl)-2-(1,5-dimethyl-1H-pyrazol-3-yl)morpholino)-piperidin-1-yl)-4H-1,2,4-triazol-3-amine 2,2,2-trifluoroacetate (11)

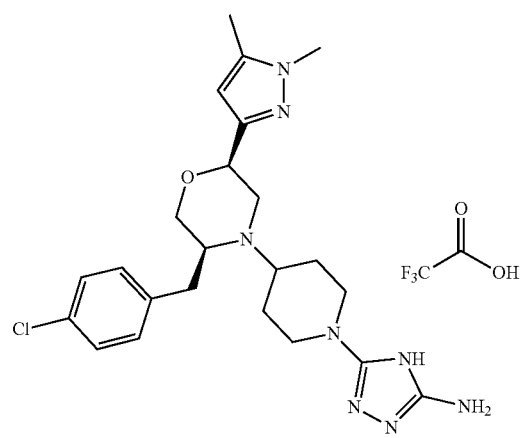

Step 1

Synthesis of (2R,5S)-tert-butyl 2-(but-2-ynoyl)-5-(4-chlorobenzyl)morpholine-4-carboxylate (11a)

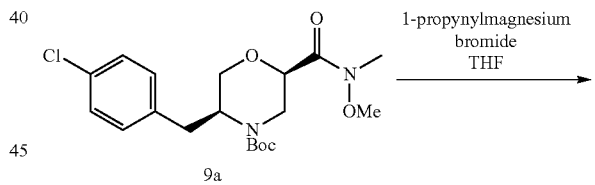

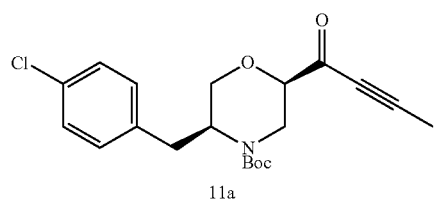

The title compound (11a) was obtained from 9a (323 mg; 0.81 mmol) according to the General Procedure VI in 99% yield (300 mg; 0.80 mmol).

ESI-MS $C_{15}H_{17}ClNO_2$ found 277.9/279.9 (M+H)+.

Step 2

Synthesis of (2R,5S)-tert-butyl 5-(4-chlorobenzyl)-2-(1,5-dimethyl-1H-pyrazol-3-yl)morpholine-4-carboxylate (11b)

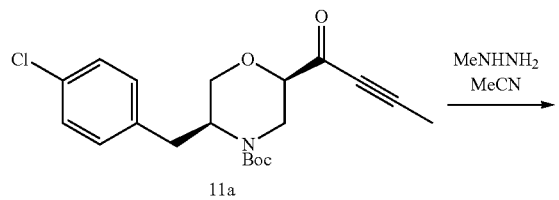

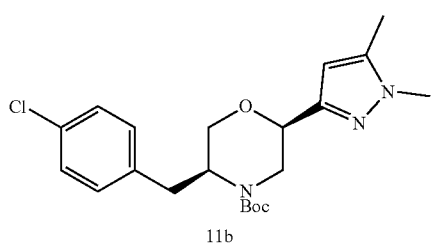

The solution of 11a (100 mg; 0.26 mmol) with methylhydrazine (28 µL; 0.52 mmol) in acetonitrile (2 mL) was stirred at room temperature for 1 hour. The reaction progress was monitored by LC-MS. When analysis indicated completion of the reaction, the reaction was concentrated in vacuo and the crude product mixture was used in the next step without additional purification. Compound 11b was obtained in 99% yield (105 mg; 0.26 mmol).

ESI-MS m/z for $C_{21}H_{29}ClN_3O_3$ found 406.2/408.2 $(M+H)^+$; $^1H$ NMR (700 MHz, DMSO-$d_6$+$D_2O$, 348 K) δ 7.29-7.24 (m, 2H), 7.24-7.13 (m, 2H), 6.08 (s, 1H), 4.27 (dd, J=11.2, 3.1 Hz, 1H), 4.15-4.01 (m, 1H), 3.93-3.81 (m, 1H), 3.77-3.71 (m, 1H), 3.68 (s, 3H), 3.63-3.58 (m, 1H), 3.28-3.15 (m, 1H), 3.06-2.94 (m, 1H), 2.93-2.82 (m, 1H), 2.22 (s, 3H), 1.22 (s, 9H).

Step 3

Synthesis of (2R,5S)-5-(4-chlorobenzyl)-2-(1,5-dimethyl-1H-pyrazol-3-yl)morpholine hydrochloride (11c)

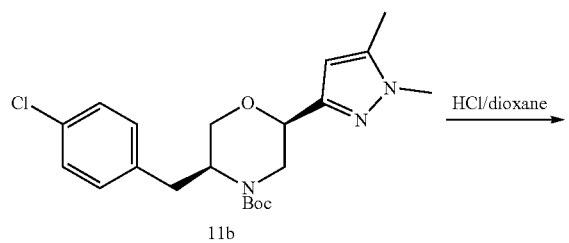

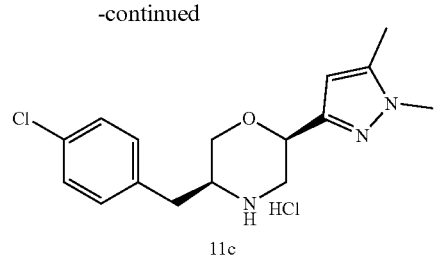

The title compound (11c) was obtained as a hydrochloride salt from 11b (105 mg; 0.26 mmol) according to the General Procedure IVa in 99% yield (89 mg; 0.26 mmol).

ESI-MS $C_{16}H_{21}ClN_3O$ found 305.9/307.9 $(M+H)^+$.

Step 4

Synthesis of 5-(4-((2R,5S)-5-(4-chlorobenzyl)-2-(1,5-dimethyl-1H-pyrazol-3-yl)morpholino)-piperidin-1-yl)-4H-1,2,4-triazol-3-amine 2,2,2-trifluoroacetate (11)

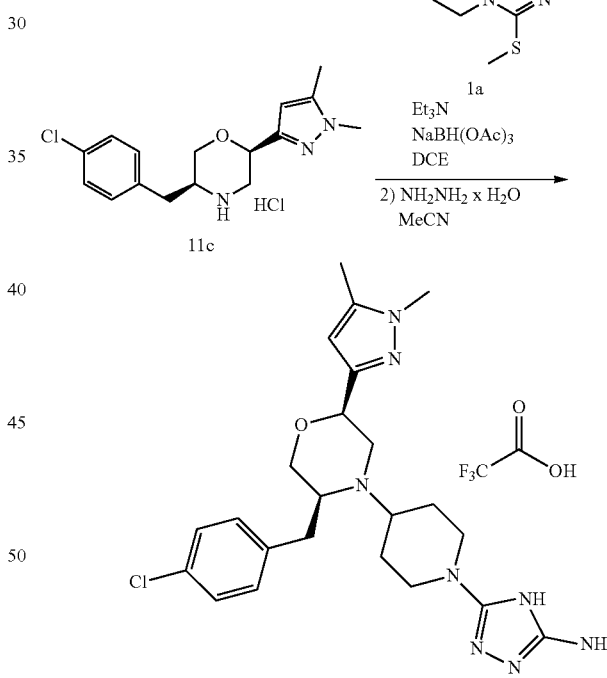

The title compound (11) was obtained as a TFA salt from 11c (89 mg; 0.26 mmol) according to the General Procedure Vb in 50% yield (75 mg; 0.13 mmol).

ESI-MS m/z for $C_{23}H_{32}ClN_8O$ found 471.4/473.4 $(M+H)^+$; $^1H$ NMR (700 MHz, DMSO-$d_6$+$D_2O$, 348 K) δ 7.40-7.35 (m, 2H), 7.34-7.28 (m, 2H), 6.17 (s, 1H), 4.76 (d, J=8.3 Hz, 1H), 3.90-3.85 (m, 2H), 3.84-3.79 (m, 1H), 3.78-3.74 (m, 1H), 3.71-3.65 (m, 5H), 3.49-3.41 (m, 2H), 3.25-3.11 (m, 2H), 2.98-2.86 (m, 2H), 2.23 (s, 3H), 2.21-2.13 (m, 2H), 1.72-1.58 (m, 2H).

Example 12

Synthesis of 5-(4-((2R,5S)-5-(4-chlorobenzyl)-2-(1H-pyrazol-5-yl)morpholino)piperidin-1-yl)-4H-1,2,4-triazol-3-amine 2,2,2-trifluoroacetate (12)

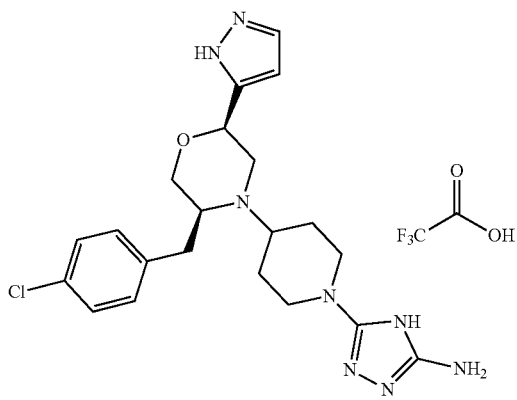

The title compound 12 was obtained as a TFA salt in 6% overall yield in a similar way to Examples 9 and 10 with the exception that, in the third step of the synthesis, hydrazine hydrate was used instead of methylhydrazine.

ESI-MS m/z for $C_{21}H_{28}ClN_8O$ found 443.2/445.2 (M+1)+; $^1$H NMR (700 MHz, DMSO-$d_6$+$D_2O$, 348 K) δ 7.68 (d, J=2.3 Hz, 1H), 7.41-7.36 (m, 2H), 7.36-7.28 (m, 2H), 6.43 (d, J=2.3 Hz, 1H), 4.93-4.85 (m, 1H), 3.90-3.83 (m, 4H), 3.80-3.76 (m, 1H), 3.74-3.66 (m, 2H), 3.60-3.56 (m, 1H), 3.24 (dd, J=13.8, 10.9 Hz, 1H), 3.17 (dd, J=14.0, 3.8 Hz, 1H), 2.99-2.89 (m, 2H), 2.23-2.17 (m, 2H), 1.72-1.63 (m, 2H).

Example 13

Synthesis of 5-(4-((2R,5S)-2-((1H-pyrazol-1-yl)methyl)-5-(4-chlorobenzyl)morpholino)-piperidin-1-yl)-4H-1,2,4-triazol-3-amine 2,2,2-trifluoroacetate (13)

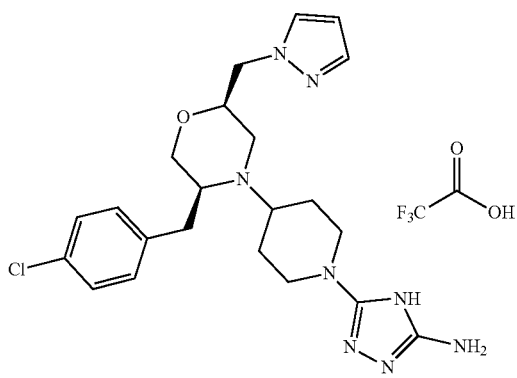

The title compound 13 was obtained as a TFA salt in 19% overall yield in a similar way to Example 8 with the exception that, in the first step of the synthesis, pyrazole was used instead of 4-cyanopyrazole.

ESI-MS m/z for $C_{22}H_{30}ClN_8O$ found 457.0/459.0 (M+1)+; $^1$H NMR (700 MHz, DMSO-$d_6$+$D_2O$, 348 K) δ 7.70 (d, J=2.0 Hz, 1H), 7.49 (d, J=1.4 Hz, 1H), 7.41-7.33 (m, 2H), 7.30-7.22 (m, 2H), 6.30 (t, J=2.0 Hz, 1H), 4.43-4.27 (m, 2H), 4.17-4.07 (m, 1H), 3.93-3.80 (m, 2H), 3.75-3.67 (m, 2H), 3.63-3.53 (m, 3H), 3.16-3.07 (m, 1H), 3.05-3.00 (m, 1H), 2.99-2.88 (m, 3H), 2.19-2.12 (m, 2H), 1.69-1.61 (m, 2H).

Example 14

Synthesis of 5-(4-((2S,5S)-5-(4-chlorobenzyl)-2-(2,2,2-trifluoroethyl)morpholino)piperidin-1-yl)-4H-1,2,4-triazol-3-amine 2,2,2-trifluoroacetate (14)

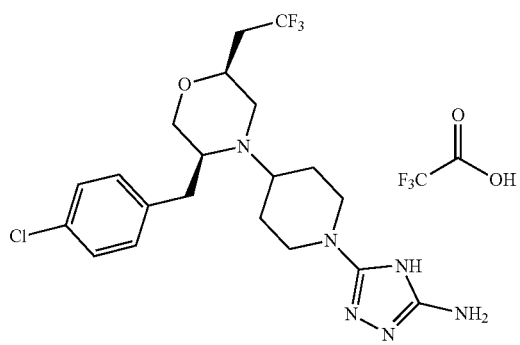

Step 1

Synthesis of (2R,5S)-tert-butyl 5-(4-chlorobenzyl)-2-((S)-2,2,2-trifluoro-1-hydroxyethyl)-morpholine-4-carboxylate (14a)

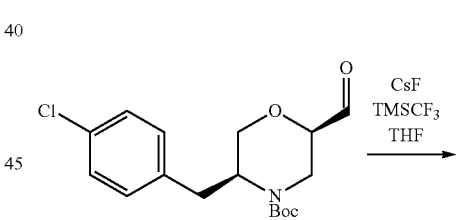

CsF (0.8 g; 5.29 mmol) was placed in flask and gently dried with a heat gun under argon flow. Then compound 2a (0.6 g; 1.76 mmol) was added dropwise as a solution in THF and the mixture was cooled to −20° C. Then CF$_3$TMS (0.39 mL; 2.65 mmol) was slowly added via syringe and reaction was allowed to warm up to room temperature. The reaction progress was monitored by LC-MS. When analysis indicated completion of the reaction, water was added and product was extracted with AcOEt. Organic solutions were dried over MgSO$_4$, filtered and concentrated in vacuo and the crude product was purified by column chromatography (hexane/AcOEt; 20:1 to 5:1 v/v). Compound 14a was obtained as a mixture of two diastereoisomers in 64% yield (462 mg; 1.13 mmol).

ESI-MS m/z for C$_{14}$H$_{16}$ClF$_3$NO$_4$ found 353.9/355.9 (M+H−tBu)$^+$; $^1$H NMR (700 MHz, DMSO-d$_6$+D$_2$O, 348 K) δ 7.32-7.24 (m, 2H), 7.22-7.13 (m, 2H), 5.59 (s, 1H), 4.11-3.87 (m, 2H), 3.80-3.71 (m, 1H), 3.56-3.48 (m, 2H), 3.18-3.02 (m, 1H), 3.00-2.91 (m, 1H), 2.86-2.78 (m, 1H), 1.32-1.11 (m, 9H).

Step 2

Synthesis of (2R,5S)-tert-butyl 5-(4-chlorobenzyl)-2-((S)-2,2,2-trifluoro-1-((phenoxy-carbonothioyl)oxy)ethyl)morpholine-4-carboxylate (14b)

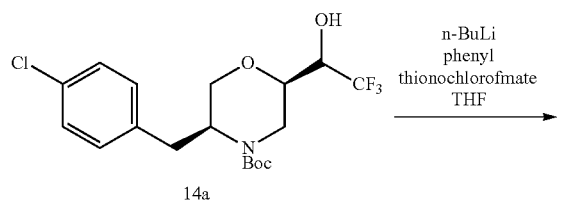

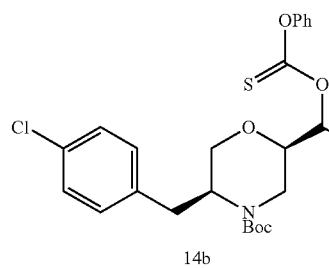

To a solution of 14a (0.2 g; 0.49 mmol) in THF (4.5 mL) cooled to −70° C., n-BuLi (0.23 mL; 0.59 mmol) was added followed by phenyl thionochloroformate (0.17 mL; 1.22 mmol) and the mixture was stirred at −70° C. for 40 minutes and then at room temperature for 1 hour. The reaction progress was monitored by LC-MS. When analysis indicated completion of the reaction, 5% NaHCO$_3$ solution was added and the product was extracted with Et$_2$O. Organic solutions were dried over MgSO$_4$, filtered and concentrated in vacuo and the crude product was used in the next step without additional purification. Compound 14b was obtained as a mixture of two diastereoisomers in 99% yield (264 mg; 0.49 mmol).

ESI-MS m/z for C$_{20}$H$_{20}$ClF$_3$NO$_3$S found 445.9/447.9 (M+H)$^+$; $^1$H NMR (700 MHz, DMSO-d$_6$+D$_2$O, 348 K) δ 7.52-7.45 (m, 2H), 7.22-7.12 (m, 5H), 6.79-6.73 (m, 2H), 6.24-6.05 (m, 1H), 4.17-4.08 (m, 1H), 4.01-3.96 (m, 1H), 3.96-3.85 (m, 1H), 3.82-3.77 (m, 1H), 3.70-3.57 (m, 1H), 3.20-3.06 (m, 1H), 2.99-2.91 (m, 1H), 2.90-2.78 (m, 1H), 1.32-1.15 (m, 9H).

Step 3

Synthesis of (2S,5S)-tert-butyl 5-(4-chlorobenzyl)-2-(2,2,2-trifluoroethyl)morpholine-4-carboxylate (14c)

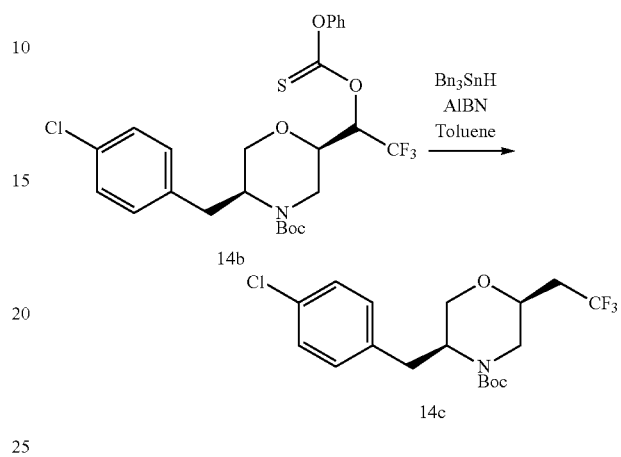

To a solution of 14b (380 mg; 0.7 mmol) in toluene (10 mL), Bn$_3$SnH (0.26 mL; 0.97 mmol) and AIBN (23 mg; 0.14 mmol) were subsequently added and the mixture was refluxed for 1.5 hour and then kept at 100° C. overnight. The reaction progress was monitored by TLC and LC-MS. When analyses indicated completion of the reaction, toluene was evaporated and crude product was then purified by column chromatography (hexane/AcOEt; 20:1 v/v). Compound 14c was obtained in 39% yield (106 mg; 0.27 mmol).

ESI-MS m/z for C$_{14}$H$_{16}$ClF$_3$NO$_3$ found 337.9/339.9 (M+H−tBu)$^+$; $^1$H NMR (700 MHz, DMSO-d$_6$+D$_2$O, 348 K) δ 7.31-7.25 (m, 2H), 7.22-7.13 (m, 2H), 4.11-3.98 (m, 1H), 3.86-3.75 (m, 1H), 3.71 (d, J=11.7 Hz, 1H), 3.64-3.58 (m, 1H), 3.56-3.51 (m, 1H), 3.05-2.90 (m, 2H), 2.86-2.77 (m, 1H), 2.55-2.52 (m, 1H), 2.50-2.46 (m, 1H), 1.30-1.11 (m, 9H); $^{19}$F NMR (235 MHz, DMSO-d$_6$) δ−65.53 (s).

Step 4

Synthesis of (2S,5S)-5-(4-chlorobenzyl)-2-(2,2,2-trifluoroethyl)morpholine hydrochloride (14d)

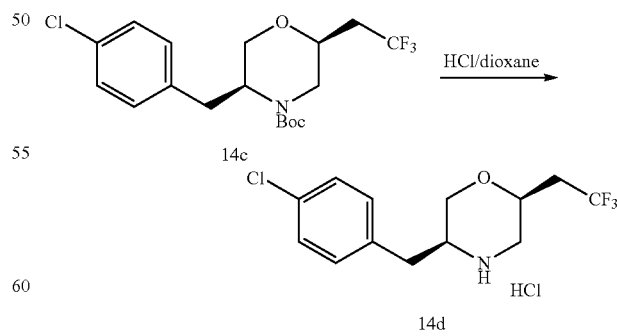

The title compound (14d) was obtained as a hydrochloride salt from 14c (106 mg; 0.27 mmol) according to the General Procedure IVa in 99% yield (89 mg; 0.27 mmol).

ESI-MS C$_{13}$H$_{16}$ClF$_3$NO found 293.9/295.9 (M+H)$^+$.

Step 5

Synthesis of 5-(4-((2S,5S)-5-(4-chlorobenzyl)-2-(2,2,2-trifluoroethyl)morpholino)piperidin-1-yl)-4H-1,2,4-triazol-3-amine 2,2,2-trifluoroacetate (14)

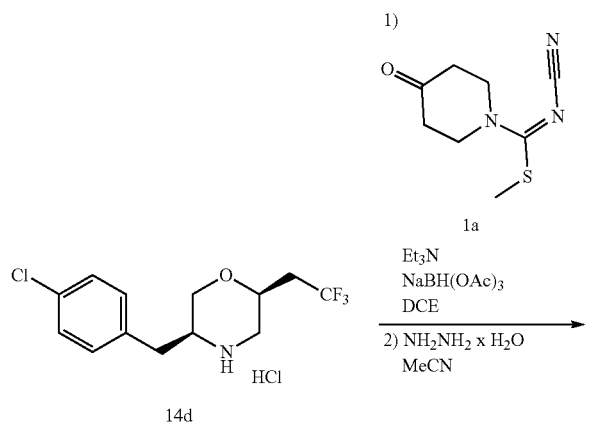

The title compound (14) was obtained as a TFA salt from 14d (89 mg; 0.27 mmol) according to the General Procedure Vb in 26% yield (40 mg; 0.07 mmol).

ESI-MS m/z for $C_{20}H_{27}ClF_3N_6O$ found 459.0/461.0 (M+H)$^+$; $^1$H NMR (700 MHz, DMSO-d$_6$+D$_2$O, 348 K) δ 7.43-7.37 (m, 2H), 7.34-7.27 (m, 2H), 4.08-3.99 (m, 1H), 3.90-3.82 (m, 2H), 3.72-3.59 (m, 3H), 3.57-3.50 (m, 1H), 3.41-3.37 (m, 1H), 3.17-3.05 (m, 3H), 2.96-2.87 (m, 2H), 2.69-2.56 (m, 2H), 2.17-2.08 (m, 2H), 1.66-1.57 (m, 2H); $^{19}$F NMR (235 MHz, DMSO-d$_6$) δ −61.72 (s), −73.92 (s).

Example 15

Synthesis of 5-(4-((2S,5S)-5-(4-chlorobenzyl)-2-(morpholinomethyl)morpholino)piperidin-1-yl)-4H-1,2,4-triazol-3-amine 2,2,2-trifluoroacetate (15)

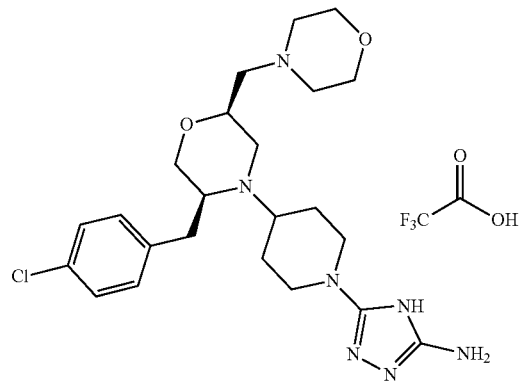

The title compound 15 was obtained as a TFA salt in 27% overall yield in a similar way to Example 8 with the exception that, in the first step of the synthesis, morpholine was used instead of 4-cyanopyrazole.

ESI-MS m/z for $C_{23}H_{35}ClN_7O_2$ found 476.2/478.2 (M+1)$^+$; $^1$H NMR (700 MHz, DMSO-d$_6$+D$_2$O, 348 K) δ 7.40-7.34 (m, 2H), 7.32-7.26 (m, 2H), 4.24-4.16 (m, 1H), 3.91-3.80 (m, 6H), 3.78-3.70 (m, 1H), 3.65-3.60 (m, 2H), 3.50-3.44 (m, 1H), 3.41-3.37 (m, 1H), 3.36-3.26 (m, 6H), 3.15-3.08 (m, 1H), 3.07-2.93 (m, 4H), 2.16-2.08 (m, 2H), 1.67-1.57 (m, 2H).

Examples 16 and 17

Synthesis of (S)-1-((2R,5S)-4-(1-(5-amino-4H-1,2,4-triazol-3-yl)piperidin-4-yl)-5-(4-chloro-benzyl)morpholin-2-yl)-2,2,2-trifluoroethanol 2,2,2-trifluoroacetate (16) and (R)-1-((2R,5S)-4-(1-(5-amino-4H-1,2,4-triazol-3-yl)piperidin-4-yl)-5-(4-chlorobenzyl)morpholin-2-yl)-2,2,2-trifluoroethanol 2,2,2-trifluoroacetate (17)

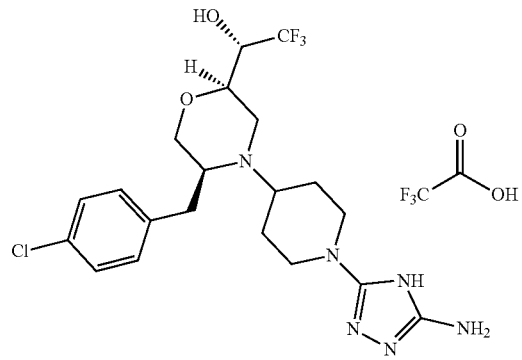

Step 1

Synthesis of 1-((5S)-5-(4-chlorobenzyl)morpholin-2-yl)-2,2,2-trifluoroethanol 2,2,2-trifluoroacetate (16a)

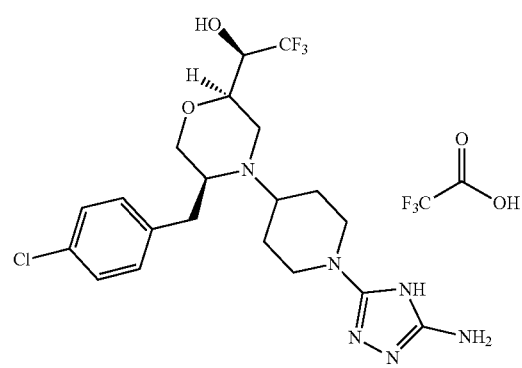

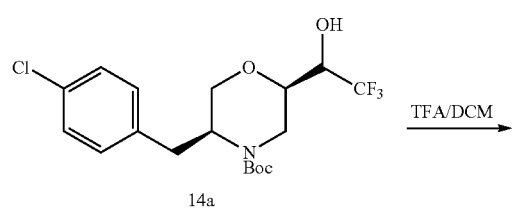

The title compound (16a) was obtained as a TFA salt from 14a (151 mg; 0.36 mmol) according to the General Procedure IVb in 99% yield (152 mg; 0.36 mmol).

ESI-MS $C_{13}H_{16}ClF_3NO_2$ found 309.9/311.9 (M+H)$^+$.

Step 2

Synthesis of (S)-1-((2R,5S)-4-(1-(5-amino-4H-1,2,4-triazol-3-yl)piperidin-4-yl)-5-(4-chloro-benzyl)morpholin-2-yl)-2,2,2-trifluoroethanol 2,2,2-trifluoroacetate (16) and (R)-1-((2R,5S)-4-(1-(5-amino-4H-1,2,4-triazol-3-yl)piperidin-4-yl)-5-(4-chlorobenzyl)morpholin-2-yl)-2,2,2-trifluoroethanol 2,2,2-trifluoroacetate (17)

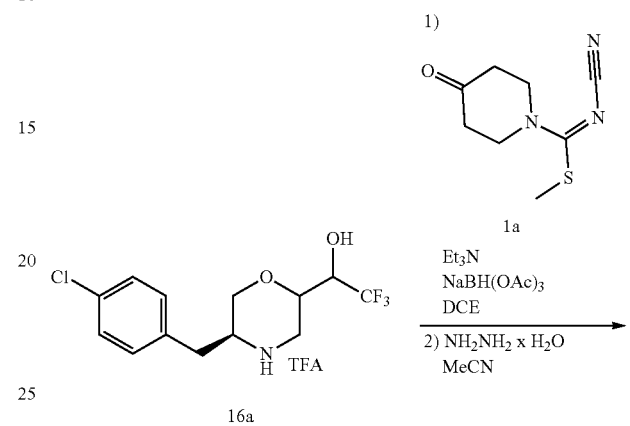

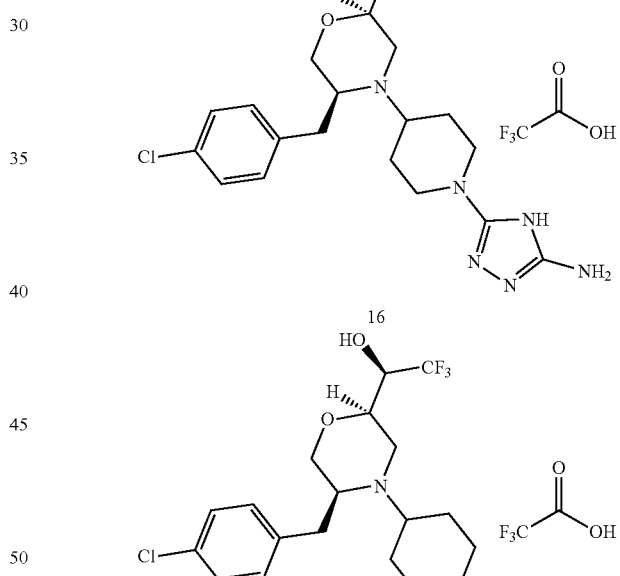

The title compounds (16 and 17) were obtained as a two diastereoisomers as a TFA salts from 16a (152 mg; 0.36 mmol) according to the General Procedure Vb. Compound 16 was obtained in 31% yield (64 mg; 0.11 mmol) and compound 17 was obtained in 22% yield (46 mg; 0.078 mmol).

For compound 16: ESI-MS m/z for $C_{20}H_{27}CF_3N_6O_2$ found 475.1/477.1 (M+H)$^+$; $^1$H NMR (700 MHz, DMSO-$d_6$+$D_2O$, 348 K) δ 7.45-7.35 (m, 2H), 7.35-7.30 (m, 2H), 4.20-4.11 (m, 1H), 4.07-3.97 (m, 1H), 3.92-3.83 (m, 2H), 3.73-3.59 (m, 4H), 3.45-3.41 (m, 1H), 3.29-3.22 (m, 1H), 3.19-3.04 (m, 2H), 3.00-2.87 (m, 2H), 2.20-2.09 (m, 2H), 1.69-1.54 (m, 2H); $^{19}$F NMR (235 MHz, DMSO-d$_6$) δ−69.99 (d, J=5.8 Hz), −70.32 (s).

For compound 17: ESI-MS m/z for C$_{20}$H$_{27}$ClF$_3$N$_6$O$_2$ found 475.1/477.1 (M+H)$^+$; $^1$H NMR (700 MHz, DMSO-d$_6$+D$_2$O, 348 K) δ 7.43-7.35 (m, 2H), 7.35-7.28 (m, 2H), 4.25-4.15 (m, 1H), 4.01-3.94 (m, 1H), 3.88-3.84 (m, 2H), 3.73-3.56 (m, 4H), 3.36-3.30 (m, 1H), 3.30-3.24 (m, 1H), 3.16-3.05 (m, 2H), 2.98-2.85 (m, 2H), 2.17-2.06 (m, 2H), 1.71-1.56 (m, 2H); $^{19}$F NMR (235 MHz, DMSO-d$_6$) δ−70.36 (s), −70.90 (s).

Examples 18

Synthesis of 5-(4-((2R,5S)-2-((S)-1-(1H-pyrazol-1-yl)ethyl)-5-(4-chlorobenzyl)morpholino)-piperidin-1-yl)-4H-1,2,4-triazol-3-amine 2,2,2-trifluoroacetate (18)

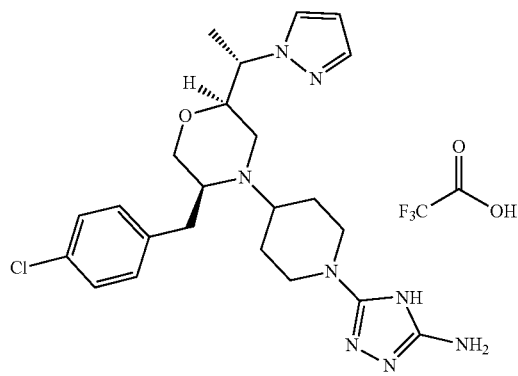

Step 1

Synthesis of (2R,5S)-tert-butyl 2-acetyl-5-(4-chlorobenzyl)morpholine-4-carboxylate (18a)

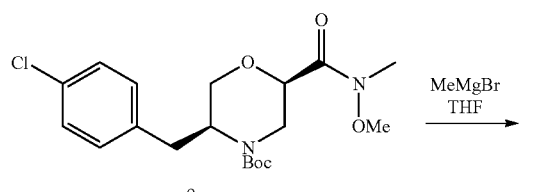

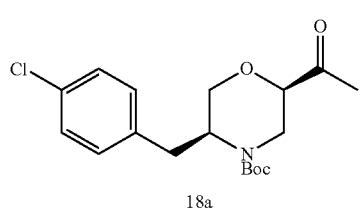

The title compound (18a) was obtained from 9a (0.8 g; 2 mmol) according to the General Procedure VI in 99% yield (0.7 g; 1.98 mmol).

ESI-MS C$_{13}$H$_{17}$ClNO$_2$ found 253.9/255.9 (M+H-Boc)$^+$; $^1$H NMR (700 MHz, DMSO-d$_6$+D$_2$O, 348 K) δ 7.31-7.24 (m, 2H), 7.23-7.17 (m, 2H), 4.11-4.06 (m, 1H), 3.97-3.89 (m, 1H), 3.87 (dd, J=11.2, 3.4 Hz, 1H), 3.82-3.78 (m, 1H), 3.59 (dd, J=11.6, 3.3 Hz, 1H), 3.00-2.90 (m, 2H), 2.87-2.75 (m, 1H), 2.20 (s, 3H), 1.21 (s, 9H).

Step 2

Synthesis of (2R,5S)-tert-butyl 5-(4-chlorobenzyl)-2-((R)-1-hydroxyethyl)morpholine-4-carboxylate (18b)

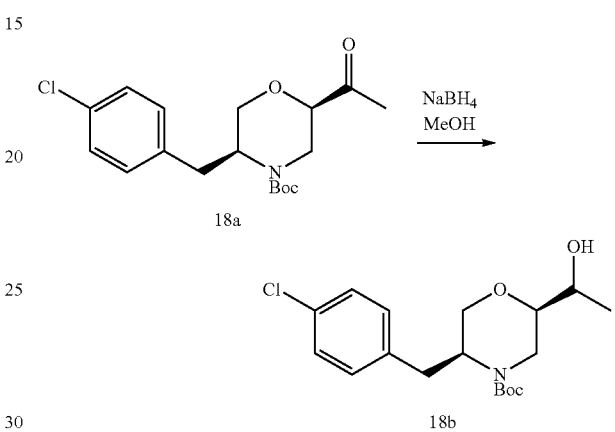

To a cooled to 0° C. solution of 18a (0.3 g; 0.85 mmol) in MeOH (4 mL), NaBH$_4$ (64 mg; 1.7 mmol) was slowly added and the mixture was allowed to warm up to room temperature and then stirred for 3 hours. The reaction progress was monitored by LC-MS. When analysis indicated completion of the reaction, MeOH was evaporated and residue was diluted with water and extracted with DCM (3×20 mL). Organic solutions were dried over MgSO$_4$, filtered and concentrated in vacuo and the crude product was used in the next step without additional purification. Compound 18b was obtained as a mixture of two diastereoisomers in 99% yield (298 mg; 0.84 mmol).

ESI-MS C$_{13}$H$_{19}$ClNO$_2$ found 256.0/258.0 (M+H-Boc)$^+$; $^1$H NMR (700 MHz, DMSO-d$_6$+D$_2$O, 348 K) δ 7.29-7.22 (m, 2H), 7.24-7.14 (m, 2H), 5.69-5.52 (m, 1H), 4.09-3.85 (m, 1H), 3.74-3.61 (m, 2H), 3.61-3.55 (m, 1H), 3.17-3.01 (m, 1H), 3.00-2.76 (m, 3H), 1.32-1.16 (m, 9H), 1.13-1.08 (m, 3H).

Step 3

Synthesis of (2R,5S)-tert-butyl 5-(4-chlorobenzyl)-2-((S)-1-((methylsulfonyl)oxy)ethyl)-morpholine-4-carboxylate (18c)

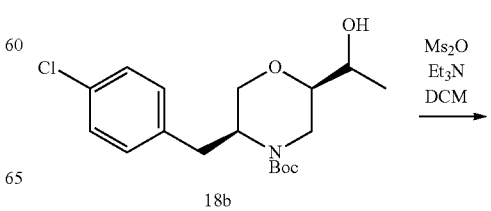

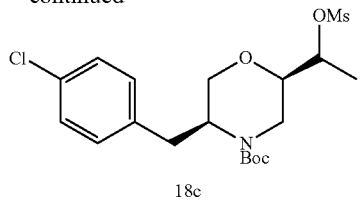

18c

The title compound (18c) was obtained as a mixture of two diastereoisomers from 18b (117 mg; 0.33 mmol) according to the General Procedure X in 97% yield (139 mg; 0.32 mmol).

ESI-MS $C_{15}H_{21}ClNO_6S$ found 377.9/379.9 (M+H−tBu)$^+$; $^1$H NMR (700 MHz, DMSO-d$_6$+D$_2$O, 348 K) δ 7.31-7.25 (m, 2H), 7.22-7.14 (m, 2H), 4.77-4.71 (m, 1H), 4.10-4.02 (m, 1H), 3.89-3.72 (m, 1H), 3.57-3.51 (m, 1H), 3.45-3.38 (m, 1H), 3.17-3.10 (m, 3H), 3.00-2.93 (m, 3H), 2.87-2.77 (m, 1H), 1.39-1.36 (m, 3H), 1.24-1.13 (m, 9H).

Step 4

Synthesis of (2R,5S)-tert-butyl 2-((S)-1-(1H-pyrazol-1-yl)ethyl)-5-(4-chlorobenzyl)morpholine-4-carboxylate (18d) and (2R,5S)-tert-butyl 2-((R)-1-(1H-pyrazol-1-yl)ethyl)-5-(4-chlorobenzyl)-morpholine-4-carboxylate (18d')

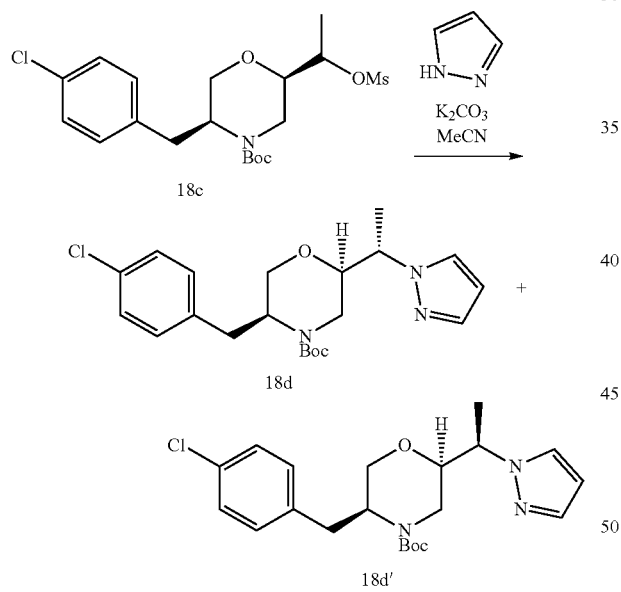

The title compounds (18d and 18d') were obtained as a two diastereoisomers from 18c (139 mg; 0.32 mmol) according to the General Procedure VIII. Compound 18d was obtained in 26% yield (34 mg; 0.084 mmol) and compound 18d' was obtained in 50% yield (66 mg; 0.16 mmol).

For compound 18d: ESI-MS $C_{21}H_{29}ClN_3O_3$ found 406.0/408.0 (M+H)$^+$; $^1$H NMR (700 MHz, DMSO-d$_6$+D$_2$O, 348 K) δ 7.72-7.70 (m, 1H), 7.48-7.45 (m, 1H), 7.29-7.24 (m, 2H), 7.17-7.12 (m, 2H), 6.29-6.23 (m, 1H), 4.47-4.37 (m, 1H), 4.17-4.11 (m, 1H), 4.08-3.97 (m, 1H), 3.78-3.71 (m, 1H), 3.62-3.55 (m, 1H), 3.54-3.50 (m, 1H), 3.32-3.15 (m, 1H), 2.91-2.84 (m, 1H), 2.84-2.72 (m, 1H), 1.50 (d, J=6.9 Hz, 3H), 1.16-1.11 (m, 9H).

For compound 18d': ESI-MS $C_{21}H_{29}ClN_3O_3$ found 406.0/408.0 (M+H)$^+$; $^1$H NMR (700 MHz, DMSO-d$_6$+D$_2$O, 348 K) δ 7.75-7.66 (m, 1H), 7.49-7.39 (m, 1H), 7.28-7.22 (m, 2H), 7.16-7.05 (m, 2H), 6.26-6.25 (m, 1H), 4.53-4.47 (m, 1H), 4.17-4.10 (m, 1H), 4.06-3.96 (m, 1H), 3.69-3.64 (m, 1H), 3.62-3.57 (m, 1H), 3.52 (s, 1H), 2.87-2.66 (m, 3H), 1.45 (d, J=7.1 Hz, 3H), 1.24-1.12 (m, 9H).

Step 5

Synthesis of (2R,5S)-2-((S)-1-(1H-pyrazol-1-yl)ethyl)-5-(4-chlorobenzyl)morpholine hydrochloride (18e)

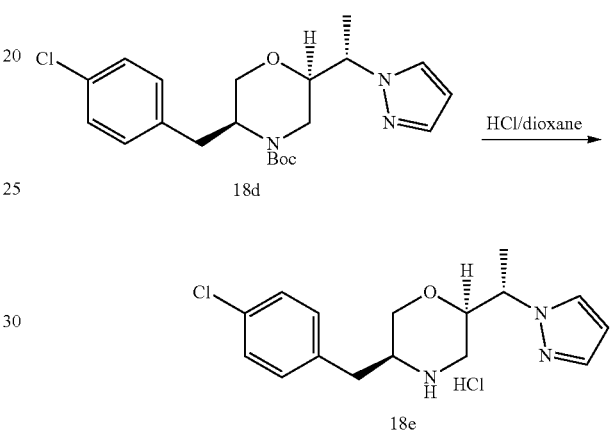

The title compound (18e) was obtained as a hydrochloride salt from 18d (34 mg; 0.084 mmol) according to the General Procedure IVa in 99% yield (28 mg; 0.083 mmol).

ESI-MS $C_{16}H_{21}ClN_3O$ found 306.0/308.0 (M+H)$^+$.

Step 6

Synthesis of 5-(4-((2R,5S)-2-((S)-1-(1H-pyrazol-1-yl)ethyl)-5-(4-chlorobenzyl)morpholino)-piperidin-1-yl)-4H-1,2,4-triazol-3-amine 2,2,2-trifluoroacetate (18)

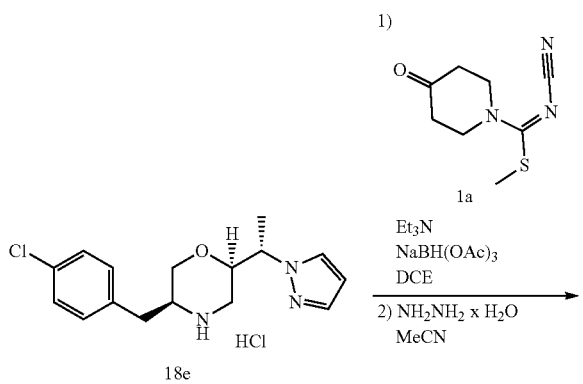

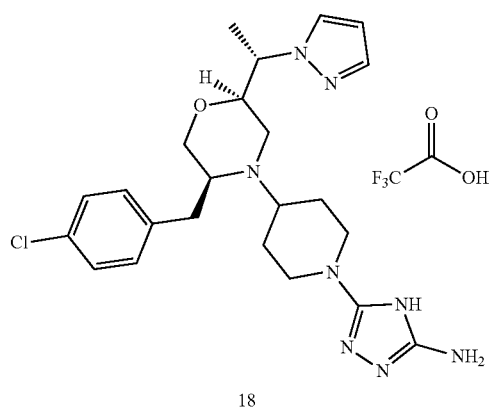

The title compound (18) was obtained as a TFA salt from 18e (28 mg; 0.083 mmol) according to the General Procedure Vb in 46% yield (22 mg; 0.038 mmol).

ESI-MS m/z for $C_{23}H_{32}ClN_8O$ found 471.2/473.2 (M+H); $^1$H NMR (700 MHz, DMSO-$d_6$+$D_2O$, 348 K) δ 7.77-7.68 (m, 1H), 7.58-7.49 (m, 1H), 7.38-7.34 (m, 2H), 7.31-7.21 (m, 2H), 6.33-6.28 (m, 1H), 4.62-4.53 (m, 1H), 4.02-3.95 (m, 1H), 3.87-3.79 (m, 2H), 3.72-3.64 (m, 2H), 3.62-3.58 (m, 1H), 3.58-3.52 (m, 1H), 3.16-3.10 (m, 1H), 3.05-2.96 (m, 2H), 2.94-2.84 (m, 3H), 2.10-1.98 (m, 2H), 1.61-1.50 (m, 5H).

Example 19

Synthesis of 5-(4-((2R,5S)-2-((R)-1-(1H-pyrazol-1-yl)ethyl)-5-(4-chlorobenzyl)morpholino)-piperidin-1-yl)-4H-1,2,4-triazol-3-amine 2,2,2-trifluoroacetate (19)

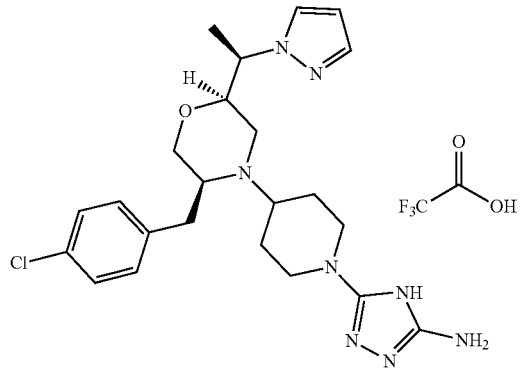

Step 1

Synthesis of (2R,5S)-2-((R)-1-(1H-pyrazol-1-yl)ethyl)-5-(4-chlorobenzyl)morpholine hydrochloride (19a)

The title compound (19a) was obtained as a hydrochloride salt from 18d' (66 mg; 0.16 mmol) according to the General Procedure IVa in 99% yield (55 mg; 0.16 mmol).

ESI-MS $C_{16}H_{21}ClN_3O$ found 306.0/308.0 (M+H)$^+$.

Step 2

Synthesis of 5-(4-((2R,5S)-2-((R)-1-(1H-pyrazol-1-yl)ethyl)-5-(4-chlorobenzyl)morpholino)-piperidin-1-yl)-4H-1,2,4-triazol-3-amine 2,2,2-trifluoroacetate (19)

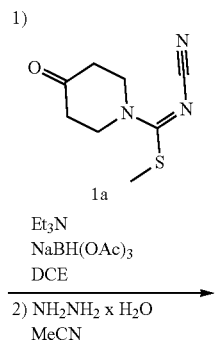

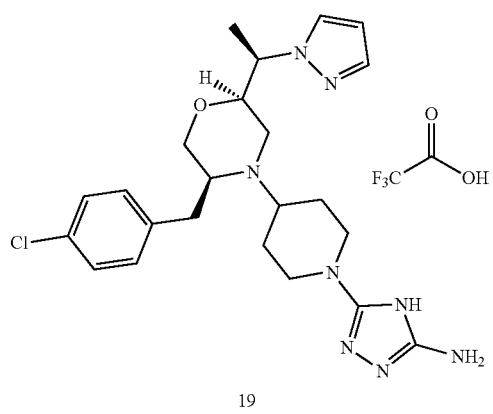

The title compound (19) was obtained as a TFA salt from 19a (55 mg; 0.16 mmol) according to the General Procedure Vb in 32% yield (30 mg; 0.051 mmol).

ESI-MS m/z for $C_{23}H_{32}ClN_8O$ found 471.1/473.1 (M+H)$^+$; $^1$H NMR (700 MHz, DMSO-d$_6$+D$_2$O, 348 K) δ 7.83-7.73 (m, 1H), 7.55-7.45 (m, 1H), 7.42-7.32 (m, 2H), 7.26-7.16 (m, 2H), 6.37-6.28 (m, 1H), 4.67-4.57 (m, 1H), 4.01-3.95 (m, 1H), 3.89-3.83 (m, 2H), 3.68-3.61 (m, 2H), 3.59-3.52 (m, 2H), 3.43-3.38 (m, 1H), 2.95-2.81 (m, 4H), 2.76-2.68 (m, 1H), 2.16-2.10 (m, 2H), 1.66-1.57 (m, 2H), 1.52 (d, J=7.1 Hz, 3H).

Example 20

Synthesis of 5-(4-((2R,5S)-5-(4-chlorobenzyl)-2-(1-fluoroethyl)morpholino)piperidin-1-yl)-4H-1,2,4-triazol-3-amine 2,2,2-trifluoroacetate (20)

Step 1

Synthesis of (2R,5S)-tert-butyl 5-(4-chlorobenzyl)-2-((R)-1-fluoroethyl)morpholine-4-carboxylate (20a)

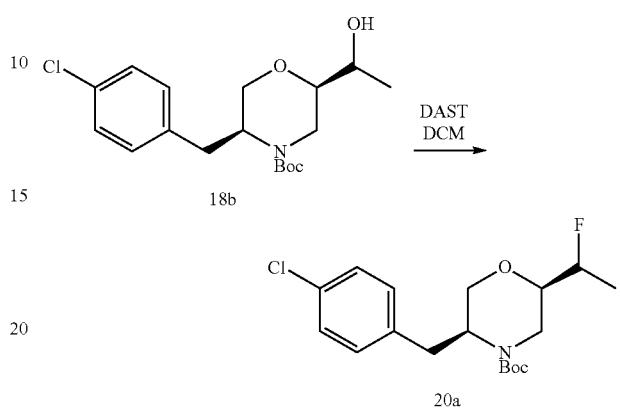

The title compound (20a) was obtained from 18b (76 mg; 0.21 mmol) according to the General Procedure VII in 71% yield (52 mg; 0.15 mmol).

ESI-MS $C_{14}H_{18}ClFNO_3$ found 301.9/303.9 (M+H−tBu); $^1$H NMR (700 MHz, DMSO-d$_6$+D$_2$O, 348 K) δ 7.34-7.22 (m, 2H), 7.22-7.13 (m, 2H), 4.76-4.59 (m, 1H), 4.11-3.96 (m, 1H), 3.80-3.66 (m, 2H), 3.59-3.50 (m, 1H), 3.39-3.31 (m, 1H), 3.07-2.89 (m, 2H), 2.87-2.77 (m, 1H), 1.35-1.26 (m, 3H), 1.27-1.12 (m, 9H).

Step 2

Synthesis of (2R,5S)-5-(4-chlorobenzyl)-2-((R)-1-fluoroethyl)morpholine hydrochloride (20b)

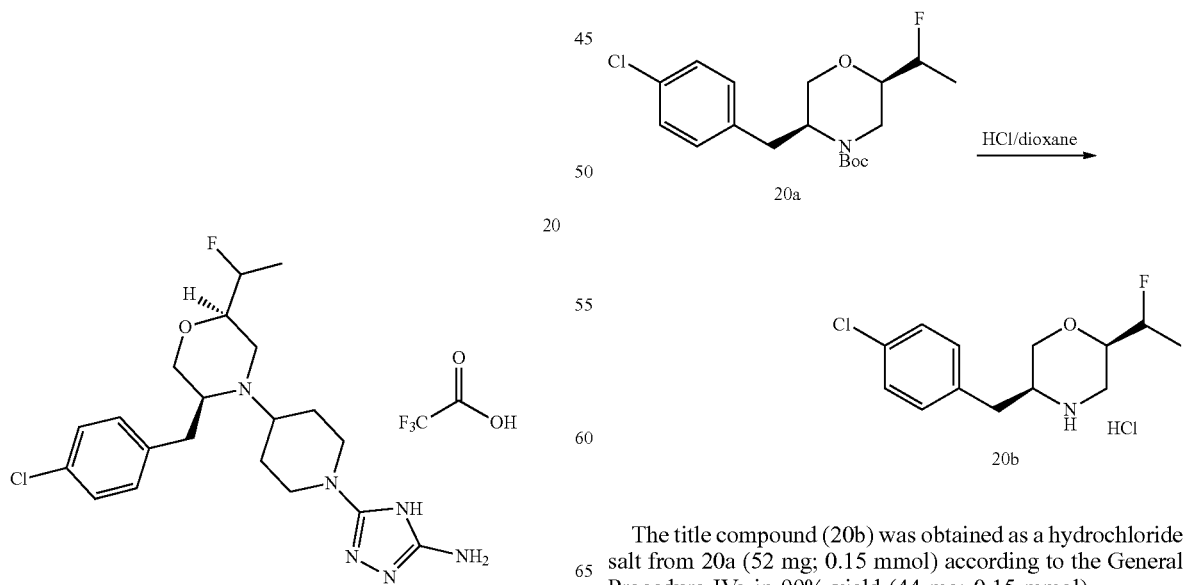

The title compound (20b) was obtained as a hydrochloride salt from 20a (52 mg; 0.15 mmol) according to the General Procedure IVa in 99% yield (44 mg; 0.15 mmol).

ESI-MS $C_{13}H_{18}ClFNO$ found 257.9/259.9 (M+H)$^+$.

Step 3

Synthesis of 5-(4-((2R,5S)-5-(4-chlorobenzyl)-2-(1-fluoroethyl)morpholino)piperidin-1-yl)-4H-1,2,4-triazol-3-amine 2,2,2-trifluoroacetate (20)

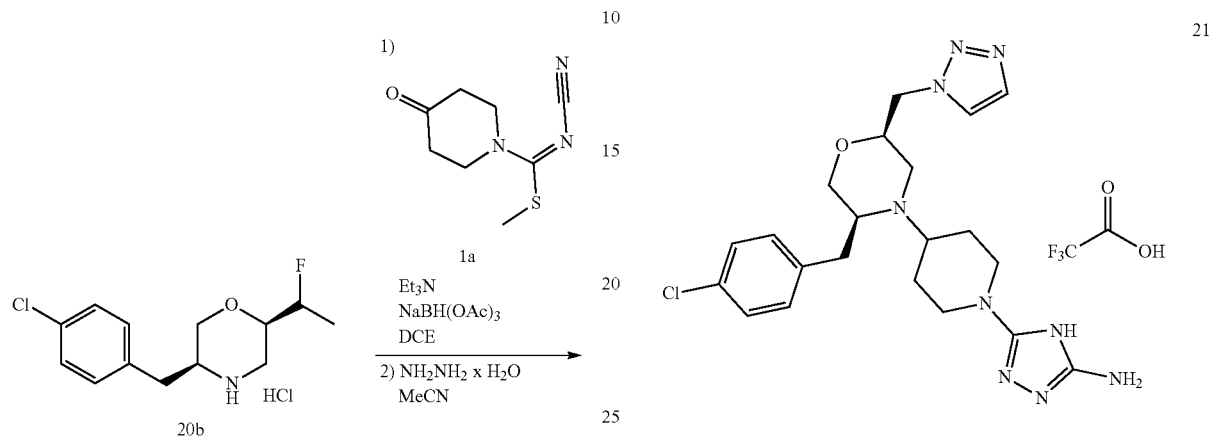

The title compound (20) was obtained as a TFA salt as a single isomer from 20b (44 mg; 0.15 mmol) according to the General Procedure Vb in 30% yield (24 mg; 0.045 mmol).

ESI-MS m/z for $C_{20}H_{29}ClFN_6O$ found 423.0/425.0 (M+H)$^+$; $^1$H NMR (700 MHz, DMSO-d$_6$+D$_2$O, 348 K) δ 7.42-7.33 (m, 2H), 7.33-7.21 (m, 2H), 4.85-4.71 (m, 1H), 3.90-3.84 (m, 2H), 3.81-3.74 (m, 1H), 3.71-3.66 (m, 3H), 3.64-3.57 (m, 1H), 3.43-3.40 (m, 1H), 3.27-3.16 (m, 1H), 3.12-3.04 (m, 2H), 2.93-2.82 (m, 2H), 2.24-2.09 (m, 2H), 1.68-1.57 (m, 2H), 1.42-1.31 (m, 3H); $^{19}$F NMR (235 MHz, DMSO-d$_6$) δ −73.97 (s).

Example 21

Synthesis of 5-(4-((2R,5S)-2-((1H-1,2,3-triazol-1-yl)methyl)-5-(4-chlorobenzyl)morpholino)-piperidin-1-yl)-4H-1,2,4-triazol-3-amine 2,2,2-trifluoroacetate (21)

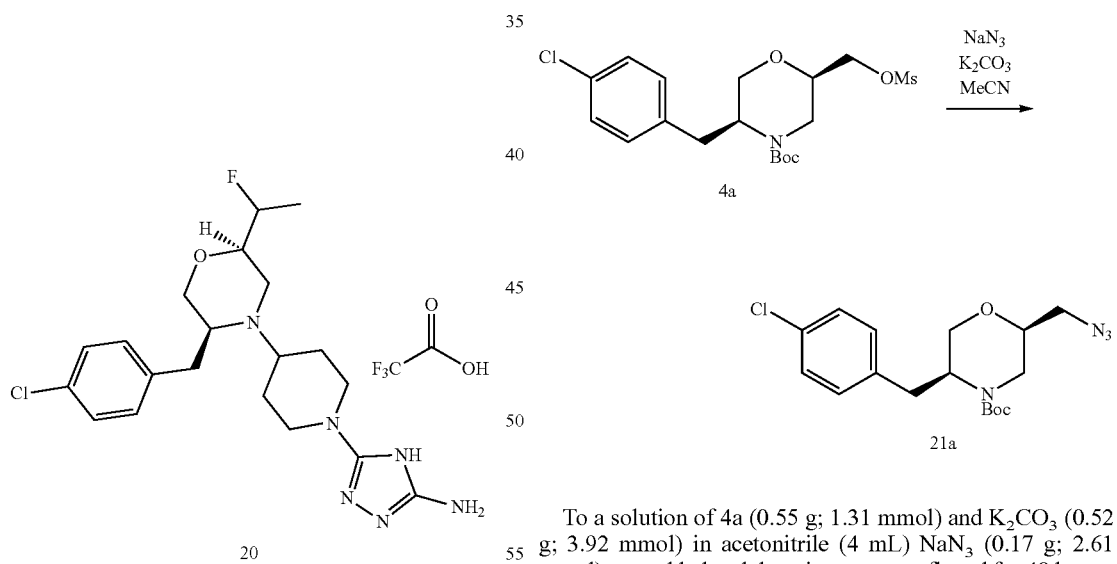

Step 1

Synthesis of (2R,5S)-tert-butyl 2-(azidomethyl)-5-(4-chlorobenzyl)morpholine-4-carboxylate (21a)

To a solution of 4a (0.55 g; 1.31 mmol) and K$_2$CO$_3$ (0.52 g; 3.92 mmol) in acetonitrile (4 mL) NaN$_3$ (0.17 g; 2.61 mmol) was added and the mixture was refluxed for 48 hours. Then another equivalent of NaN$_3$ (85 mg; 1.3 mmol) and two equivalents of K$_2$CO$_3$ (0.36 g; 2.6 mmol) were added and the resulting mixture was refluxed for 72 hours. The reaction progress was monitored by LC-MS. When analysis indicated completion of the reaction, the reaction mixture was taken into water and AcOEt. Organic layer was washed with brine and then dried over MgSO$_4$, filtered and concentrated in vacuo and the crude product was used to the next step without additional purification. Compound 21a was obtained in 65% yield (0.31 g; 0.85 mmol).

ESI-MS $C_{17}H_{24}ClN_4O_3$ found 367.2/369.2 (M+H)$^+$.

Step 2

Synthesis of (2R,5S)-2-(azidomethyl)-5-(4-chlorobenzyl)morpholine hydrochloride (21b)

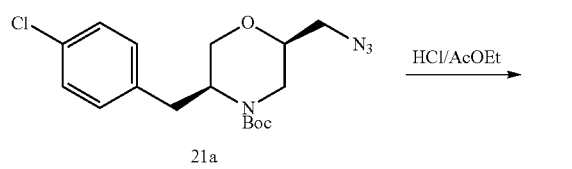

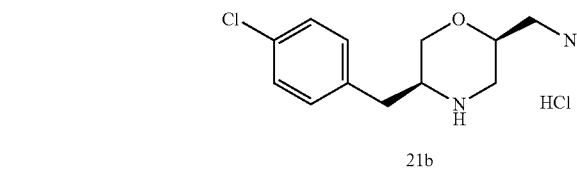

The title compound (21b) was obtained as a hydrochloride salt from 21a (130 mg; 0.28 mmol) according to the General Procedure IVa in 99% yield (85 mg; 0.28 mmol).

ESI-MS $C_{12}H_{16}ClN_4O$ found 267.1/269.1 (M+H)$^+$.

Step 3

Synthesis of (2R,5S)-5-(4-chlorobenzyl)-2-((4-(trimethylsilyl)-1H-1,2,3-triazol-1-yl)methyl)-morpholine (21c)

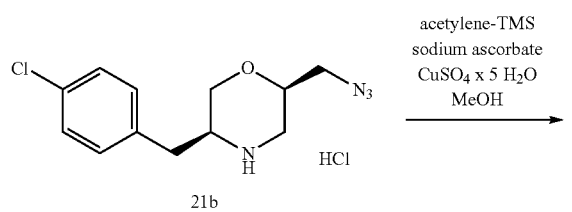

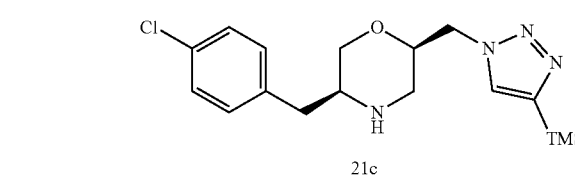

To a solution of 21b (85 mg; 0.28 mmol) in MeOH (4 mL) TMS-acetylene (78 μL; 0.56 mmol) was added followed by CuSO$_4$×5 H$_2$O (70 mg; 0.28 mmol) and sodium ascorbate (111 mg; 0.56 mmol) and the mixture was stirred at room temperature overnight. The reaction progress was monitored by LC-MS. When analysis indicated completion of the reaction, the reaction mixture was filtered through Celite and filtrate was evaporated in vacuo and the crude product was used to the next step without additional purification. Compound 21c was obtained in 75% yield (75 mg; 0.21 mmol).

ESI-MS $C_{17}H_{25}ClN_4OSi$ found 365.2/367.2 (M+H)$^+$.

Step 4

Synthesis of 5-(4-((2R,5S)-5-(4-chlorobenzyl)-2-((4-(trimethylsilyl)-1H-1,2,3-triazol-1-yl)-methyl)morpholino)piperidin-1-yl)-4H-1,2,4-triazol-3-amine 2,2,2-trifluoroacetate (21d)

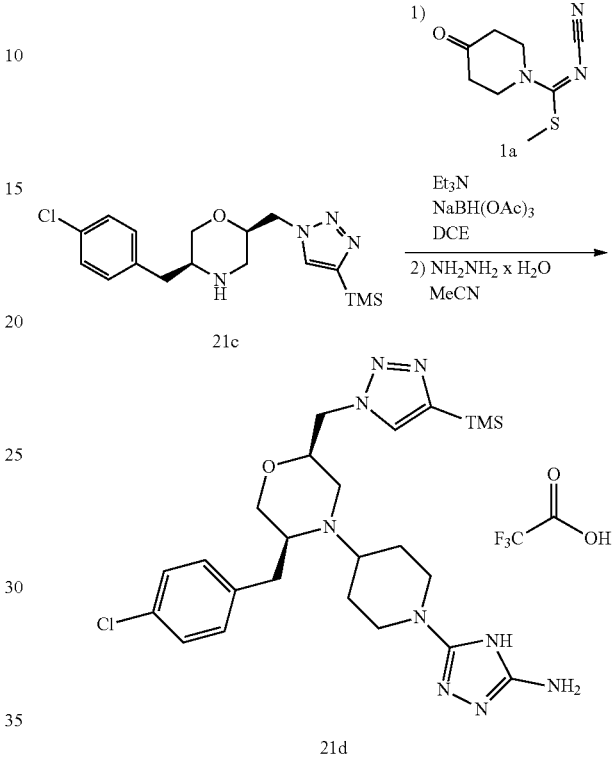

The title compound (21d) was obtained as a TFA salt from 21c (75 mg; 0.21 mmol) according to the General Procedure Vb in 16% yield (22 mg; 0.034 mmol).

ESI-MS m/z for $C_{24}H_{37}ClN_9OSi$ found 530.3/532.3 (M+H)$^+$.

Step 5

Synthesis of 5-(4-((2R,5S)-2-((1H-1,2,3-triazol-1-yl)methyl)-5-(4-chlorobenzyl)morpholino)-piperidin-1-yl)-4H-1,2,4-triazol-3-amine 2,2,2-trifluoroacetate (21)

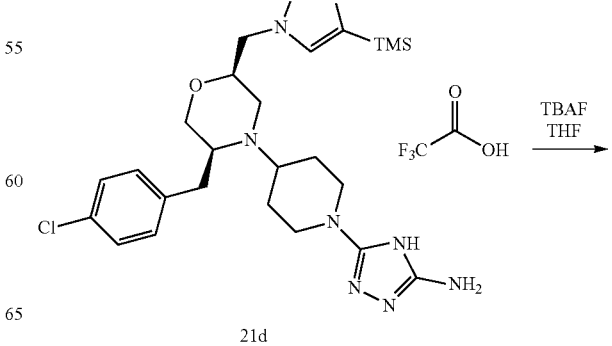

165
-continued

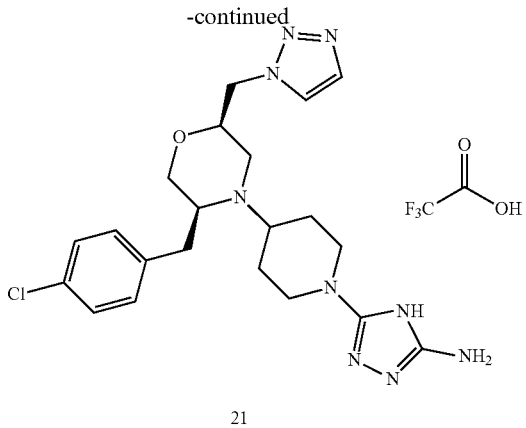

21

To a solution of 21d (18 mg; 0.03 mmol) in THF (2 mL) TBAF (1 M in THF; 30 μL; 0.03 mmol) was added and the mixture was stirred at room temperature overnight. The reaction progress was monitored by LC-MS. When analysis indicated completion of the reaction, the reaction mixture was concentrated in vacuo and the crude product was purified by preparative reversed-phase column chromatography (phenyl/hexyl, water/MeCN+1% TFA, 99:1 to 40:60, 30 min). Compound 21 was obtained as a TFA salt in 20% yield (3.5 mg; 0.006 mmol).

ESI-MS $C_{21}H_{29}ClN_9O$ found 458.2/460.2 $(M+H)^+$; $^1H$ NMR (700 MHz, Methanol-$d_4$) δ 8.32-8.24 (m, 1H), 8.08-7.98 (m, 1H), 7.46-7.37 (m, 2H), 7.34-7.26 (m, 2H), 4.95-4.89 (m, 2H), 4.51-4.42 (m, 1H), 4.07-4.01 (m, 2H), 4.00-3.87 (m, 3H), 3.86-3.72 (m, 2H), 3.28-3.22 (m, 1H), 3.19-3.08 (m, 3H), 3.08-2.98 (m, 1H), 2.43-2.35 (m, 2H), 2.10-1.98 (m, 2H).

Example 22

Synthesis of 5-(4-((2R,5S)-5-(4-chlorobenzyl)-2-(3-methylisoxazol-5-yl)morpholino)piperidin-1-yl)-4H-1,2,4-triazol-3-amine 2,2,2-trifluoroacetate (22)

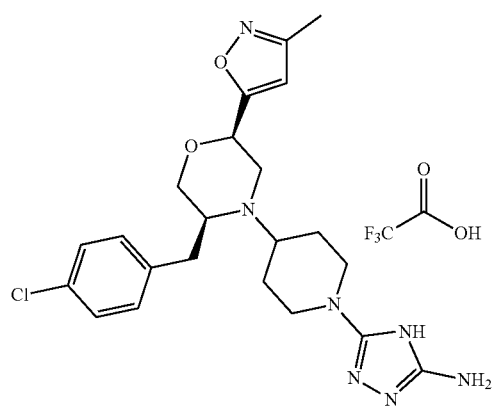

22

Step 1

Synthesis of (2R,5S)-tert-butyl 5-(4-chlorobenzyl)-2-(3-methylisoxazol-5-yl)morpholine-4-carboxylate (22a)

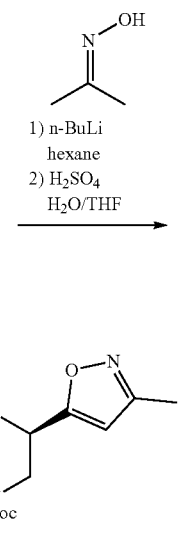

To a cooled to 0° C. solution of an oxime (55 mg; 074 mmol) in THF (1.5 mL) a solution of n-butyllithium (2.5 M in hexanes; 0.6 mL; 1.49 mmol) was added dropwise and the mixture was stirred for 30 minutes. Then the solution of 9a (246 mg; 0.62 mmol) in THF (3 mL) was added dropwise over 15 minutes. After 30 minutes to this mixture a solution of $H_2SO_4$ (0.13 mL) in THF/water (1.5 mL/0.4 mL) was added and the resulting mixture was refluxed for 1 hour. The reaction progress was monitored by LC-MS. When analysis indicated completion of the reaction, the reaction mixture was cooled to 0° C. and the reaction was neutralized with 5% $NaHCO_3$. Then water was added and the mixture was extracted with $Et_2O$. Organic layer was then dried over $MgSO_4$, filtered and concentrated in vacuo and the crude product was used in the next step without additional purification. Compound 22a was obtained in 97% yield (235 mg; 0.6 mmol).

ESI-MS $C_{20}H_{26}ClN_2O_4$ found 393.2/395.2 $(M+H)^+$.

Step 2

Synthesis of (2R,5S)-5-(4-chlorobenzyl)-2-(3-methylisoxazol-5-yl)morpholine hydrochloride (22b)

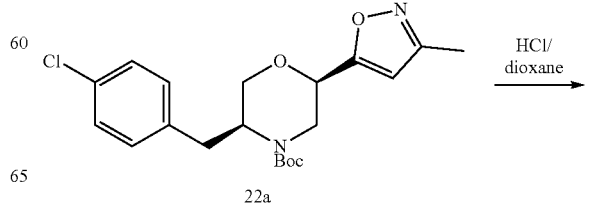

22a

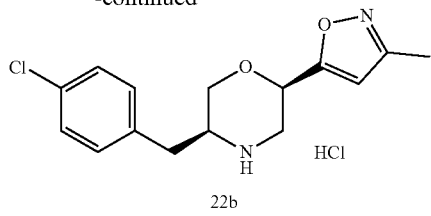

The title compound (22b) was obtained as a hydrochloride salt from 22a (235 mg; 0.6 mmol) according to the General Procedure IVa in 99% yield (194 mg; 0.59 mmol).

ESI-MS $C_{12}H_{16}ClN_4O$ found 293.1/295.1 $(M+H)^+$.

Step 3

Synthesis of 5-(4-((2R,5S)-5-(4-chlorobenzyl)-2-(3-methylisoxazol-5-yl)morpholino)piperidin-1-yl)-4H-1,2,4-triazol-3-amine 2,2,2-trifluoroacetate (22)

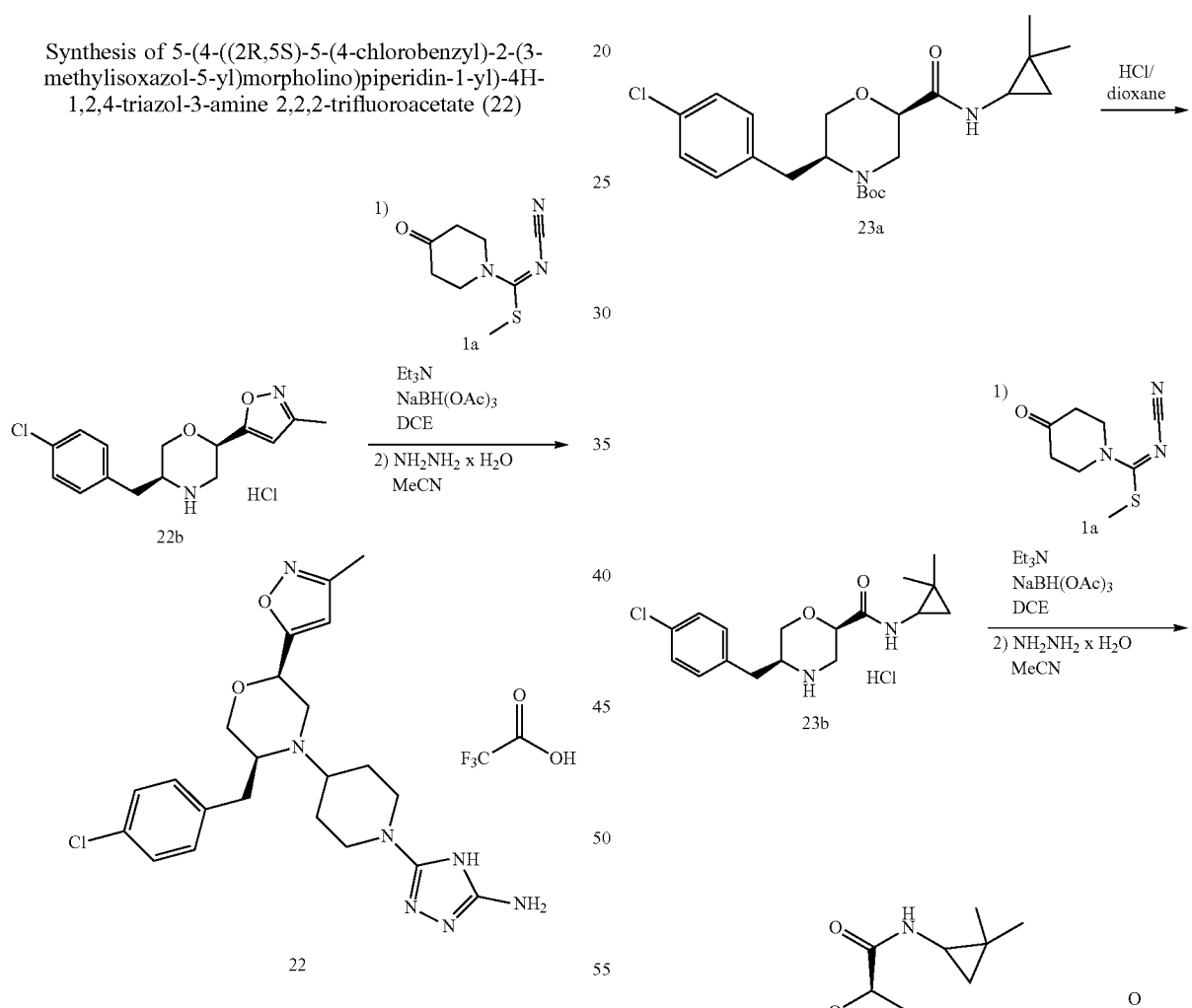

The title compound (22) was obtained as a TFA salt from 22b (194 mg; 0.59 mmol) according to the General Procedure Vb in 27% yield (90 mg; 0.16 mmol).

ESI-MS m/z for $C_{22}H_{29}ClN_7O_2$ found 458.3/460.3 $(M+H)^+$; $^1H$ NMR (700 MHz, DMSO-$d_6$+$D_2O$, 348 K) δ 7.41-7.34 (m, 2H), 7.31-7.23 (m, 2H), 6.46 (s, 1H), 4.94-4.87 (m, 1H), 3.83-3.77 (m, 2H), 3.77-3.72 (m, 1H), 3.66-3.63 (m, 1H), 3.51-3.46 (m, 1H), 3.38-3.32 (m, 2H), 3.30-3.22 (m, 1H), 3.10-3.02 (m, 2H), 3.00-2.92 (m, 2H), 2.25 (s, 3H), 2.10-2.02 (m, 2H), 1.63-1.53 (m, 2H).

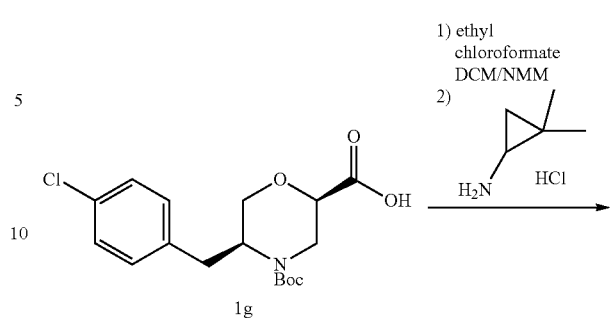

Synthesis of Example 23

Example 23

Synthesis of (2R,5S)-4-(1-(5-amino-4H-1,2,4-tri-azol-3-yl)piperidin-4-yl)-5-(4-chlorobenzyl)-N-(2,2-dimethylcyclopropyl)morpholine-2-carboxamide 2,2,2-trifluoroacetate (23)

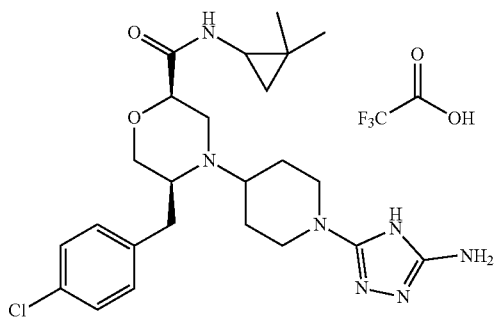

Step 1

Synthesis of (2R,5S)-tert-butyl 5-(4-chlorobenzyl)-2-((2,2-dimethylcyclopropyl)carbamoyl)-morpholine-4-carboxylate (23a)

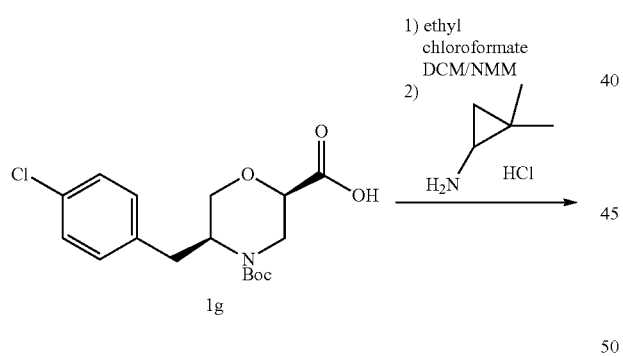

The title compound (22b) was obtained from 1g (200 mg; 0.56 mmol) according to the General Procedure XII in 89% yield (210 mg; 0.5 mmol).

ESI-MS $C_{22}H_{32}ClN_2O_4$ found 423.2/425.2 (M+H)$^+$.

Step 2

Synthesis of (2R,5S)-5-(4-chlorobenzyl)-N-(2,2-dimethylcyclopropyl)morpholine-2-carboxamide hydrochloride (23b)

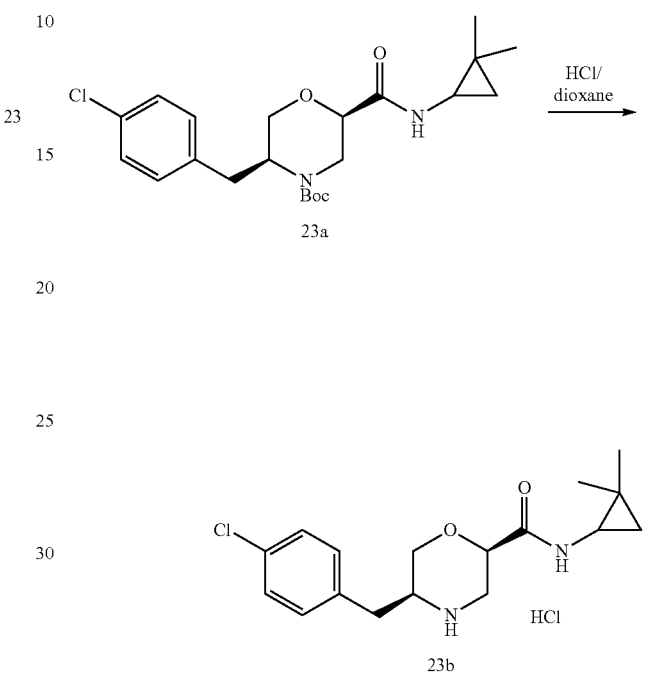

The title compound (23b) was obtained as a hydrochloride salt from 23a (210 mg; 0.5 mmol) according to the General Procedure IVa in 78% yield (140 mg; 0.39 mmol).

ESI-MS $C_{17}H_{24}ClN_2O_2$ found 323.1/325.1 (M+H)$^+$.

Step 3

Synthesis of (2R,5S)-4-(1-(5-amino-4H-1,2,4-tri-azol-3-yl)piperidin-4-yl)-5-(4-chlorobenzyl)-N-(2,2-dimethylcyclopropyl)morpholine-2-carboxamide 2,2,2-trifluoroacetate (23)

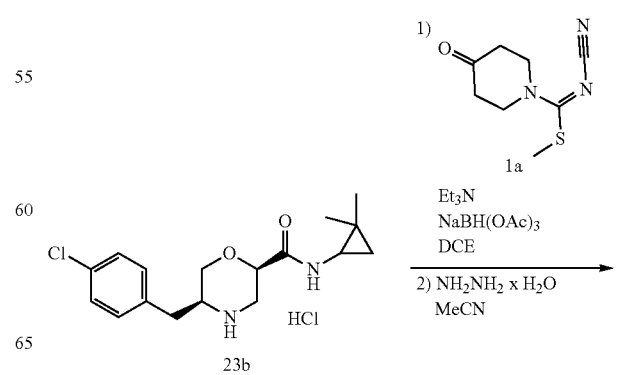

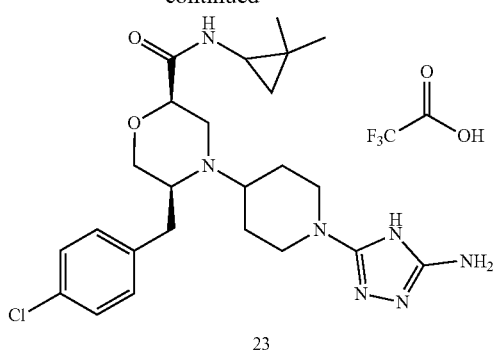

The title compound (23) was obtained as a TFA salt from 23b (140 mg; 0.39 mmol) according to the General Procedure Vb in 46% yield (111 mg; 0.18 mmol).

ESI-MS m/z for $C_{24}H_{35}ClN_7O_2$ found 488.0/490.0 $(M+H)^+$; $^1H$ NMR (700 MHz, DMSO-$d_6$+$D_2O$, 348 K) δ 7.39-7.35 (m, 2H), 7.33-7.30 (m, 2H), 4.28-4.19 (m, 1H), 3.89-3.79 (m, 2H), 3.71-3.66 (m, 2H), 3.64-3.58 (m, 1H), 3.55-3.49 (m, 1H), 3.42-3.38 (m, 1H), 3.27-3.11 (m, 1H), 3.11-3.03 (m, 2H), 2.98-2.89 (m, 2H), 2.44-2.37 (m, 1H), 2.15-2.03 (m, 2H), 1.69-1.58 (m, 2H), 1.06-1.02 (m, 3H), 1.02-0.96 (m, 3H), 0.70-0.64 (m, 1H), 0.53-0.47 (m, 1H).

Example 24

Synthesis of (2R,5S)-4-(1-(5-amino-4H-1,2,4-triazol-3-yl)piperidin-4-yl)-5-(4-chlorobenzyl)-N-cyclopropylmorpholine-2-carboxamide 2,2,2-trifluoroacetate (24)

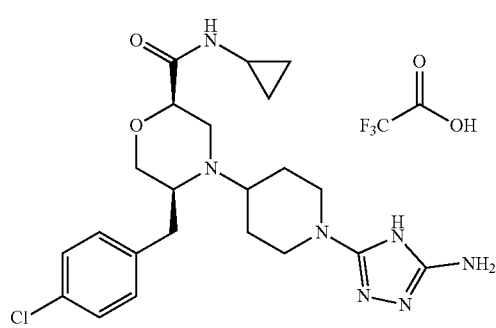

The title compound 24 was obtained as a TFA salt in 27% overall yield in a similar way to Example 23 with the exception that, in the first step of the synthesis, cyclopropylamine was used instead of 2,2-dimethylcyclopropane-1-amine hydrochloride.

ESI-MS m/z for $C_{22}H_{31}ClN_7O_2$ found 460.2/462.2 $(M+1)^+$; $^1H$ NMR (700 MHz, DMSO-$d_6$+$D_2O$, 348 K) δ 7.40-7.36 (m, 2H), 7.34-7.30 (m, 2H), 4.20-4.13 (m, 1H), 3.88-3.79 (m, 2H), 3.72-3.66 (m, 2H), 3.59 (s, 1H), 3.54-3.46 (m, 2H), 3.22-3.14 (m, 1H), 3.12-3.00 (m, 2H), 2.99-2.86 (m, 2H), 2.72-2.66 (m, 1H), 2.15-2.04 (m, 2H), 1.68-1.55 (m, 2H), 0.72-0.63 (m, 2H), 0.59-0.49 (m, 2H).

Example 25

Synthesis of (2R,5S)-4-(1-(5-amino-4H-1,2,4-triazol-3-yl)piperidin-4-yl)-5-(4-chlorobenzyl)-N-(2,2-difluoroethyl)morpholine-2-carboxamide 2,2,2-trifluoroacetate (25)

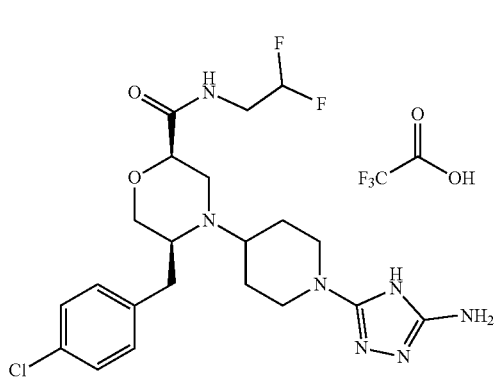

The title compound 25 was obtained as a TFA salt in 36% overall yield in a similar way to Example 23 with the exception that, in the first step of the synthesis, 2,2-difluoroethylamine was used instead of 2,2-dimethylcyclopropane-1-amine hydrochloride.

ESI-MS m/z for $C_{21}H_{29}ClF_2N_7O_2$ found 484.2/486.2 $(M+1)^+$; $^1H$ NMR (700 MHz, DMSO-$d_6$+$D_2O$, 348 K) δ 7.40-7.36 (m, 2H), 7.34-7.32 (m, 2H), 6.02 (tt, J=55.8, 3.9 Hz, 1H), 4.32-4.23 (m, 1H), 3.85-3.79 (m, 2H), 3.77-3.68 (m, 2H), 3.66-3.50 (m, 4H), 3.49-3.46 (m, 1H), 3.22-3.12 (m, 1H), 3.10-3.03 (m, 2H), 2.99-2.90 (m, 2H), 2.15-2.03 (m, 2H), 1.69-1.58 (m, 2H); $^{19}F$ NMR (235 MHz, DMSO-$d_6$) δ −70.40 (s), −118.12 (dt, J=55.9, 15.4 Hz).

Example 26

Synthesis of (2R,5S)-4-(1-(5-amino-4H-1,2,4-triazol-3-yl)piperidin-4-yl)-5-(4-chlorobenzyl)-N-(2,2,2-trifluoroethyl)morpholine-2-carboxamide 2,2,2-trifluoroacetate (26)

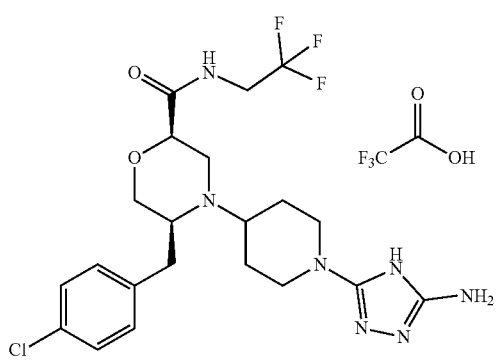

The title compound 26 was obtained as a TFA salt in 23% overall yield in a similar way to Example 23 with the exception that, in the first step of the synthesis, 2,2,2-trifluoroethylamine hydrochloride was used instead of 2,2-dimethylcyclopropane-1-amine hydrochloride.

ESI-MS m/z for $C_{21}H_{27}ClF_3N_7O_2$ found 502.1/504.1 (M+1)$^+$; $^1$H NMR (700 MHz, DMSO-$d_6$+$D_2O$, 348 K) δ 7.42-7.35 (m, 2H), 7.35-7.28 (m, 2H), 4.32-4.25 (m, 1H), 4.00-3.93 (m, 1H), 3.93-3.87 (m, 1H), 3.87-3.73 (m, 2H), 3.73-3.63 (m, 2H), 3.61-3.51 (m, 1H), 3.42-3.35 (m, 2H), 3.19-3.10 (m, 1H), 3.10-3.01 (m, 2H), 3.01-2.90 (m, 2H), 2.11-1.97 (m, 2H), 1.72-1.58 (m, 2H); $^{19}$F NMR (235 MHz, DMSO-$d_6$) δ −74.06 (s), −77.80 (s).

Example 27

Synthesis of 5-(4-((2R,5S)-2-((1H-1,2,4-triazol-1-yl)methyl)-5-(4-chlorobenzyl)morpholino)piperidin-1-yl)-4H-1,2,4-triazol-3-amine 2,2,2-trifluoroacetate (27)

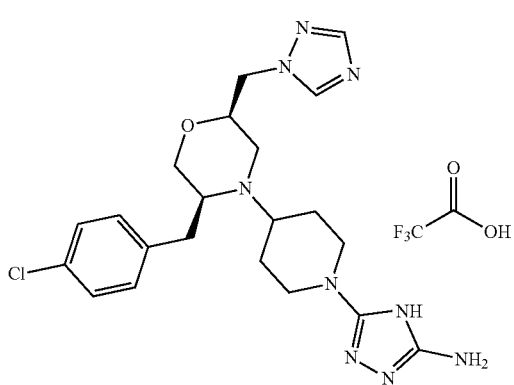

Step 1

Synthesis of tert-butyl 4-((2R,5S)-5-(4-chlorobenzyl)-2-(hydroxymethyl)morpholino)piperidine-1-carboxylate (27a)

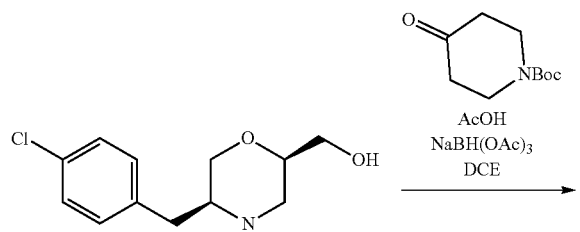

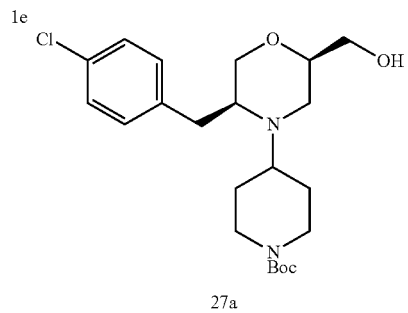

The title compound (27a) was obtained from 1e (1.91 g; 7.92 mmol) according to the General Procedure IX in 74% yield (2.49 g; 5.86 mmol).

ESI-MS $C_{22}H_{34}ClN_2O_4$ found 425.2/427.2 (M+H)$^+$; $^1$H NMR (700 MHz, CDCl$_3$) δ 7.30-7.27 (m, 2H), 7.18-7.06 (m, 2H), 4.13-4.00 (m, 2H), 3.74-3.64 (m, 4H), 3.56-3.48 (m, 1H), 3.06-2.93 (m, 2H), 2.93-2.83 (m, 2H), 2.78-2.70 (m, 2H), 2.70-2.64 (m, 1H), 2.58-2.51 (m, 1H), 2.04-1.98 (m, 1H), 1.98-1.87 (m, 2H), 1.50-1.39 (m, 11H).

Step 2

Synthesis of tert-butyl 4-((2R,5S)-5-(4-chlorobenzyl)-2-(((methylsulfonyl)oxy)methyl)morpholino)piperidine-1-carboxylate (27b)

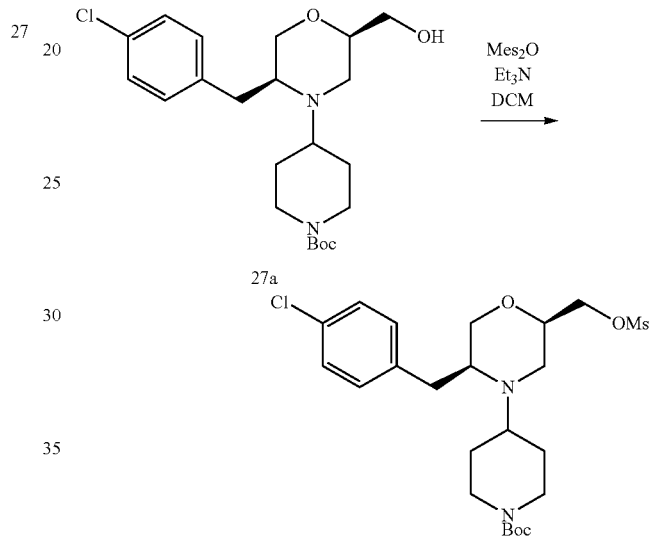

The title compound (27b) was obtained from 27a (1.27 g; 2.99 mmol) according to the General Procedure X in 99% yield (1.5 g; 2.96 mmol).
ESI-MS $C_{23}H_{36}ClN_2O_6S$ found 503.2/505.2 (M+H)$^+$.

Step 3

Synthesis of tert-butyl 4-((2R,5S)-2-((1H-1,2,4-triazol-1-yl)methyl)-5-(4-chlorobenzyl)-morpholino)piperidine-1-carboxylate (27c)

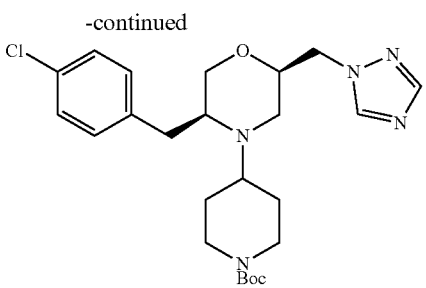

27c

The title compound (27c) was obtained from 27b (0.18 g; 0.36 mmol) according to the General Procedure VIII in 82% yield (143 mg; 0.3 mmol).

ESI-MS $C_{24}H_{35}ClN_5O_3$ found 476.2/478.2 (M+H)$^+$; H NMR (700 MHz, CDCl$_3$) δ 8.26 (s, 1H), 7.99 (s, 1H), 7.29-7.26 (m, 2H), 7.09-7.04 (m, 2H), 4.38-4.28 (m, 2H), 4.10-3.98 (m, 2H), 3.94-3.83 (m, 1H), 3.70-3.57 (m, 1H), 3.49-3.44 (m, 1H), 2.95-2.83 (m, 3H), 2.83-2.75 (m, 2H), 2.70-2.61 (m, 2H), 2.47-2.38 (m, 1H), 1.95-1.81 (m, 2H), 1.50-1.36 (m, 11H).

Step 4

Synthesis of (2R,5S)-2-((1H-1,2,4-triazol-1-yl)methyl)-5-(4-chlorobenzyl)-4-(piperidin-4-yl)-morpholine 2,2,2-trifluoroacetate (27d)

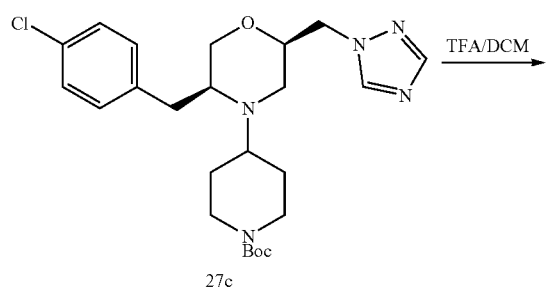

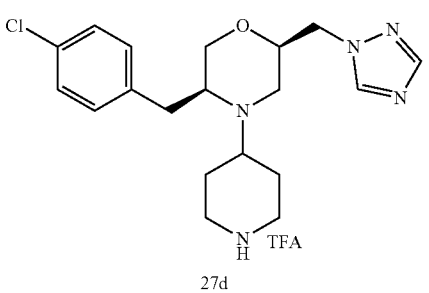

27d

The title compound (27d) was obtained as a TFA salt from 27c (143 mg; 0.3 mmol) according to the General Procedure IVb in 99% yield (145 mg; 0.3 mmol).

ESI-MS $C_{19}H_{27}ClN_5O$ found 376.2/378.2 (M+H)$^+$; $^1$H NMR (700 MHz, CDCl$_3$) δ 8.58 (s, 1H), 8.08 (s, 1H), 7.37-7.33 (m, 2H), 7.26-7.18 (m, 2H), 4.62-4.56 (m, 1H), 4.56-4.47 (m, 1H), 4.23-4.18 (m, 1H), 3.73-3.58 (m, 7H), 3.20-3.06 (m, 3H), 3.05-3.01 (m, 1H), 2.97-2.88 (m, 1H), 2.51-2.42 (m, 2H), 2.03-1.92 (m, 2H).

Step 5

Synthesis of 5-(4-((2R,5S)-2-((1H-1,2,4-triazol-1-yl)methyl)-5-(4-chlorobenzyl)morpholino)-piperidin-1-yl)-4H-1,2,4-triazol-3-amine 2,2,2-trifluoroacetate (27)

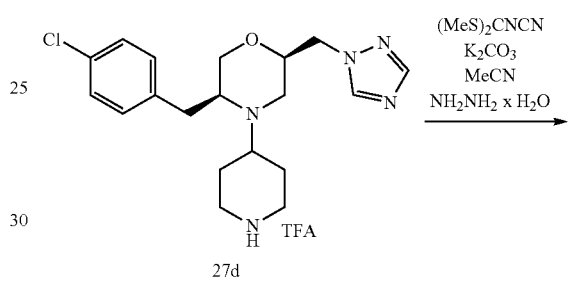

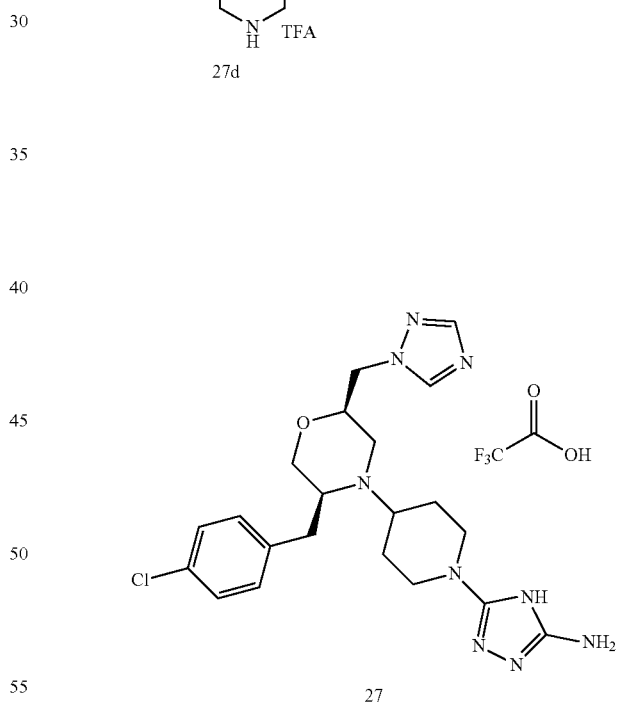

27

The title compound (27) was obtained as a TFA salt from 27d (145 mg; 0.3 mmol) according to the General Procedure Va in 11% yield (18 mg; 0.032 mmol).

ESI-MS $C_{21}H_{29}ClN_9O$ found 458.1/460.1 (M+H)$^+$; $^1$H NMR (700 MHz, D$_2$O) δ 8.64 (s, 1H), 8.16 (s, 1H), 7.42-7.33 (m, 2H), 7.22-7.12 (m, 2H), 4.62-4.48 (m, 2H), 4.33-4.22 (m, 1H), 3.95-3.82 (m, 3H), 3.81-3.66 (m, 4H), 3.25-3.20 (m, 1H), 3.11-3.03 (m, 3H), 3.02-2.89 (m, 1H), 2.38-2.33 (m, 2H), 1.81-1.70 (m, 2H).

Example 28

Synthesis of 5-(4-((2S,5S)-5-(4-chlorobenzyl)-2-(pyrrolidin-1-ylmethyl)morpholino)piperidin-1-yl)-4H-1,2,4-triazol-3-amine 2,2,2-trifluoroacetate (28)

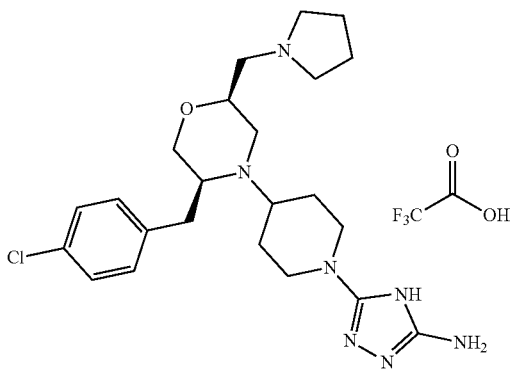

The title compound 28 was obtained as a TFA salt in 24% overall yield in a similar way to Example 27 with the exception that, in the third step of the synthesis, pyrrolidine was used instead of 1,2,4-triazole and in the fourth step of the synthesis, the synthesis was carried out according to the General Procedure IVa instead of General Procedure IVb.

ESI-MS m/z for $C_{23}H_{35}ClN_7O$ found 460.1/462.1 (M+1)$^+$; $^1$H NMR (700 MHz, D$_2$O) δ 7.43-7.34 (m, 2H), 7.31-7.22 (m, 2H), 4.25-4.17 (m, 1H), 3.95-3.85 (m, 4H), 3.79-3.64 (m, 5H), 3.59-3.54 (m, 1H), 3.38-3.33 (m, 1H), 3.29-3.03 (m, 7H), 2.37-2.27 (m, 2H), 2.20-2.10 (m, 2H), 2.03-1.94 (m, 2H), 1.85-1.70 (m, 2H).

Example 29

Synthesis of 5-(4-((2S,5S)-5-(4-chlorobenzyl)-2-((3,3-difluoropyrrolidin-1-yl)methyl)-morpholino)piperidin-1-yl)-4H-1,2,4-triazol-3-amine 2,2,2-trifluoroacetate (29)

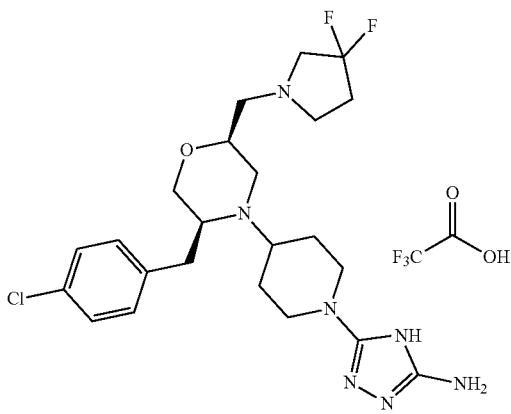

The title compound 29 was obtained as a TFA salt in 5% overall yield in a similar way to Example 27 with the exception that, in the third step of the synthesis, 3,3-difluoropyrrolidine hydrochloride was used instead of 1,2,4-triazole and in the fourth step of the synthesis, the synthesis was carried out according to the General Procedure IVa instead of General Procedure IVb.

ESI-MS m/z for $C_{23}H_{33}ClF_2N_7O$ found 496.1/498.1 (M+1)$^+$; $^1$H NMR (700 MHz, D$_2$O) δ 7.43-7.37 (m, 2H), 7.28-7.23 (m, 2H), 4.27-4.20 (m, 1H), 4.03-3.72 (m, 10H), 3.72-3.64 (m, 2H), 3.60-3.52 (m, 1H), 3.30-3.15 (m, 3H), 3.11-2.99 (m, 2H), 2.76-2.64 (m, 2H), 2.40-2.25 (m, 2H), 1.82-1.68 (m, 2H).

Example 30

Synthesis of (S)-1-(((2S,5S)-4-(1-(5-amino-4H-1,2,4-triazol-3-yl)piperidin-4-yl)-5-(4-chlorobenzyl)morpholin-2-yl)methyl)pyrrolidin-3-ol 2,2,2-trifluoroacetate (30)

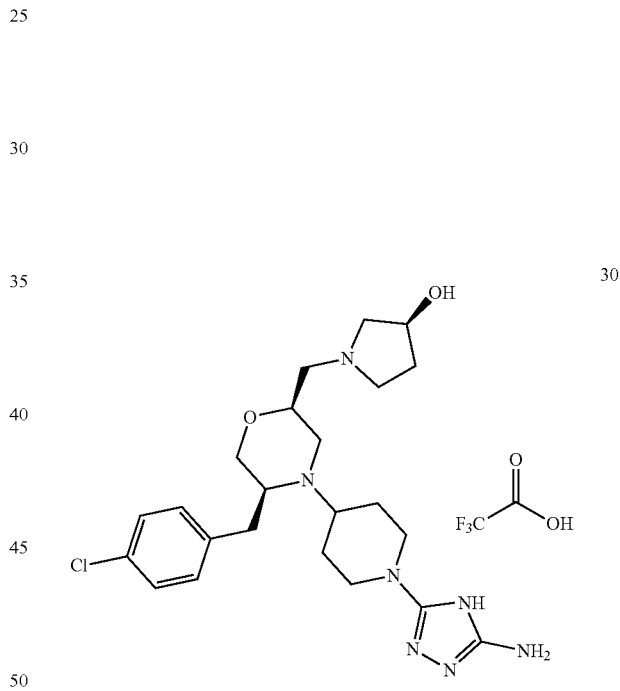

The title compound 30 was obtained as a TFA salt in 19% overall yield in a similar way to Example 27 with the exception that, in the third step of the synthesis, (S)-3-hydroxypyrrolidine was used instead of 1,2,4-triazole and in the fourth step of the synthesis, the synthesis was carried out according to the General Procedure IVa instead of General Procedure IVb.

ESI-MS m/z for $C_{23}H_{35}ClN_7O_2$ found 476.1/478.1 (M+1)$^+$; $^1$H NMR (700 MHz, Methanol-d$_4$) δ 7.42-7.37 (m, 2H), 7.34-7.28 (m, 2H), 4.65-4.58 (m, 1H), 4.31-4.21 (m, 1H), 4.02-3.93 (m, 2H), 3.90-3.79 (m, 3H), 3.79-3.66 (m, 2H), 3.65-3.34 (m, 6H), 3.28-3.21 (m, 1H), 3.19-3.03 (m, 4H), 2.48-2.21 (m, 3H), 2.17-2.02 (m, 1H), 1.89-1.74 (m, 2H).

Example 31

Synthesis of (R)-1-(((2S,5S)-4-(1-(5-amino-4H-1,2,4-triazol-3-yl)piperidin-4-yl)-5-(4-chlorobenzyl)morpholin-2-yl)methyl)pyrrolidin-3-ol 2,2,2-trifluoroacetate (31)

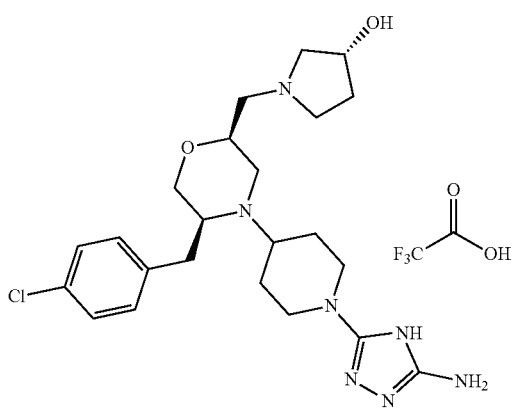

The title compound 31 was obtained as a TFA salt in 30% overall yield in a similar way to Example 27 with the exception that, in the third step of the synthesis, (R)-3-hydroxypyrrolidine was used instead of 1,2,4-triazole and in the fourth step of the synthesis, the synthesis was carried out according to the General Procedure IVa instead of General Procedure IVb.

ESI-MS m/z for $C_{23}H_{35}ClN_7O_2$ found 476.1/478.1 (M+1)$^+$; $^1$H NMR (700 MHz, Methanol-$d_4$) δ 7.45-7.36 (m, 2H), 7.38-7.28 (m, 2H), 4.34-4.21 (m, 1H), 4.02-3.94 (m, 2H), 3.89-3.42 (m, 11H), 3.28-3.05 (m, 6H), 2.58-1.99 (m, 4H), 1.93-1.73 (m, 2H).

Example 32

Synthesis of 5-(4-((2R,5S)-5-(4-chlorobenzyl)-2-((methylsulfinyl)methyl)morpholino)piperidin-1-yl)-4H-1,2,4-triazol-3-amine dihydrochloride (32)

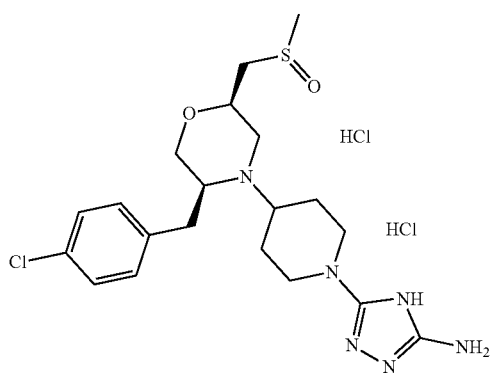

Step 1

Synthesis of (2R,5S)-tert-butyl 5-(4-chlorobenzyl)-2-((methylthio)methyl)morpholine-4-carboxylate (32a)

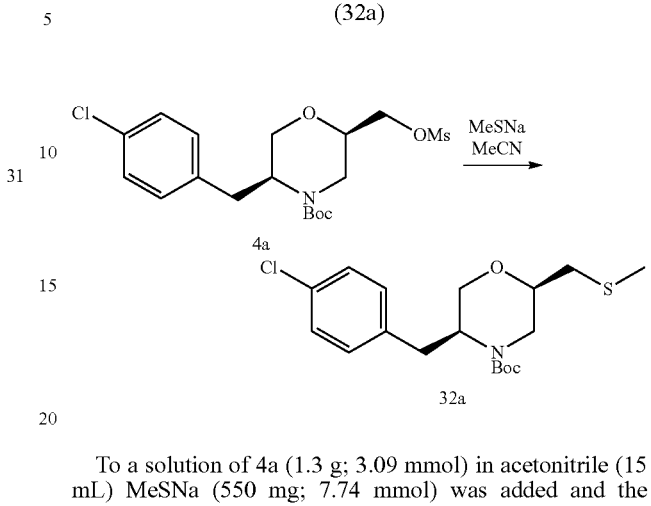

To a solution of 4a (1.3 g; 3.09 mmol) in acetonitrile (15 mL) MeSNa (550 mg; 7.74 mmol) was added and the reaction mixture was stirred at 80° C. overnight. The reaction progress was monitored by LC-MS analysis. After analytical control indicated completion of the reaction, the mixture was dissolved in DCM and then washed with 2 M NaOH, brine, dried over $Na_2SO_4$, filtered and concentrated in vacuo and the crude product was used in the next step without additional purification. Compound 32a was obtained in 79% yield (0.9 g; 2.43 mmol).

ESI-MS m/z for $C_{18}H_{27}ClNO_3S$ found 372.1/374.1 (M+1)$^+$.

Step 2

Synthesis of (2R,5S)-tert-butyl 5-(4-chlorobenzyl)-2-((methylsulfinyl)methyl)morpholine-4-carboxylate (32b)

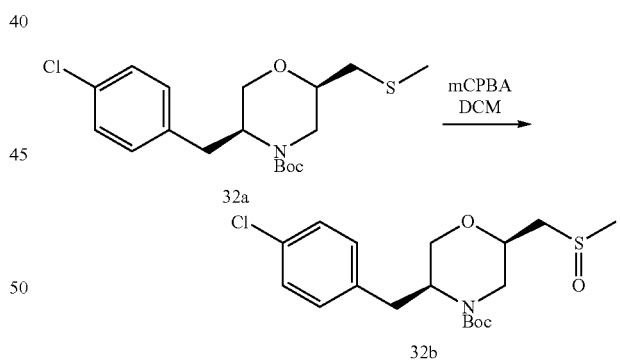

To a pre-cooled (0° C.) solution of 32a (0.6 g; 1.61 mmol) in DCM (15 mL) mCPBA (0.39 g; 1.61 mmol) was added in several portions. The reaction was stirred at room temperature for 3 hours. The reaction progress was monitored by LC-MS analysis. After analytical control indicated completion of the reaction, the reaction mixture was washed with 10% $Na_2S_2O_3$, saturated $NaHCO_3$, brine, dried over $Na_2SO_4$, filtered and concentrated in vacuo and the crude product was used in the next step without additional purification. Compound 32b was obtained in 82% yield (0.51 g; 1.32 mmol).

ESI-MS m/z for $C_{18}H_{27}ClNO_4S$ found 388.1/390.1 (M+1)$^+$.

Step 3

Synthesis of (2R,5S)-5-(4-chlorobenzyl)-2-((methylsulfinyl)methyl)morpholine (32c)

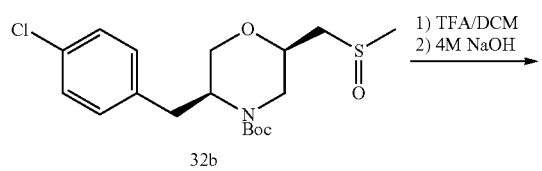

The title compound (32c) was obtained as a free base in 92% yield (350 mg; 1.22 mmol) from 32b (0.51 g; 1.32 mmol) according to the General Procedure IVb followed by basic (4 M NaOH) extraction with DCM.

Step 4

Synthesis of tert-butyl 4-((2R,5S)-5-(4-chlorobenzyl)-2-((methylsulfinyl)methyl)morpholino)-piperidine-1-carboxylate (32d)

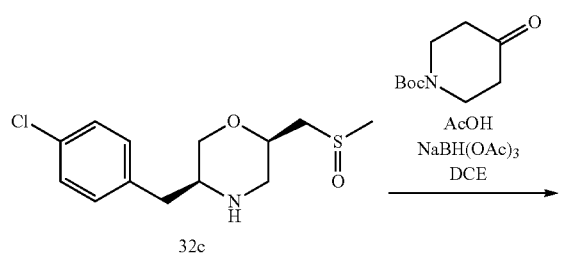

The title compound (32d) was obtained from 32c (350 mg; 1.22 mmol) according to the General Procedure IX in 99% yield (569 mg; 1.21 mmol).

ESI-MS m/z for $C_{23}H_{36}ClN_2O_4S$ found 471.2/473.2 $(M+1)^+$

Step 5

Synthesis of (2R,5S)-5-(4-chlorobenzyl)-2-((methylsulfinyl)methyl)-4-(piperidin-4-yl)-morpholine 2,2,2-trifluoroacetate (32e)

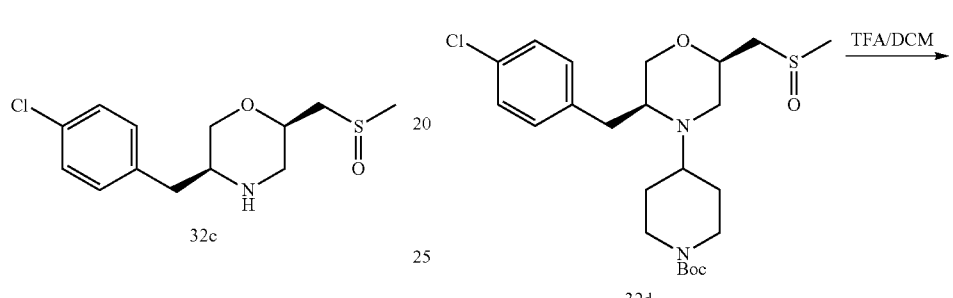

The title compound (32e) was obtained as a TFA salt from 32d (569 mg; 1.21 mmol) according to the General Procedure IVb in 99% yield (581 mg; 1.2 mmol).

Step 6

Synthesis of 5-(4-((2R,5S)-5-(4-chlorobenzyl)-2-((methylsulfinyl)methyl)morpholino)piperidin-1-yl)-4H-1,2,4-triazol-3-amine dihydrochloride (32)

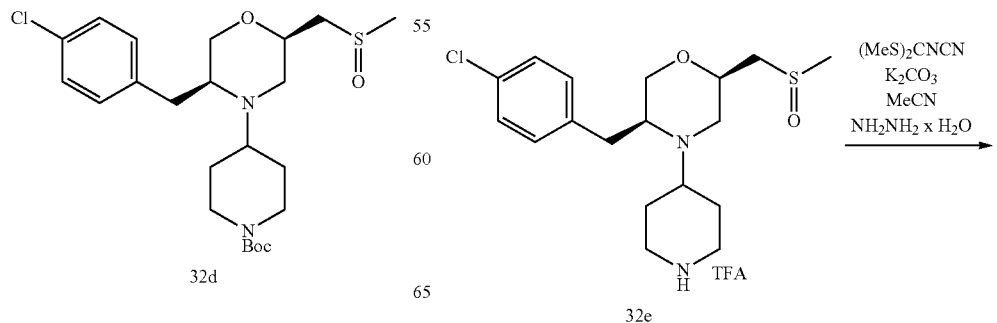

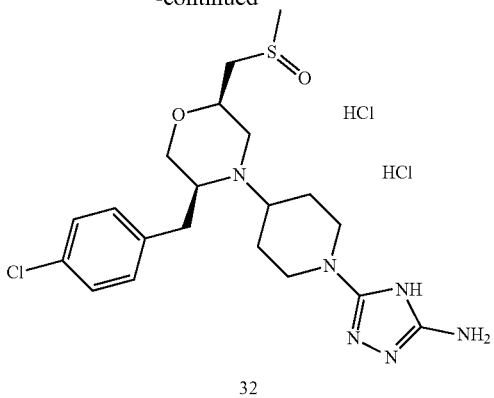

32

The title compound (32) was obtained as a dihydrochloride salt from 32e (581 mg; 1.2 mmol) according to the General Procedure Va in 8% yield (48 mg; 0.091 mmol).

ESI-MS $C_{20}H_{30}ClN_6O_2S$ found 453.1/455.1 (M+H)$^+$; $^1$H NMR (400 MHz, Methanol-$d_4$) δ 7.42-7.26 (m, 4H), 4.38-4.22 (m, 1H), 4.10-3.69 (m, 7H), 3.62-3.50 (m, 1H), 3.39-3.33 (m, 1H), 3.25-3.02 (m, 5H), 2.79-2.72 (m, 3H), 2.46-2.32 (m, 2H), 2.02-1.86 (m, 2H).

Example 33

Synthesis of 5-(4-((2R,5S)-5-(4-chlorobenzyl)-2-((methylsulfonyl)methyl)morpholino)piperidin-1-yl)-4H-1,2,4-triazol-3-amine dihydrochloride (33)

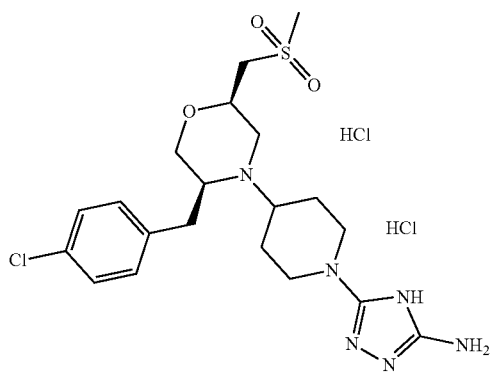

33

Step 1

Synthesis of (2R,5S)-tert-butyl 5-(4-chlorobenzyl)-2-((methylsulfonyl)methyl)morpholine-4-carboxylate (33a)

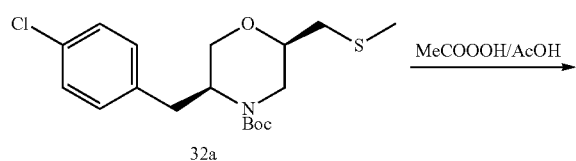

33a

To a compound 32a (0.32 g; 0.86 mmol) peracetic acid (35% in AcOH; 0.33 mL; 1.72 mmol) was added and this solution was stirred at room temperature overnight. Then the reaction was concentrated and the residue was transferred to AcOEt/1 M NaOH. Phases were separated and the organic one was washed with brine, dried over Na$_2$SO$_4$, filtered and concentrated in vacuo and the crude product was used in the next step without additional purification. Compound 33a was obtained in 99% yield (0.34 g; 0.85 mmol).

ESI-MS m/z for $C_{18}H_{27}ClNO_5S$ found 404.1/406.1 (M+1)$^+$; $^1$H NMR (700 MHz, DMSO-$d_6$+$D_2O$, 348 K) δ 7.33-7.26 (m, 2H), 7.24-7.18 (m, 2H), 4.11-4.05 (m, 1H), 3.87-3.82 (m, 1H), 3.81-3.77 (m, 1H), 3.77-3.73 (m, 1H), 3.61-3.54 (m, 1H), 3.34-3.29 (m, 1H), 3.06-2.94 (m, 5H), 2.86-2.79 (m, 1H), 1.98-1.95 (m, 1H), 1.27-1.14 (m, 9H).

Step 2

Synthesis of (2R,5S)-5-(4-chlorobenzyl)-2-((methylsulfonyl)methyl)morpholine (33b)

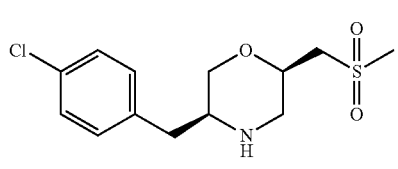

33a

33b

The title compound (33b) was obtained as a free base in 99% yield (149 mg; 0.49 mmol) from 33a (198 mg; 0.49 mmol) according to the General Procedure IVb followed by basic (4 M NaOH) extraction with DCM.

Step 3

Synthesis of tert-butyl 4-((2R,5S)-5-(4-chlorobenzyl)-2-((methylsulfonyl)methyl)morpholino)-piperidine-1-carboxylate (33c)

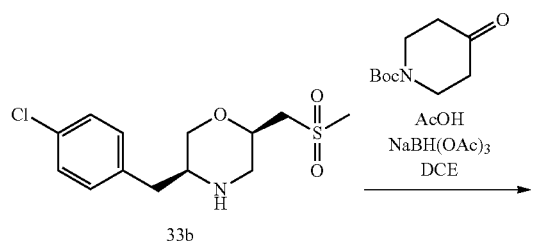

The title compound (33c) was obtained from 33b (149 mg; 0.49 mmol) according to the General Procedure IX in 99% yield (238 mg; 0.49 mmol).

ESI-MS m/z for $C_{23}H_{36}ClN_2O_5S$ found 487.2/489.2 $(M+1)^+$.

Step 4

Synthesis of (2R,5S)-5-(4-chlorobenzyl)-2-((methylsulfonyl)methyl)-4-(piperidin-4-yl)-morpholine 2,2,2-trifluoroacetate (33d)

The title compound (33d) was obtained as a TFA salt from 33c (238 mg; 0.49 mmol) according to the General Procedure IVb in 99% yield (245 mg; 0.49 mmol).

Step 5

Synthesis of 5-(4-((2R,5S)-5-(4-chlorobenzyl)-2-((methylsulfonyl)methyl)morpholino)piperidin-1-yl)-4H-1,2,4-triazol-3-amine dihydrochloride (33)

The title compound (33) was obtained as a dihydrochloride salt from 33d (245 mg; 0.49 mmol) according to the General Procedure Va in 33% yield (86 mg; 0.16 mmol).

ESI-MS $C_{20}H_{30}ClN_6O_3S$ found 469.1/471.1 $(M+H)^+$; $^1H$ NMR (400 MHz, Methanol-$d_4$) δ 7.43-7.29 (m, 4H), 4.53-4.38 (m, 1H), 4.03-3.61 (m, 8H), 3.53-3.39 (m, 2H), 3.37-3.32 (m, 1H), 3.25-3.18 (m, 1H), 3.16-3.04 (m, 5H), 2.44-2.28 (m, 2H), 2.02-1.83 (m, 2H).

Example 34

Synthesis of 5-(4-((2R,5S)-5-(4-chlorobenzyl)-2-(3-methyl-1H-pyrazol-5-yl)morpholino)-piperidin-1-yl)-4H-1,2,4-triazol-3-amine 2,2,2-trifluoroacetate (34)

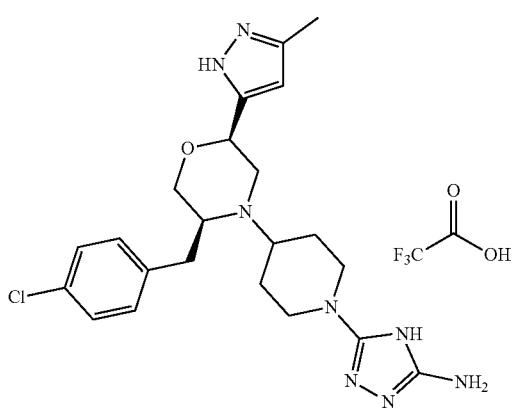

The title compound 34 was obtained as a TFA salt in 61% overall yield in a similar way to Example 11 with the exception that, in the second step of the synthesis, hydrazine hydrate was used instead of methylhydrazine.

ESI-MS m/z for $C_{22}H_{30}ClN_8O$ found 457.3/459.3 (M+1)$^+$; $^1$H NMR (700 MHz, DMSO-d$_6$+D$_2$O, 348 K) δ 7.41-7.36 (m, 2H), 7.36-7.28 (m, 2H), 6.16 (s, 1H), 4.86-4.78 (m, 1H), 3.90-3.82 (m, 3H), 3.81-3.77 (m, 1H), 3.74-3.65 (m, 2H), 3.54-3.44 (m, 2H), 3.25-3.20 (m, 1H), 3.19-3.14 (m, 1H), 3.00-2.91 (m, 2H), 2.25-2.14 (m, 5H), 1.75-1.62 (m, 2H).

Example 35

Synthesis of 1-(((2R,5S)-4-(1-(5-amino-4H-1,2,4-triazol-3-yl)piperidin-4-yl)-5-(4-chlorobenzyl)-morpholin-2-yl)methyl)piperidin-2-one 2,2,2-trifluoroacetate (35)

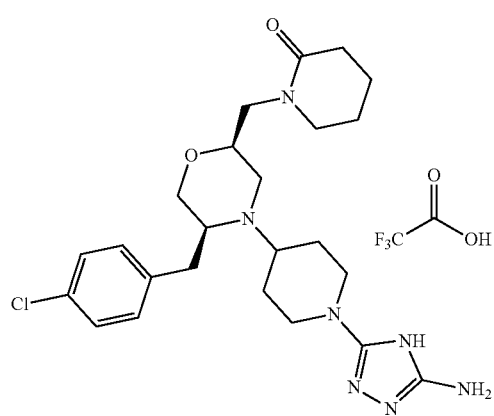

Step 1

Synthesis of (2S,5S)-tert-butyl 5-(4-chlorobenzyl)-2-((2-oxopiperidin-1-yl)methyl)morpholine-4-carboxylate (35a)

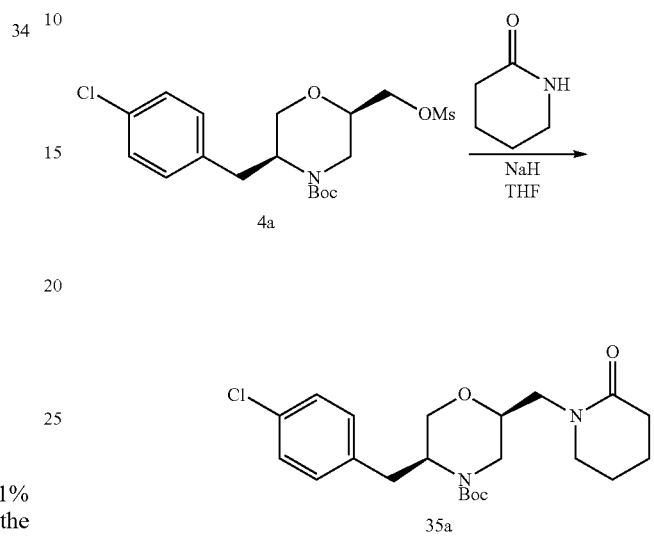

The title compound (35a) was obtained from 4a (200 mg; 0.47 mmol) according to the General Procedure XI in 99% yield (196 mg; 0.47 mmol).

ESI-MS $C_{17}H_{24}ClN_2O_2$ found 323.1/325.1 (M+H-Boc)$^+$.

Step 2

Synthesis of 1-(((2R,5S)-5-(4-chlorobenzyl)morpholin-2-yl)methyl)piperidin-2-one hydrochloride (35b)

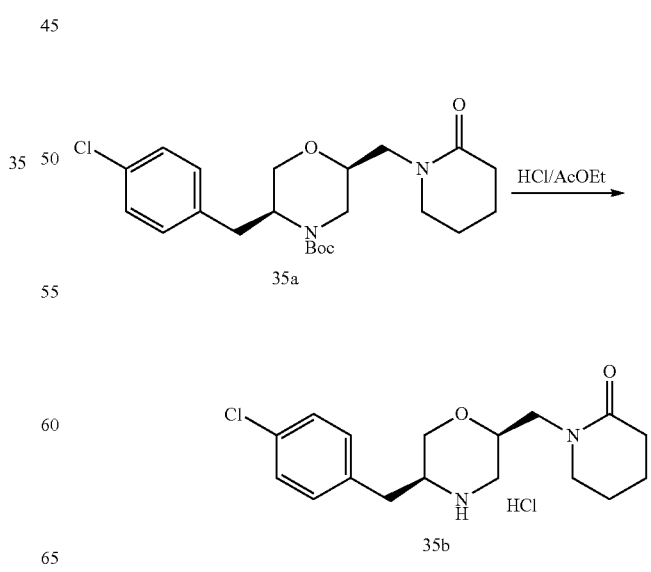

The title compound (35b) was obtained as a hydrochloride salt from 35a (330 mg; 0.78 mmol) according to the General Procedure IVa in 99% yield (277 mg; 0.77 mmol).

ESI-MS $C_{17}H_{24}ClN_2O_2$ found 323.1/325.1 (M+H)⁺.

Step 3

Synthesis of 1-(((2R,5S)-4-(1-(5-amino-4H-1,2,4-triazol-3-yl)piperidin-4-yl)-5-(4-chlorobenzyl)-morpholin-2-yl)methyl)piperidin-2-one 2,2,2-trifluoroacetate (35)

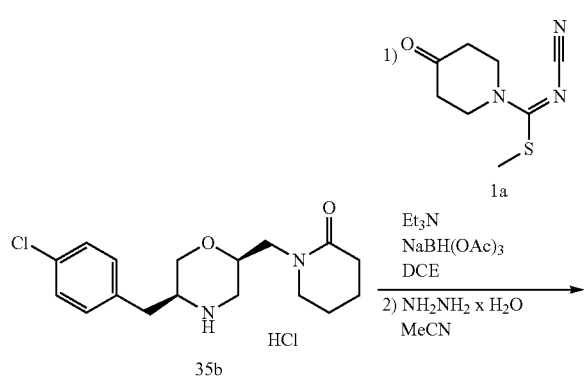

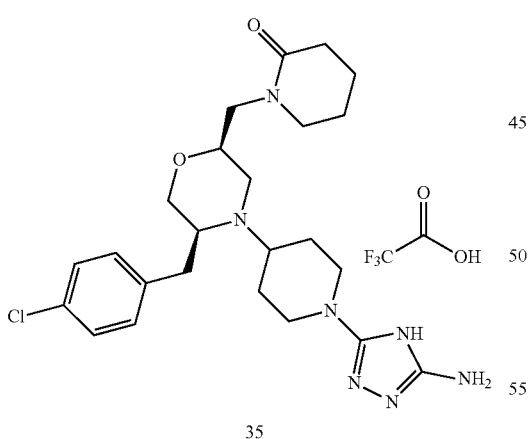

35

The title compound (35) was obtained as a TFA salt from 35b (277 mg; 0.77 mmol) according to the General Procedure Vb in 2% yield (10 mg; 0.017 mmol).

ESI-MS $C_{24}H_{34}ClN_7O_2$ found 488.1/4901.1 (M+H)⁺; ¹H NMR (400 MHz, Methanol-d₄) δ 7.45-7.38 (m, 2H), 7.29 (m, 2H), 4.09-3.99 (m, 3H), 3.87-3.78 (m, 2H), 3.78-3.66 (m, 3H), 3.66-3.47 (m, 4H), 3.28-3.01 (m, 5H), 2.47-2.28 (m, 4H), 1.93-1.74 (m, 6H).

Example 36

Synthesis of 5-(4-((2R,5S)-5-(4-chlorobenzyl)-2-((4-fluoro-1H-pyrazol-1-yl)methyl)-morpholino)piperidin-1-yl)-4H-1,2,4-triazol-3-amine 2,2,2-trifluoroacetate (36)

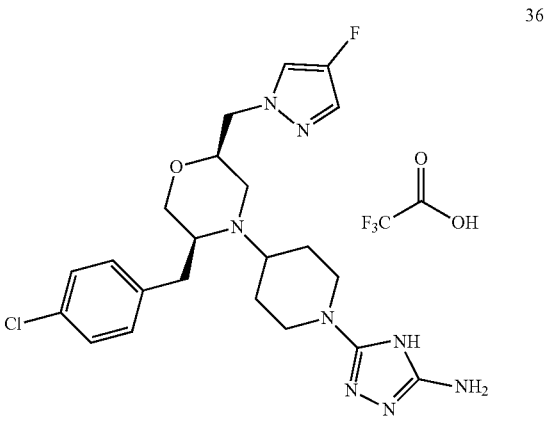 [SMILES: Nc1nnc(N2CCC(N3C[C@H](Cn4cc(F)cn4)OC[C@@H]3Cc3ccc(Cl)cc3)CC2)[nH]1 ; O=C(O)C(F)(F)F]

36

The title compound 36 was obtained as a TFA salt in 33% overall yield in a similar way to Example 8 with the exception that, in the first step of the synthesis, 4-fluoro-1H-pyrazole was used instead of 4-cyanopyrazole.

ESI-MS m/z for $C_{22}H_{29}ClFN_8O$ found 475.2/477.2 (M+1)⁺; ¹H NMR (700 MHz, DMSO-d₆+D₂O, 348 K) δ 7.78 (d, J=4.6 Hz, 1H), 7.47 (d, J=4.2 Hz, 1H), 7.41-7.35 (m, 2H), 7.28-7.24 (m, 2H), 4.33-4.22 (m, 2H), 4.13-4.05 (m, 1H), 3.89-3.84 (m, 2H), 3.71-3.64 (m, 2H), 3.61-3.57 (m, 2H), 3.47-3.44 (m, 1H), 3.08-3.01 (m, 2H), 2.98-2.90 (m, 3H), 2.18-2.11 (m, 2H), 1.67-1.58 (m, 2H); ¹⁹F NMR (235 MHz, DMSO-d₆) δ −69.20 (s).

Example 37

Synthesis of 5-(4-((2S,5S)-5-(4-chlorobenzyl)-2-((3-fluoroazetidin-1-yl)methyl)morpholino)-piperidin-1-yl)-4H-1,2,4-triazol-3-amine 2,2,2-trifluoroacetate (37)

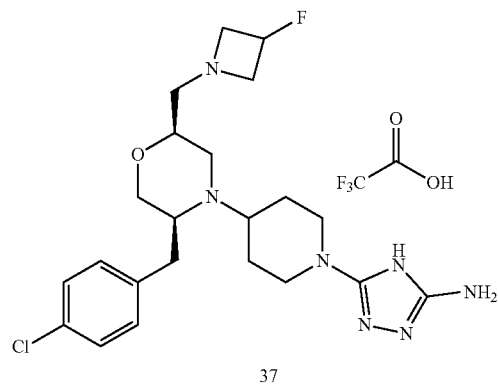

37

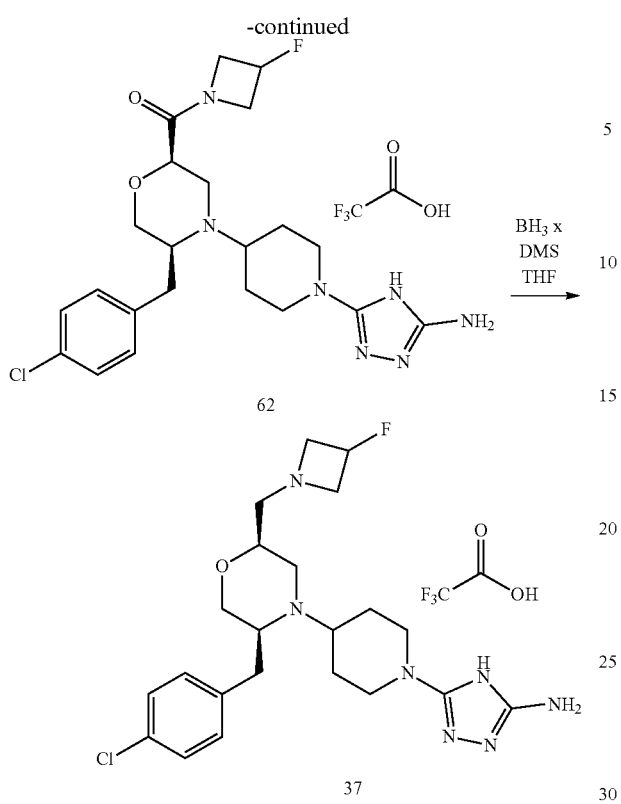

The title compound (37) was obtained as a TFA salt from 62 (75 mg; 0.13 mmol) according to the General Procedure Ia in 53% yield (40 mg; 0.069 mmol).

ESI-MS $C_{22}H_{32}ClFN_7O$ found 464.2/466.2 (M+H)$^+$; H NMR (700 MHz, D$_2$O) δ 7.41-7.36 (m, 2H), 7.31-7.22 (m, 2H), 5.43 (d, J=56.3 Hz, 1H), 4.65-4.28 (m, 3H), 4.19-4.11 (m, 1H), 3.97-3.84 (m, 4H), 3.83-3.41 (m, 6H), 3.30-3.14 (m, 3H), 3.10-3.01 (m, 2H), 2.43-2.25 (m, 2H), 1.83-1.65 (m, 2H).

Example 38

Synthesis of 5-(4-((2S,5S)-5-(4-chlorobenzyl)-2-((4,4-difluoropiperidin-1-yl)methyl)-morpholino)piperidin-1-yl)-4H-1,2,4-triazol-3-amine 2,2,2-trifluoroacetate (38)

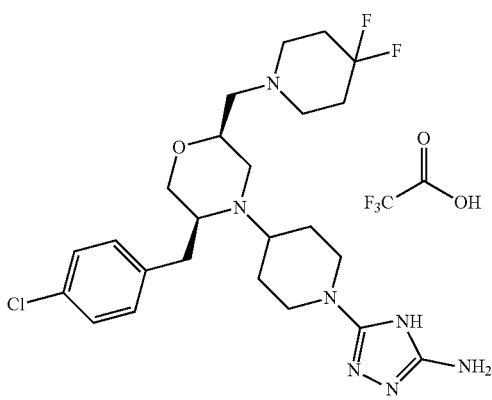

The title compound 38 was obtained as a TFA salt in 21% overall yield in a similar way to Example 27 with the exception that, in the third step of the synthesis, 4,4-difluoropiperidine hydrochloride was used instead of 1,2,4-triazole.

ESI-MS $C_{24}H_{35}ClF_2N_7O$ found 510.3/512.3 (M+H)$^+$; H NMR (700 MHz, D$_2$O) δ 7.43-7.37 (m, 2H), 7.30-7.23 (m, 2H), 4.35-4.28 (m, 1H), 3.98-3.85 (m, 4H), 3.80-3.48 (m, 7H), 3.43-3.40 (m, 1H), 3.32-3.22 (m, 2H), 3.22-3.14 (m, 1H), 3.10-3.01 (m, 2H), 2.47-2.26 (m, 6H), 1.83-1.62 (m, 2H).

Example 39

Synthesis of 5-(4-((2R,5S)-5-(4-chlorobenzyl)-2-((2,2,2-trifluoroethoxy)methyl)morpholino)-piperidin-1-yl)-4H-1,2,4-triazol-3-amine 2,2,2-trifluoroacetate (39)

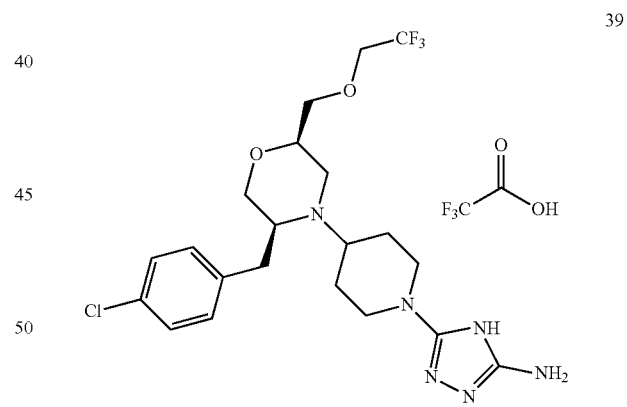

The title compound 39 was obtained as a TFA salt in 22% overall yield in a similar way to Example 35 with the exception that, in the first step of the synthesis, 2,2,2-trifluoroethanol was used instead of 2-piperidone and compound 27b was used instead of compound 4a.

ESI-MS $C_{21}H_{29}ClF_3N_6O_2$ found 489.2/491.2 (M+H)$^+$; $^1$H NMR (700 MHz, D$_2$O) δ 7.43-7.32 (m, 2H), 7.29-7.20 (m, 2H), 4.12-3.99 (m, 3H), 3.92-3.83 (m, 6H), 3.83-3.68 (m, 2H), 3.68-3.56 (m, 1H), 3.44-3.33 (m, 1H), 3.29-3.12 (m, 2H), 3.11-3.01 (m, 2H), 2.43-2.28 (m, 2H), 1.84-1.62 (m, 2H).

Example 40

Synthesis of 5-(4-((2R,5S)-5-(4-chlorobenzyl)-2-((difluoromethoxy)methyl)morpholino)-piperidin-1-yl)-4H-1,2,4-triazol-3-amine 2,2,2-trifluoroacetate (40)

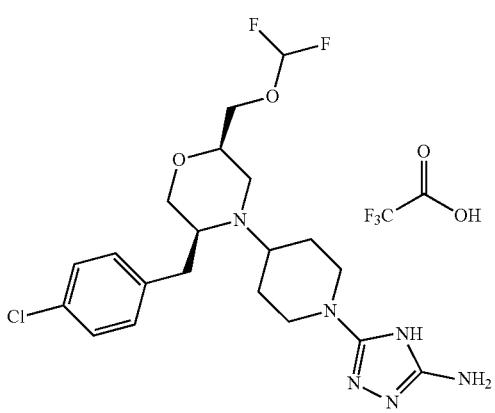

Step 1

Synthesis of (2R,5S)-tert-butyl 5-(4-chlorobenzyl)-2-((difluoromethoxy)methyl)morpholine-4-carboxylate (40a)

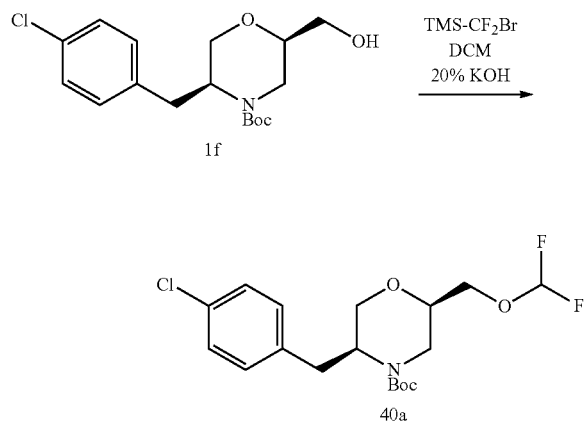

To the vigorously stirred pre-cooled (0° C.) biphasic mixture of KOH (0.98 g; 17.5 mmol) in water (4 mL) and the solution of 1f (500 mg, 1.46 mmol) in DCM (3 mL) the solution of TMS-CF$_2$—Br (1.2 g; 5.86 mmol) in DCM (1 mL) was added dropwise. The reaction was stirred at 0° C. overnight. The phases were separated, aqueous one was additionally extracted several times with DCM. Combined solutions were dried over Na$_2$SO$_4$ filtered and evaporated to dryness. The crude product was used in the next step without additional purification. Compound 40a was obtained in 72% yield (0.41 g; 1.05 mmol).

ESI-MS m/z for $C_{18}H_{25}ClF_2NO_4$ found 392.1/394.1 (M+1)$^+$.

Step 2

Synthesis of (2R,5S)-5-(4-chlorobenzyl)-2-((difluoromethoxy)methyl)morpholine (40b)

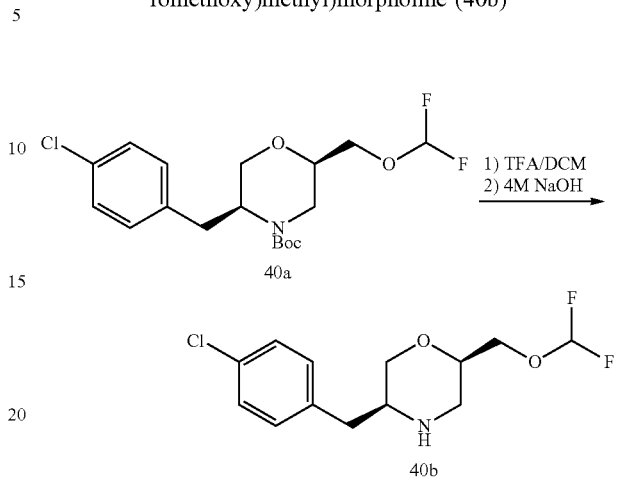

The title compound (40b) was obtained as a free base in 99% yield (303 mg; 1.04 mmol) from 40a (0.41 g; 1.05 mmol) according to the General Procedure IVb followed by basic (4 M NaOH) extraction with DCM.

Step 3

Synthesis of tert-butyl 4-((2R,5S)-5-(4-chlorobenzyl)-2-((difluoromethoxy)methyl)morpholino)-piperidine-1-carboxylate (40c)

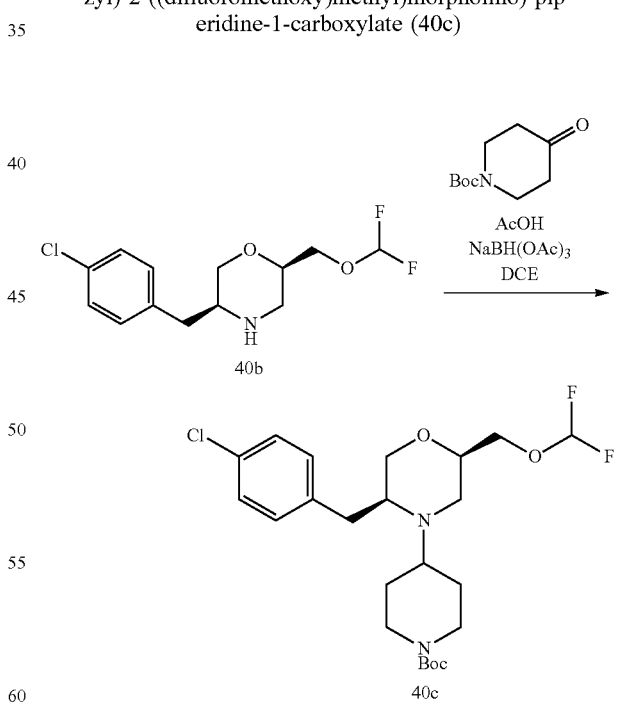

The title compound (40c) was obtained from 40b (303 mg; 1.04 mmol) according to the General Procedure IX in 99% yield (488 mg; 1.03 mmol).

ESI-MS m/z for $C_{23}H_{34}ClF_2N_2O_4$ found 475.2/477.2 (M+1)$^+$.

Step 4

Synthesis of (2R,5S)-5-(4-chlorobenzyl)-2-((difluoromethoxy)methyl)-4-(piperidin-4-yl)-morpholine 2,2,2-trifluoroacetate (40d)

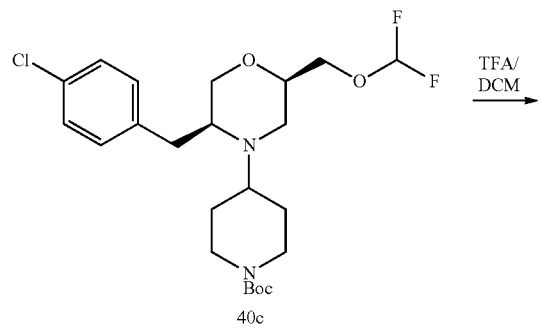
40c

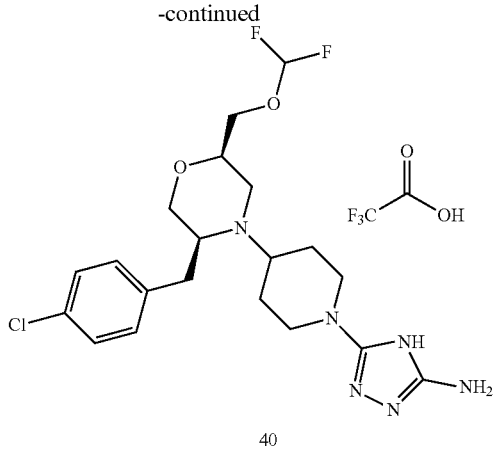
40

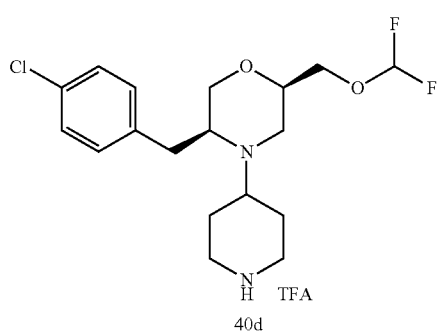
40d

The title compound (40d) was obtained as a TFA salt from 40c (488 mg; 1.03 mmol) according to the General Procedure IVb in 99% yield (498 mg; 1.02 mmol).

Step 5

Synthesis of 5-(4-((2R,5S)-5-(4-chlorobenzyl)-2-((difluoromethoxy)methyl)morpholino)-piperidin-1-yl)-4H-1,2,4-triazol-3-amine 2,2,2-trifluoroacetate (40)

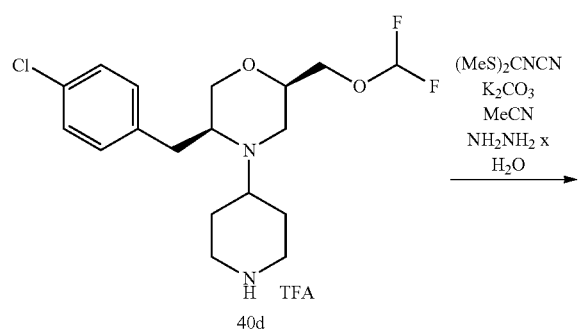
40d

The title compound (40) was obtained as a TFA salt from 40d (498 mg; 1.02 mmol) according to the General Procedure Va in 27% yield (157 mg; 0.28 mmol).

ESI-MS $C_{20}H_{28}ClF_2N_6O_2$ found 457.1/459.1 $(M+H)^+$; $^1$H NMR (400 MHz, Methanol-$d_4$) δ 7.40-7.35 (m, 2H), 7.34-7.30 (m, 2H), 6.49 (t, J=74.7 Hz, 1H), 4.17-3.96 (m, 5H), 3.85-3.59 (m, 5H), 3.39-3.34 (m, 1H), 3.27-2.99 (m, 4H), 2.43-2.29 (m, 2H), 1.89-1.70 (m, 2H).

Example 41

Synthesis of 5-(4-((2R,5S)-5-(4-chlorobenzyl)-2-((methylthio)methyl)morpholino)piperidin-1-yl)-4H-1,2,4-triazol-3-amine dihydrochloride (41)

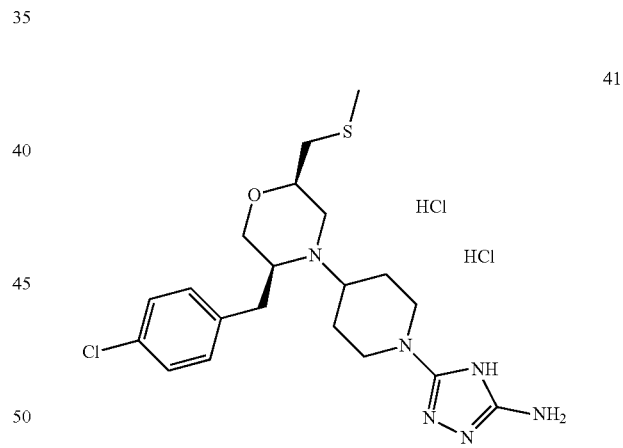
41

Step 1

Synthesis of (2R,5S)-5-(4-chlorobenzyl)-2-((methylthio)methyl)morpholine (41a)

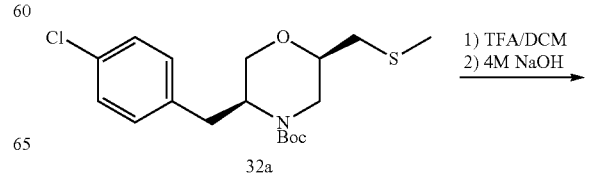
32a

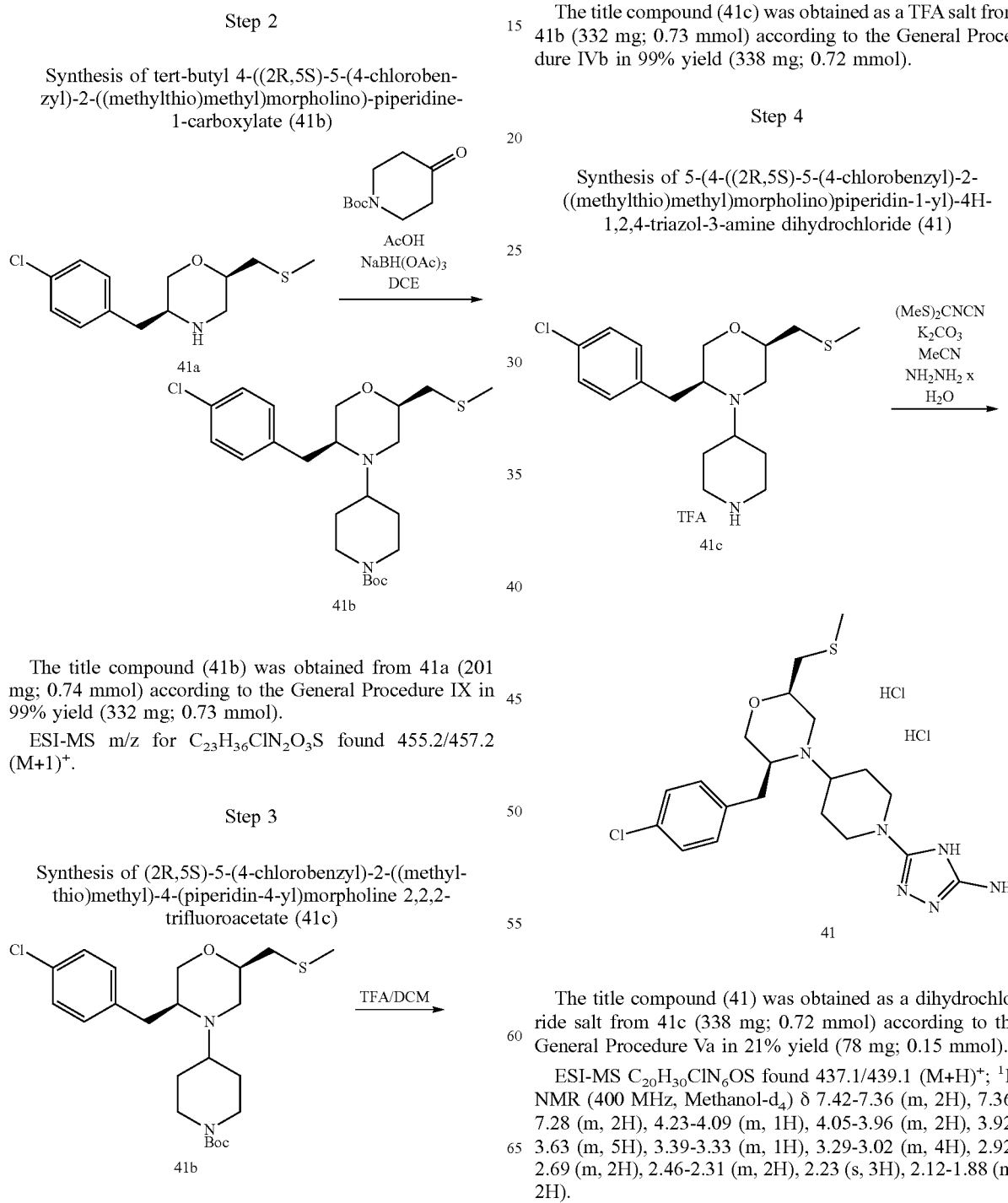

The title compound (41a) was obtained as a free base in 99% yield (201 mg; 0.74 mmol) from 32a (275 mg; 0.74 mmol) according to the General Procedure IVb followed by basic (4 M NaOH) extraction with DCM.

Step 2

Synthesis of tert-butyl 4-((2R,5S)-5-(4-chlorobenzyl)-2-((methylthio)methyl)morpholino)-piperidine-1-carboxylate (41b)

The title compound (41b) was obtained from 41a (201 mg; 0.74 mmol) according to the General Procedure IX in 99% yield (332 mg; 0.73 mmol).

ESI-MS m/z for $C_{23}H_{36}ClN_2O_3S$ found 455.2/457.2 $(M+1)^+$.

Step 3

Synthesis of (2R,5S)-5-(4-chlorobenzyl)-2-((methylthio)methyl)-4-(piperidin-4-yl)morpholine 2,2,2-trifluoroacetate (41c)

The title compound (41c) was obtained as a TFA salt from 41b (332 mg; 0.73 mmol) according to the General Procedure IVb in 99% yield (338 mg; 0.72 mmol).

Step 4

Synthesis of 5-(4-((2R,5S)-5-(4-chlorobenzyl)-2-((methylthio)methyl)morpholino)piperidin-1-yl)-4H-1,2,4-triazol-3-amine dihydrochloride (41)

The title compound (41) was obtained as a dihydrochloride salt from 41c (338 mg; 0.72 mmol) according to the General Procedure Va in 21% yield (78 mg; 0.15 mmol).

ESI-MS $C_{20}H_{30}ClN_6OS$ found 437.1/439.1 $(M+H)^+$; $^1H$ NMR (400 MHz, Methanol-$d_4$) δ 7.42-7.36 (m, 2H), 7.36-7.28 (m, 2H), 4.23-4.09 (m, 1H), 4.05-3.96 (m, 2H), 3.92-3.63 (m, 5H), 3.39-3.33 (m, 1H), 3.29-3.02 (m, 4H), 2.92-2.69 (m, 2H), 2.46-2.31 (m, 2H), 2.23 (s, 3H), 2.12-1.88 (m, 2H).

Example 42

Synthesis of 5-(4-((2R,5S)-5-(4-chlorobenzyl)-2-(1,1-difluoroethyl)morpholino)piperidin-1-yl)-4H-1,2,4-triazol-3-amine dihydrochloride (42)

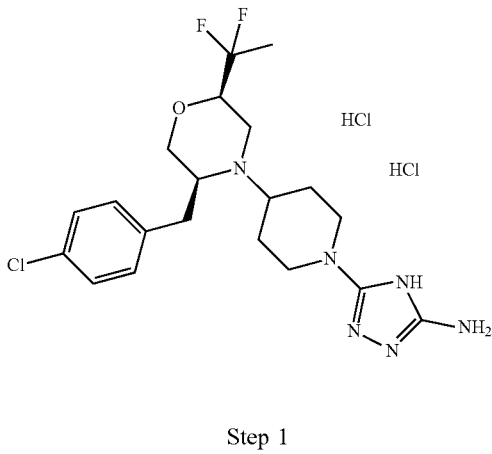

Step 1

Synthesis of (2R,5S)-tert-butyl 5-(4-chlorobenzyl)-2-(1,1-difluoroethyl)morpholine-4-carboxylate (42a)

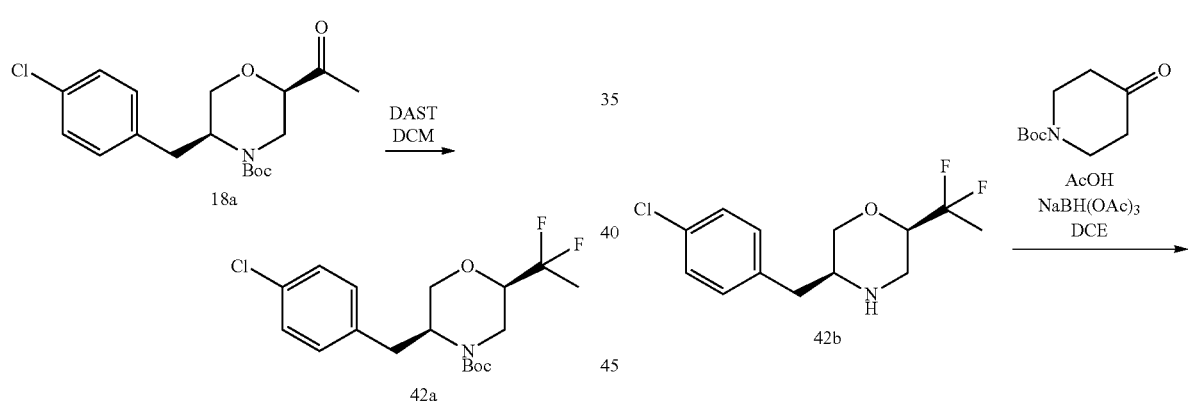

The title compound (42a) was obtained from 18a (420 mg; 1.19 mmol) according to the General Procedure VII in 92% yield (409 mg; 1.09 mmol).

Step 2

Synthesis of (2R,5S)-5-(4-chlorobenzyl)-2-(1,1-difluoroethyl)morpholine (42b)

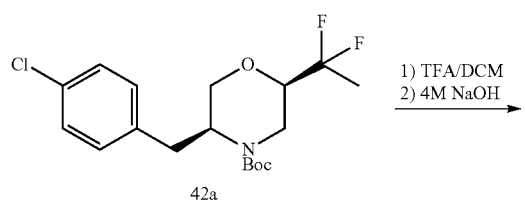

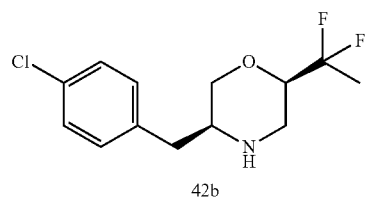

The title compound (42b) was obtained as a free base in 99% yield (297 mg; 1.08 mmol) from 42a (409 mg; 1.09 mmol) according to the General Procedure IVb followed by basic (4 M NaOH) extraction with DCM.

Step 3

Synthesis of tert-butyl 4-((2R,5S)-5-(4-chlorobenzyl)-2-(1,1-difluoroethyl)morpholino)-piperidine-1-carboxylate (42c)

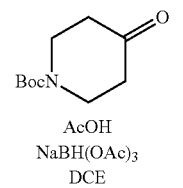

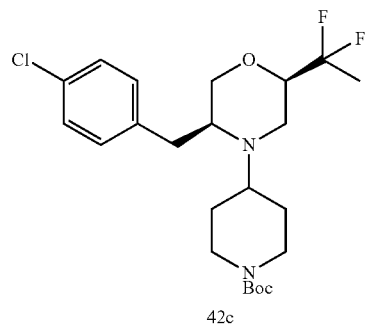

The title compound (42c) was obtained from 42b (297 mg; 1.08 mmol) according to the General Procedure IX in 99% yield (490 mg; 1.07 mmol).

Step 4

Synthesis of (2R,5S)-5-(4-chlorobenzyl)-2-(1,1-difluoroethyl)-4-(piperidin-4-yl)morpholine 2,2,2-trifluoroacetate (42d)

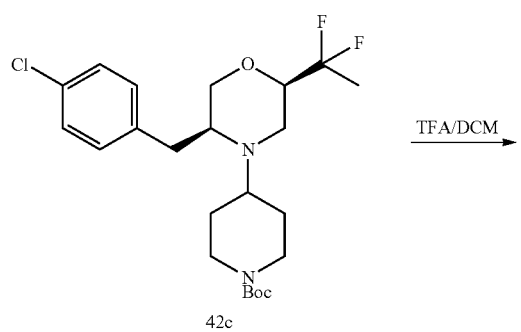

The title compound (42d) was obtained as a TFA salt from 42c (490 mg; 1.07 mmol) according to the General Procedure IVb in 99% yield (500 mg; 1.06 mmol).

Step 5

Synthesis of 5-(4-((2R,5S)-5-(4-chlorobenzyl)-2-(1,1-difluoroethyl)morpholino)piperidin-1-yl)-4H-1,2,4-triazol-3-amine dihydrochloride (42)

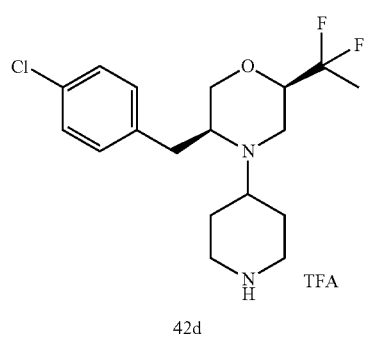

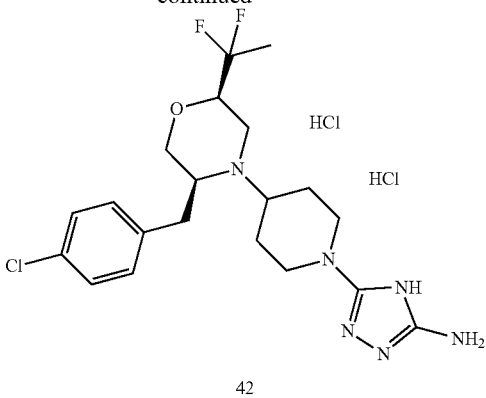

The title compound (42) was obtained as a dihydrochloride salt from 42d (500 mg; 1.06 mmol) according to the General Procedure Va in 28% yield (155 mg; 0.3 mmol).

ESI-MS $C_{20}H_{28}ClF_2N_6O$ found 441.1/443.1 $(M+H)^+$; $^1H$ NMR (400 MHz, Methanol-$d_4$) δ 7.45-7.36 (m, 2H), 7.36-7.28 (m, 2H), 4.33-4.17 (m, 1H), 4.08-3.91 (m, 4H), 3.90-3.77 (m, 2H), 3.74-3.65 (m, 1H), 3.57-3.42 (m, 1H), 3.27-3.02 (m, 4H), 2.44-2.32 (m, 2H), 2.10-1.92 (m, 2H), 1.76 (t, J=19.5 Hz, 3H).

Example 43

Synthesis of 5-(4-((2R,5S)-5-(4-chlorobenzyl)-2-((2,2-difluoroethoxy)methyl)morpholino)-piperidin-1-yl)-4H-1,2,4-triazol-3-amine 2,2,2-trifluoroacetate (43)

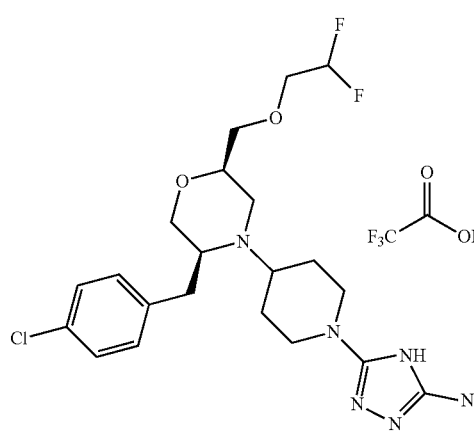

Step 1

Synthesis of (2R,5S)-5-(4-chlorobenzyl)-2-((2,2-difluoroethoxy)methyl)morpholine (43a)

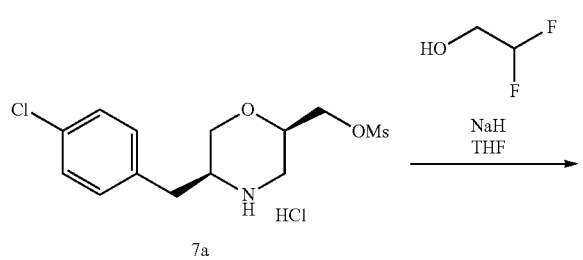

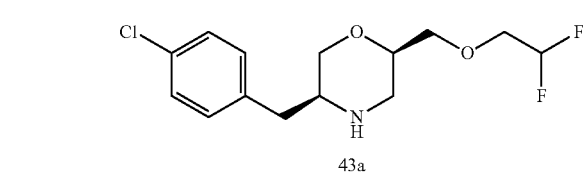

The title compound (43a) was obtained from 7a (171 mg; 0.48 mmol) according to the General Procedure XI in 99% yield (146 mg; 0.48 mmol).

ESI-MS $C_{14}H_{19}ClF_2NO_2$ found 306.1/308.1 (M+H)$^+$.

Step 2

Synthesis of 5-(4-((2R,5S)-5-(4-chlorobenzyl)-2-((2,2-difluoroethoxy)methyl)morpholino)-piperidin-1-yl)-4H-1,2,4-triazol-3-amine 2,2,2-trifluoroacetate (43)

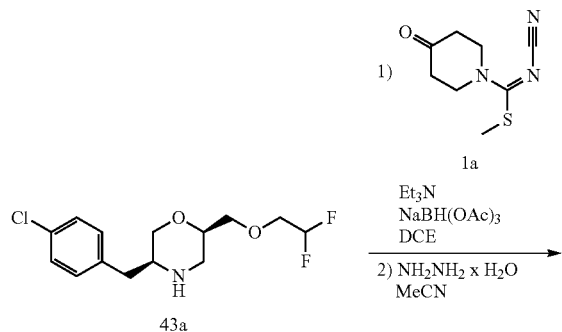

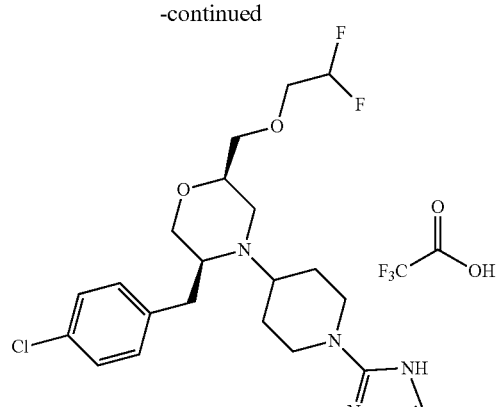

The title compound (43) was obtained as a TFA salt from 43a (146 mg; 0.48 mmol) according to the General Procedure Vb in 15% yield (41 mg; 0.07 mmol).

ESI-MS $C_{21}H_{30}ClF_2N_6O_2$ found 471.0/473.0 (M+H)$^+$; H NMR (700 MHz, DMSO-$d_6$+$D_2O$, 348 K) δ 7.42-7.35 (m, 2H), 7.35-7.22 (m, 2H), 6.08 (tt, J=54.9, 3.6 Hz, 1H), 3.96-3.85 (m, 3H), 3.84-3.55 (m, 9H), 3.19-3.07 (m, 3H), 2.96-2.84 (m, 2H), 2.26-2.08 (m, 2H), 1.74-1.54 (m, 2H).

Example 44

Synthesis of 5-(4-((2R,5S)-2-((4-chloro-1H-pyrazol-1-yl)methyl)-5-(4-chlorobenzyl)-morpholino)piperidin-1-yl)-4H-1,2,4-triazol-3-amine 2,2,2-trifluoroacetate (44)

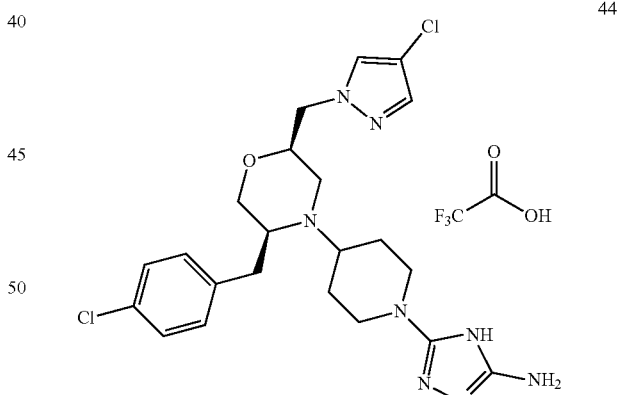

The title compound 44 was obtained as a TFA salt in 26% overall yield in a similar way to Example 8 with the exception that, in the first step of the synthesis, 4-chloro-1H-pyrazole was used instead of 4-cyanopyrazole.

ESI-MS m/z for $C_{22}H_{29}Cl_2N_8O$ found 491.1/493.1 (M+1)$^+$; $^1$H NMR (700 MHz, DMSO-$d_6$+$D_2O$, 348 K) δ 7.88 (d, J=0.6 Hz, 1H), 7.55 (d, J=0.6 Hz, 1H), 7.38-7.35 (m, 2H), 7.26-7.23 (m, 2H), 4.37-4.27 (m, 2H), 4.16-4.05 (m, 1H), 3.90-3.82 (m, 2H), 3.70-3.63 (m, 2H), 3.62-3.52 (m, 3H), 3.14-3.01 (m, 2H), 3.00-2.89 (m, 3H), 2.20-2.12 (m, 2H), 1.73-1.53 (m, 2H).

Example 45

Synthesis of (2R,5S)-4-(1-(5-amino-4H-1,2,4-triazol-3-yl)piperidin-4-yl)-5-(4-chlorobenzyl)-N-(2-(methylsulfonyl)ethyl)morpholine-2-carboxamide 2,2,2-trifluoroacetate (45)

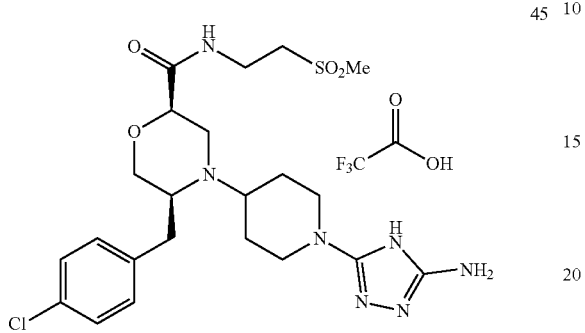

The title compound 45 was obtained as a TFA salt in 21% overall yield in a similar way to Example 23 with the exception that, in the first step of the synthesis, 2-(methylsulfonyl)ethane-amine hydrochloride was used instead of 2,2-dimethylcyclopropane-1-amine hydrochloride.

ESI-MS m/z for $C_{22}H_{33}ClN_7O_4S$ found 526.2/528.2 (M+1)$^+$; $^1$H NMR (700 MHz, DMSO-d$_6$+D$_2$O, 348 K) δ 7.43-7.34 (m, 2H), 7.36-7.28 (m, 2H), 4.26-4.18 (m, 1H), 3.88-3.76 (m, 2H), 3.75-3.55 (m, 5H), 3.41-3.38 (m, 1H), 3.35-3.30 (m, 2H), 3.19-3.10 (m, 1H), 3.09-3.01 (m, 2H), 3.00 (s, 3H), 2.97-2.89 (m, 2H), 2.12-2.00 (m, 2H), 1.68-1.52 (m, 2H).

Example 46

Synthesis of (2R,5S)-4-(1-(5-amino-4H-1,2,4-triazol-3-yl)piperidin-4-yl)-5-(4-chlorobenzyl)-N-(2-(N-methylsulfamoyl)ethyl)morpholine-2-carboxamide 2,2,2-trifluoroacetate (46)

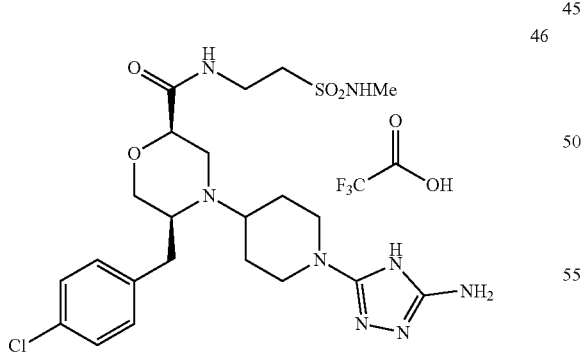

The title compound 46 was obtained as a TFA salt in 22% overall yield in a similar way to Example 23 with the exception that, in the first step of the synthesis, 2-amino-N-methylethane-sulfonamide hydrochloride was used instead of 2,2-dimethylcyclopropane-1-amine hydrochloride.

ESI-MS m/z for $C_{22}H_{34}ClN_8O_4S$ found 541.1/543.1 (M+1)$^+$; $^1$H NMR (700 MHz, DMSO-d$_6$+D$_2$O, 348 K) δ 7.40-7.36 (m, 2H), 7.34-7.29 (m, 2H), 4.23-4.18 (m, 1H), 3.86-3.79 (m, 2H), 3.70-3.65 (m, 2H), 3.58-3.49 (m, 3H), 3.39-3.36 (m, 1H), 3.26-3.19 (m, 2H), 3.18-3.09 (m, 1H), 3.08-3.01 (m, 2H), 2.99-2.90 (m, 2H), 2.67-2.58 (m, 3H), 2.11-2.01 (m, 2H), 1.67-1.54 (m, 2H).

Example 47

Synthesis of 5-(4-((2R,5S)-2-((1H-imidazol-1-yl)methyl)-5-(4-chlorobenzyl)morpholino)-piperidin-1-yl)-4H-1,2,4-triazol-3-amine 2,2,2-trifluoroacetate (47)

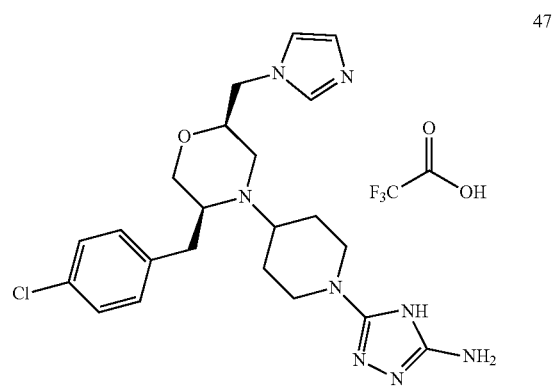 [SMILES: Nc1nnc(N2CCC(N3C[C@H](Cn4ccnc4)OC[C@@H]3Cc3ccc(Cl)cc3)CC2)[nH]1 ; O=C(O)C(F)(F)F]

The title compound 47 was obtained as a TFA salt in 9% overall yield in a similar way to Example 27 with the exception that, in the third step of the synthesis, imidazole was used instead of 1,2,4-triazole and in the fourth step of the synthesis, the synthesis was carried out according to the General Procedure IVa instead of General Procedure IVb.

ESI-MS m/z for $C_{22}H_{30}ClN_8O$ found 457.1/459.1 (M+1)$^+$; $^1$H NMR (700 MHz, D$_2$O) δ 8.85-8.72 (m, 1H), 7.59-7.53 (m, 1H), 7.53-7.46 (m, 1H), 7.43-7.35 (m, 2H), 7.30-7.20 (m, 2H), 4.61-4.52 (m, 1H), 4.51-4.43 (m, 1H), 4.26-4.19 (m, 1H), 3.91-3.82 (m, 4H), 3.80-3.72 (m, 2H), 3.70-3.60 (m, 1H), 3.26-3.20 (m, 1H), 3.15-3.11 (m, 2H), 3.09-3.03 (m, 2H), 2.40-2.31 (m, 2H), 1.83-1.69 (m, 2H).

Example 48

Synthesis of ((2R,5S)-4-(1-(5-amino-4H-1,2,4-triazol-3-yl)piperidin-4-yl)-5-(4-chlorobenzyl)morpholin-2-yl)methyl dimethylcarbamate 2,2,2-trifluoroacetate (48)

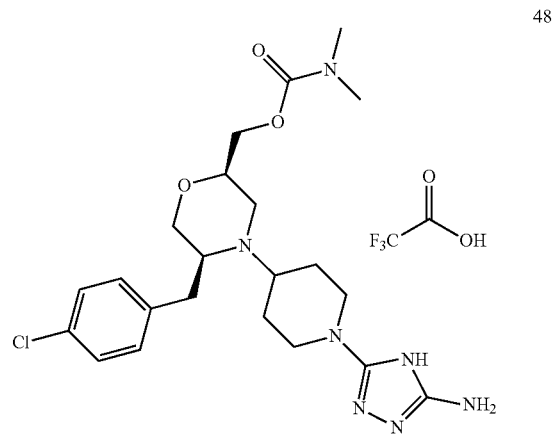 [SMILES: CN(C)C(=O)OC[C@H]1CN(C2CCN(c3nnc(N)[nH]3)CC2)[C@@H](Cc2ccc(Cl)cc2)CO1 ; O=C(O)C(F)(F)F]

207

Step 1

Synthesis of tert-butyl 4-((2R,5S)-5-(4-chlorobenzyl)-2-(((dimethylcarbamoyl)oxy)methyl)-morpholino)piperidine-1-carboxylate (48a)

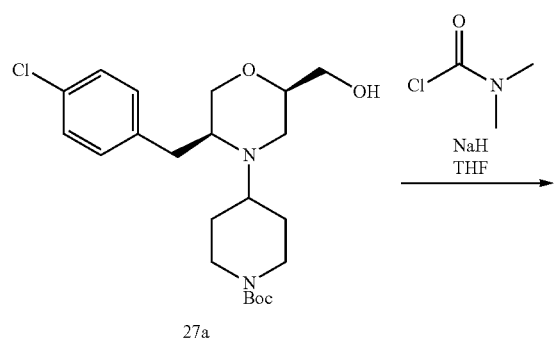

To a solution of 27a (152 mg; 0.36 mmol) in THF (2.5 mL) sodium hydride (60% in oil; 43 mg; 1.08 mmol) and dimethyl carbamoyl chloride (65 µL; 1.08 mmol) were added and the resulting mixture was stirred at room temperature for 5.5 hours. The reaction progress was monitored by LC-MS. When analysis indicated completion of the reaction, the reaction mixture was cooled to 0° C. and water was carefully added and then the product was extracted with DCM (3×). Combined organic layers were dried over MgSO$_4$, filtered and concentrated in vacuo and the crude product was used in the next step without additional purification. Compound 48a was obtained in 88% yield (158 mg; 0.32 mmol).

ESI-MS C$_{25}$H$_{39}$ClN$_3$O$_5$ found 496.1/498.1 (M+H)$^+$; H NMR (700 MHz, CDCl$_3$) δ 7.28-7.21 (m, 2H), 7.19-7.07 (m, 2H), 4.21-4.13 (m, 2H), 4.11-4.03 (m, 1H), 3.81-3.75 (m, 1H), 3.68 (dd, J=11.4, 1.5 Hz, 1H), 3.52-3.47 (m, 1H), 3.02-2.92 (m, 7H), 2.91-2.86 (m, 1H), 2.79-2.75 (m, 1H), 2.72-2.64 (m, 2H), 2.56-2.46 (m, 1H), 1.97-1.86 (m, 2H), 1.61-1.56 (m, 2H), 1.50-1.45 (m, 9H), 1.29-1.24 (m, 2H), 0.94-0.85 (m, 1H).

208

Step 2

Synthesis of ((2R,5S)-5-(4-chlorobenzyl)-4-(piperidin-4-yl)morpholin-2-yl)methyl dimethylcarbamate hydrochloride (48b)

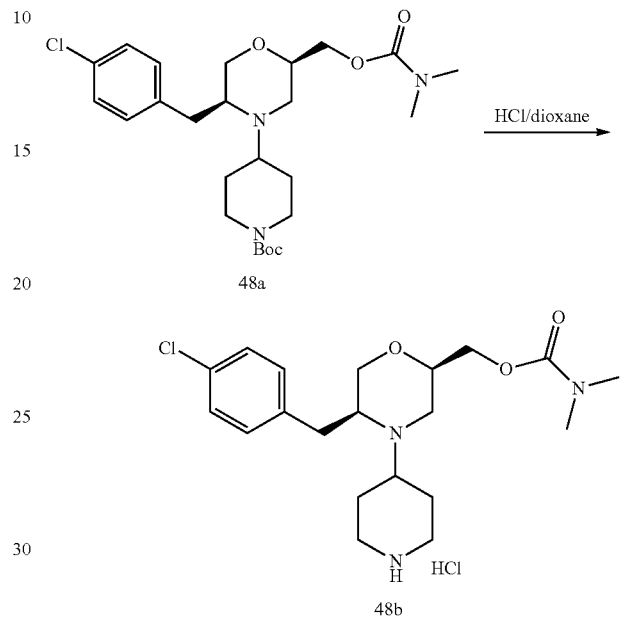

The title compound (48b) was obtained as a hydrochloride salt from 48 (156 mg; 0.31 mmol) according to the General Procedure IVa in 98% yield (131 mg; 0.30 mmol).

ESI-MS C$_{20}$H$_{31}$ClN$_3$O$_3$ found 395.9/397.9 (M+H)$^+$ $^1$H NMR (700 MHz, D$_2$O) δ 7.43-7.37 (m, 2H), 7.29-7.20 (m, 2H), 4.33 (dd, J=12.3, 2.9 Hz, 1H), 4.21-4.15 (m, 1H), 4.15-4.09 (m, 1H), 3.89-3.73 (m, 4H), 3.68-3.58 (m, 3H), 3.36-3.30 (m, 1H), 3.19-3.05 (m, 4H), 2.95 (s, 3H), 2.89 (s, 3H), 2.58-2.48 (m, 2H), 1.98-1.83 (m, 2H).

Step 3

Synthesis of ((2R,5S)-4-(1-(5-amino-4H-1,2,4-triazol-3-yl)piperidin-4-yl)-5-(4-chlorobenzyl)-morpholin-2-yl)methyl dimethylcarbamate 2,2,2-trifluoroacetate (48)

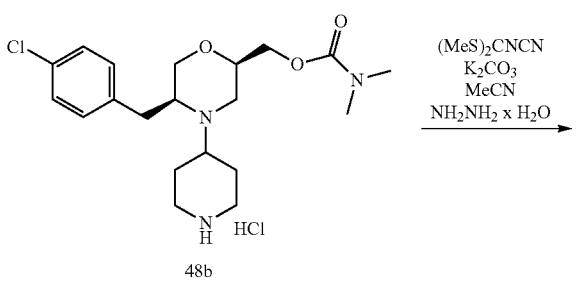

209
-continued

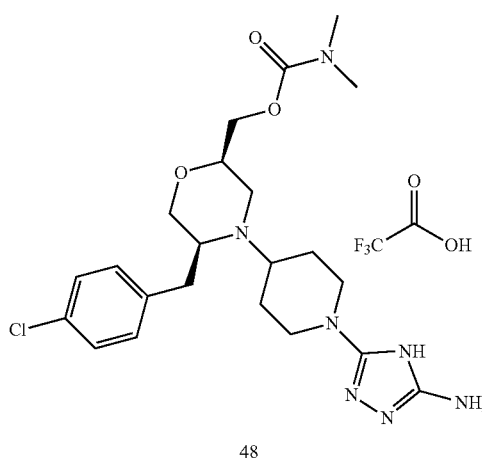

48

The title compound (48) was obtained as a TFA salt from 48b (109 mg; 0.25 mmol) according to the General Procedure Va in 28% yield (42 mg; 0.071 mmol).

ESI-MS $C_{22}H_{33}ClN_7O_3$ found 478.3/480.3 (M+H)$^+$; $^1$H NMR (700 MHz, D$_2$O) δ 7.44-7.35 (m, 2H), 7.27-7.19 (m, 2H), 4.41-4.30 (m, 1H), 4.26-4.10 (m, 2H), 3.93-3.85 (m, 3H), 3.85-3.80 (m, 1H), 3.80-3.71 (m, 2H), 3.71-3.65 (m, 1H), 3.41-3.33 (m, 1H), 3.24-3.14 (m, 2H), 3.12-3.03 (m, 2H), 2.95 (s, 3H), 2.89 (s, 3H), 2.40-2.32 (m, 2H), 1.82-1.68 (m, 2H).

Example 49

Synthesis of 5-(4-((2R,5S)-5-(4-chlorobenzyl)-2-(4-methyloxazol-2-yl)morpholino)piperidin-1-yl)-4H-1,2,4-triazol-3-amine 2,2,2-trifluoroacetate (49)

210
Step 1

Synthesis of (2R,5S)-tert-butyl 5-(4-chlorobenzyl)-2-(4-methyloxazol-2-yl)morpholine-4-carboxylate (49a)

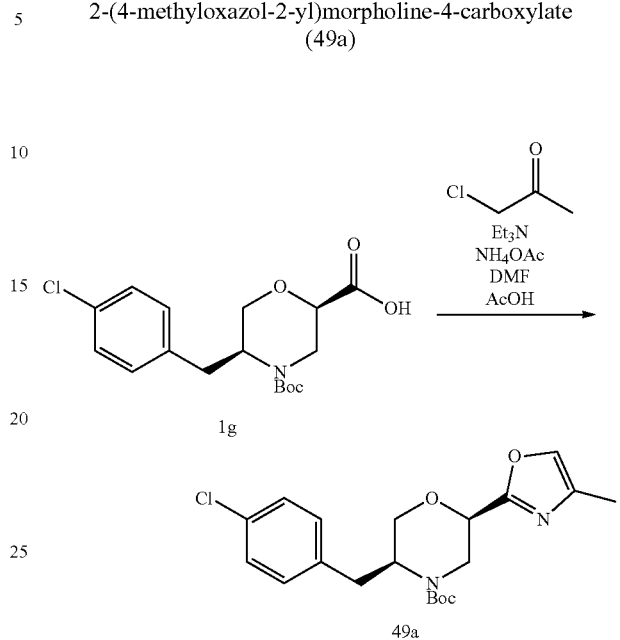

To a solution of 1g (150 mg; 0.42 mmol) and Et$_3$N (71 μL; 0.5 mmol) in DMF (5 mL) under argon atmosphere chloroacetone (38 μL; 0.46 mmol) and ammonium acetate (195 mg; 2.52 mmol) were added and the resulting mixture was stirred at room temperature. The reaction progress was monitored by LC-MS. When analysis indicated completion of the reaction, AcOEt was added and the mixture was then washed with 0.5 M HCl, NaHCO$_3$. Combined organic layers were dried over Na$_2$SO$_4$, filtered and concentrated in vacuo and the crude product was dissolved in AcOH (8 mL) and the solution was stirred at 115° C. The reaction progress was monitored by LC-MS. When analysis indicated completion of the reaction, mixture was evaporated with MeOH (3×). Crude product was used in the next step without additional purification. Compound 49a was obtained in 99% yield (165 mg; 0.42 mmol).

ESI-MS $C_{20}H_{26}ClN_2O_4$ found 393.2/395.2 (M+H)$^+$

Step 2

Synthesis of (2R,5S)-5-(4-chlorobenzyl)-2-(4-methyloxazol-2-yl)morpholine 2,2,2-trifluoroacetate (49b)

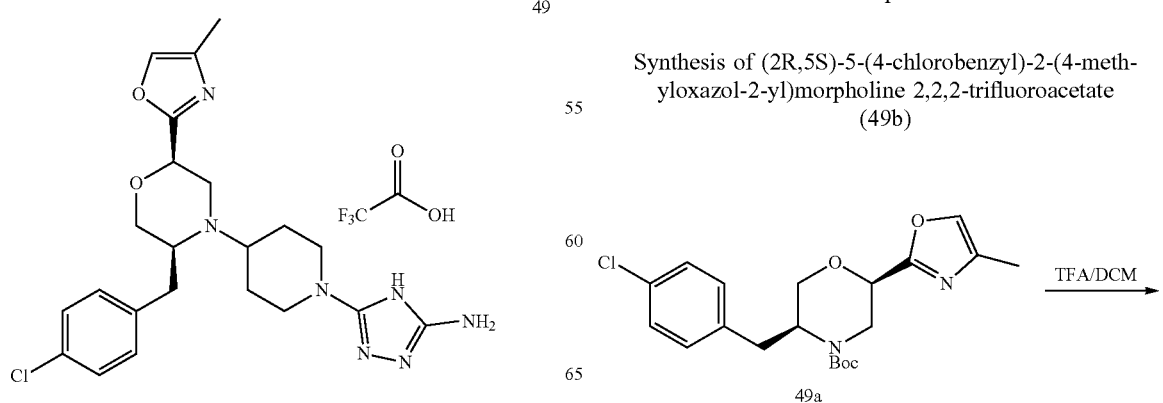

49a

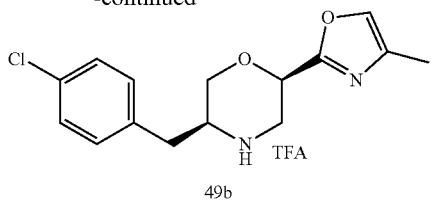

49b

The title compound (49b) was obtained as a TFA salt from 49a (165 mg; 0.42 mmol) according to the General Procedure IVb in 99% yield (171 mg; 0.42 mmol).

Step 3

Synthesis of 5-(4-((2R,5S)-5-(4-chlorobenzyl)-2-(4-methyloxazol-2-yl)morpholino)piperidin-1-yl)-4H-1,2,4-triazol-3-amine 2,2,2-trifluoroacetate (49)

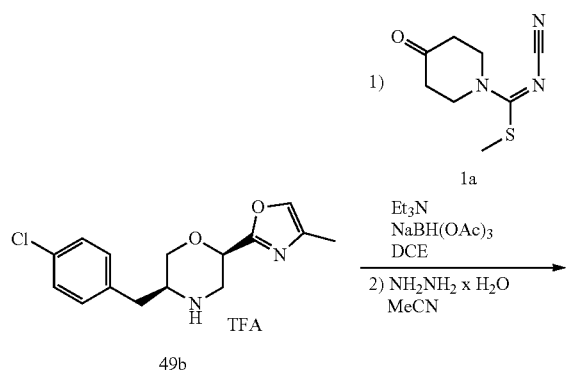

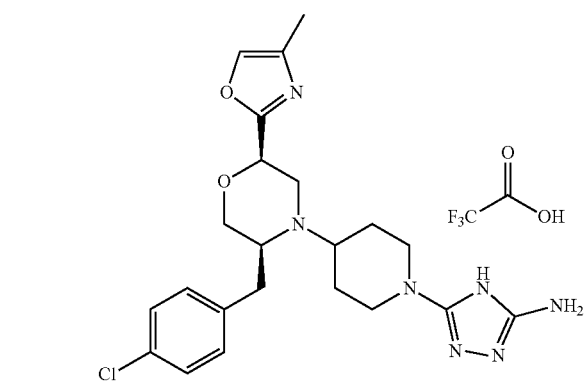

49

The title compound (49) was obtained as a TFA salt from 49b (171 mg; 0.42 mmol) according to the General Procedure Vb in 3% yield (7 mg; 0.012 mmol).
ESI-MS $C_{22}H_{29}ClN_7O_2$ found 458.1/460.1 (M+H)⁺; ¹H NMR (400 MHz, Methanol-$d_4$) δ 7.76-7.67 (m, 2H), 7.40-7.24 (m, 2H), 4.99-4.93 (m, 1H), 4.02-3.93 (m, 2H), 3.87-3.71 (m, 4H), 3.68-3.58 (m, 2H), 3.28-3.03 (m, 4H), 2.34-2.25 (m, 2H), 2.18 (s, 3H), 1.87-1.70 (m, 2H).

Example 50

Synthesis of 5-(4-((2R,5S)-5-(4-chlorobenzyl)-2-(4,5-dimethyloxazol-2-yl)morpholino)piperidin-1-yl)-4H-1,2,4-triazol-3-amine 2,2,2-trifluoroacetate (50)

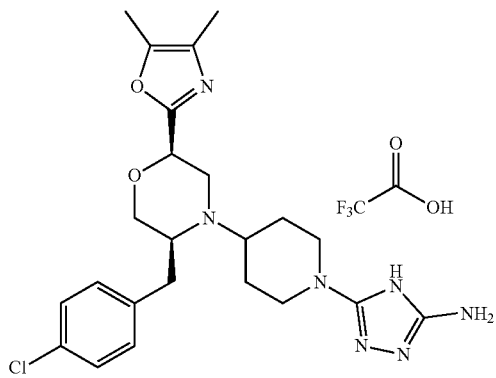

50

Step 1

Synthesis of (2R,5S)-tert-butyl 5-(4-chlorobenzyl)-2-(4,5-dimethyloxazol-2-yl)morpholine-4-carboxylate (50a)

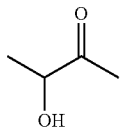

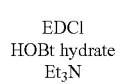

1g

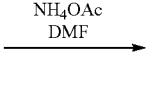

50a

A solution of 1g (150 mg; 0.42 mmol), 3-hydroxy-2-butanone (56 mg; 0.63 mmol), EDCI (121 mg; 0.63 mmol), HOBt hydrate (86 mg; 0.63 mmol) and $Et_3N$ (177 μL; 1.26 mmol) in DMF (4 mL) was stirred at room temperature overnight. The reaction progress was monitored by TLC. When analysis indicated completion of the reaction, water and AcOEt were added and the mixture was then washed with 0.5 M HCl, NaHCO₃. Combined organic layers were dried over Na₂SO₄, filtered and concentrated in vacuo and to the crude product AcOH (8 mL) and NH₄OAc (195 mg; 2.52 mmol) were added and the mixture was refluxed for 4 hours. Then the mixture was evaporated with MeOH (2×). Crude product was used in the next step without additional purification. Compound 50a was obtained in 99% yield (171 mg; 0.42 mmol).

ESI-MS $C_{21}H_{28}ClN_2O_4$ found 407.2/409.2 (M+H)⁺.

Step 2

Synthesis of (2R,5S)-5-(4-chlorobenzyl)-2-(4,5-dimethyloxazol-2-yl)morpholine 2,2,2-trifluoroacetate (50b)

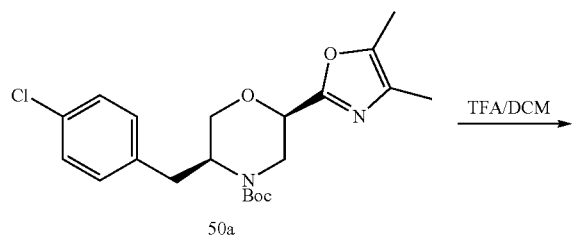

The title compound (50b) was obtained as a TFA salt from 50a (171 mg; 0.42 mmol) according to the General Procedure IVb in 99% yield (176 mg; 0.42 mmol).

Step 3

Synthesis of 5-(4-((2R,5S)-5-(4-chlorobenzyl)-2-(4,5-dimethyloxazol-2-yl)morpholino)piperidin-1-yl)-4H-1,2,4-triazol-3-amine 2,2,2-trifluoroacetate (50)

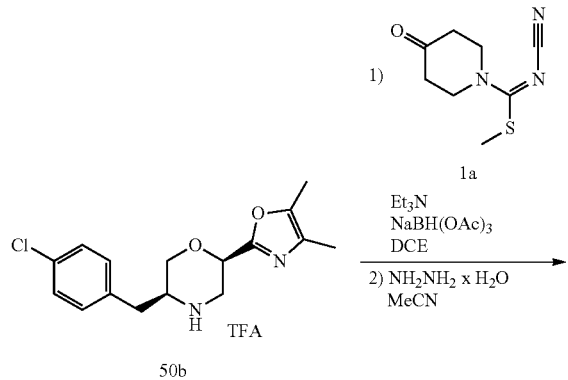

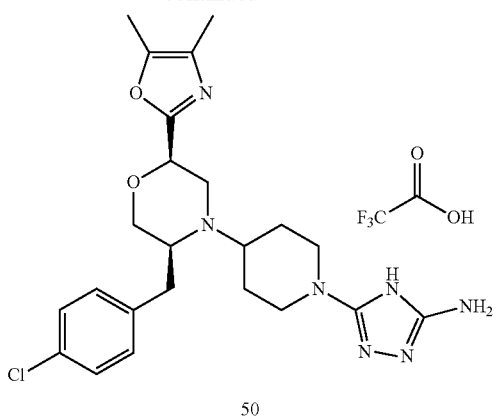

The title compound (50) was obtained as a TFA salt from 50b (176 mg; 0.42 mmol) according to the General Procedure Vb in 5% yield (12 mg; 0.02 mmol).

ESI-MS $C_{22}H_{29}ClN_7O_2$ found 472.2/474.2 (M+H)⁺; ¹H NMR (400 MHz, Methanol-d₄) δ 7.41-7.36 (m, 2H), 7.35-7.31 (m, 2H), 4.99-4.94 (m, 1H), 4.00-3.92 (m, 2H), 3.88-3.72 (m, 5H), 3.71-3.62 (m, 1H), 3.28-3.00 (m, 4H), 2.40-2.25 (m, 5H), 2.16-2.08 (m, 3H), 1.88-1.74 (m, 2H).

Example 51

Synthesis of 5-(4-((2S,5S)-5-(4-chlorobenzyl)-2-((3-methylazetidin-1-yl)methyl)morpholino)-piperidin-1-yl)-4H-1,2,4-triazol-3-amine 2,2,2-trifluoroacetate (51)

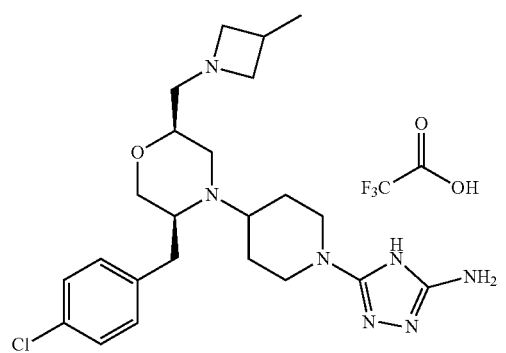

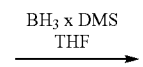

-continued

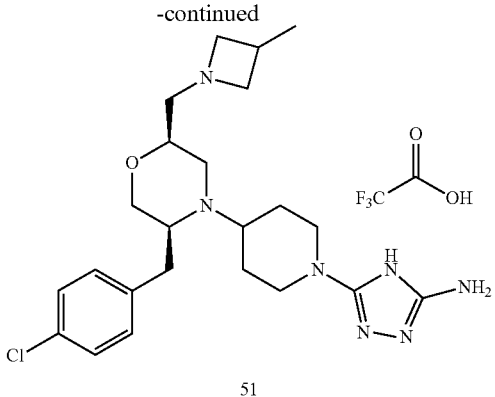

51

The title compound (51) was obtained as a TFA salt from 61 (85 mg; 0.14 mmol) according to the General Procedure Ia in 57% yield (46 mg; 0.08 mmol).

ESI-MS $C_{23}H_{35}ClN_7O$ found 460.2/462.2 (M+H)$^+$; $^1$H NMR (700 MHz, D$_2$O) δ 7.46-7.35 (m, 2H), 7.28-7.19 (m, 2H), 4.38-4.28 (m, 1H), 4.26-4.17 (m, 1H), 4.11-4.03 (m, 1H), 4.03-3.83 (m, 5H), 3.81-3.60 (m, 4H), 3.53-3.45 (m, 1H), 3.44-3.37 (m, 1H), 3.27-3.12 (m, 3H), 3.08-2.91 (m, 3H), 2.37-2.25 (m, 2H), 1.80-1.66 (m, 2H), 1.31-1.14 (m, 3H).

Example 52

Synthesis of 5-(4-((2S,5S)-5-(4-chlorobenzyl)-2-(piperidin-1-ylmethyl)morpholino)piperidin-1-yl)-4H-1,2,4-triazol-3-amine 2,2,2-trifluoroacetate (52)

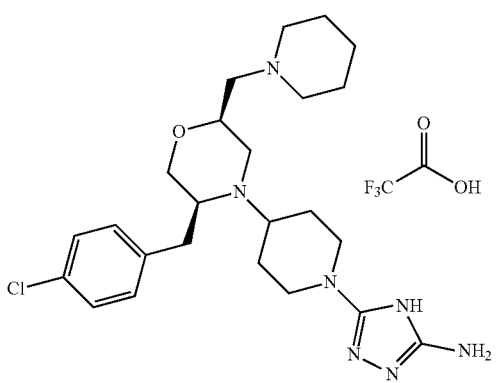

52

The title compound 52 was obtained as a TFA salt in 22% overall yield in a similar way to Example 27 with the exception that, in the third step of the synthesis, piperidine was used instead of 1,2,4-triazole and in the fourth step of the synthesis, the synthesis was carried out according to the General Procedure IVa instead of General Procedure IVb.

ESI-MS $C_{24}H_{37}ClN_7O$ found 474.3/476.3 (M+H)$^+$; $^1$H NMR (700 MHz, D$_2$O) δ 7.45-7.36 (m, 2H), 7.30-7.19 (m, 2H), 4.36-4.22 (m, 1H), 3.95-3.91 (m, 1H), 3.91-3.84 (m, 3H), 3.81-3.70 (m, 2H), 3.68-3.62 (m, 1H), 3.59-3.50 (m, 2H), 3.46-3.35 (m, 1H), 3.33-3.28 (m, 1H), 3.28-3.23 (m, 2H), 3.20-3.13 (m, 1H), 3.09-3.02 (m, 3H), 3.00-2.91 (m, 1H), 2.39-2.28 (m, 2H), 1.94-1.88 (m, 2H), 1.82-1.66 (m, 5H), 1.53-1.38 (m, 1H).

Example 53

Synthesis of ((2R,5S)-4-(1-(5-amino-4H-1,2,4-triazol-3-yl)piperidin-4-yl)-5-(4-chlorobenzyl)-morpholin-2-yl)(4,4-difluoropiperidin-1-yl)methanone 2,2,2-trifluoroacetate (53)

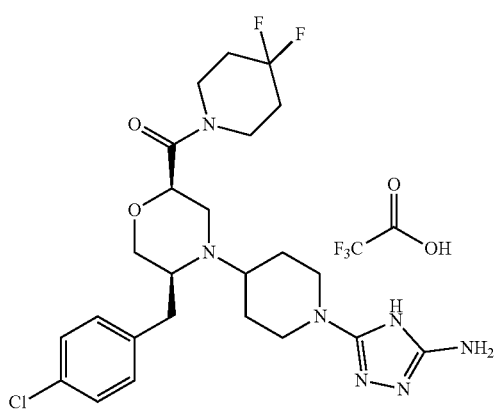

53

The title compound 53 was obtained as a TFA salt in 47% overall yield in a similar way to Example 23 with the exception that, in the first step of the synthesis, 4,4-difluoropiperidine hydrochloride was used instead of 2,2-dimethylcyclopropane-1-amine hydrochloride.

ESI-MS m/z for $C_{24}H_{33}ClF_2N_7O_2$ found 524.1/526.1 (M+1)$^+$; $^1$H NMR (700 MHz, DMSO-d$_6$+D$_2$O, 348 K) δ 7.42-7.33 (m, 2H), 7.33-7.23 (m, 2H), 4.74-4.57 (m, 1H), 3.92-3.83 (m, 2H), 3.83-3.75 (m, 1H), 3.71-3.57 (m, 8H), 3.35-3.27 (m, 1H), 3.22-3.12 (m, 1H), 3.06-2.98 (m, 1H), 2.96-2.82 (m, 2H), 2.11-1.95 (m, 6H), 1.73-1.54 (m, 2H); $^{19}$F NMR (235 MHz, DMSO-d$_6$) δ −70.18 (s), −91.93 (d, J=104.0 Hz).

Example 54

Synthesis of ((2R,5S)-4-(1-(5-amino-4H-1,2,4-triazol-3-yl)piperidin-4-yl)-5-(4-chlorobenzyl)-morpholin-2-yl)(3,3-difluoropyrrolidin-1-yl)methanone 2,2,2-trifluoroacetate (54)

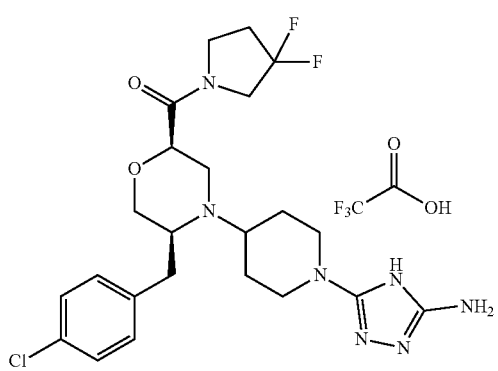

54

The title compound 54 was obtained as a TFA salt in 3% overall yield in a similar way to Example 23 with the exception that, in the first step of the synthesis, 3,3-difluoropyrrolidine was used instead of 2,2-dimethylcyclopropane-1-amine hydrochloride.

ESI-MS m/z for $C_{23}H_{31}ClF_2N_7O_2$ found 510.1/512.1 (M+1)$^+$; $^1$H NMR (700 MHz, DMSO-d$_6$+D$_2$O, 348 K) δ 7.42-7.35 (m, 2H), 7.32-7.24 (m, 2H), 4.51 (d, J=59.2 Hz, 1H), 4.05-3.94 (m, 1H), 3.90-3.75 (m, 5H), 3.73-3.57 (m, 4H), 3.42-3.35 (m, 2H), 3.16-3.09 (m, 1H), 3.09-3.01 (m, 1H), 2.96-2.86 (m, 2H), 2.48-2.35 (m, 2H), 2.15-1.97 (m, 2H), 1.74-1.58 (m, 2H).

Example 55

Synthesis of 5-(4-((2S,4R)-2-(4-chlorobenzyl)-4-morpholinopyrrolidin-1-yl)piperidin-1-yl)-4H-1,2,4-triazol-3-amine 2,2,2-trifluoroacetate (55)

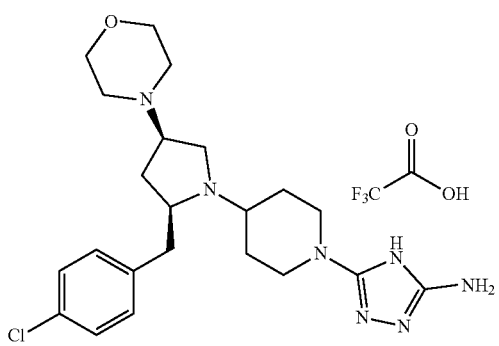

Step 1

Synthesis of (2R,4S)-1-tert-butyl 2-methyl 4-hydroxypyrrolidine-1,2-dicarboxylate (55a)

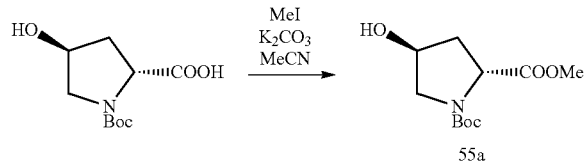 [SMILES: CC(C)(C)OC(=O)N1C[C@@H](O)C[C@@H]1C(=O)O ; COC(=O)[C@H]1C[C@H](O)CN1C(=O)OC(C)(C)C]

To a solution of N-Boc-trans-4-hydroxy-D-proline (10.00 g; 43.25 mmol) in acetonitrile (100 mL), potassium carbonate (11.95 g; 86.50 mmol) was added followed by methyl iodide (5.40 mL, 86.50 mmol) and resulting mixture was stirred overnight. LC-MS indicated presence of substrate. Another portion of potassium carbonate (5.98 g; 43.25 mmol) and methyl iodide was added (2.7 mL; 43.25 mmol) and reaction was stirred for 2 days after which time LC-MS indicated completion of the reaction. Reaction mixture was filtered and solid residue was washed with EtOAc. After evaporation of filtrate the product 55a was obtained as a yellowish oil in 88% yield (9.37 g; 38.22 mmol).

ESI-MS m/z for $C_{11}H_{19}NO_5$ found 145.9 (M+H-Boc)$^+$, 268.0 (M+Na)$^+$.

Step 2

Synthesis of (2R,4S)-1-tert-butyl 2-methyl 4-((tert-butyldimethylsilyl)oxy)pyrrolidine-1,2-dicarboxylate (55b)

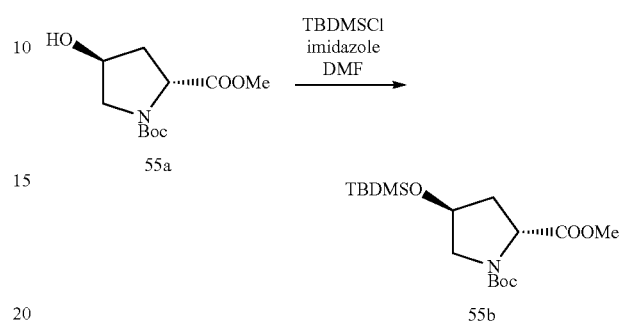

To a solution of 55a (5 g; 20.38 mmol) in DMF (60 mL), imidazole (6.94 g; 101.90 mmol) was added followed by TBDMSCl (4.61 g; 30.57 mmol) and reaction was stirred overnight. When LC-MS analysis indicated completion of the reaction, reaction mixture was taken between water and EtOAc. Organic layer was washed with water, brine, dried over anhydrous MgSO$_4$, filtered and concentrated. Crude product was purified by column chromatography (hexane/EtOAc 8:1 v/v) to give 55b as a colorless oil in 92% yield (6.7 g; 18.63 mmol).

ESI-MS m/z for $C_{17}H_{33}NO_5Si$ found 260.2 (M+H-Boc)$^+$, 382.1 (M+Na)$^+$; $^1$H NMR (700 MHz, CDCl$_3$) δ [4.43-4.40 (m); 4.33 (d, J=7.7 Hz); 2H], [3.74 (s); 3.72 (s); 3H], [3.61 (dd, J=11.2, 4.6 Hz); 3.57 (dd, J=11.0, 4.8 Hz); 1H], [3.40 (dd, J=11.4, 1.3 Hz); 3.37 (dd, J=11.2, 2.4 Hz); 1H], 2.20-2.14 (m, 1H), 2.04-1.98 (m, 1H), [1.46 (s); 1.41 (s); 9H], 087 (s, 9H), 0.06 (s, 6H).

Step 3

Synthesis of (2R,4S)-1-(tert-butoxycarbonyl)-4-((tert-butyldimethylsilyl)oxy)pyrrolidine-2-carboxylic Acid (55c)

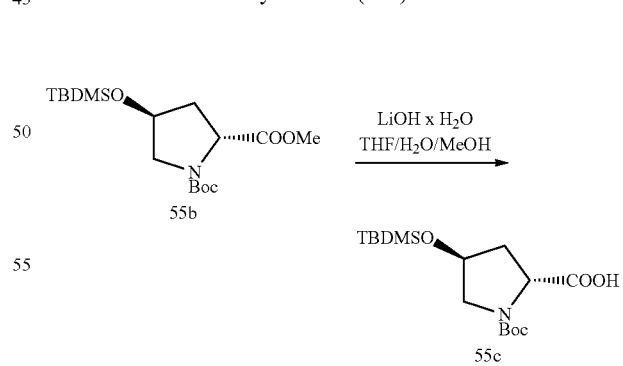

Compound 55b (6.70 g; 18.63 mmol) was dissolved in a mixture of 200 mL THF and 100 mL MeOH. Solution of lithium hydroxide hydrate in 100 mL of water was added to the reaction mixture and resulting mixture was stirred overnight. After LC-MS control indicated completion of the reaction, reaction mixture was concentrated. Water residue was acidified to pH 4 with 2 N HCl at 0° C. and product was extracted with EtOAc. Organic layer was washed with brine, dried over anhydrous MgSO₄, filtered and concentrated in vacuo to give product 55c as a yellowish oil in 80% yield (5.13 g; 14.85 mmol).

ESI-MS m/z for $C_{16}H_{31}NO_5Si$ found 246.1 (M+H-Boc)⁺, 368.1 (M+Na)⁺, 344.1 (M-H)-

Step 4

Synthesis of (2R,4S)-tert-butyl 4-((tert-butyldimethylsilyl)oxy)-2-(methoxy(methyl)carbamoyl)-pyrrolidine-1-carboxylate (55d)

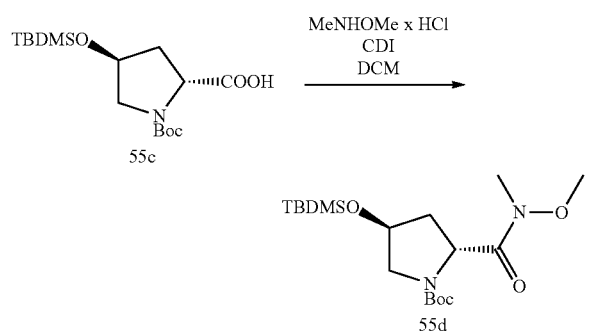

To a solution of compound 55c (10 g; 14.85 mmol) in DCM (40 mL), triethylamine (5.2 mL; 37.12 mmol) was added, followed by carbonyldiimidazole (CDI; 3.61 g; 22.28 mmol), and the reaction was stirred for 1 hour. N,O-Dimethylhydroxylamine hydrochloride (2.17 g; 22.28 mmol) was added and the reaction was stirred overnight, after which time LC-MS control indicated completion of the reaction. The reaction mixture was washed with water and brine. Organic layer was dried over anhydrous MgSO₄, filtered and concentrated. Crude product was purified by column chromatography (hexane/EtOAc 5:1 v/v) to give 55d as a colorless oil in 72% yield (4.15 g; 10.68 mmol).

ESI-MS m/z for $C_{18}H_{36}N_2O_5Si$ found 289.7/290.3 (M+H-Boc)⁺, 411.1/412.3 (M+Na)⁺; ¹H NMR (700 MHz, CDCl₃) δ [4.82 (brs); 4.73 (t, J=7.0 Hz); 1H], 4.45 (dq, 1H, J=18.0, 4.8 Hz), [3.79 (s); 3.72 (s); 3H], [3.68 (dd, J=11.0, 5.3 Hz); 3.64 (dd, J=11.0, 5.3 Hz); 1H], [3.40 (dd, J=11.0, 3.1 Hz); 3.32 (dd, J=10.8, 3.7 Hz); 1H], 3.20 (s, 3H), 2.18-2.12 (m, 1H), 2.00-1.95 (m, 1H), [1.45 (s); 1.41 (s); 9H], 0.88 (s, 9H), 0.06 (s, 6H).

Step 5

Synthesis of (2R,4S)-tert-butyl 4-((tert-butyldimethylsilyl)oxy)-2-(4-chlorobenzoyl)pyrrolidine-1-carboxylate (55e)

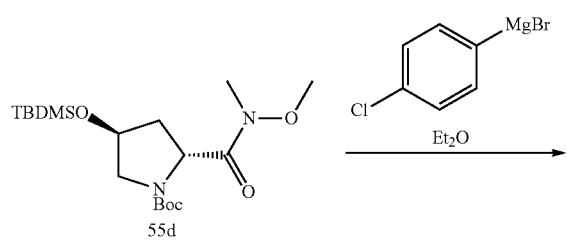

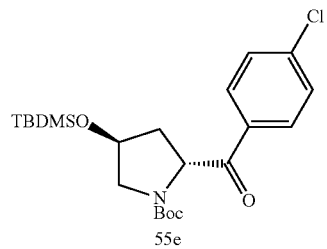

The title compound (55e) was obtained from 55d (1.00 g; 2.57 mmol) according to the General Procedure VI in 86% yield (970 mg; 2.20 mmol).

ESI-MS m/z for $C_{22}H_{34}ClNO_4Si$ found 340.0/341.9 (M+H-Boc)⁺, 462.1 (M+Na)⁺; ¹H NMR (700 MHz, DMSO-d₆+D₂O) 7.97-7.95 (m, 2H), 7.61-7.59 (m, 2H), 5.27-5.22 (m, 1H), 4.44-4.39 (m, 1H), [3.52 (dd, J=11.4, 4.4 Hz); 3.48 (dd, J=11.4, 4.4 Hz); 1H], [3.34 (m); 3.30 (m); 1H], 2.24-2.19 (m, 1H), [1.92 (ddd, J=12.9, 7.8, 4.8 Hz); 1.85 (ddd, J=13.0, 7.7, 4.8 Hz); 1H], [1.34 (s); 1.11 (s); 9H], 0.83 (s, 9H), [0.04 (s); 0.03 (s); 6H].

Step 6

Synthesis of (3S,5S)-5-(4-chlorobenzyl)pyrrolidin-3-ol (55f)

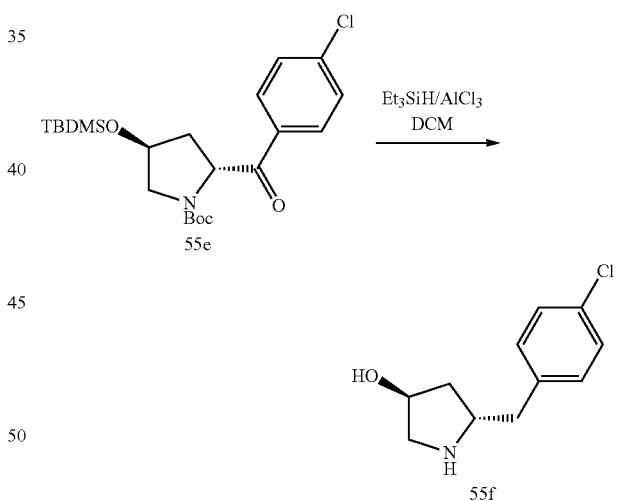

To a solution of compound 55e (970 mg; 2.20 mmol) in DCM (11 mL) AlCl₃ (880 mg; 6.60 mmol) was added under argon, followed by triethylsilane (1.05 mL; 6.60 mmol). Reaction was stirred for 45 minutes after which LC-MS control indicated completion of the reaction. Reaction was quenched with 4 M NaOH, saturated with sodium chloride, and filtrated through Celite. Product was extracted from water phase with DCM (3×20 mL). Combined organic layers were dried over anhydrous MgSO₄, filtered and concentrated in vacuo to give 55f as a yellowish oil in 99% yield (460 mg; 2.18 mmol).

ESI-MS m/z for $C_{11}H_{15}ClNO$ found 211.9 (M+H)⁺.

Step 7

Synthesis of (2S,4S)-tert-butyl 2-(4-chlorobenzyl)-4-hydroxypyrrolidine-1-carboxylate (55g)

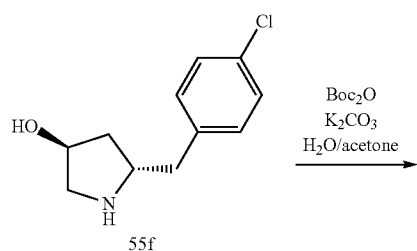

To a solution of compound 55f (840 mg; 3.97 mmol) in acetone (8 mL), water (8 mL) was added and pH was adjusted to 12 with K$_2$CO$_3$ (1.1 g; 7.94 mmol). Boc$_2$O (954 mg; 4.37 mmol) was added in one portion and reaction was stirred overnight after which time LC-MS control indicated completion of the reaction. Reaction mixture was concentrated to remove acetone. Water residue was saturated with NaCl and extracted with EtOAc. Organic layer was washed with brine, dried over anhydrous MgSO$_4$, filtered and concentrated in vacuo. Crude product was purified by column chromatography (hexane/EtOAc 1:1 v/v) to give 55g as a colorless oil in 6% yield (71 mg; 0.23 mmol).

ESI-MS m/z for C$_{16}$H$_{22}$ClNO$_3$ found 211.0/213.9 (M+H-Boc)$^+$, 256.0/257.8 (M+H-$^t$Bu)$^+$, 333.9 (M+Na)$^+$.

Step 8

Synthesis of (2S,4S)-tert-butyl 2-(4-chlorobenzyl)-4-((methylsulfonyl)oxy)pyrrolidine-1-carboxylate (55h)

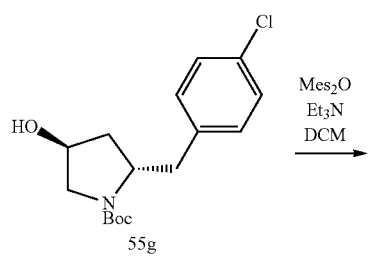

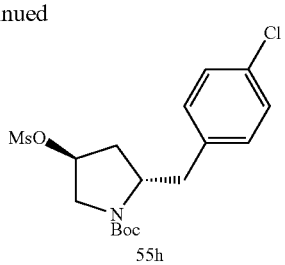

The title compound (55h) was obtained from 55g (240 mg; 0.76 mmol) according to the General Procedure X in 96% yield (284 mg; 0.73 mmol).

ESI-MS m/z for C$_{13}$H$_{17}$ClNO$_5$S found 333.8/335.8 (M+H−tBu)$^+$.

Step 9

Synthesis of (2S,4R)-tert-butyl 2-(4-chlorobenzyl)-4-morpholinopyrrolidine-1-carboxylate (55i)

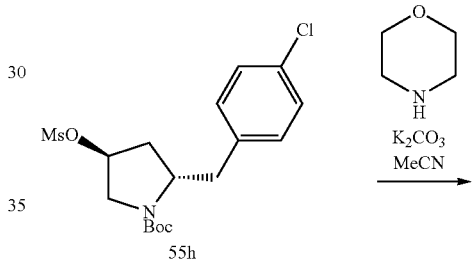

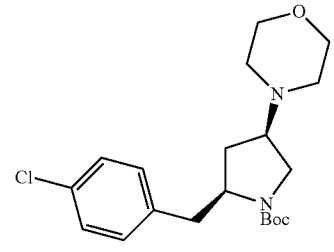

The title compound (55i) was obtained from 55h (284 mg; 0.73 mmol) according to the General Procedure VII in 82% yield (230 mg; 0.6 mmol).

ESI-MS m/z for C$_{20}$H$_{30}$ClN$_2$O$_3$ found 381.2/383.2 (M+H)$^+$; $^1$H NMR (700 MHz, DMSO-d$_6$+D$_2$O, 348 K) δ 7.36-7.26 (m, 2H), 7.20-7.14 (m, 2H), 3.92-3.85 (m, 1H), 3.74-3.66 (m, 1H), 3.56-3.52 (m, 4H), 3.11-3.05 (m, 1H), 2.79-2.69 (m, 2H), 2.37-2.32 (m, 2H), 2.31-2.24 (m, 2H), 2.05-1.97 (m, 1H), 1.45-1.42 (m, 1H), 1.41-1.40 (m, 9H), 1.40-1.36 (m, 1H).

Step 10

Synthesis of 4-((3R,5S)-5-(4-chlorobenzyl)pyrrolidin-3-yl)morpholine hydrochloride (55j)

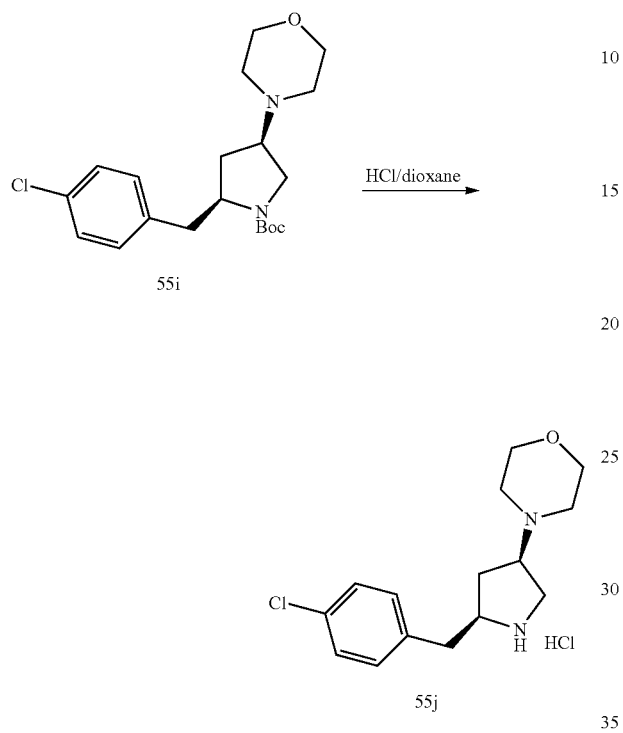

The title compound (55j) was obtained as a hydrochloride salt from 55i (230 mg; 0.6 mmol) according to the General Procedure IVa in 99% yield (187 mg; 0.59 mmol).

ESI-MS m/z for $C_{15}H_{22}ClN_2O$ found 280.9/282.9 $(M+H)^+$;

Step 11

Synthesis of 5-(4-((2S,4R)-2-(4-chlorobenzyl)-4-morpholinopyrrolidin-1-yl)piperidin-1-yl)-4H-1,2,4-triazol-3-amine 2,2,2-trifluoroacetate (55)

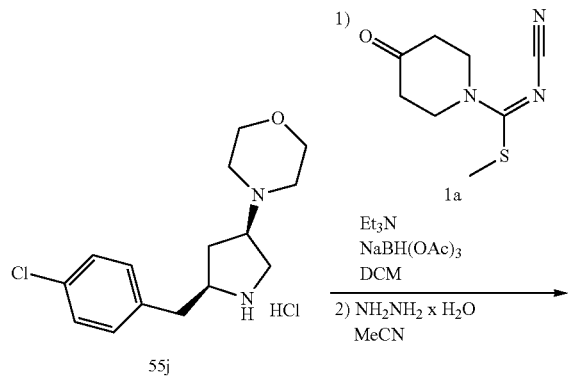

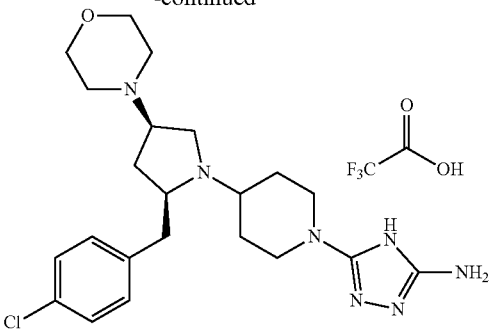

The title compound (55) was obtained as a TFA salt from 55j (187 mg; 0.59 mmol) according to the General Procedure Vb in 29% yield (94 mg; 0.17 mmol).

ESI-MS $C_{22}H_{33}ClN_7O$ found 446.2/448.2 $(M+H)^+$; $^1H$ NMR (700 MHz, DMSO-$d_6$+$D_2O$, 348 K) δ 7.40-7.35 (m, 2H), 7.35-7.27 (m, 2H), 3.92-3.83 (m, 2H), 3.77-3.64 (m, 5H), 3.35-3.19 (m, 4H), 2.91-2.81 (m, 3H), 2.81-2.68 (m, 4H), 2.53-2.52 (m, 1H), 2.15-2.11 (m, 1H), 2.03-1.88 (m, 2H), 1.77-1.56 (m, 3H).

Example 56

Synthesis of (S)-5-(4-(2-(4-chlorobenzyl)-4,4-difluoropyrrolidin-1-yl)piperidin-1-yl)-4H-1,2,4-triazol-3-amine dihydrochloride (56)

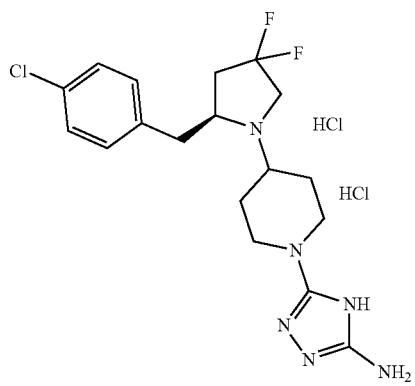

Step 1

Synthesis of (S)-tert-butyl 2-(4-chlorobenzyl)-4-oxopyrrolidine-1-carboxylate (56a)

225

-continued

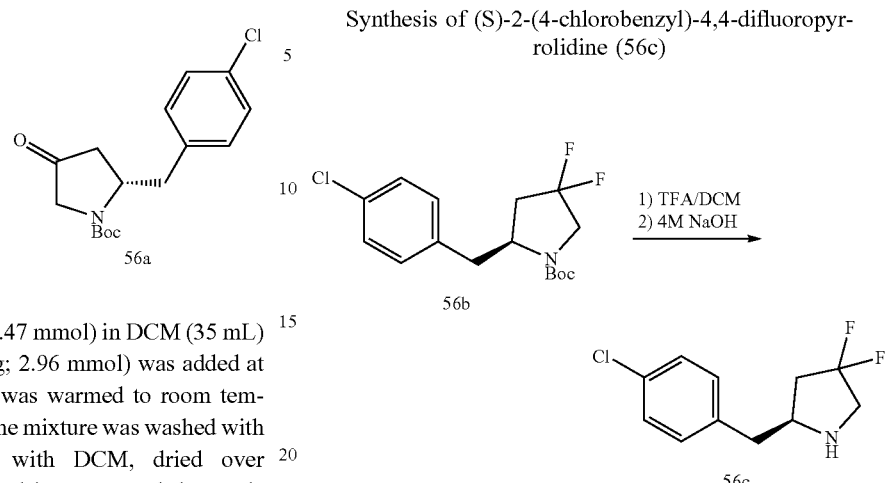

56a

To a solution of 55g (0.77 g; 2.47 mmol) in DCM (35 mL) Dess-Martin periodinane (1.26 g; 2.96 mmol) was added at 0° C. and the reaction mixture was warmed to room temperature and stirred for 1 hour. The mixture was washed with saturated $Na_2S_2O_3$, extracted with DCM, dried over $Na_2SO_4$, filtered and concentrated in vacuo and the crude product was used in the next step without additional purification. Compound 56a was obtained in 96% yield (0.73 g; 2.36 mmol).

Step 2

Synthesis of (S)-tert-butyl 2-(4-chlorobenzyl)-4,4-difluoropyrrolidine-1-carboxylate (56b)

The title compound (56b) was obtained from 56a (330 mg; 1.07 mmol) according to the General Procedure VII in 74% yield (260 mg; 0.79 mmol).

ESI-MS m/z for $C_{16}H_{21}ClF_2NO_2$ found 332.1/334.1 $(M+H)^+$.

226

Step 3

Synthesis of (S)-2-(4-chlorobenzyl)-4,4-difluoropyrrolidine (56c)

The title compound (56c) was obtained as a free base in 87% yield (159 mg; 0.69 mmol) from 56b (260 mg; 0.79 mmol) according to the General Procedure IVb followed by basic (4 M NaOH) extraction with DCM.

Step 4

Synthesis of (S)-tert-butyl 4-(2-(4-chlorobenzyl)-4,4-difluoropyrrolidin-1-yl)piperidine-1-carboxylate (56d)

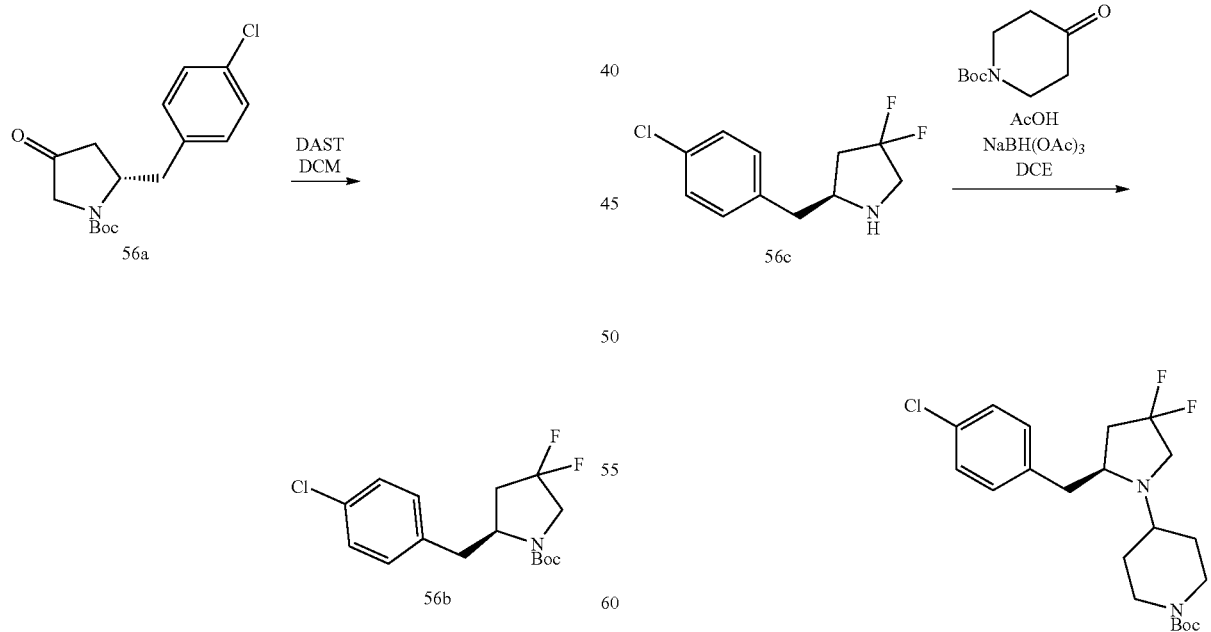

The title compound (56d) was obtained from 56c (159 mg; 0.69 mmol) according to the General Procedure IX in 99% yield (282 mg; 0.68 mmol).

Step 5

Synthesis of (S)-4-(2-(4-chlorobenzyl)-4,4-difluoropyrrolidin-1-yl)piperidine 2,2,2-trifluoroacetate (56e)

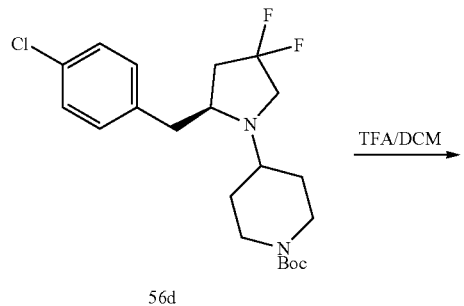

56d

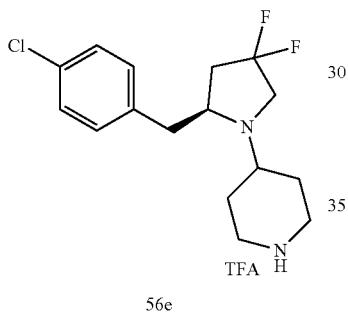

56e

The title compound (56e) was obtained as a TFA salt from 56d (282 mg; 0.68 mmol) according to the General Procedure IVb in 99% yield (287 mg; 0.67 mmol).

Step 6

Synthesis of (S)-5-(4-(2-(4-chlorobenzyl)-4,4-difluoropyrrolidin-1-yl)piperidin-1-yl)-4H-1,2,4-triazol-3-amine dihydrochloride (56)

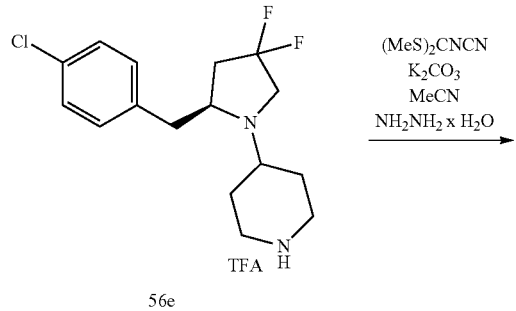

56e

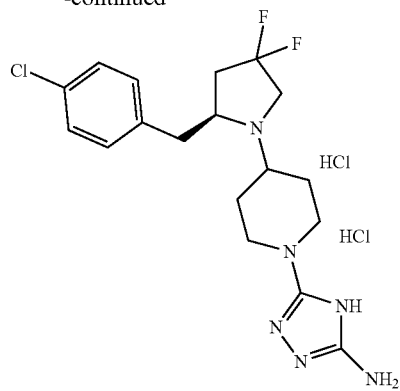

56

The title compound (56) was obtained as a dihydrochloride salt from 56e (287 mg; 0.67 mmol) according to the General Procedure Va in 39% yield (120 mg; 0.26 mmol). ESI-MS $C_{18}H_{24}ClF_2N_6$ found 397.2/399.2 (M+H)$^+$; $^1$H NMR (400 MHz, Methanol-$d_4$) δ 7.42-7.29 (m, 4H), 4.47-4.33 (m, 1H), 4.13-3.92 (m, 4H), 3.88-3.75 (m, 1H), 3.54-3.45 (m, 1H), 3.12-2.99 (m, 3H), 2.65-2.43 (m, 2H), 2.36-2.14 (m, 2H), 2.01-1.81 (m, 2H).

Example 57

Synthesis of (R)-5-(2-(4-chlorobenzyl)-5,5-difluoro-[1,4'-bipiperidin]-1'-yl)-4H-1,2,4-triazol-3-amine 2,2,2-trifluoroacetate (57)

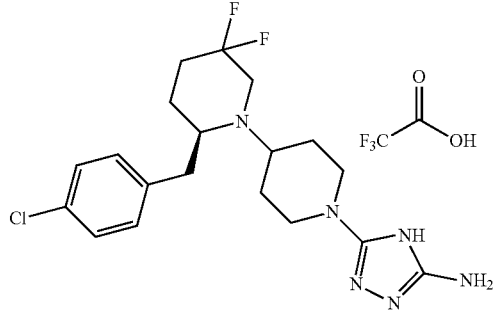

57

Step 1

Synthesis of (S)-2-((tert-butoxycarbonyl)amino)-3-(4-chlorophenyl)propanoic Acid (57a)

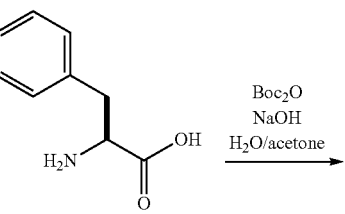

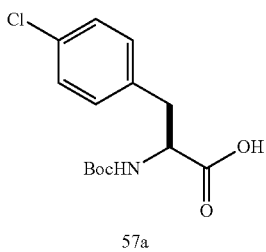

57a

To a solution of p-chloro-L-phenylalanine (18.0 g, 75 mmol) in acetone-water (150 mL 150 mL) sodium hydroxide (6 g, 150 mmol) was added at 0° C. Then di-tert-butyl dicarbonate (16.4 g, 75 mmol) was added. The reaction mixture was stirred at room temperature overnight. Acetone was evaporated. Aqueous layer was acidified to pH 2 with 2 M HCl and extracted with ethyl acetate. Organic layer was dried over magnesium sulfate, filtered and concentrated under reduced pressure. The crude product was crystallized from hexane to obtain 57a as a white solid in 80% yield (18.0 g; 60 mmol).

ESI-MS m/z for $C_{14}H_{19}ClNO_4$ found 299.8/301.8 $(M+H)^+$; $^1H$ NMR (500 MHz, DMSO-$d_6$) δ: 7.29 (d, J=8.3 Hz, 2H), 7.21 (d, J=8.3 Hz, 2H), 7.02 (d, J=7.3 Hz, 1H), 4.08-3.99 (m, 1H), 2.96 (dd, J=4.3, 13.7 Hz, 1H), 2.76 (dd, J=10.5, 13.6 Hz, 1H).

Step 2

Synthesis of (S)-tert-butyl(3-(4-chlorophenyl)-1-(2,2-dimethyl-4,6-dioxo-1,3-dioxan-5-yl)-1-oxopropan-2-yl)carbamate (57b)

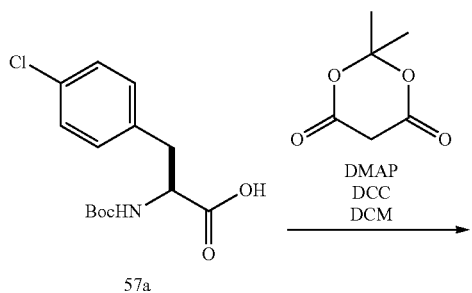

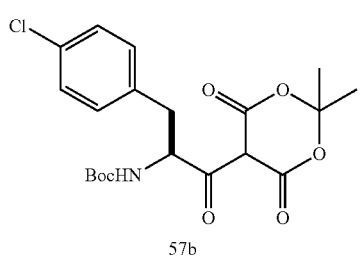

57b

To a solution of 57a (4 g, 13.34 mmol), DMAP (2.45 g; 20.02 mmol) and Meldrum's acid (2.31 g; 16.01 mmol) in anhydrous DCM (27 mL) DCC (3.3 g; 16.01 mmol) was added portionwise at 0° C. over 10 minutes and the mixture was allowed to room temperature and stirred for 22 hours. The reaction progress was monitored by LC-MS. When analysis indicated completion of the reaction, the mixture was filtered through Celite pad in order to remove insoluble solid which was washed with DCM and discarded. The filtrate was washed with 1 M HCl (30 mL) and brine (30 mL), dried over $Na_2SO_4$, filtered and concentrated in vacuo and the crude product was used in the next step without additional purification. Compound 57b was obtained in 99% yield (5.61 g; 13.21 mmol).

ESI-MS m/z for $C_{20}H_{24}ClNO_7Na$ found 448.1/450.1 $(M+Na)^+$.

Step 3

Synthesis of (R)-tert-butyl(1-(4-chlorophenyl)-3-(2,2-dimethyl-4,6-dioxo-1,3-dioxan-5-yl)-propan-2-yl)carbamate (57c)

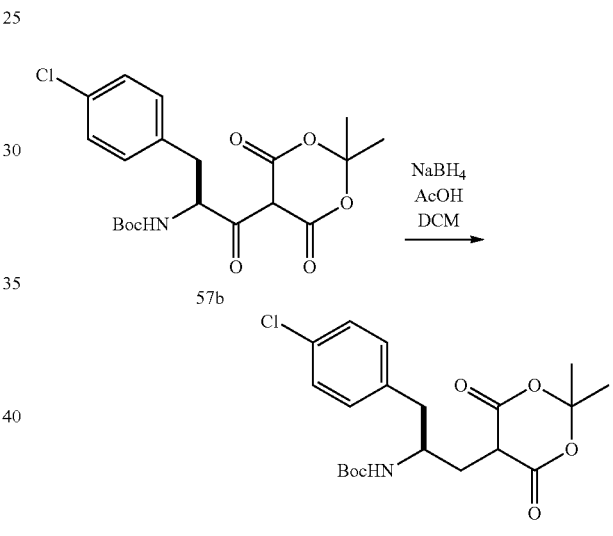

To a cooled to 0° C. solution of 57b (9.35 g, 21.96 mmol) and glacial acetic acid (12.6 mL; 219.56 mmol) in DCM (110 mL) NaBH$_4$ (2.08 g; 54.89 mmol) was added portionwise over 20 minutes and the mixture was allowed to room temperature and stirred for 18 hours. The reaction progress was monitored by LC-MS. When analysis indicated completion of the reaction, phases were separated and an organic phase was washed with brine (100 mL). An aqueous phase was washed additionally with DCM (3×40 mL) and discarded. Combined organic solutions were washed with brine (2×50 mL), then with saturated aqueous NaHCO$_3$ diluted with water (100 mL; 1:1 v/v) until pH 6-7 and with brine (50 mL). Due to emulsion CHCl$_3$ was added to the organic phase during a final washing. Combined organic solutions were dried over Na$_2$SO$_4$, filtered and concentrated in vacuo and the crude product was used in the next step without additional purification. Compound 57c was obtained in 99% yield (8.94 g; 21.74 mmol).

ESI-MS m/z for $C_{20}H_{26}ClNO_6Na$ found 434.1/436.1 $(M+Na)^+$.

Step 4

Synthesis of (R)-tert-butyl 2-(4-chlorobenzyl)-5-oxopyrrolidine-1-carboxylate (57d)

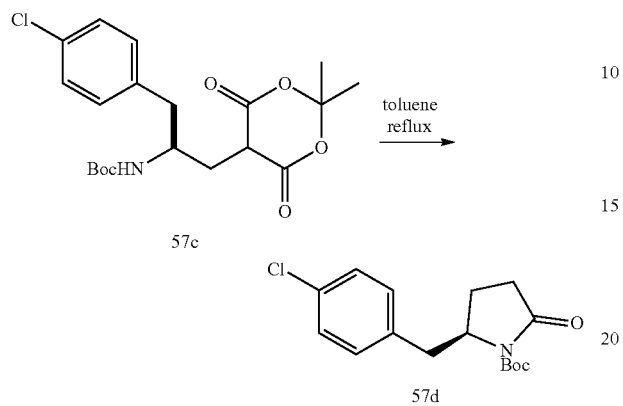

The solution of 57c (8.94 g; 21.74 mmol) in toluene (110 mL) was heated to reflux for 15 hours. The reaction progress was monitored by LC-MS. When analysis indicated completion of the reaction, the mixture was concentrated and the remaining oily residue was dissolved in AcOEt and then coevaporated with silica gel. The crude product was purified by flash column chromatography (hexane/AcOEt, 80:20 to 70:30). Compound 57d was obtained as a dense orange oil in 80% yield (5.35 g; 17.31 mmol).

ESI-MS m/z for $C_{16}H_{20}ClNO_3Na$ found 332.1/334.1 $(M+Na)^+$.

Step 5

Synthesis of ((R)-1-(4-chlorobenzyl)-4-oxo-5-dimethylsulfoxonium-pentyl)-carbamic Acid tert-butyl ester (57e)

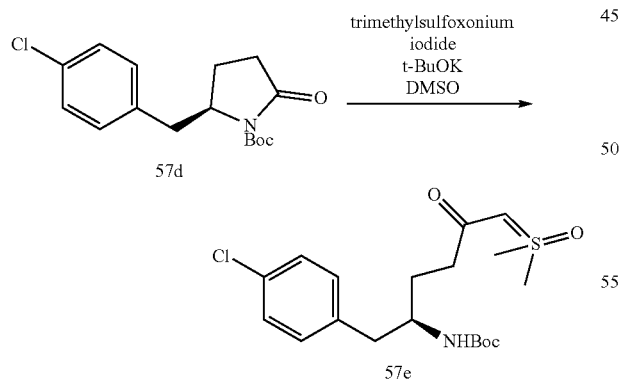

To a suspension of trimethylsulfoxonium iodide (4.56 g; 20.72 mmol) in anhydrous DMSO (18 mL) under nitrogen atmosphere, t-BuOK (2.13 g; 19 mmol) was added and the mixture was stirred at room temperature for 2 hours until the mixture became clear. In an another flask 57d (5.35 g, 17.31 mmol) was dissolved in DMSO (17 mL) and to this solution the previously prepared ylide was transferred via syringe and the mixture was stirred at room temperature for 17 hours. The reaction progress was monitored by LC-MS. When analysis indicated completion of the reaction, water (200 mL) was added and the product was extracted with AcOEt (200 mL, then 2×50 mL). Combined organic solutions were washed with water (50 mL) and brine (50 mL), dried over $Na_2SO_4$, filtered and concentrated in vacuo and the crude product was used in the next step without additional purification. Compound 57e was obtained as a white solid in 93% yield (6.46 g; 16.1 mmol).

ESI-MS m/z for $C_{19}H_{29}ClNO_4S$ found 402.1/404.1 $(M+Na)^+$.

Step 6

Synthesis of (R)-tert-butyl 2-(4-chlorobenzyl)-5-oxopiperidine-1-carboxylate (57f)

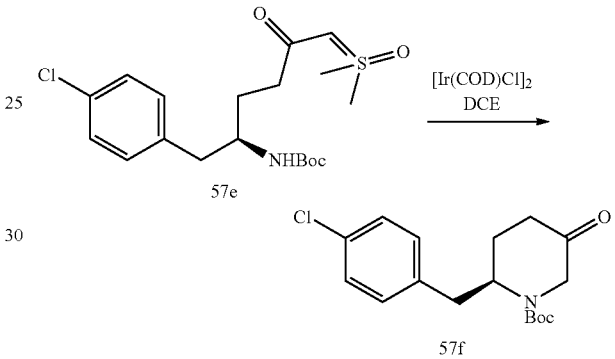

To a solution of iridium catalyst (42 mg; 0.06 mmol) in a degassed DCE (20 mL) under nitrogen atmosphere, a solution of 57e (2.5 g; 6.22 mmol) in a degassed DCE (105 mL) was added dropwise via syringe pump (20 mL/hour) over 5 hours at 70° C. After this time the mixture was stirred at 70° C. for 30 minutes. The reaction progress was monitored by LC-MS. When analysis indicated completion of the reaction, the mixture was concentrated and the oily residue was dissolved in DCM and co-evaporated with silica gel. The crude product was purified by flash column chromatography (hexane/AcOEt, 100:0 to 70:30). Compound 57f was obtained as a thick orange oil in 86% yield (1.73 g; 5.35 mmol).

ESI-MS m/z for $C_{17}H_{23}ClNO_3$ found 325.0/327.0 $(M+Na)^+$.

Step 7

Synthesis of (R)-tert-butyl 2-(4-chlorobenzyl)-5,5-difluoropiperidine-1-carboxylate (57g)

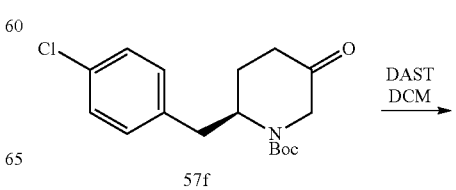

233

-continued

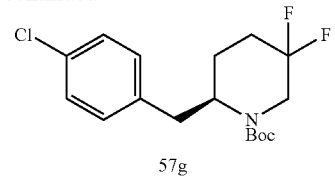

57g

The title compound (57g) was obtained from 57f (150 mg; 0.46 mmol) according to the General Procedure VII in 99% yield (159 mg; 0.46 mmol).

ESI-MS m/z for $C_{13}H_{15}ClF_2NO_2$ found 290.1/292.1 (M+H−tBu)⁺.

Step 8

Synthesis of (R)-2-(4-chlorobenzyl)-5,5-difluoropiperidine hydrochloride (57h)

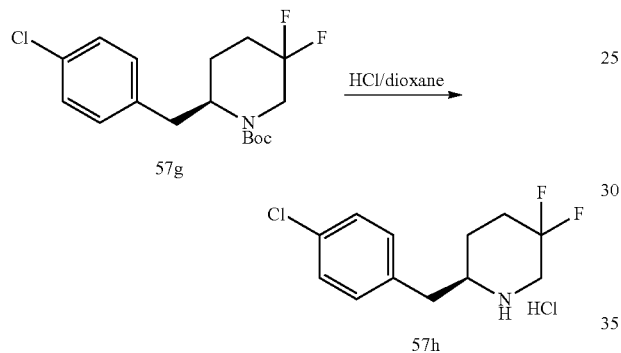

The title compound (57h) was obtained as a hydrochloride salt from 57g (159 mg; 0.46 mmol) according to the General Procedure IVa in 99% yield (130 mg; 0.46 mmol).

ESI-MS m/z for $C_{12}H_{15}ClF_2N$ found 246.1/248.1 (M+H)⁺.

Step 9

Synthesis of (R)-5-(2-(4-chlorobenzyl)-5,5-difluoro-[1,4'-bipiperidin]-1'-yl)-4H-1,2,4-triazol-3-amine 2,2,2-trifluoroacetate (57)

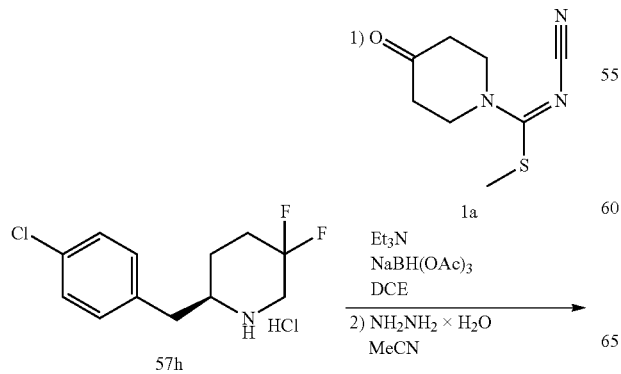

234

-continued

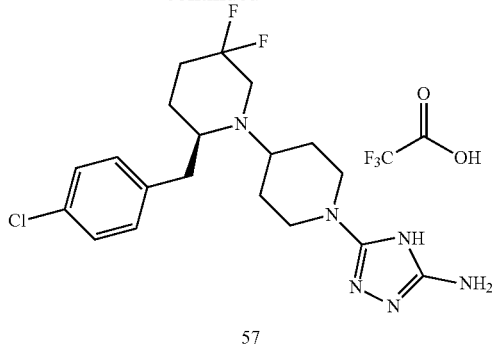

57

The title compound (57) was obtained as a TFA salt from 57h (130 mg; 0.46 mmol) according to the General Procedure Vb in 13% yield (31 mg; 0.059 mmol).

ESI-MS $C_{19}H_{26}CF_2N_6$ found 411.3/413.3 (M+H)⁺; ¹H NMR (400 MHz, Methanol-d₄) δ 7.43-7.36 (m, 2H), 7.36-7.27 (m, 2H), 4.01-3.69 (m, 5H), 3.64-3.52 (m, 1H), 3.50-3.39 (m, 1H), 3.17-2.96 (m, 2H), 2.87-2.80 (m, 1H), 2.36-2.20 (m, 1H), 2.20-1.75 (m, 7H).

Example 58

Synthesis of 5-((2R,5R)-2-(4-chlorobenzyl)-5-morpholino-[1,4'-bipiperidin]-1'-yl)-4H-1,2,4-triazol-3-amine 2,2,2-trifluoroacetate (58)

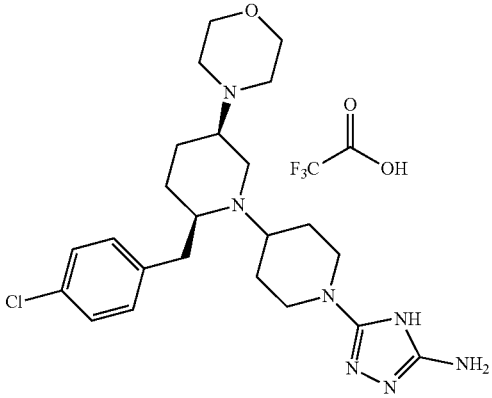

Step 1

Synthesis of (2R,5R)-tert-butyl 2-(4-chlorobenzyl)-5-morpholinopiperidine-1-carboxylate (58a)

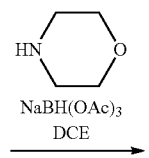

235

-continued

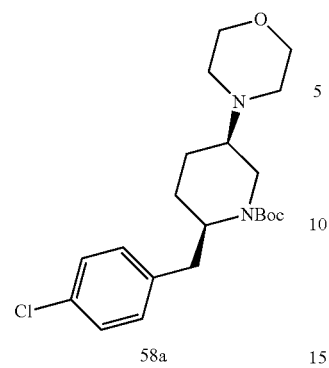

58a

The title compound (58a) was obtained from 57f (234 mg; 0.72 mmol) according to the General Procedure IX in 99% yield (280 mg; 0.71 mmol).

ESI-MS m/z for $C_{21}H_{32}ClN_2O_3$ found 395.2/397.2 (M+H)$^+$

Step 2

Synthesis of 4-((3R,6R)-6-(4-chlorobenzyl)piperidin-3-yl)morpholine dihydrochloride (58b)

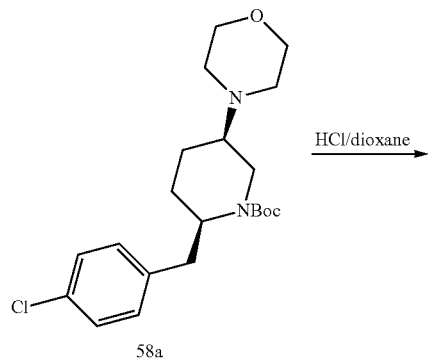

The title compound (58b) was obtained as a dihydrochloride salt from 58a (280 mg; 0.71 mmol) according to the General Procedure IVa in 99% yield (258 mg; 0.7 mmol).

ESI-MS m/z for $C_{16}H_{24}ClN_2O$ found 295.2/297.2 (M+H)$^+$.

236

Step 3

Synthesis of (2R,5R)-tert-butyl 2-(4-chlorobenzyl)-5-morpholino-[1,4'-bipiperidine]-1'-carboxylate (58c)

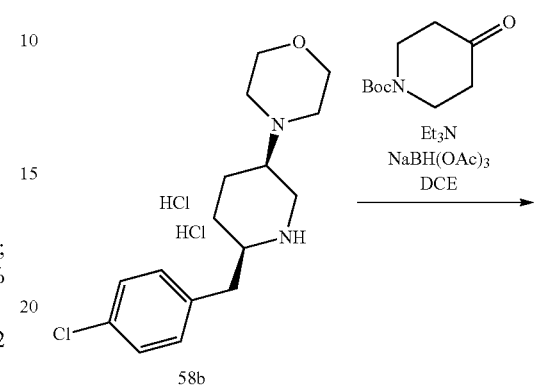

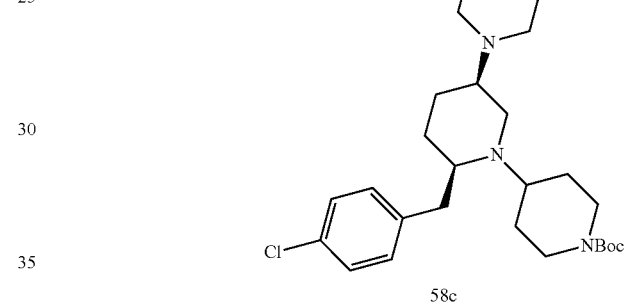

The title compound (58c) was obtained from 58b (258 mg; 0.7 mmol) according to the General Procedure IX in 99% yield (331 mg; 0.69 mmol).

ESI-MS m/z for $C_{26}H_{41}ClN_3O_3$ found 478.2/480.2 (M+H)$^+$.

Step 4

Synthesis of 4-((3R,6R)-6-(4-chlorobenzyl)-[1,4'-bipiperidin]-3-yl)morpholine (58d)

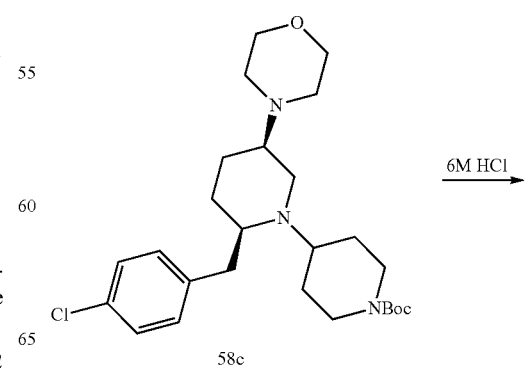

237

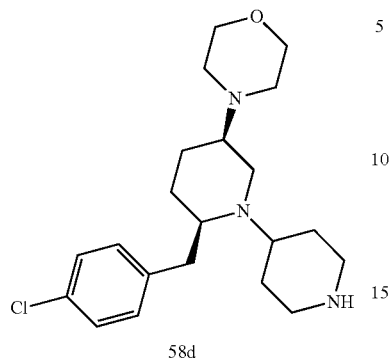

58d

The mixture of 58c (331 mg; 0.69 mmol) in 6 M HCl (5 mL) was stirred at room temperature for 18 hours. The reaction progress was monitored by LC-MS. When analysis indicated completion of the reaction, the mixture was alkalized with 4 M NaOH until pH 14 and the product was extracted with CHCl₃ (3×20 mL). Combined organic solutions were dried over Na₂SO₄, filtered and concentrated in vacuo and the crude product was used in the next step without additional purification. Compound 58d was obtained in 99% yield (257 mg; 0.68 mmol).

ESI-MS m/z for $C_{21}H_{33}ClN_3O$ found 378.2/380.2 $(M+H)^+$.

Step 5

Synthesis of 5-((2R,5R)-2-(4-chlorobenzyl)-5-morpholino-[1,4'-bipiperidin]-1'-yl)-4H-1,2,4-triazol-3-amine 2,2,2-trifluoroacetate (58)

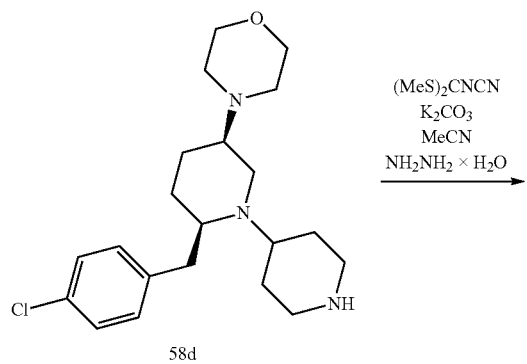

58d

238

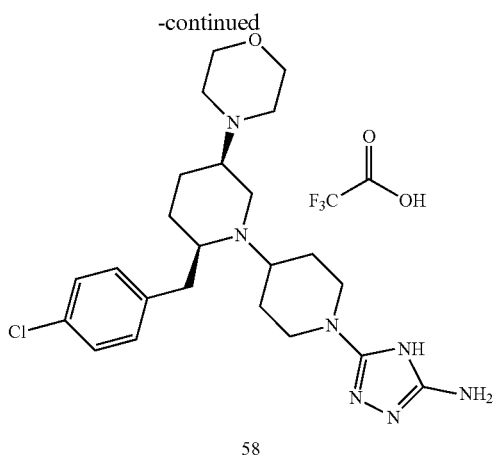

58

The title compound (58) was obtained as a TFA salt from 58d (257 mg; 0.68 mmol) according to the General Procedure Va in 25% yield (95 mg; 0.17 mmol).

ESI-MS $C_{23}H_{35}ClN_7O$ found 460.2/462.2 $(M+H)^+$; ¹H NMR (400 MHz, Methanol-d₄) δ 7.43-7.35 (m, 2H), 7.35-7.25 (m, 2H), 4.12-3.78 (m, 8H), 3.78-3.61 (m, 2H), 3.59-3.46 (m, 1H), 3.37-3.31 (m, 1H), 3.29-3.17 (m, 2H), 3.17-3.02 (m, 2H), 2.99-2.87 (m, 1H), 2.84-2.73 (m, 1H), 2.31-1.57 (m, 9H).

Example 59

Synthesis of (2S)-1'-(5-amino-4H-1,2,4-triazol-3-yl)-2-(4-chlorobenzyl)-4-methyl-[1,4'-bipiperidin]-4-ol 2,2,2-trifluoroacetate (59)

59

Step 1

Synthesis of tert-butyl (S)—(1-(4-chlorophenyl)-4-diazo-3-oxobutan-2-yl)carbamate (59a)

57a

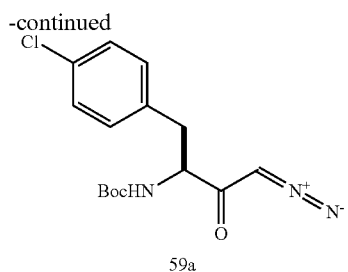

59a

To a solution of acid 57a (17.2 g, 57 mmol) in TH (200 mL) triethylamine (17 mL, 120 mmol) and methyl chloroformate (4.87 mL, 63 mmol) were added at −10° C. After 15 min a solution of diazomethane (342 mmol) in diethyl ether (400 mL) was added at −30° C. The reaction mixture was stirred overnight at room temperature. The excess of diazomethane was decomposed with acetic acid (15 mL). The mixture was diluted with diethyl ether and washed with 5% NaHCO$_3$, saturated NH$_4$Cl, and brine. The organic layer was dried over MgSO$_4$, filtered and concentrated in vacuo to give product 59a as an orange solid in 96% yield (18.0 g; 55.7 mmol).

ESI-MS m/z for $C_{15}H_{19}ClN_3O_3$ found 324.1/326.1 (M+H)$^+$; $^1$H NMR (700 MHz, CDCl$_3$) δ7.28 (d, J=8.3 Hz, 2H), 7.13 (d, J=8.2 Hz, 2H), 5.26 (br s, 1H), 5.07 (br s, 1H), 4.40 (br s, 1H), 3.03 (dd, J=7.0, 14.0 Hz, 1H), 2.97 (dd, J=6.1, 13.5 Hz, 1H), 1.42 (s, 9H).

Step 2

Synthesis of (S)-3-((tert-butoxycarbonyl)amino)-4-(4-chlorophenyl)butanoic Acid (59b)

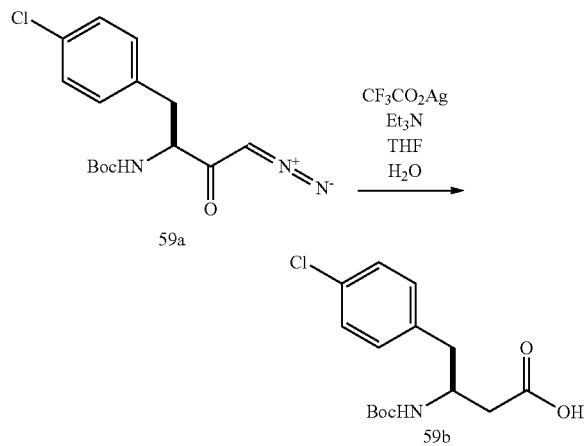

To a solution of compound 59a (18 g, 65 mmol) in THF:water (135:15 mL) was added a solution of silver trifluoroacetate (1.57 g, 7.1 mmol) in triethylamine (25 mL, 182 mmol) at −5° C. The reaction mixture was stirred for 1 hour. After this time solvent was removed at reduced pressure. The residue was diluted with saturated aq. NaHCO$_3$, and the mixture was extracted with diethyl ether. 1 M HCl was added to the aqueous layer at 0° C. until pH 2-3, and the mixture was extracted three times with ethyl acetate. The organic layers were collected, dried over MgSO$_4$ and concentrated in vacuo. The crude product was crystallized from diethyl ether to obtain 59b as a white solid in 34% yield (7 g; 22.36 mmol).

ESI-MS m/z for $C_{15}H_{21}ClNO_4$ found 312.3/314.3 (M−H)$^−$; $^1$H NMR (500 MHz, DMSO-d$_6$) δ 12.14 (s, 1H), 7.28 (d, J=8.3 Hz, 2H), 7.14 (d, J=8.3 Hz, 2H), 6.76 (d, J=8.7 Hz, 1H), 3.90-3.86 (m, 1H), 2.68 (dd, J=5.27, 13.4 Hz, 1H), 2.60 (dd, J=8.5, 13.4 Hz, 1H), 2.30 (t, J=7.0 Hz, 2H), 1.25 (s, 9H).

Step 3

Synthesis of tert-butyl (S)—(1-(4-chlorophenyl)-4-(methoxy(methyl)amino)-4-oxobutan-2-yl)-carbamate (59c)

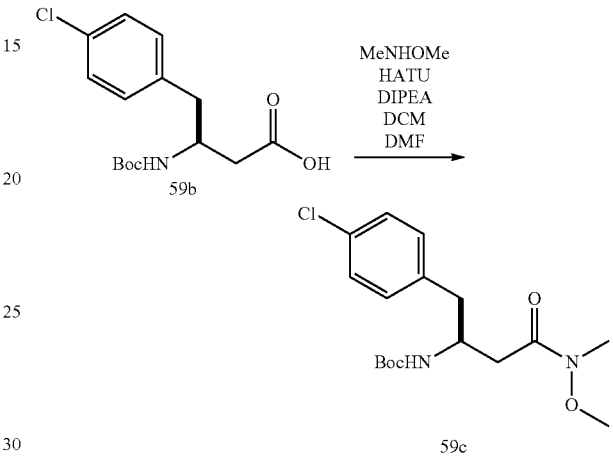

To a solution of 59b (7 g; 22.36 mmol) in DCM/DMF (10:1 v/v; 40 mL:4 mL), DIPEA (8.1 mL; 46.96 mmol) and N,O-dimethylhydroxylamine hydrochloride (2.4 g; 24.6 mmol) were added. Then TBTU (7.9 g; 24.6 mmol) was added to the reaction mixture and the reaction was stirred at room temperature overnight. The reaction progress was monitored by LC-MS. When analysis indicated completion of the reaction, the mixture was diluted with DCM, then washed with 2 M HCl and brine. Organic layer was dried over anhydrous MgSO$_4$, filtered and concentrated in vacuo. The crude product was purified by flash column chromatography (hexane/AcOEt, 20:1 to 1:1). Compound 59c was obtained in 93% yield (7.4 g; 20.79 mmol).

ESI-MS m/z for $C_{17}H_{25}ClN_2O_4Na$ found 380.1/382.1 (M+Na)$^+$; $^1$H NMR (500 MHz, CDCl$_3$) δ 7.25 (d, J=8.5 Hz, 2H), 7.13 (d, J=8.3 Hz, 2H), 5.48 (br s, 1H), 4.14-4.10 (m, 1H), 3.57 (s, 3H), 3.17 (s, 3H), 3.00-2.94 (m, 1H), 2.84 (dd, J=7.9, 13.6 Hz, 1H), 2.58 (qd, J=3.8, 16.4 Hz, 2H), 1.39 (s, 9H).

Step 4

Synthesis of tert-butyl (S)—(1-(4-chlorophenyl)-4-oxohex-5-en-2-yl)carbamate (59d)

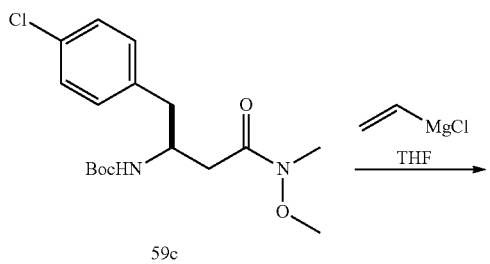

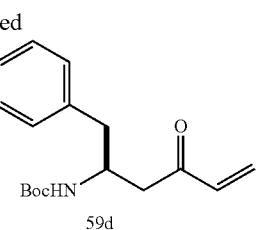

The title compound (59d) was obtained from 59c (6.9 g, 19.3 mmol) according to the General Procedure VI in 32% yield (2 g; 6.19 mmol).

ESI-MS m/z for $C_{17}H_{23}ClNO_3$ found 323.8/325.8 $(M+H)^+$.

Step 5

Synthesis of tert-butyl (S)-2-(4-chlorobenzyl)-4-oxopiperidine-1-carboxylate (59e)

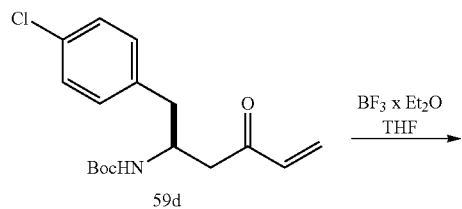

To a solution of 59d (1.1 g, 3.4 mmol) in THF (10 mL) boron trifluoride diethyl ether complex (4.27 mL, 34 mmol) was added. The reaction mixture was stirred at room temperature overnight. Then the mixture was diluted with ethyl acetate and washed with 4 M NaOH. Organic layer was dried over $MgSO_4$, filtered and concentrated in vacuo. The crude product was purified by flash column chromatography (hexane/AcOEt, 6:1 to 2:1). Compound 59e was obtained in 44% yield (480 mg; 1.49 mmol).

ESI-MS m/z for $C_{17}H_{22}ClNO_3Na$ found 346.1/348.1 $(M+Na)^+$; $^1H$ NMR (500 MHz, $CDCl_3$) δ 7.26 (d, J=8.3 Hz, 2H), 7.09 (d, J=6.6 Hz, 2H), 4.74 (br s, 1H), 4.37 (br s, 1H), 3.30 (qd, J=3.7, 11.5 Hz, 1H), 2.81 (dd, J=7.3, 13.6 Hz, 1H), 2.68 (dd, J=7.9, 13.7 Hz, 1H), 2.60 (dd, J=6.8, 14.5 Hz, 1H), 2.54-2.49 (m, 1H), 2.39-2.34 (m, 2H), 1.40 (s, 9H).

Step 6

Synthesis of (2S)-tert-butyl 2-(4-chlorobenzyl)-4-hydroxy-4-methylpiperidine-1-carboxylate (59f)

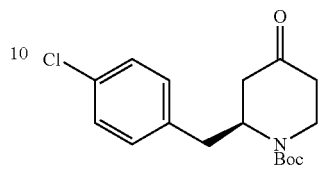

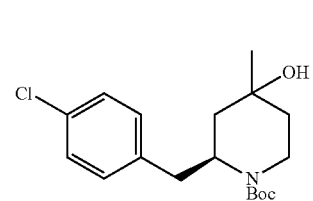

The title compound (59f) was obtained from 59e (0.15 g, 0.46 mmol) according to the General Procedure VI in 76% yield (0.12 g; 0.35 mmol).

ESI-MS m/z for $C_{18}H_{27}ClNO_3$ found 340.2/342.2 $(M+H)$; $^1H$ NMR (700 MHz, DMSO-$d_6$) δ 7.31-7.26 (m, 2H), 7.23-7.11 (m, 2H), 4.24-4.18 (m, 1H), 4.16-4.12 (m, 1H), 3.86-3.77 (m, 1H), 3.22-3.14 (m, 1H), 3.10-3.07 (m, 1H), 2.99-2.94 (m, 1H), 1.58-1.51 (m, 2H), 1.43-1.32 (m, 2H), 1.24 (s, 9H), 1.13 (s, 3H).

Step 7

Synthesis of (2S)-2-(4-chlorobenzyl)-4-methylpiperidin-4-ol hydrochloride (59g)

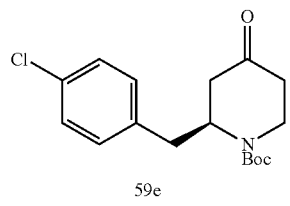

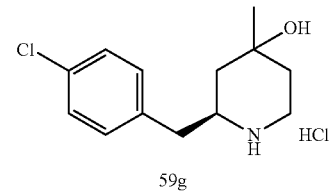

The title compound (59g) was obtained as a hydrochloride salt from 59f (0.12 g; 0.35 mmol) according to the General Procedure IVa in 99% yield (96 mg; 0.35 mmol).

ESI-MS m/z for $C_{13}H_{19}ClNO$ found 239.9/241.9 $(M+H)^+$.

Step 8

Synthesis of (2S)-1'-(5-amino-4H-1,2,4-triazol-3-yl)-2-(4-chlorobenzyl)-4-methyl-[1,4'-bipiperidin]-4-ol 2,2,2-trifluoroacetate (59)

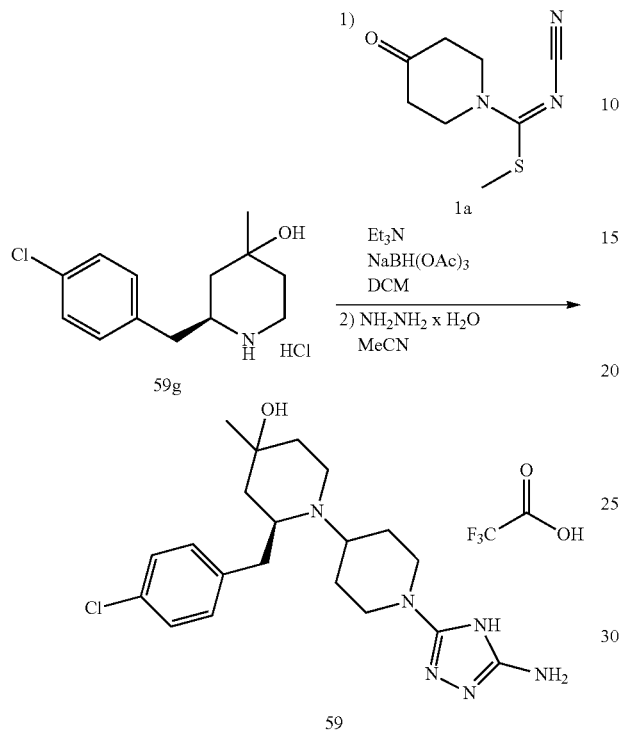

The title compound (59) was obtained as a TFA salt from 59g (77 mg; 0.28 mmol) according to the General Procedure Vb in 5% yield (8 mg; 0.015 mmol).

ESI-MS $C_{20}H_{30}ClN_6O$ found 405.1/407.1 (M+H)$^+$; $^1$H NMR (700 MHz, D$_2$O, 333 K) δ 7.77-7.68 (m, 2H), 7.68-7.53 (m, 2H), 4.25-4.09 (m, 3H), 4.09-4.01 (m, 1H), 3.97-3.87 (m, 1H), 3.81-3.65 (m, 1H), 3.51-3.23 (m, 3H), 3.17-3.11 (m, 1H), 2.47-1.98 (m, 8H), 1.58 (s, 3H).

Example 60

Synthesis of ((2R,5S)-4-(1-(5-amino-4H-1,2,4-triazol-3-yl)piperidin-4-yl)-5-(4-chlorobenzyl)-morpholin-2-yl)(pyrrolidin-1-yl)methanone 2,2,2-trifluoroacetate (60)

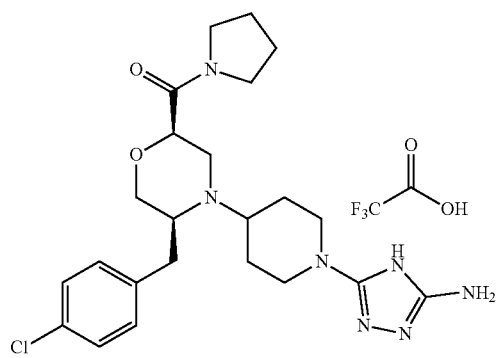

The title compound 60 was obtained as a TFA salt in 27% overall yield in a similar way to Example 23 with the exception that, in the first step of the synthesis, pyrrolidine was used instead of 2,2-dimethylcyclopropane-1-amine hydrochloride.

ESI-MS m/z for $C_{23}H_{33}ClN_7O_2$ found 474.2/476.2 (M+1)$^+$; $^1$H NMR (700 MHz, DMSO-d$_6$) δ 7.43-7.35 (m, 2H), 7.34-7.26 (m, 2H), 4.55-4.42 (m, 1H), 3.84-3.76 (m, 3H), 3.76-3.69 (m, 2H), 3.66-3.59 (m, 1H), 3.54-3.40 (m, 4H), 3.37-3.26 (m, 2H), 3.23-3.18 (m, 1H), 3.17-3.10 (m, 1H), 3.10-3.03 (m, 1H), 2.97-2.87 (m, 2H), 2.18-2.11 (m, 1H), 1.89-1.82 (m, 2H), 1.80-1.74 (m, 2H), 1.67-1.59 (m, 2H).

Example 61

Synthesis of ((2R,5S)-4-(1-(5-amino-4H-1,2,4-triazol-3-yl)piperidin-4-yl)-5-(4-chlorobenzyl)-morpholin-2-yl)(3-methylazetidin-1-yl)methanone 2,2,2-trifluoroacetate (61)

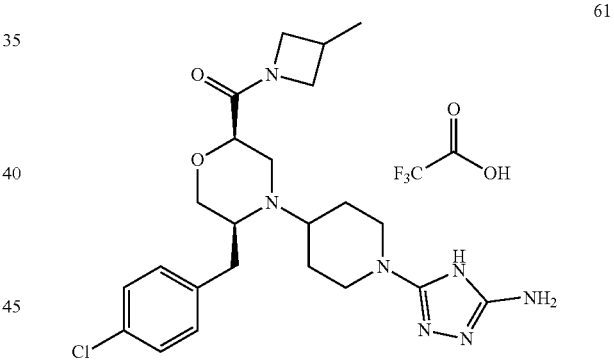

The title compound 61 was obtained as a TFA salt in 47% overall yield in a similar way to Example 23 with the exception that, in the first step of the synthesis, 3-methylazetidine hydrochloride was used instead of 2,2-dimethylcyclopropane-1-amine hydrochloride and in the second step of the synthesis, the synthesis was carried out according to the General Procedure IVb instead of General Procedure IVa.

ESI-MS m/z for $C_{23}H_{33}ClN_7O_2$ found 474.1/476.1 (M+1)$^+$; $^1$H NMR (700 MHz, DMSO-d$_6$+D$_2$O, 348 K) δ 7.42-7.35 (m, 2H), 7.35-7.23 (m, 2H), 4.45-4.29 (m, 2H), 4.09-4.01 (m, 1H), 3.88-3.78 (m, 3H), 3.71-3.60 (m, 3H), 3.58-3.54 (m, 1H), 3.50-3.46 (m, 1H), 3.37-3.28 (m, 2H), 3.14-3.09 (m, 1H), 3.09-3.01 (m, 1H), 2.96-2.84 (m, 2H), 2.77-2.70 (m, 1H), 2.12-2.02 (m, 2H), 1.70-1.57 (m, 2H), 1.19 (s, 3H).

Example 62

Synthesis of ((2R,5S)-4-(1-(5-amino-4H-1,2,4-triazol-3-yl)piperidin-4-yl)-5-(4-chlorobenzyl)-morpholin-2-yl)(3-fluoroazetidin-1-yl)methanone 2,2,2-trifluoroacetate (62)

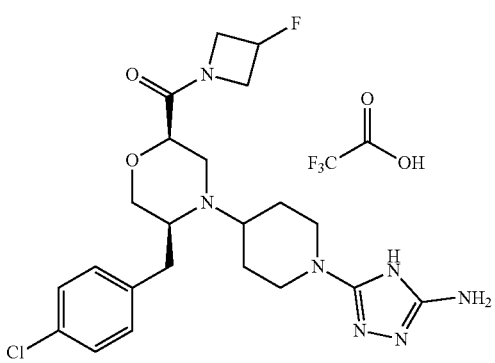

The title compound 62 was obtained as a TFA salt in 32% overall yield in a similar way to Example 23 with the exception that, in the first step of the synthesis, 3-fluoroazetidine hydrochloride was used instead of 2,2-dimethylcyclopropane-1-amine hydrochloride and in the second step of the synthesis, the synthesis was carried out according to the General Procedure IVb instead of General Procedure IVa.

ESI-MS m/z for $C_{22}H_{30}ClFN_7O_2$ found 478.2/480.2 (M+1)$^+$; $^1$H NMR (700 MHz, DMSO-d$_6$+D$_2$O, 348 K) δ 7.41-7.34 (m, 2H), 7.34-7.26 (m, 2H), 5.50-5.33 (m, 1H), 4.73-4.22 (m, 3H), 4.05-3.79 (m, 3H), 3.68-3.47 (m, 3H), 3.35-3.24 (m, 4H), 3.11-2.99 (m, 2H), 2.97-2.88 (m, 2H), 2.12-2.02 (m, 2H), 1.65-1.55 (m, 2H); $^{19}$F NMR (235 MHz, DMSO-d$_6$) δ−70.24 (s), −170.40−−183.01 (m).

Example 63

Synthesis of ((2R,5S)-4-(1-(5-amino-4H-1,2,4-triazol-3-yl)piperidin-4-yl)-5-(4-chlorobenzyl)-morpholin-2-yl)(morpholino)methanone 2,2,2-trifluoroacetate (63)

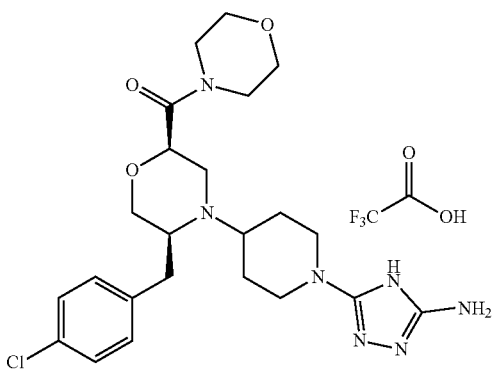

The title compound 63 was obtained as a TFA salt in 28% overall yield in a similar way to Example 23 with the exception that, in the first step of the synthesis, morpholine was used instead of 2,2-dimethylcyclopropane-1-amine hydrochloride.

ESI-MS m/z for $C_{23}H_{33}ClN_7O_3$ found 490.1/492.1 (M+1)$^+$; $^1$H NMR (700 MHz, DMSO-d$_6$+D$_2$O, 348 K) δ 7.42-7.35 (m, 2H), 7.34-7.25 (m, 2H), 4.69-4.60 (m, 1H), 3.89-3.81 (m, 2H), 3.81-3.77 (m, 1H), 3.75-3.71 (m, 1H), 3.70-3.57 (m, 6H), 3.55-3.52 (m, 2H), 3.48-3.43 (m, 2H), 3.41-3.30 (m, 2H), 3.18-3.12 (m, 1H), 3.06-3.00 (m, 1H), 2.95-2.82 (m, 2H), 2.15-2.03 (m, 2H), 1.72-1.61 (m, 2H).

Example 64

Synthesis of 2-((2R,5S)-4-(1-(5-amino-4H-1,2,4-triazol-3-yl)piperidin-4-yl)-5-(4-bromobenzyl)-morpholin-2-yl)propan-2-ol 2,2,2-trifluoroacetate (64)

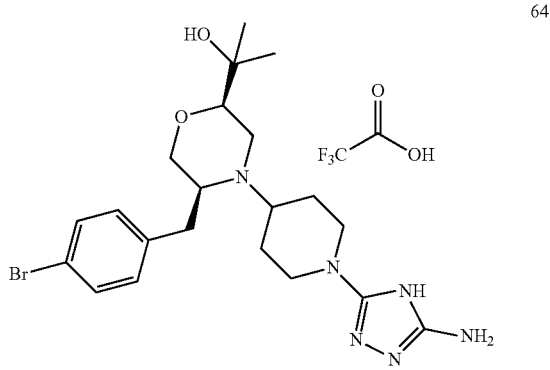

Step 1

Synthesis of (2S)-2-amino-3-(4-bromophenyl)propan-1-ol (64a)

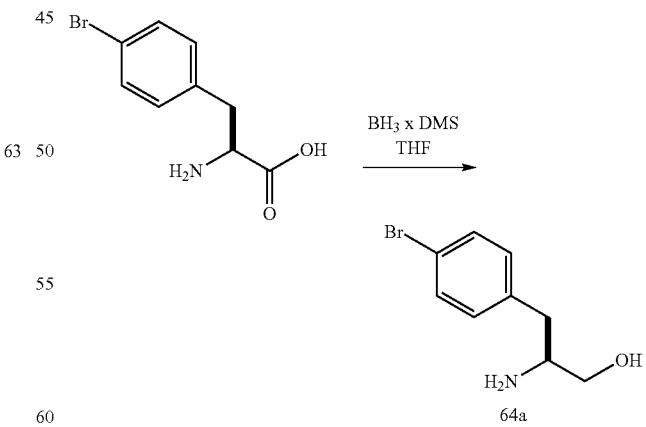

The title compound (64a) was obtained from optically pure L-p-bromophenylalanine ((2S)-2-amino-3-(4-bromophenyl)propanoic acid) (2.8 g; 11.47 mmol) according to the General Procedure Ia in 87% yield (2.6 g; 11.36 mmol).

ESI-MS m/z for $C_9H_{13}BrNO$ found 229.8/231.8 (M+H)$^+$.

Step 2

Synthesis of (R)-2-bromo-N—((S)-1-(4-bromophenyl)-3-hydroxypropan-2-yl)-3-(tert-butoxy)-propanamide (64b)

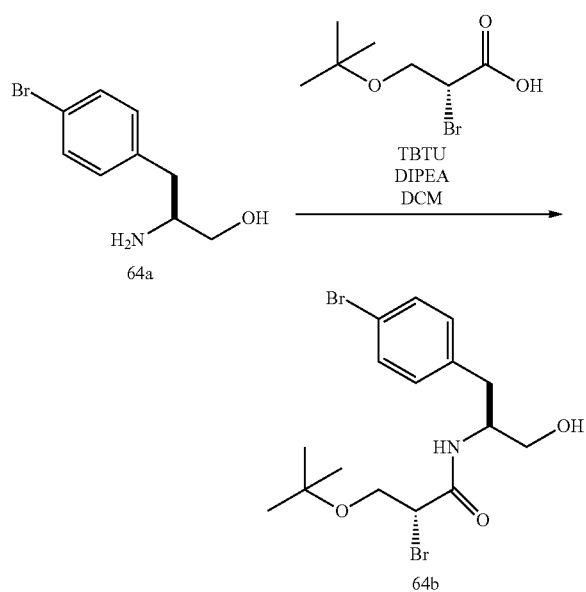

The title compound (64b) was obtained from 64a (30 g; 112.5 mmol) according to the General Procedure III in 70% yield (34.26 g; 78.75 mmol).

Step 3

Synthesis of (2S,5S)-5-(4-bromobenzyl)-2-(tert-butoxymethyl)morpholin-3-one (64c)

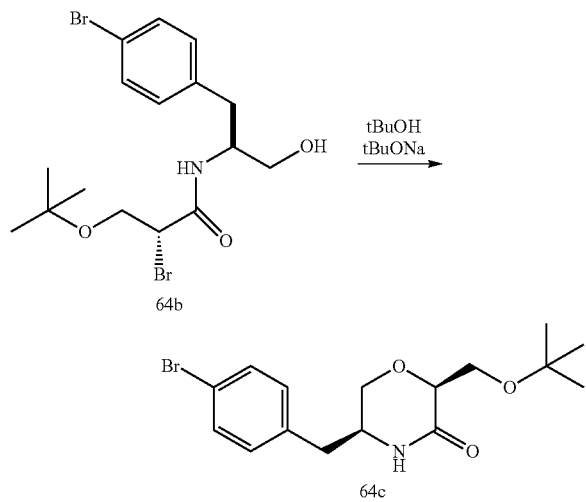

To a solution of 64b (4.75 g; 10.87 mmol) in tBuOH (20 mL) tBuONa (1.56 g; 16.29 mmol) was added and reaction was stirred at room temperature for 1 hour. The reaction progress was monitored by LC-MS. When analysis indicated completion of the reaction, to this mixture water (10 mL) was added and then 1 M HCl was added dropwise to pH 4 and tBuOH was removed in vacuo. The residue was diluted with brine and extracted with AcOEt (2×). Combined organic solutions were dried over anhydrous MgSO$_4$, filtered and concentrated in vacuo and the crude product was used in the next step without additional purification. Compound 64c was obtained in 99% yield (3.82 g; 10.76 mmol).

ESI-MS m/z for $C_{16}H_{23}BrNO_3$ found 355.8/357.8 (M+H)$^+$.

Step 4

Synthesis of ((2R,5S)-5-(4-bromobenzyl)morpholin-2-yl)methanol (64d)

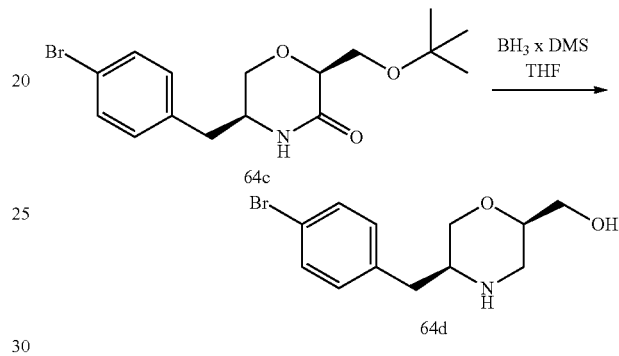

The title compound (64d) was obtained from 64c (3.82 g; 10.76 mmol) according to the General Procedure Ib in 75% yield (2.3 g; 8.07 mmol).

ESI-MS m/z for $C_{12}H_{17}BrNO_2$ found 285.7/287.7 (M+H)$^+$.

Step 5

Synthesis of (2R,5S)-tert-butyl 5-(4-bromobenzyl)-2-(hydroxymethyl)morpholine-4-carboxylate (64e)

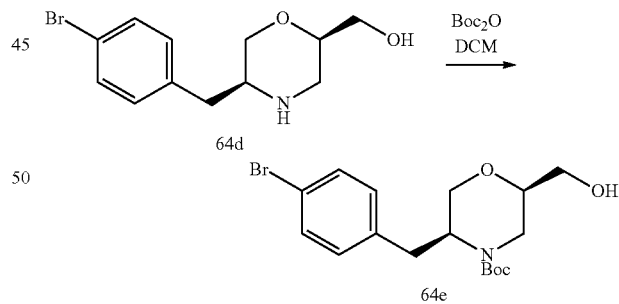

To a solution of amino alcohol 64d (2.25 g, 7.86 mmol) in dichloromethane (80 mL), di-tert-butyl dicarbonate (Boc$_2$O) (1.62 g, 7.47 mmol) was added and the reaction mixture was stirred at room temperature overnight, after which time TLC showed almost complete consumption of the starting material. Volatiles were removed in vacuo and the residue was purified by column chromatography (DCM/MeOH 100:1 v/v). Compound 64e was obtained in 82% yield (2.48 g; 6.44 mmol).

ESI-MS m/z for $C_{17}H_{24}ClBrNO_4Na$ found 408.1/410.1 (M+Na)$^+$.

Step 6

Synthesis of (2R,5S)-5-(4-bromobenzyl)-4-(tert-butoxycarbonyl)morpholine-2-carboxylic acid (64f)

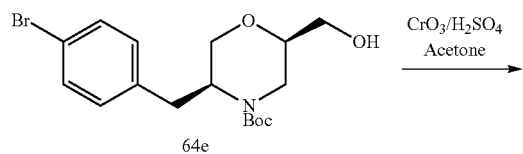

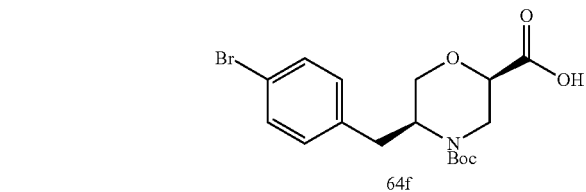

To a cooled to 0° C. solution of alcohol 64e (2.48 g; 6.44 mmol) in acetone (65 mL), Jones reagent (1.7 M; 9.4 mL; 16 mmol) was added dropwise. The reaction mixture was stirred at 0° C. for 1.5 hour, and then isopropanol (iPrOH) (10 mL) was added. After 10 minutes ethyl acetate was added and the mixture was filtered through a pad of Celite. The filtrate was washed with brine, dried over $MgSO_4$ and evaporated affording the title compound 64f as white foam in 89% yield (2.3 g; 5.76 mmol).

ESI-MS m/z for $C_{17}H_{23}BrNO_5$ found 399.8/401.8 $(M+H)^+$.

Step 7

Synthesis of (2R,5S)-4-tert-butyl 2-methyl 5-(4-bromobenzyl)morpholine-2,4-dicarboxylate (64g)

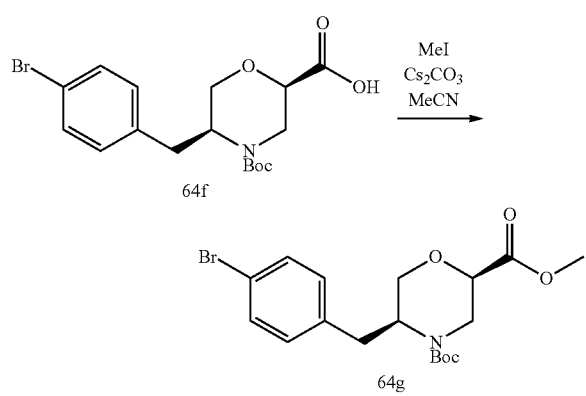

To a solution of Boc-protected amino acid 64f (3 g, 7.5 mmol) in acetonitrile (10 mL), cesium carbonate (7.33 g, 22.5 mmol) was added followed by methyl iodide (MeI) (1.4 mL, 22.5 mmol) at room temperature. After reaction was completed as judged by TLC, to the reaction mixture DCM (50 mL) was added and the mixture was filtered off. The filtrate was concentrated in vacuo and the residue was purified by flash column chromatography (DCM/MeOH 200:1 to 100:1 v/v). Compound 64g was obtained in 69% yield (2.15 g; 5.2 mmol).

ESI-MS m/z for $C_{18}H_{25}BrNO_5$ found 414.1/416.1 $(M+H)^+$.

Step 8

Synthesis of (2R,5S)-tert-butyl 5-(4-bromobenzyl)-2-(2-hydroxypropan-2-yl)morpholine-4-carboxylate (64h)

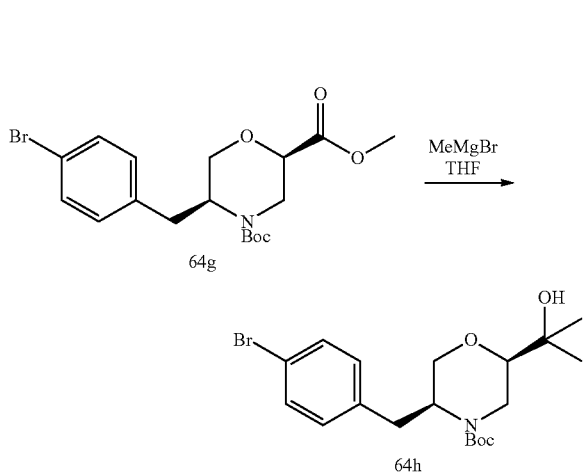 [SMILES: COC(=O)[C@H]1CN(C(=O)OC(C)(C)C)[C@@H](Cc2ccc(Br)cc2)CO1 ; CC(C)(C)OC(=O)N1C[C@H](C(C)(C)O)OC[C@@H]1Cc1ccc(Br)cc1]

The title compound (64h) was obtained from 64g (2.15 g; 5.2 mmol) according to the General Procedure VI in 73% yield (1.56 g; 3.78 mmol).

ESI-MS $C_{19}H_{29}BrNO_4$ found 414.0/416.0 $(M+H)^+$.

Step 9

Synthesis of 2-((2R,5S)-5-(4-bromobenzyl)morpholin-2-yl)propan-2-ol hydrochloride (64i)

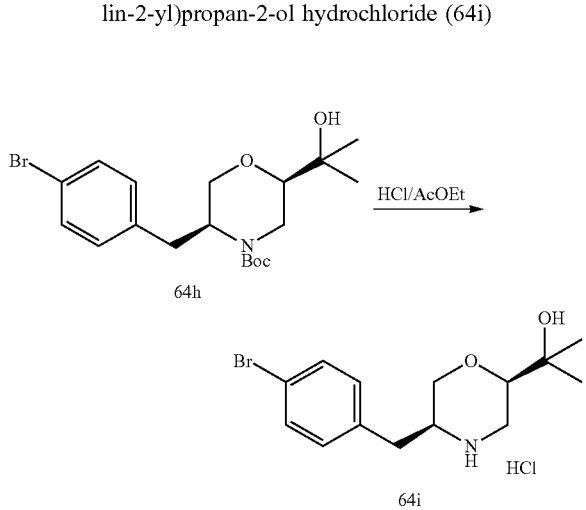

The title compound (64i) was obtained as a hydrochloride salt from 64h (1.56 g; 3.78 mmol) according to the General Procedure IVa in 99% yield (1.31 g; 3.74 mmol).

Step 10

Synthesis of tert-butyl 4-((2R,5S)-5-(4-bromobenzyl)-2-(2-hydroxypropan-2-yl)morpholino)-piperidine-1-carboxylate (64j)

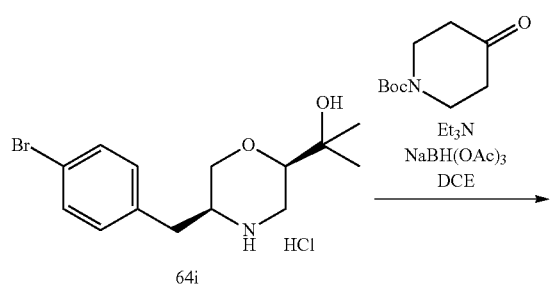

The title compound (64j) was obtained from 64i (0.75 g; 2.38 mmol) according to the General Procedure IX in 92% yield (1.08 g; 2.18 mmol).

ESI-MS $C_{24}H_{38}BrN_2O_4$ found 496.9/498.9 (M+H)$^+$.

Step 11

Synthesis of 2-((2R,5S)-5-(4-bromobenzyl)-4-(piperidin-4-yl)morpholin-2-yl)propan-2-ol hydrochloride (64k)

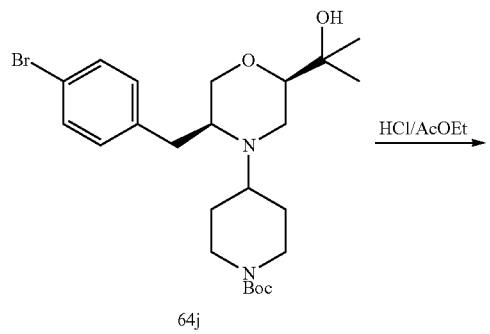

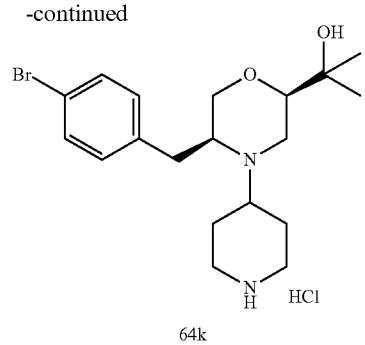

The title compound (64k) was obtained as a hydrochloride salt from 64j (1.08 g; 2.18 mmol) according to the General Procedure IVa in 95% yield (0.9 g; 2.08 mmol).

ESI-MS $C_{19}H_{30}BrN_2O_2$ found 396.9/398.9 (M+H)$^+$.

Step 12

Synthesis of 2-((2R,5S)-4-(1-(5-amino-4H-1,2,4-triazol-3-yl)piperidin-4-yl)-5-(4-bromobenzyl)morpholin-2-yl)propan-2-ol 2,2,2-trifluoroacetate (64)

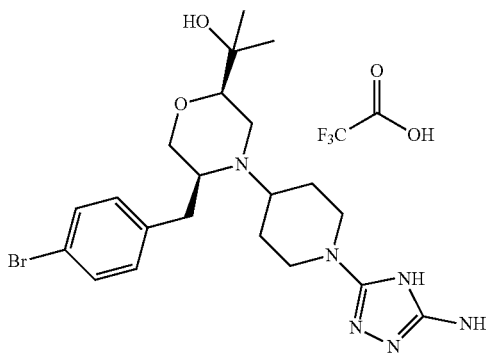

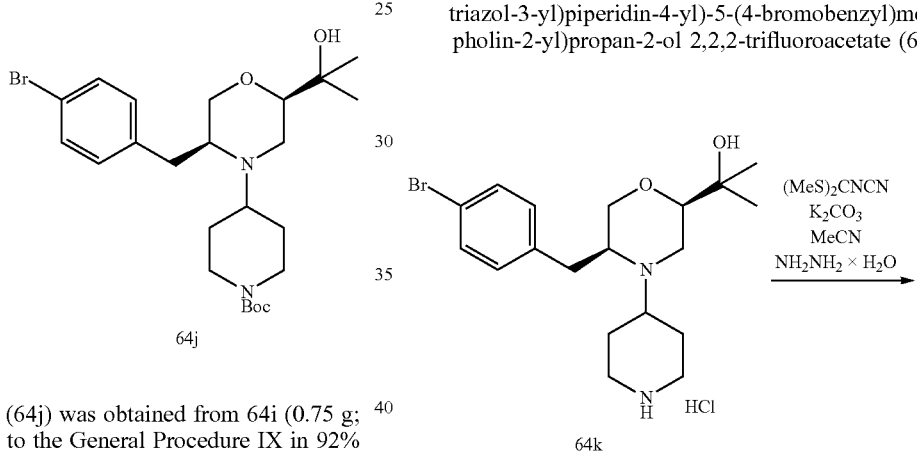

The title compound (64) was obtained as a TFA salt from 64k (120 mg; 0.28 mmol) according to the General Procedure Va in 71% yield (116 mg; 0.2 mmol).

ESI-MS m/z for $C_{21}H_{32}BrN_6O_2$ found 478.8/480.8 (M+H)$^+$; $^1$H NMR (700 MHz, DMSO-d$_6$+D$_2$O, 348 K) δ 7.56-7.50 (m, 2H), 7.29-7.22 (m, 2H), 3.97-3.86 (m, 2H), 3.77-3.64 (m, 4H), 3.54-3.48 (m, 2H), 3.21-3.16 (m, 1H), 3.15-3.05 (m, 2H), 3.04-2.93 (m, 2H), 2.27-2.10 (m, 2H), 1.73-1.60 (m, 2H), 1.19 (s, 6H).

Example 65

Synthesis of (2R,5S)-4-(1-(5-amino-4H-1,2,4-triazol-3-yl)piperidin-4-yl)-5-(4-chlorobenzyl)-N-isopropylmorpholine-2-carboxamide 2,2,2-trifluoroacetate (65)

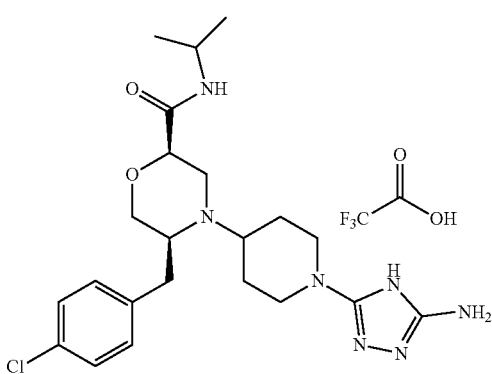

The title compound 65 was obtained as a TFA salt in 21% overall yield in a similar way to Example 23 with the exception that, in the first step of the synthesis, isopropylamine was used instead of 2,2-dimethylcyclopropane-1-amine hydrochloride.

ESI-MS m/z for $C_{22}H_{33}ClN_7O_2$ found 462.2/464.2 (M+1)$^+$; $^1$H NMR (700 MHz, DMSO-d$_6$+D$_2$O, 348 K) δ 7.40-7.37 (m, 2H), 7.35-7.32 (m, 2H), 4.24-4.15 (m, 1H), 3.97-3.89 (m, 1H), 3.87-3.80 (m, 2H), 3.73-3.69 (m, 2H), 3.65-3.58 (m, 1H), 3.58-3.49 (m, 1H), 3.47-3.44 (m, 1H), 3.23-3.13 (m, 1H), 3.10-3.04 (m, 2H), 3.00-2.88 (m, 2H), 2.17-2.01 (m, 2H), 1.69-1.58 (m, 2H), 1.15-1.07 (m, 6H).

Example 66

Synthesis of (2R,5S)-4-(1-(5-amino-4H-1,2,4-triazol-3-yl)piperidin-4-yl)-N-(tert-butyl)-5-(4-chlorobenzyl)morpholine-2-carboxamide 2,2,2-trifluoroacetate (66)

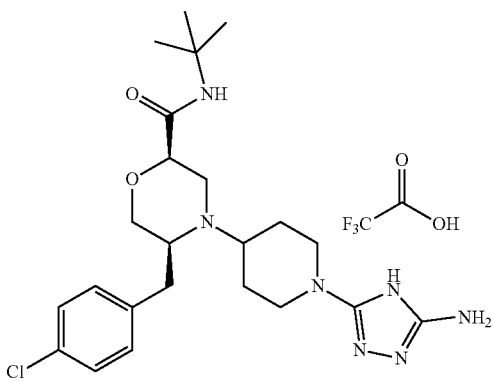

The title compound 66 was obtained as a TFA salt in 41% overall yield in a similar way to Example 23 with the exception that, in the first step of the synthesis, tert-butylamine was used instead of 2,2-dimethylcyclopropane-1-amine hydrochloride.

ESI-MS m/z for $C_{23}H_{35}ClN_7O_2$ found 476.0/478.0 (M+1)$^+$; $^1$H NMR (700 MHz, DMSO-d$_6$+D$_2$O, 348 K) δ 7.42-7.37 (m, 2H), 7.37-7.29 (m, 2H), 4.16-4.09 (m, 1H), 3.90-3.78 (m, 2H), 3.74-3.68 (m, 2H), 3.62-3.55 (m, 1H), 3.54-3.46 (m, 1H), 3.45-3.42 (m, 1H), 3.17-3.03 (m, 3H), 2.96-2.89 (m, 2H), 2.15-2.02 (m, 2H), 1.69-1.57 (m, 2H), 1.31 (s, 9H).

Example 67

Synthesis of (R)-1-((2R,5S)-4-(1-(5-amino-4H-1,2,4-triazol-3-yl)piperidin-4-yl)-5-(4-chlorobenzyl)morpholin-2-yl)ethanol 2,2,2-trifluoroacetate (67)

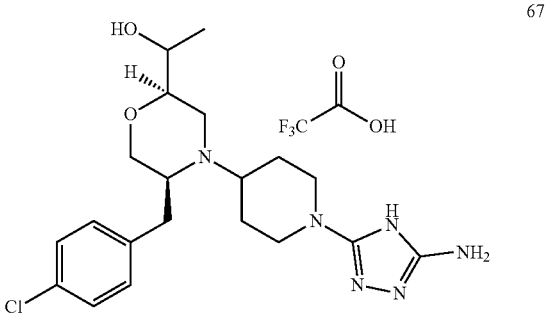

Step 1

Synthesis of (R)-1-((2R,5S)-5-(4-chlorobenzyl)morpholin-2-yl)ethanol 2,2,2-trifluoroacetate (67a)

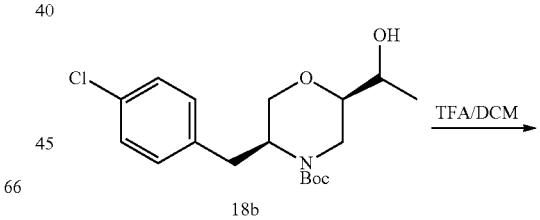

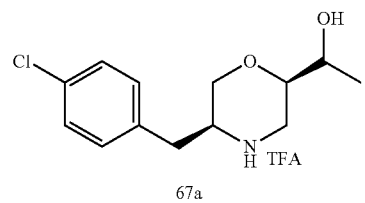

The title compound (67a) was obtained as a TFA salt from 18b (405 mg; 1.14 mmol) according to the General Procedure IVb in 99% yield (417 mg; 1.13 mmol).

Step 2

Synthesis of tert-butyl 4-((2R,5S)-5-(4-chlorobenzyl)-2-((R)-1-hydroxyethyl)morpholino)-piperidine-1-carboxylate (67b)

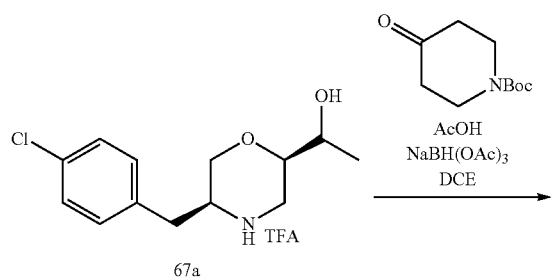

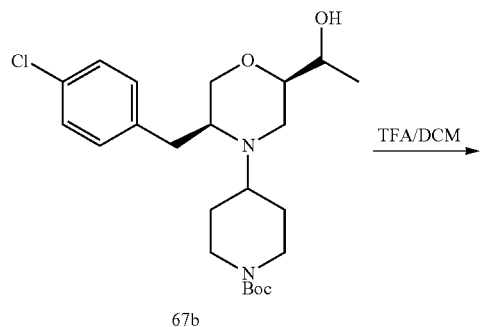

The title compound (67b) was obtained from 67a (417 mg; 1.13 mmol) according to the General Procedure IX in 99% yield (491 mg; 1.12 mmol).

ESI-MS m/z for $C_{23}H_{36}ClN_2O_4$ found 439.2/441.2 $(M+1)^+$.

Step 3

Synthesis of (R)-1-((2R,5S)-5-(4-chlorobenzyl)-4-(piperidin-4-yl)morpholin-2-yl)ethanol 2,2,2-trifluoroacetate (67c)

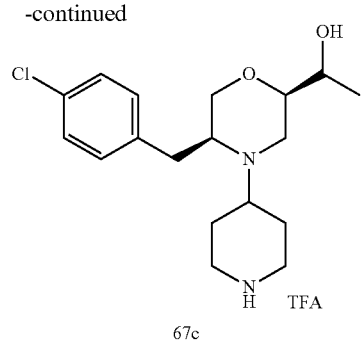

The title compound (67c) was obtained as a TFA salt from 67b (491 mg; 1.12 mmol) according to the General Procedure IVb in 99% yield (502 mg; 1.11 mmol).

Step 4

Synthesis of (R)-1-((2R,5S)-4-(1-(5-amino-4H-1,2,4-triazol-3-yl)piperidin-4-yl)-5-(4-chlorobenzyl)morpholin-2-yl)ethanol 2,2,2-trifluoroacetate (67)

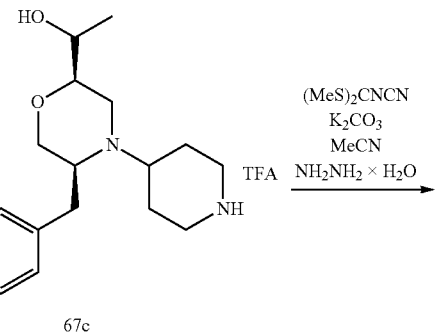

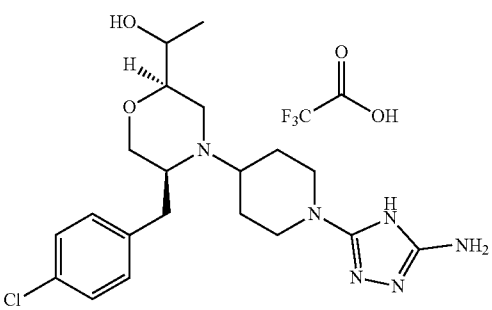

The title compound (67) was obtained as a TFA salt from 67c (502 mg; 1.11 mmol) according to the General Procedure Va in 11% yield (63 mg; 0.2 mmol).

ESI-MS m/z for $C_{20}H_{30}ClN_6O_2$ found 421.2/423.2 $(M+H)^+$; $^1H$ NMR (400 MHz, Methanol-$d_4$) δ 7.42-7.28 (m, 4H), 4.05-3.94 (m, 3H), 3.88-3.62 (m, 6H), 3.61-3.51 (m, 1H), 3.28-3.24 (m, 1H), 3.20-3.13 (m, 1H), 3.11-2.99 (m, 2H), 2.43-2.30 (m, 2H), 1.89-1.71 (m, 2H), 1.30 (d, J=6.6 Hz, 3H).

Example 68

Synthesis of 3-((2R,5S)-4-(1-(5-amino-4H-1,2,4-triazol-3-yl)piperidin-4-yl)-5-(4-chlorobenzyl)-morpholin-2-yl)pentan-3-ol 2,2,2-trifluoroacetate (68)

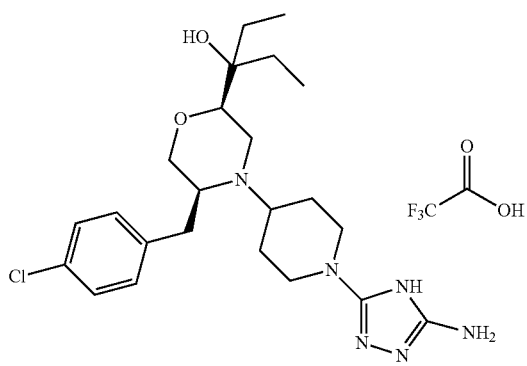

Step 1

Synthesis of (2R,5S)-tert-butyl 5-(4-chlorobenzyl)-2-(3-hydroxypentan-3-yl)morpholine-4-carboxylate (68a)

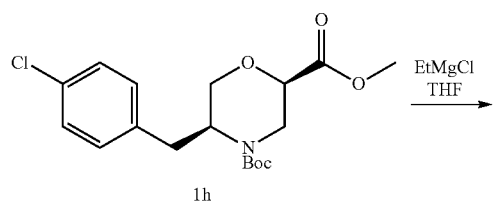

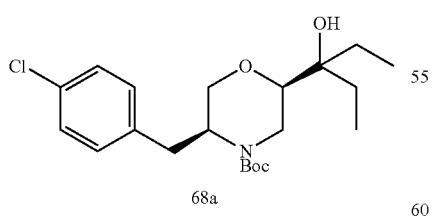

The title compound (68a) was obtained from 1h (220 mg; 0.6 mmol) according to the General Procedure VI in 99% yield (234 mg; 0.59 mmol).

ESI-MS m/z for $C_{17}H_{23}ClNO_3$ found 324.1/326.1 (M+H–tBu–H$_2$O)$^+$;

Step 2

Synthesis of 3-((2R,5S)-5-(4-chlorobenzyl)morpholin-2-yl)pentan-3-ol 2,2,2-trifluoroacetate (68b)

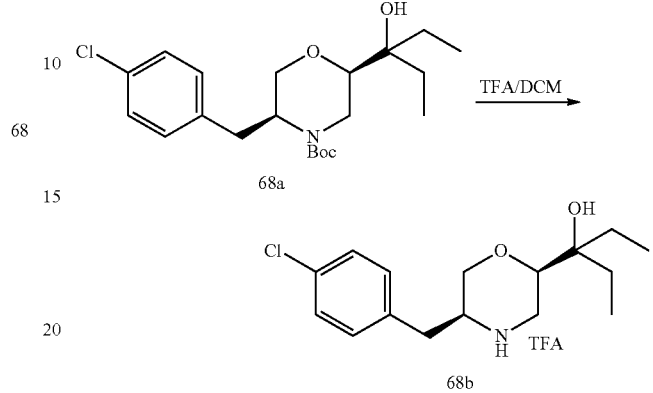

The title compound (68b) was obtained as a TFA salt from 68a (234 mg; 0.59 mmol) according to the General Procedure IVb in 99% yield (238 mg; 0.58 mmol).

Step 3

Synthesis of 3-((2R,5S)-4-(1-(5-amino-4H-1,2,4-triazol-3-yl)piperidin-4-yl)-5-(4-chlorobenzyl)-morpholin-2-yl)pentan-3-ol 2,2,2-trifluoroacetate (68)

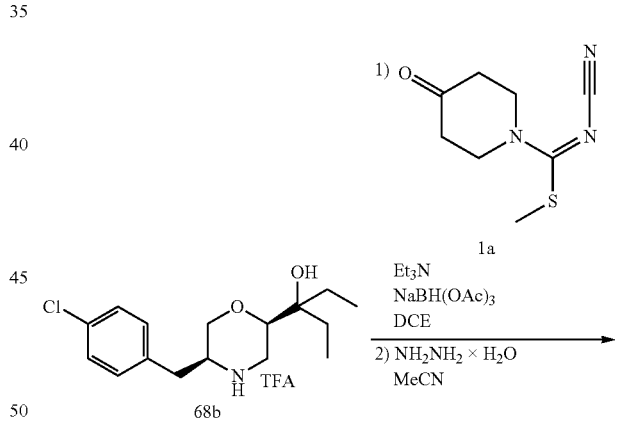

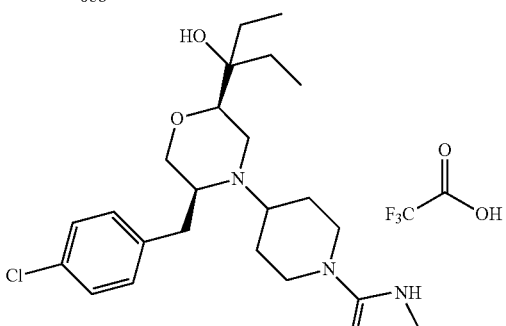

The title compound (68) was obtained as a TFA salt from 68b (238 mg; 0.58 mmol) according to the General Procedure Vb in 28% yield (94 mg; 0.16 mmol).

ESI-MS m/z for $C_{23}H_{36}ClN_6O_2$ found 463.1/465.1 $(M+H)^+$; $^1H$ NMR (700 MHz, DMSO-$d_6$+$D_2O$, 348 K) δ 7.42-7.35 (m, 2H), 7.35-7.30 (m, 2H), 3.95-3.87 (m, 2H), 3.74-3.61 (m, 5H), 3.41-3.36 (m, 1H), 3.30-3.21 (m, 1H), 3.15-3.05 (m, 2H), 2.99-2.85 (m, 2H), 2.27-2.11 (m, 2H), 1.73-1.35 (m, 6H), 0.92-0.76 (m, 6H).

Example 69

Synthesis of (2R,5S)-4-(1-(5-amino-4H-1,2,4-triazol-3-yl)piperidin-4-yl)-5-(4-chlorobenzyl)-N-isobutylmorpholine-2-carboxamide 2,2,2-trifluoroacetate (69)

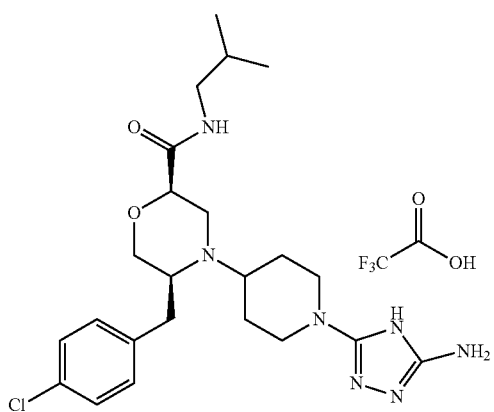

69

The title compound 69 was obtained as a TFA salt in 34% overall yield in a similar way to Example 23 with the exception that, in the first step of the synthesis, isobutyl amine was used instead of 2,2-dimethylcyclopropane-1-amine hydrochloride.

ESI-MS m/z for $C_{23}H_{35}ClN_7O_2$ found 476.0/478.0 $(M+1)^+$; $^1H$ NMR (700 MHz, DMSO-$d_6$+$D_2O$, 348 K) δ 7.40-7.36 (m, 2H), 7.36-7.31 (m, 2H), 4.24-4.20 (m, 1H), 3.87-3.80 (m, 2H), 3.72-3.67 (m, 2H), 3.60-3.55 (m, 1H), 3.50-3.43 (m, 2H), 3.16-3.11 (m, 1H), 3.08-3.04 (m, 2H), 3.01-2.90 (m, 4H), 2.14-2.04 (m, 2H), 1.81-1.73 (m, 1H), 1.65-1.57 (m, 2H), 0.89-0.80 (m, 6H).

Example 70

Synthesis of (3R,6R)-1'-(5-amino-4H-1,2,4-triazol-3-yl)-6-(4-chlorobenzyl)-[1,4'-bipiperidin]-3-ol 2,2,2-trifluoroacetate (70)

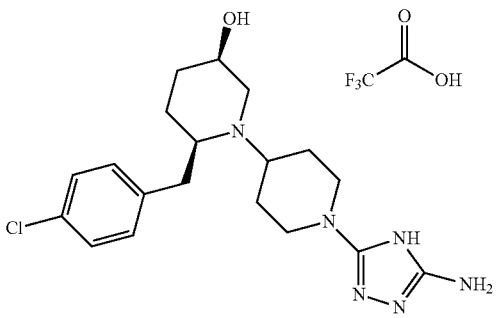

70

Step 1

Synthesis of (2R,5R)-tert-butyl 2-(4-chlorobenzyl)-5-hydroxypiperidine-1-carboxylate (70a)

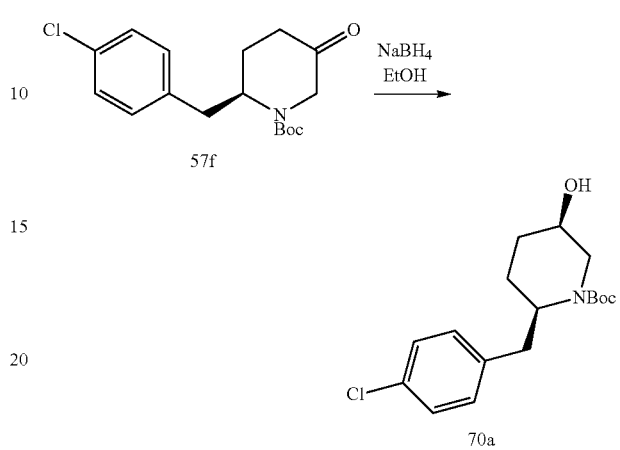

To a solution of 57f (136 mg; 0.42 mmol) in EtOH (8.4 mL) NaBH$_4$ (24 mg; 0.63 mmol) was added at −5° C. and the mixture was stirred at this temperature for 4 hours. The reaction progress was monitored by LC-MS. When analysis indicated completion of the reaction, the mixture was concentrated and saturated aqueous NH$_4$Cl (20 mL) was added and the product was extracted with DCM (4×15 mL). Combined organic solutions were dried over Na$_2$SO$_4$, filtered and concentrated in vacuo and the crude product was used in the next step without additional purification. Compound 70a was obtained in 99% yield (137 mg; 0.42 mmol).

ESI-MS m/z for $C_{12}H_{17}ClNO$ found 226.1/228.1 (M+H-Boc)$^+$.

Step 2

Synthesis of (3R,6R)-6-(4-chlorobenzyl)piperidin-3-ol hydrochloride (70b)

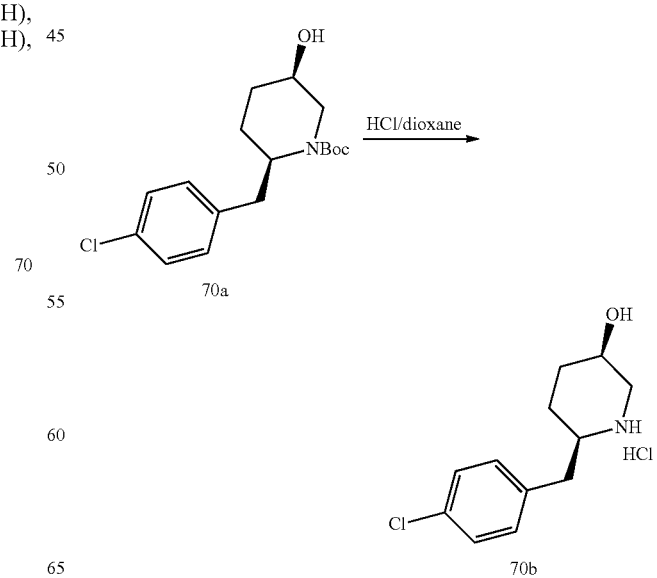

The title compound (70b) was obtained as a hydrochloride salt from 70a (137 mg; 0.42 mmol) according to the General Procedure IVa in 99% yield (110 mg; 0.42 mmol).

ESI-MS m/z for $C_{12}H_{17}ClNO$ found 226.1/228.1 $(M+H)^+$.

Step 3

Synthesis of (3R,6R)-1'-(5-amino-4H-1,2,4-triazol-3-yl)-6-(4-chlorobenzyl)-[1,4'-bipiperidin]-3-ol 2,2,2-trifluoroacetate (70)

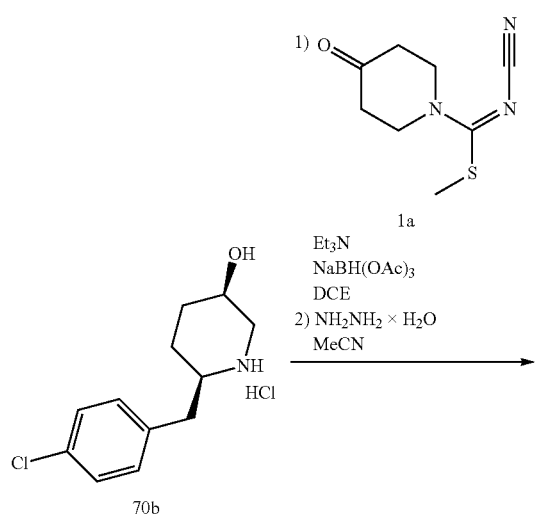

The title compound (70) was obtained as a TFA salt from 70b (110 mg; 0.42 mmol) according to the General Procedure Vb in 40% yield (59 mg; 0.17 mmol).

ESI-MS m/z for $C_{19}H_{28}ClN_6O$ found 391.2/393.2 $(M+H)^+$; $^1H$ NMR (400 MHz, Methanol-$d_4$) δ 7.44-7.34 (m, 2H), 7.34-7.25 (m, 2H), 4.18-4.08 (m, 1H), 4.04-3.85 (m, 3H), 3.77-3.65 (m, 1H), 3.58-3.39 (m, 2H), 3.22-3.03 (m, 2H), 2.99-2.85 (m, 1H), 2.80-2.66 (m, 1H), 2.15-1.90 (m, 4H), 1.90-1.78 (m, 2H), 1.73-1.59 (m, 2H).

Example 71

Synthesis of 5-((2R,5R)-2-(4-chlorobenzyl)-5-methoxy-[1,4'-bipiperidin]-1'-yl)-4H-1,2,4-triazol-3-amine 2,2,2-trifluoroacetate (71)

71

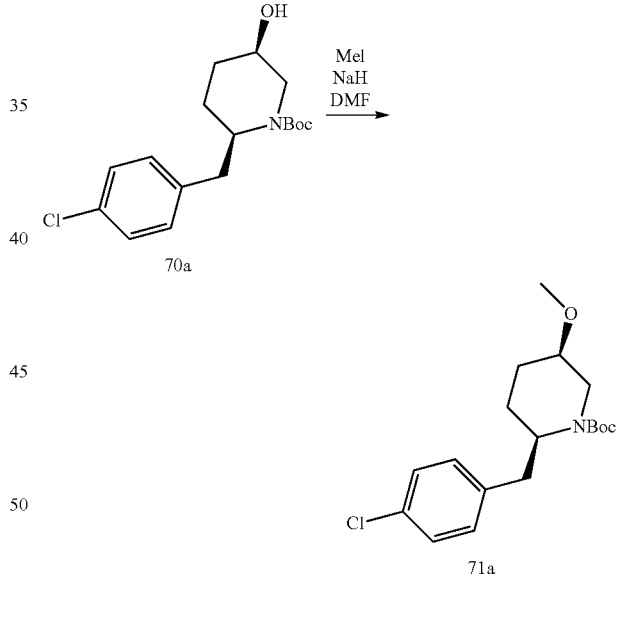

Step 1

Synthesis of (2R,5R)-tert-butyl 2-(4-chlorobenzyl)-5-methoxypiperidine-1-carboxylate (71a)

To a solution of 70a (191 mg; 0.59 mmol) in anhydrous DMF (5.9 mL) under nitrogen atmosphere NaH (60% dispersion in oil; 70 mg; 1.76 mmol) was added in one portion at 0° C. and after 5 minutes MeI (73 µL; 1.17 mmol) was added and the mixture was stirred at this temperature for 1 hour. The reaction progress was monitored by LC-MS. Catalytic amount of imidazole (10 mg), NaH (60% dispersion in oil; 140 mg; 3.52 mmol) and MeI (0.3 mL; 4.81 mmol) were added and the mixture was stirred at 0° C. for another 2 hours. LC-MS showed completion of the reaction. An excess of NaH was carefully decomposed with saturated aqueous $NH_4Cl$ (20 mL) and the product was extracted with $Et_2O$ (3×20 mL). Combined organic solutions were washed with water (2×10 mL) and brine (10 mL), dried over Na$_2$SO$_4$, filtered and concentrated in vacuo and the crude product was used in the next step without additional purification. Compound 71a was obtained in 99% yield (200 mg; 0.58 mmol).

ESI-MS m/z for C$_{13}$H$_{19}$ClNO found 240.1/242.1 (M+H-Boc)$^+$.

Step 2

Synthesis of (2R,5R)-2-(4-chlorobenzyl)-5-methoxypiperidine hydrochloride (71b)

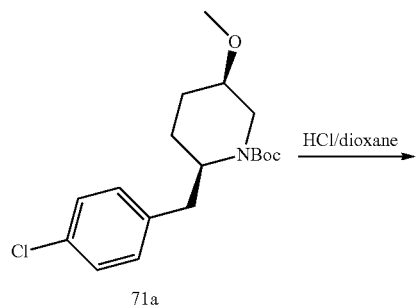

71a

71b

The title compound (71b) was obtained as a hydrochloride salt from 71a (200 mg; 0.58 mmol) according to the General Procedure IVa in 99% yield (157 mg; 0.57 mmol).

ESI-MS m/z for C$_{13}$H$_{19}$ClNO found 240.1/242.1 (M+H)$^+$.

Step 3

Synthesis of 5-((2R,5R)-2-(4-chlorobenzyl)-5-methoxy-[1,4'-bipiperidin]-1'-yl)-4H-1,2,4-triazol-3-amine 2,2,2-trifluoroacetate (71)

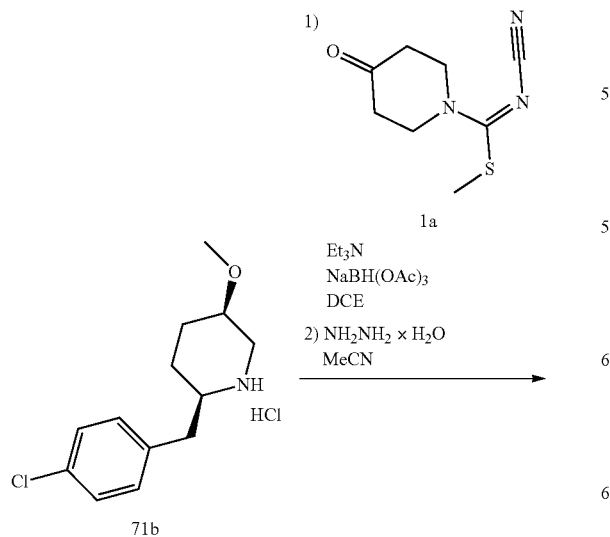

71b

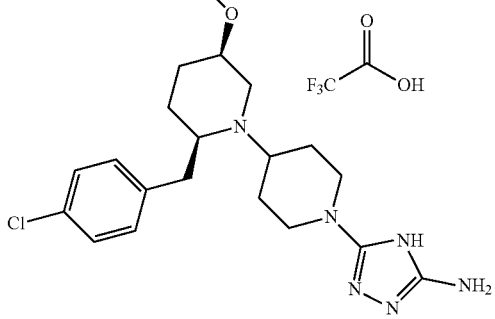

71

The title compound (71) was obtained as a TFA salt from 71b (157 mg; 0.57 mmol) according to the General Procedure Vb in 51% yield (151 mg; 0.29 mmol).

ESI-MS m/z for C$_{20}$H$_{30}$ClN$_6$O found 405.3/407.3 (M+H)$^+$; $^1$H NMR (400 MHz, Methanol-d$_4$) δ 7.41-7.35 (m, 2H), 7.31-7.25 (m, 2H), 4.02-3.85 (m, 3H), 3.78-3.58 (m, 3H), 3.55-3.45 (m, 1H), 3.39 (s, 3H), 3.18-3.05 (m, 2H), 3.01-2.89 (m, 1H), 2.81-2.68 (m, 1H), 2.11-1.78 (m, 6H), 1.69-1.51 (m, 2H).

Example 72

Synthesis of 5-(4-((4R)-4-(4-chlorobenzyl)-3-azabicyclo[4.1.0]heptan-3-yl)piperidin-1-yl)-4H-1,2,4-triazol-3-amine 2,2,2-trifluoroacetate (72)

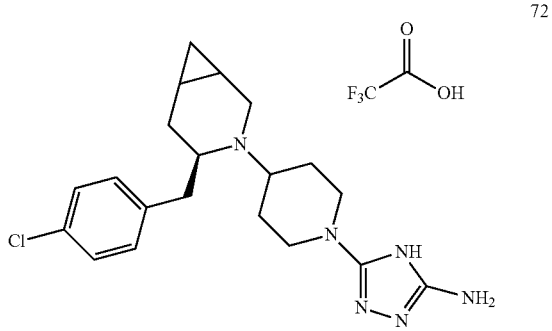 [SMILES: Nc1nnc(N2CCC(N3CC4CC4C[C@@H]3Cc3ccc(Cl)cc3)CC2)[nH]1 ; O=C(O)C(F)(F)F]

72

Step 1

Synthesis of (S,Z)—N-(2-(4-chlorophenyl)ethylidene)-2-methylpropane-2-sulfinamide (72a)

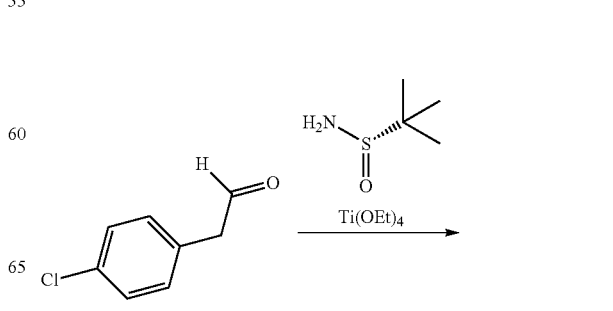

-continued

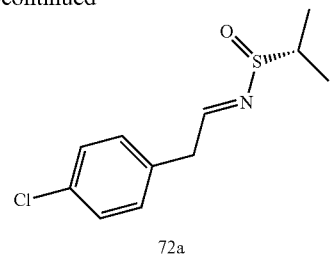

72a

A solution of p-chlorophenylacetaldehyde (6.5 g; 42.04 mmol), (S)-2-methyl-2-propane-sulfinamide (5.09 g; 42.04 mmol), Ti(OEt)$_4$ (17.63 mL; 84.08 mmol) in anhydrous DCM (84 mL) was refluxed for 2 hours, then slightly heated overnight with stirring. Anhydrous MgSO$_4$ was added (16.8 g; 139.52 mmol) and after 15 minutes the reaction was filtered through a pad of Celite. The filtrate was concentrated and the crude product was purified by column chromatography (hexane/AcOEt 2:1 v/v) and 72a was obtained in 67% yield (7.35 g, 28.5 mmol).

ESI-MS m/z for C$_{12}$H$_{17}$ClNOS found 258.1/260.1 (M+H)$^+$.

Step 2

Synthesis of (S)—N—((R)-1-(4-chlorophenyl)pent-4-en-2-yl)-2-methylpropane-2-sulfinamide (72b)

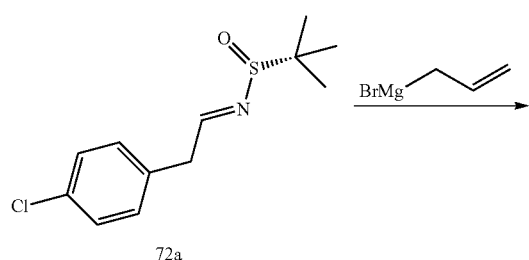

The title compound (72b) was obtained from 77a (7.35 g, 28.5 mmol) according to the General Procedure VI in 58% yield (5.0 g, 16.7 mmol).

ESI-MS m/z for C$_{15}$H$_{23}$ClNOS found 300.1/302.1 (M+H)$^+$; $^1$H NMR (500 MHz, CDCl$_3$) δ 7.21 (AA'BB', J=8.3 Hz, 2H), 7.08 (AA'BB', J=8.5 Hz, 2H), 5.81-5.71 (m, 1H), 5.18-5.10 (m, 2H), 3.54-3.46 (m, 1H), 3.33-3.28 (m, 1H), 2.78 (dd, J=7.1, 13.7 Hz, 1H), 2.69 (dd, J=6.4, 13.7 Hz, 1H), 2.40-2.32 (m, 1H), 2.31-2.23 (m, 1H), 1.08 (s, 9H).

Step 3

Synthesis of (S)—N-allyl-N—((R)-1-(4-chlorophenyl)pent-4-en-2-yl)-2-methylpropane-2-sulfinamide (72c)

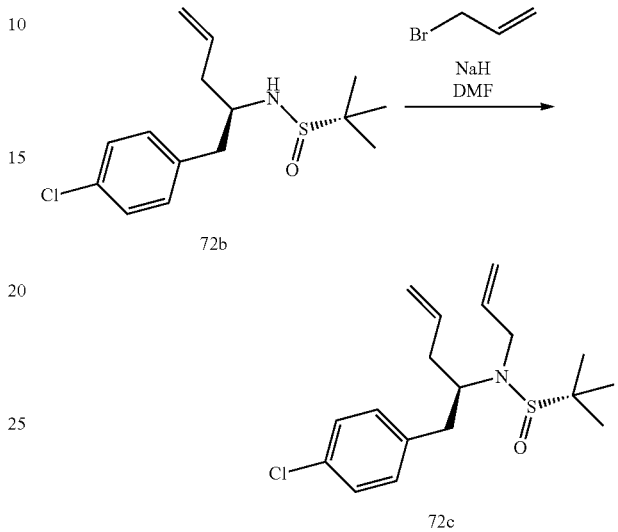

To a solution of 72b (1 g, 3.33 mmol) in anhydrous DMF (6 mL) under nitrogen atmosphere NaH (60% dispersion in oil; 265 mg; 6.66 mmol) was added in one portion and after 20 minutes allyl bromide (0.43 mL; 5 mmol) was added dropwise and the mixture was stirred for 1 hour. The reaction progress was monitored by LC-MS. When analysis indicated completion of the reaction, the reaction mixture was poured into a saturated aqueous NH$_4$Cl and extracted with Et$_2$O. Combined organic solutions were washed with brine, dried over MgSO$_4$, filtered and concentrated in vacuo and the crude product was purified by column chromatography (hexane/AcOEt 3:1 v/v) and 72c was obtained in 71% yield (0.78 g, 2.29 mmol).

ESI MS m/z for C$_{18}$H$_{27}$ClNOS found 340.2/342.2 (M+H)$^+$.

Step 4

Synthesis of (R)-1-((S)-tert-butylsulfinyl)-2-(4-chlorobenzyl)-1,2,3,6-tetrahydropyridine (72d)

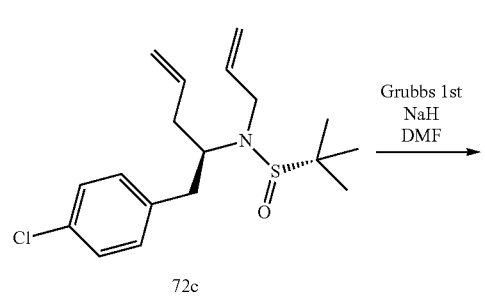

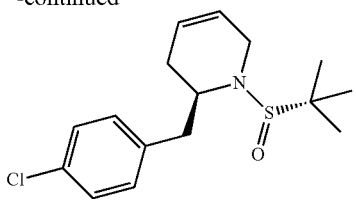

72d

To a solution of 72c (0.78 g, 2.29 mmol) in DCM (46 mL) 1st generation Grubbs catalyst (91 mg; 0.11 mmol) was added and the reaction mixture was refluxed for 1.5 hours. After this time, reaction mixture was cooled down and concentrated in vacuo and the crude product was purified by column chromatography (hexane/AcOEt 10:1 v/v). Compound 72d was obtained in 94% yield (0.67 g, 2.15 mmol).

ESI-MS m/z for $C_{16}H_{23}ClNOS$ found 312.2/314.2 $(M+H)^+$.

Step 5

Synthesis of (4R)-3-((R)-tert-butylsulfinyl)-4-(4-chlorobenzyl)-3-azabicyclo[4.1.0]heptane (72e)

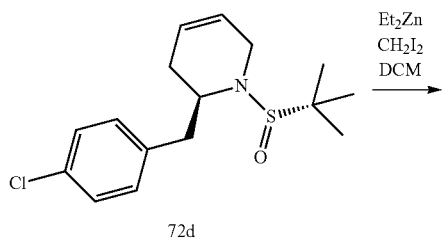

72d

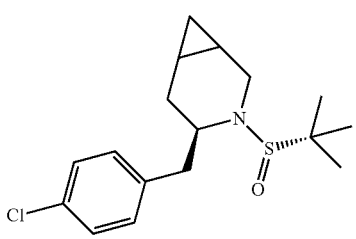

72e

To a solution of 72d (0.6 g; 1.92 mmol) in DCM (12 mL) $Et_2Zn$ (1 M in hexane; 15.4 mL; 15.38 mmol) was added dropwise at 15° C. and after 10 minutes at this temperature the mixture was cooled to 0° C. Then the solution of diiodomethane (1.2 mL; 15.38 mmol) in DCM (5 mL) was added dropwise and the mixture was stirred at room temperature overnight. The reaction progress was monitored by LC-MS. Another portion of $Et_2Zn$ (1 M in hexane; 7 mL; 7.69 mmol) was added at 15° C. to the reaction mixture and then diiodomethane (0.6 mL; 7.69 mmol) was added at 0° C. and the reaction was stirred overnight. LC-MS showed completion of the reaction. After this time, reaction mixture was poured into saturated solution of $NH_4Cl$ and stirred for 20 minutes. Phases were separated, aqueous one was extracted with DCM. Combined organic solutions were washed with brine, dried over $MgSO_4$, filtered and concentrated in vacuo and the crude product was purified by column chromatography (hexane/AcOEt 5:1 to 4:1 v/v). Compound 72d was obtained in 9% yield (60 mg, 0.18 mmol).

ESI-MS m/z for $C_{17}H_{25}ClNOS$ found 325.9/327.9 $(M+H)^+$.

Step 6

Synthesis of (4R)-4-(4-chlorobenzyl)-3-azabicyclo[4.1.0]heptane hydrochloride (72f)

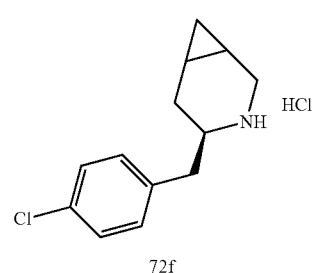

72e

72f

The title compound (72f) was obtained as a hydrochloride salt from 72e (60 mg, 0.18 mmol) according to the General Procedure IVa in 99% yield (46 mg; 0.18 mmol).

ESI-MS m/z for $C_{13}H_{17}ClN$ found 221.9/223.9 $(M+H)^+$.

Step 7

Synthesis of 5-(4-((4R)-4-(4-chlorobenzyl)-3-azabicyclo[4.1.0]heptan-3-yl)piperidin-1-yl)-4H-1,2,4-triazol-3-amine 2,2,2-trifluoroacetate (72)

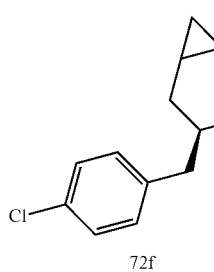

72f

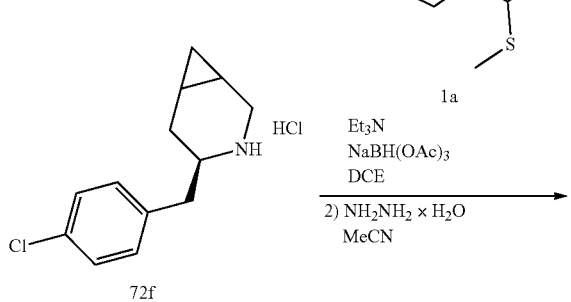

1a

269
-continued

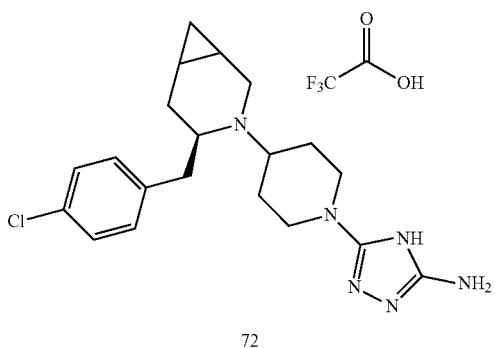

72

The title compound (72) was obtained as a TFA salt from 72f (200 mg; 0.77 mmol) according to the General Procedure Vb in 18% yield (69 mg; 0.14 mmol).

ESI-MS m/z for $C_{20}H_{28}ClN_6$ found 387.1/389.1 (M+H)$^+$;
$^1$H NMR (700 MHz, D$_2$O, 333 K) δ 7.81-7.69 (m, 2H), 7.68-7.54 (m, 2H), 4.20-4.02 (m, 3H), 3.98-3.78 (m, 2H), 3.56-3.44 (m, 1H), 3.41-3.21 (m, 3H), 3.07-2.91 (m, 1H), 2.54-2.32 (m, 3H), 2.27-2.08 (m, 2H), 1.74-1.53 (m, 3H), 1.37-1.22 (m, 1H), 0.73-0.60 (m, 1H).

Example 73

Synthesis of 5-(4-((7S,9aR)-7-(4-chlorobenzyl)hexahydropyrazino[2,1-c][1,4]oxazin-8(1H)-yl)piperidin-1-yl)-4H-1,2,4-triazol-3-amine hydrochloride (73)

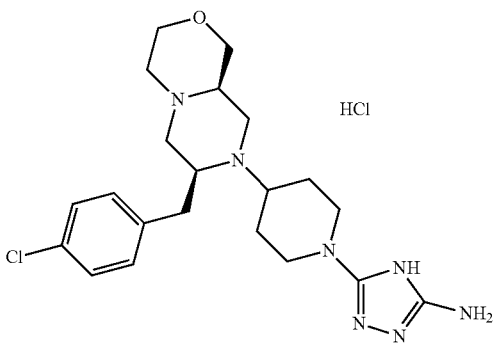

73

270

Step 1

Synthesis of (S)-methyl 4-((S)-2-((tert-butoxycarbonyl)amino)-3-(4-chlorophenyl)propanoyl)-morpholine-3-carboxylate (73a)

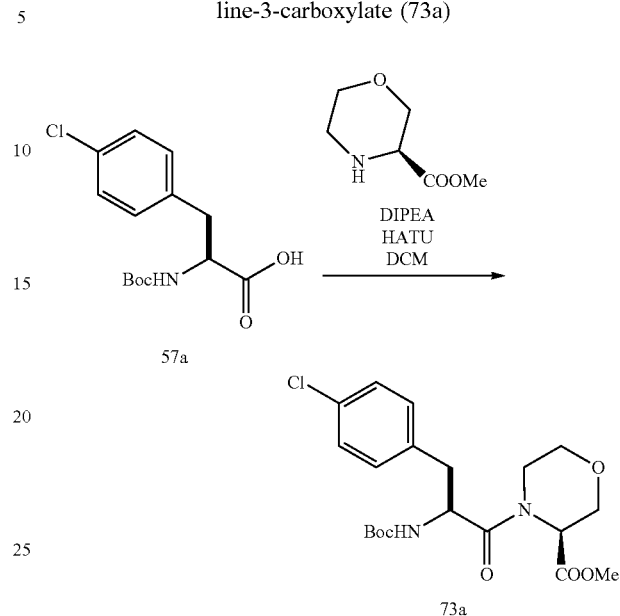

The title compound (73a) was obtained from 57a (2.64 g, 8.81 mmol) according to the General Procedure III in 77% yield (2.89 g; 6.79 mmol).

ESI-MS m/z for $C_{20}H_{28}ClN_2O_6$ found 427.1/429.1 (M+H)$^+$.

Step 2

Synthesis of (S)-methyl 4-((S)-2-amino-3-(4-chlorophenyl)propyl)morpholine-3-carboxylate hydrochloride (73b)

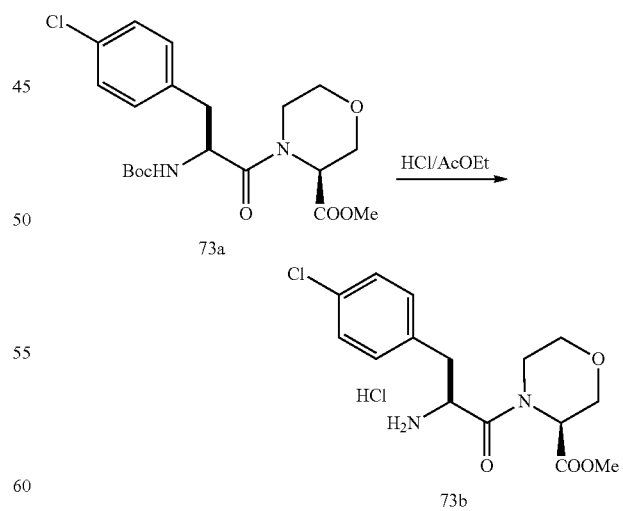

The title compound (73b) was obtained as a hydrochloride salt from 73a (2.89 g; 6.79 mmol) according to the General Procedure IVa in 99% yield (2.31 g; 6.62 mmol).

ESI-MS m/z for $C_{15}H_{22}ClN_2O_3$ found 313.1/315.1 (M+H)$^+$.

Step 3

Synthesis of (7S,9aS)-7-(4-chlorobenzyl)hexahydro-pyrazino[2,1-c][1,4]oxazine-6,9-dione (73c)

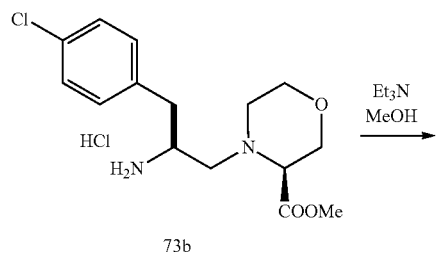

73b

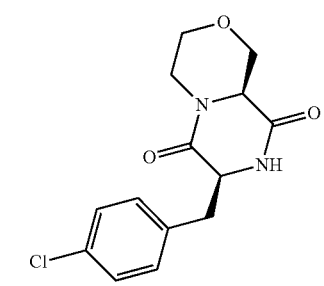

73c

To a solution of 73b (2.31 g; 6.62 mmol) in MeOH (70 mL) Et$_3$N (4.77 mL; 33.96 mmol) was added and the reaction mixture was stirred at ambient temperature for 2 hours. The reaction progress was monitored by LC-MS. Then the reaction mixture was concentrated in vacuo and the crude product was purified by flash column chromatography (DCM/MeOH 100:1 to 50:1 v/v). Compound 73c was obtained as a light yellow foam in 61% yield (1.18 g, 4.01 mmol).

ESI-MS m/z for $C_{14}H_{16}ClN_2O_3$ found 295.1/297.1 (M+H)$^+$.

Step 4

Synthesis of (7S,9aR)-7-(4-chlorobenzyl)octahydro-pyrazino[2,1-c][1,4]oxazine (73d)

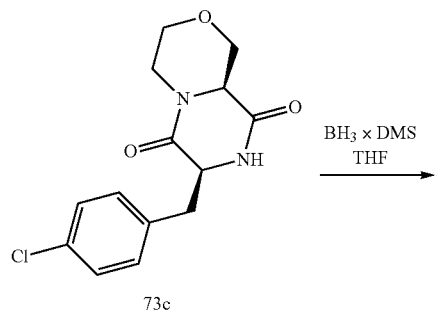

73c

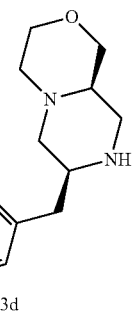

73d

The title compound (73d) was obtained from 73c (1.1 g; 3.73 mmol) according to the General Procedure Ib in 96% yield (0.95 g; 3.57 mmol).

ESI-MS m/z for $C_{14}H_{20}ClN_2O$ found 266.8/268.8 (M+H)$^+$

Step 5

Synthesis of tert-butyl 4-((7S,9aR)-7-(4-chlorobenzyl)hexahydropyrazino[2,1-c][1,4]oxazin-8(1H)-yl)piperidine-1-carboxylate (73e)

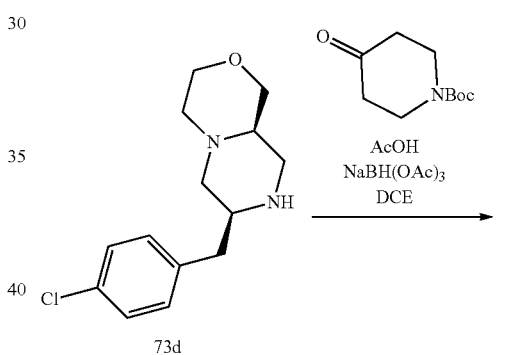

73d

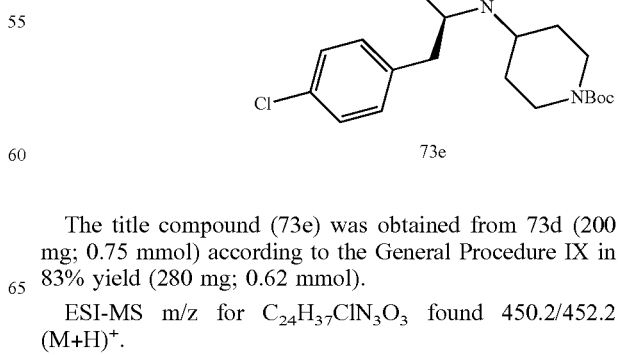

73e

The title compound (73e) was obtained from 73d (200 mg; 0.75 mmol) according to the General Procedure IX in 83% yield (280 mg; 0.62 mmol).

ESI-MS m/z for $C_{24}H_{37}ClN_3O_3$ found 450.2/452.2 (M+H)$^+$.

273

Step 6

Synthesis of (7S,9aR)-7-(4-chlorobenzyl)-8-(piperidin-4-yl)octahydropyrazino[2,1-c][1,4]oxazine hydrochloride (73f)

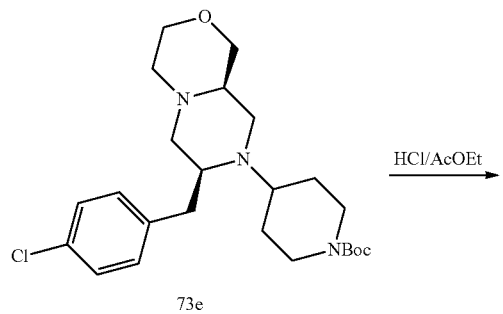

73e

HCl/AcOEt →

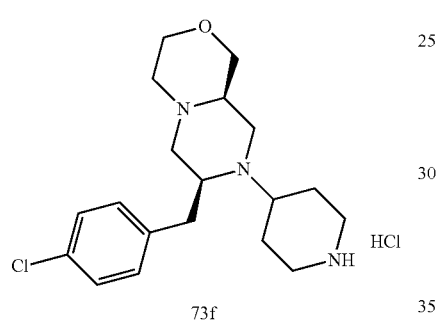

73f

The title compound (73f) was obtained as a hydrochloride salt from 73e (250 mg; 0.56 mmol) according to the General Procedure IVa in 93% yield (200 mg; 0.52 mmol).

ESI-MS m/z for $C_{19}H_{29}ClN_3O$ found 350.1/352.1 (M+H)⁺.

Step 7

Synthesis of 5-(4-((7S,9aR)-7-(4-chlorobenzyl)hexahydropyrazino[2,1-c][1,4]oxazin-8(1H)-yl)piperidin-1-yl)-4H-1,2,4-triazol-3-amine hydrochloride (73)

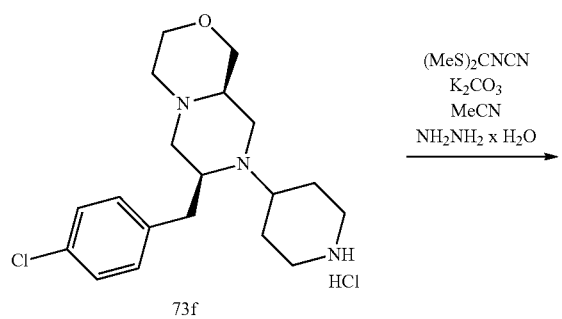

73f (MeS)₂CNCN
K₂CO₃
MeCN
NH₂NH₂ x H₂O →

274

-continued

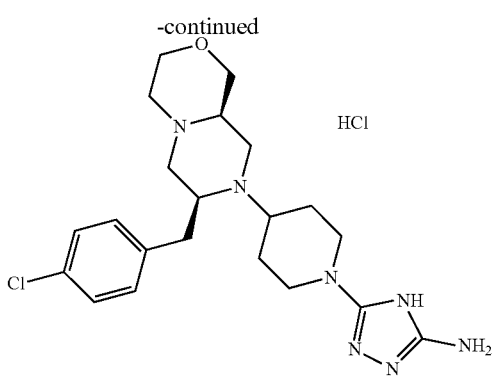

73

The title compound (73) was obtained as a hydrochloride salt from 73f (190 mg; 0.49 mmol) according to the General Procedure Va in 57% yield (130 mg; 0.28 mmol).

ESI-MS m/z for $C_{21}H_{31}ClN_7O$ found 432.1/434.1 (M+H)⁺; ¹H NMR (250 MHz, DMSO-d₆+D₂O, 348 K) δ 7.41-7.28 (m, 4H), 3.90-3.65 (m, 6H), 3.41-3.23 (m, 3H), 3.15-2.85 (m, 4H), 2.82-2.61 (m, 4H), 2.56-2.52 (m, 1H), 2.43-2.33 (m, 1H), 2.18-2.02 (m, 2H), 1.82-1.49 (m, 2H).

Example 74

Synthesis of ((2R,5S)-4-(1-(5-amino-4H-1,2,4-triazol-3-yl)piperidin-4-yl)-5-(4-chlorobenzyl)-morpholin-2-yl)methanol hydrochloride (74)

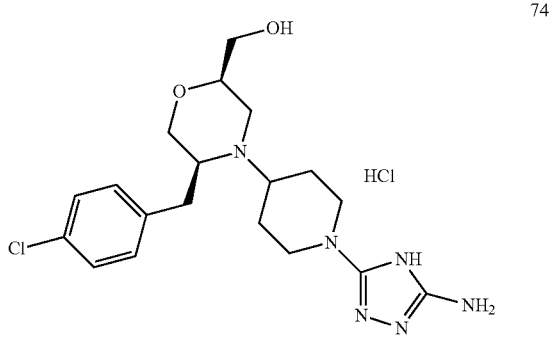 [SMILES: Nc1nnc(N2CCC(N3C[C@H](CO)OC[C@@H]3Cc3ccc(Cl)cc3)CC2)[nH]1 ; Cl]

74

Step 1

Synthesis of ((2R,5S)-5-(4-chlorobenzyl)-4-(piperidin-4-yl)morpholin-2-yl)methanol 2,2,2-trifluoroacetate (74a)

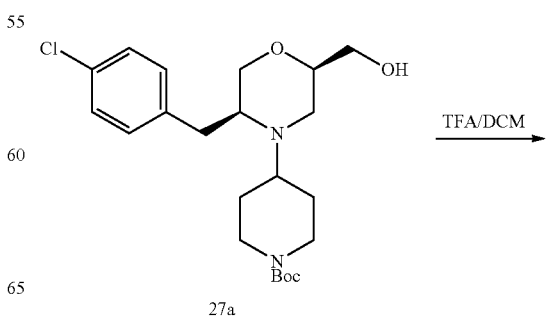

27a

TFA/DCM →

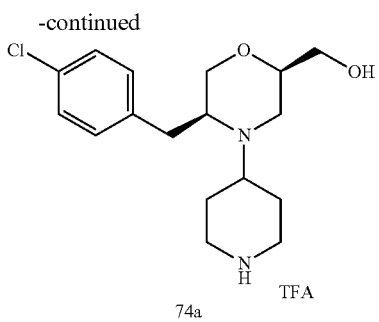

74a

The title compound (74a) was obtained as a TFA salt from 27a (180 mg; 0.42 mmol) according to the General Procedure IVa in 99% yield (184 mg; 0.42 mmol).

ESI-MS m/z for $C_{17}H_{26}ClN_2O_2$ found 324.9/326.9 $(M+H)^+$.

Step 2

Synthesis of ((2R,5S)-4-(1-(5-amino-4H-1,2,4-triazol-3-yl)piperidin-4-yl)-5-(4-chlorobenzyl)-morpholin-2-yl)methanol hydrochloride (74)

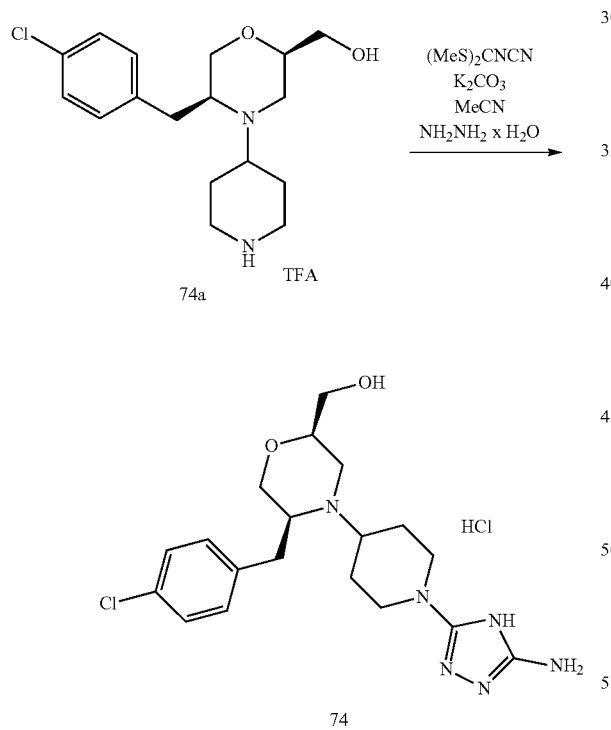

74

The title compound (74) was obtained as a hydrochloride salt from 74a (184 mg; 0.42 mmol) according to the General Procedure Va in 18% yield (40 mg; 0.077 mmol).

ESI-MS m/z for $C_{19}H_{28}ClN_6O_2$ found 407.3/409.3 $(M+H)^+$; $^1$H NMR (700 MHz, DMSO-$d_6$+$D_2$O) δ 7.43-7.37 (m, 2H), 7.37-7.29 (m, 2H), 3.96-3.80 (m, 4H), 3.77-3.65 (m, 2H), 3.65-3.52 (m, 4H), 3.21-3.07 (m, 3H), 3.04-2.95 (m, 2H), 2.29-2.18 (m, 2H), 1.87-1.74 (m, 2H).

Example 75

Synthesis of 5-(4-((2S,5S)-5-(4-bromobenzyl)-2-methylmorpholino)piperidin-1-yl)-4H-1,2,4-triazol-3-amine 2,2,2-trifluoroacetate (75)

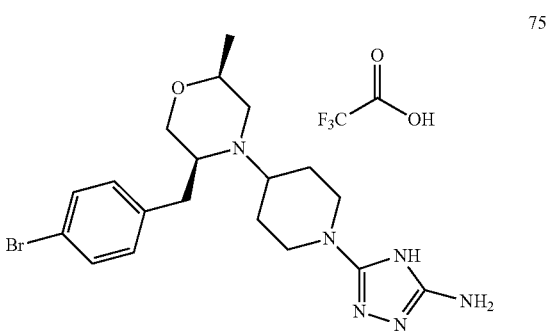

75

Step 1

Synthesis of N—((S)-1-(4-bromophenyl)-3-hydroxypropan-2-yl)-2-chloropropanamide (75a)

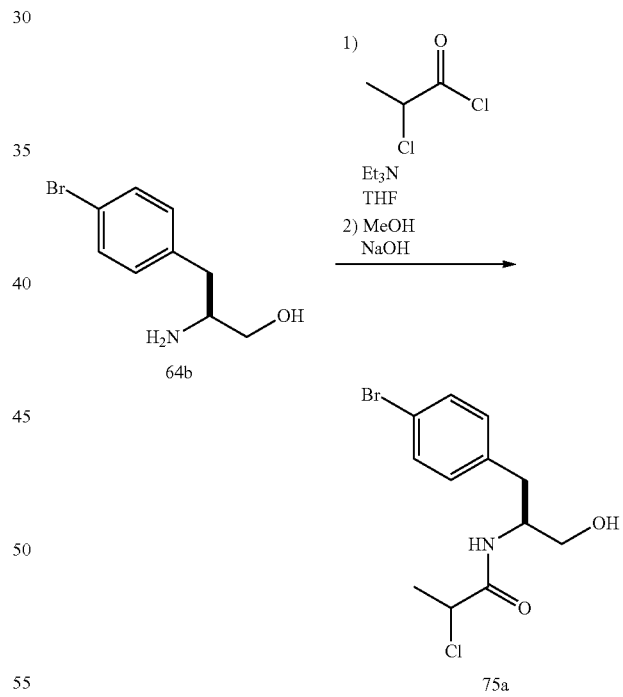

To a solution of 64a (1.5 g; 5.62 mmol) in THF (15 mL) Et$_3$N (2.33 mL; 16.86 mmol) was added and the reaction mixture was cooled to −10° C. and then a solution of 2-chloropropionylchloride (0.55 mL; 5.62 mmol) in THF (5 mL) was added dropwise and the mixture was stirred at −10° C. for 20 minutes and then 30 minutes at ambient temperature. The reaction progress was monitored by LC-MS. When analysis indicated completion of the reaction, the mixture was diluted with water and extracted with AcOEt. Combined organic solutions were washed with 0.5 M HCl, dried over MgSO₄, filtered and concentrated in vacuo and the crude product was dissolved in MeOH (10 mL) and to this solution 4 M NaOH (1 mL) was added and the mixture was stirred at room temperature for 1 hour. The reaction progress was monitored by LC-MS. When analysis indicated completion of the reaction, to this mixture water (5 mL) was added and then MeOH was removed in vacuo. The residue was diluted with brine and extracted with AcOEt (2×). Combined organic solutions were dried over anhydrous MgSO₄, filtered and concentrated in vacuo. The crude product used in the next step without additional purification. Compound 75a was obtained in 99% yield (1.77 g; 5.56 mmol).

ESI-MS m/z for $C_{12}H_{16}BrClNO_2$ found 319.7/321.7 (M+H)⁺.

Step 2

Synthesis of (2S,5S)-5-(4-bromobenzyl)-2-methyl-morpholin-3-one (75b)

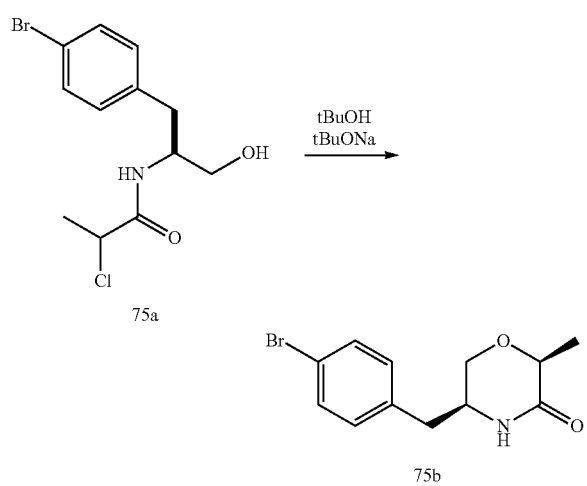

To a solution of 75a (1.77 g; 5.56 mmol) in tBuOH (10 mL) tBuONa (0.4 g; 4.18 mmol) was added and reaction was stirred at room temperature overnight. The reaction progress was monitored by LC-MS. When analysis indicated completion of the reaction, to this mixture 0.5 M HCl was added dropwise to pH 3 and extracted with AcOEt (2×). Combined organic solutions were dried over anhydrous MgSO₄, filtered and concentrated in vacuo and the crude product was used in the next step without additional purification. Compound 75b was obtained in 54% yield (0.85 g; 3 mmol).

ESI-MS m/z for $C_{12}H_{15}BrNO_2$ found 283.8/285.8 (M+H)⁺.

Step 3

Synthesis of (2S,5S)-5-(4-bromobenzyl)-2-methyl-morpholine (75c)

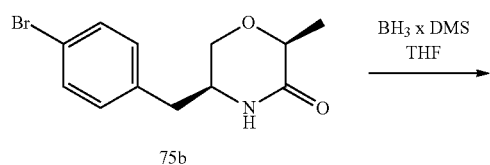

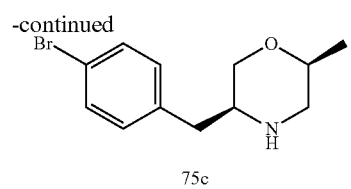

The title compound (75c) was obtained from 75b (0.74 g; 2.6 mmol) according to the General Procedure Ib in 97% yield (0.68 g; 2.53 mmol).

ESI-MS m/z for $C_{12}H_{17}BrNO$ found 269.9/271.9 (M+H)⁺.

Step 4

Synthesis of tert-butyl 4-((2S,5S)-5-(4-bromoben-zyl)-2-methylmorpholino)piperidine-1-carboxylate (75d)

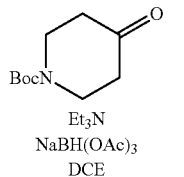

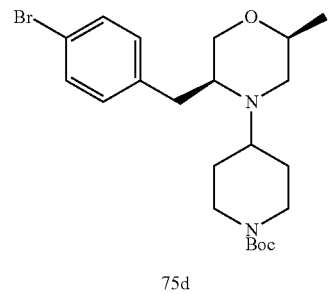

The title compound (75d) was obtained from 75c (0.67 g; 2.48 mmol) according to the General Procedure IX in 75% yield (0.84 g; 1.86 mmol).

ESI-MS m/z for $C_{22}H_{34}BrN_2O_3$ found 452.9/454.9 (M+H)⁺.

Step 5

Synthesis of (2S,5S)-5-(4-bromobenzyl)-2-methyl-4-(piperidin-4-yl)morpholine hydrochloride (75e)

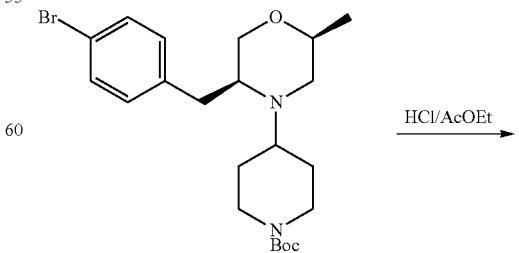

-continued

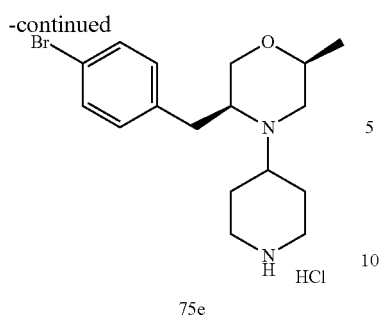

75e

The title compound (75e) was obtained from 75d (0.62 g; 1.37 mmol) according to the General Procedure IVa in 90% yield (0.48 g; 1.23 mmol).

ESI-MS m/z for $C_{17}H_{26}BrN_2O$ found 352.8/354.8 (M+H)$^+$.

Step 6

Synthesis of 5-(4-((2S,5S)-5-(4-bromobenzyl)-2-methylmorpholino)piperidin-1-yl)-4H-1,2,4-triazol-3-amine 2,2,2-trifluoroacetate (75)

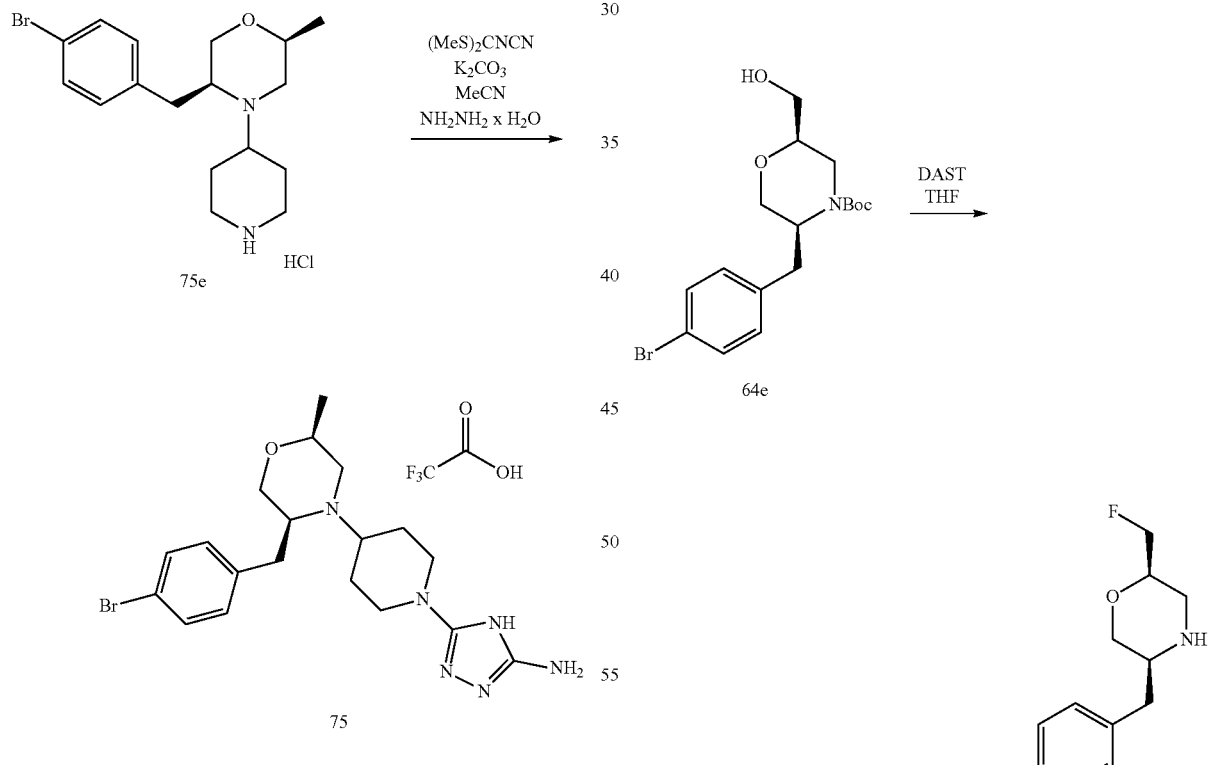

The title compound (75) was obtained as a TFA salt from 75e (100 mg; 0.28 mmol) according to the General Procedure Va in 71% yield (112 mg; 0.2 mmol).

ESI-MS m/z for $C_{19}H_{28}BrN_6O$ found 434.9/436.9 (M+H)$^+$; $^1$H NMR (700 MHz, DMSO-d$_6$+D$_2$O, 348 K) δ 7.56-7.48 (m, 2H), 7.30-7.22 (m, 2H), 3.92-3.81 (m, 3H), 3.71-3.57 (m, 4H), 3.21-2.89 (m, 6H), 2.27-2.14 (m, 2H), 1.74-1.56 (m, 2H), 1.23 (d, J=6.2 Hz, 3H).

Example 76

Synthesis of 5-(4-((2R,5S)-5-(4-bromobenzyl)-2-(fluoromethyl)morpholino)piperidin-1-yl)-4H-1,2,4-triazol-3-amine 2,2,2-trifluoroacetate (76)

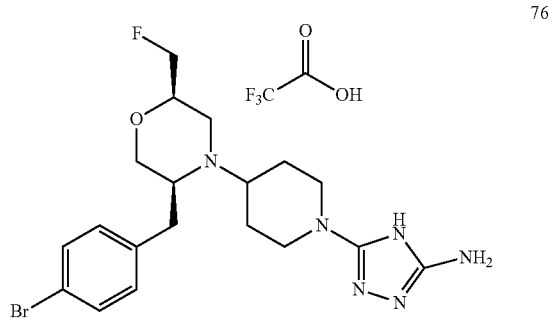 [SMILES: Nc1nnc(N2CCC(N3C[C@H](CF)OC[C@@H]3Cc3ccc(Br)cc3)CC2)[nH]1 ; O=C(O)C(F)(F)F]

Step 1

Synthesis of tert-butyl (2R,5S)-5-(4-bromobenzyl)-2-(fluoromethyl)morpholine-4-carboxylate (76a)

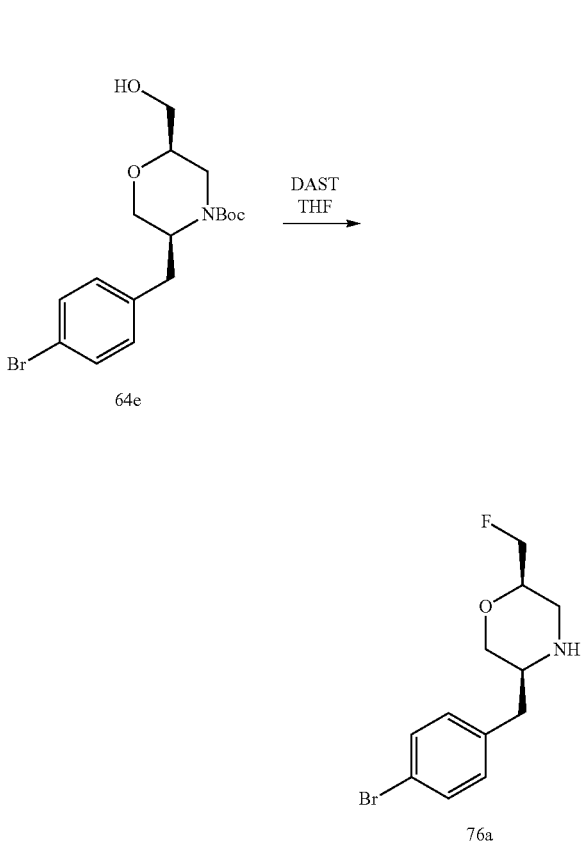 [SMILES: CC(C)(C)OC(=O)N1C[C@H](CO)OC[C@@H]1Cc1ccc(Br)cc1 ; FC[C@H]1CN[C@@H](Cc2ccc(Br)cc2)CO1]

The title compound (76a) was obtained from 64e (300 mg; 0.78 mmol) according to the General Procedure VII in 26% yield (77 mg; 0.2 mmol).

ESI-MS $C_{12}H_{16}BrFNO$ found 288.0/290.0 (M+H-Boc)$^+$.

Step 2

Synthesis of (2R,5S)-5-(4-bromobenzyl)-2-(fluoromethyl)morpholine hydrochloride (76b)

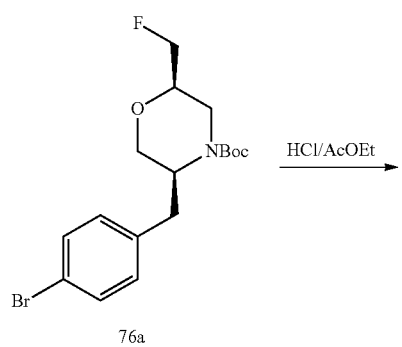

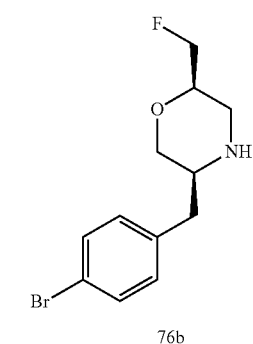

The title compound (76b) was obtained as a hydrochloride salt from 76a (77 mg; 0.2 mmol) according to the General Procedure IVa in 99% yield (65 mg; 0.2 mmol).

ESI-MS $C_{12}H_{16}BrFNO$ found 288.0/290.0 (M+H)$^+$; $^1$H NMR (700 MHz, Methanol-$d_4$) δ7.57-7.54 (m, 2H), 7.29-7.25 (m, 2H), 4.66-4.61 (m, 1H), 4.60-4.53 (m, 1H), 4.07-3.98 (m, 1H), 3.87-3.79 (m, 2H), 3.68-3.63 (m, 1H), 3.45-3.39 (m, 1H), 3.32-3.24 (m, 2H), 3.07-2.99 (m, 1H).

Step 3

Synthesis of tert-butyl 4-((2R,5S)-5-(4-bromobenzyl)-2-(fluoromethyl)morpholino)piperidine-1-carboxylate (76c)

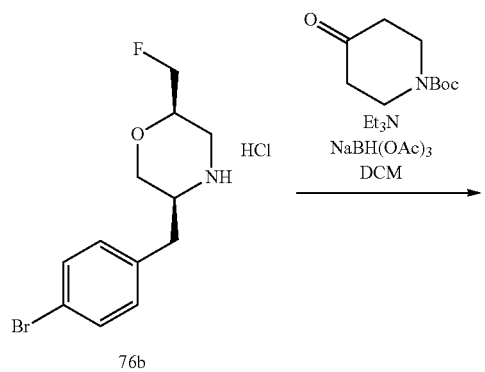

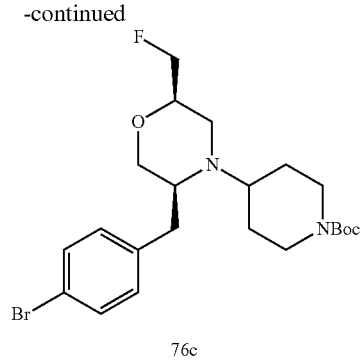

The title compound (76c) was obtained from 76b (65 mg; 0.2 mmol) according to the General Procedure IX in 56% yield (52 mg; 0.11 mmol).

ESI-MS m/z for $C_{22}H_{33}BrFN_2O_3$ found 471.2/473.2 (M+H)$^+$; $^1$H NMR (700 MHz, CDCl$_3$) δ 7.45-7.41 (m, 2H), 7.09-7.06 (m, 2H), 4.57-4.41 (m, 2H), 4.15-4.01 (m, 2H), 3.83-3.77 (m, 1H), 3.71-3.67 (m, 1H), 3.55-3.47 (m, 1H), 3.04-2.97 (m, 1H), 2.96-2.85 (m, 3H), 2.83-2.75 (m, 1H), 2.72-2.66 (m, 2H), 2.60-2.54 (m, 1H), 1.99-1.89 (m, 2H), 1.49 (s, 9H), 1.46-1.38 (m, 2H).

Step 4

Synthesis of (2R,5S)-5-(4-bromobenzyl)-2-(fluoromethyl)-4-(piperidin-4-yl)morpholine dihydrochloride (76d)

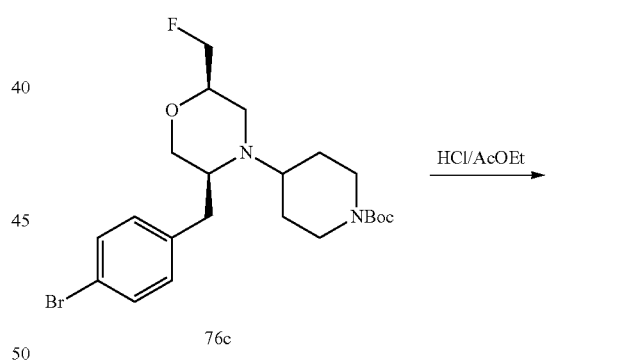

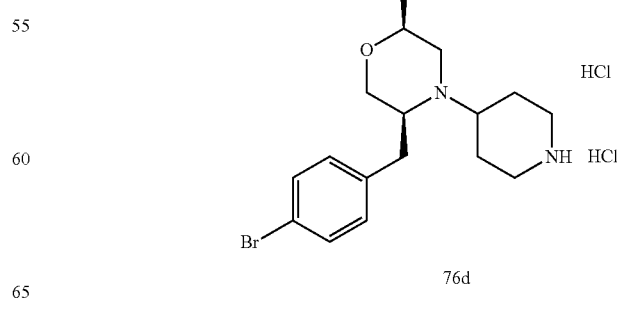

The title compound (76d) was obtained as a dihydrochloride salt from 76c (52 mg; 0.11 mmol) according to the General Procedure IVa in 98% yield (48 mg; 0.108 mmol).

ESI-MS $C_{17}H_{24}BrFN_2O$ found 271.1/273.1 (M+H)$^+$; $^1$H NMR (700 MHz, Methanol-$d_4$) δ 7.58-7.55 (m, 2H), 7.32-7.28 (m, 2H), 4.71-4.54 (m, 2H), 4.25-4.14 (m, 1H), 4.02-3.95 (m, 1H), 3.91-3.84 (m, 2H), 3.84-3.78 (m, 1H), 3.78-3.71 (m, 1H), 3.70-3.65 (m, 2H), 3.44-3.37 (m, 1H), 3.28-3.17 (m, 3H), 3.17-3.10 (m, 1H), 2.62-2.54 (m, 2H), 2.27-2.15 (m, 2H).

Step 5

Synthesis of 5-(4-((2R,5S)-5-(4-bromobenzyl)-2-(fluoromethyl)morpholino)piperidin-1-yl)-4H-1,2,4-triazol-3-amine 2,2,2-trifluoroacetate (76)

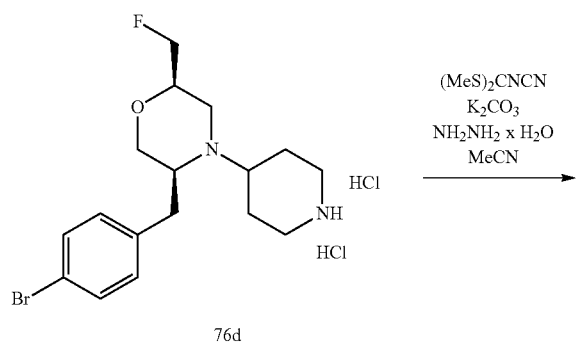

The title compound (76) was obtained as a TFA salt from 76d (48 mg; 0.108 mmol) according to the General Procedure Va in 29% yield (17 mg; 0.03 mmol).

ESI-MS m/z for $C_{19}H_{27}BrN_6O$ found 452.9/454.9 (M+H)$^+$; $^1$H NMR (700 MHz, Methanol-$d_4$) δ 7.58-7.54 (m, 2H), 7.30-7.26 (m, 2H), 4.71-4.52 (m, 2H), 4.08-3.98 (m, 3H), 3.90-3.81 (m, 2H), 3.79-3.71 (m, 2H), 3.71-3.66 (m, 1H), 3.40-3.34 (m, 1H), 3.29-3.22 (m, 1H), 3.20-3.14 (m, 1H), 3.11-3.02 (m, 2H), 2.39-2.32 (m, 2H), 1.89-1.75 (m, 2H).

Example 77

Synthesis of (S)-5-(4-(6-(4-(trifluoromethyl)benzyl)-5,6-dihydroimidazo[1,5-a]pyrazin-7(8H)-yl)piperidin-1-yl)-4H-1,2,4-triazol-3-amine 2,2,2-trifluoroacetate (77)

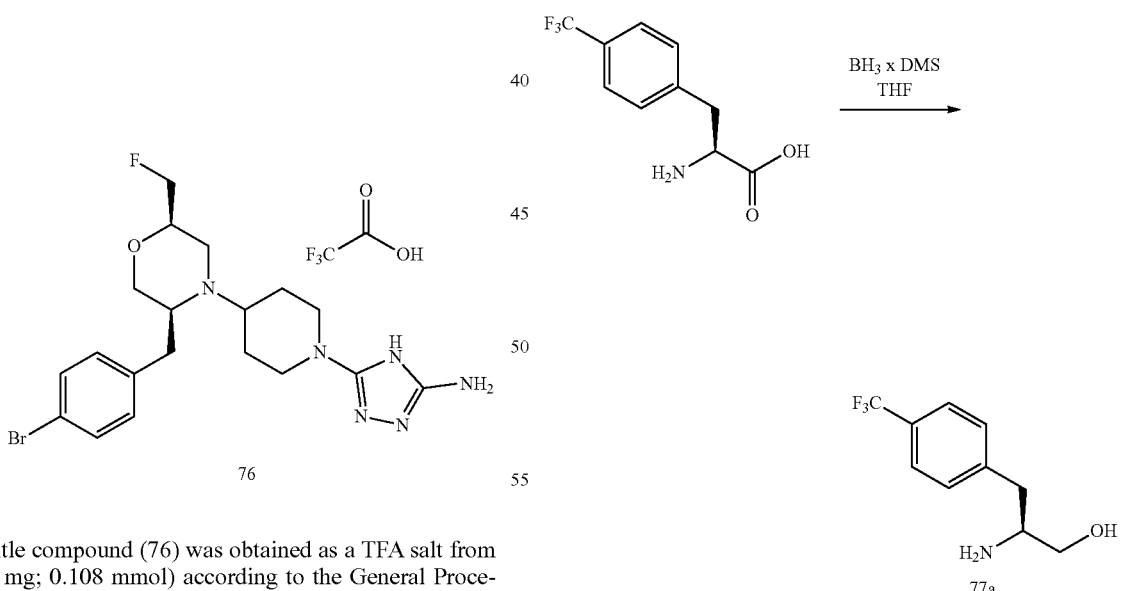

Step 1

Synthesis of (S)-2-amino-3-(4-(trifluoromethyl)phenyl)propan-1-ol (77a)

The title compound (77a) was obtained from optically pure (S)-2-amino-3-(4-(trifluoromethyl)phenyl)propanoic acid (7 g; 30 mmol) according to the General Procedure Ia in 99% yield (6.5 g; 29.7 mmol).

ESI-MS m/z for $C_{10}H_{13}F_3NO$ found 220.1 (M+H)$^+$.

Step 2

Synthesis of tert-butyl (S)—(1-hydroxy-3-(4-(trifluoromethyl)phenyl)propan-2-yl)carbamate (77b)

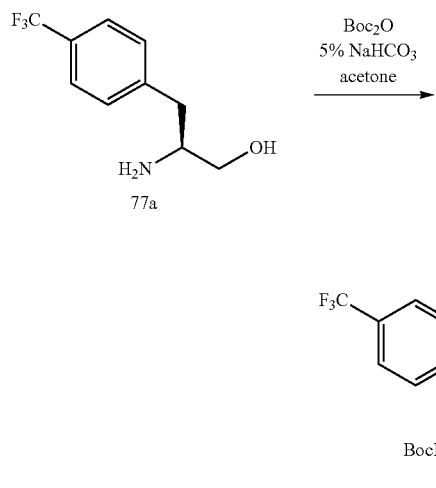

To a suspension of compound 77a (3 g; 13.69 mmol) in 5% NaHCO₃ (aqueous solution; 70 mL) a solution of Boc₂O (3.28 g; 15.05 mmol) in acetone (70 mL) was added in one portion and reaction was stirred at room temperature overnight after which time LC-MS control indicated completion of the reaction. Reaction mixture was concentrated to remove acetone. Water residue was acidified with 2 M HCl to pH 4 and extracted with EtOAc (2×). Combined organic layers were dried over anhydrous MgSO₄, filtered and concentrated in vacuo. The crude product was used in the next step without additional purification. Compound 77b was obtained in 99% yield (4.32 g; 13.55 mmol).

ESI-MS m/z for $C_{10}H_{12}F_3NO$ found 219.9 (M+H-Boc)⁺; for $C_{15}H_{21}F_3NO_3$ found 341.9 (M+Na)⁺.

Step 3

Synthesis of methyl (S)-1-(2-((tert-butoxycarbonyl)amino)-3-(4-(trifluoromethyl)phenyl)propyl)-1H-imidazole-5-carboxylate (77c)

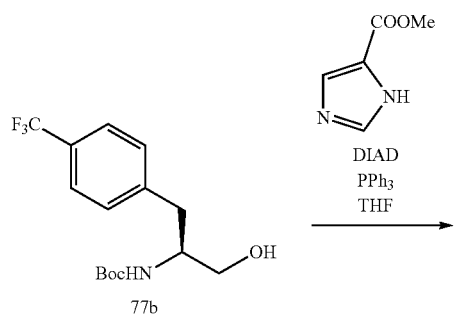

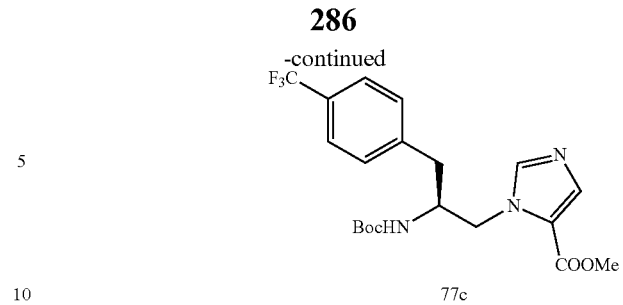

The solution of 77b (1.1 g; 3.45 mmol), PPh₃ (1.51 g; 5.77 mmol) and methyl 1H-imidazole-5-carboxylate (535 mg; 4.24 mmol) in THF (40 mL) was cooled to −15° C. and then DIAD (1.14 mL; 5.78 mmol) was added dropwise. The reaction mixture was stirred for 30 minutes below 0° C., then at room temperature for 3 days. The reaction progress was monitored by LC-MS. When analysis indicated completion of the reaction, the solvent was removed in vacuo and the crude product was purified by flash column chromatography (DCM/MeOH; 100:0 to 100/1 v/v). Compound 77c was obtained in 35% yield (520 mg; 1.22 mmol).

Step 4

Synthesis of (R)-6-(4-(trifluoromethyl)benzyl)-6,7-dihydroimidazo[1,5-a]pyrazin-8(5H)-one (77d)

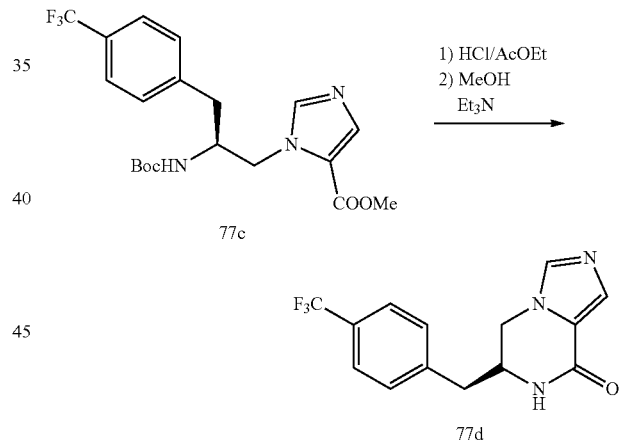

The solution of 77c (520 mg; 1.22 mmol) in HCl/AcOEt (3 M; 8 mL) was stirred at room temperature for 1 hour. The reaction progress was monitored by LC-MS. When analysis indicated completion of the reaction, the solvent was removed in vacuo and the crude solid was dissolved in MeOH (16 mL). Then to this solution Et₃N (1 mL) was added and the reaction mixture was stirred at room temperature overnight, then warmed up to 50° C. and stirred for 2 days. The solvent was removed in vacuo and the residue was redissolved in AcOEt and washed with 5% NaHCO₃. The organic layer was dried over anhydrous MgSO₄, filtered and concentrated in vacuo. The crude product was used in the next step without additional purification. Compound 77d was obtained as a grey foam in 89% yield (320 mg; 1.08 mmol).

ESI-MS m/z for $C_{14}H_{13}F_3N_3O$ found 295.8 (M+H)⁺.

Step 5

Synthesis of (R)-6-(4-(trifluoromethyl)benzyl)-5,6,7,8-tetrahydroimidazo[1,5-a]pyrazine hydrochloride (77e)

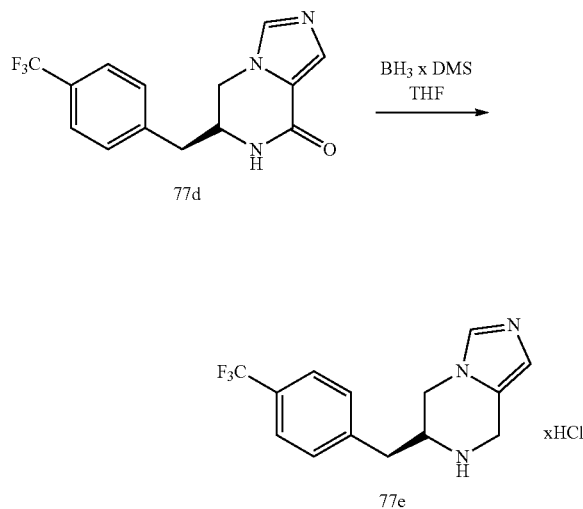

The title compound (77e) was obtained as a hydrochloride salt as a grey solid from 77d (320 mg; 1.08 mmol) according to the General Procedure Ib in 71% yield (244 mg; 0.77 mmol).

ESI-MS m/z for $C_{14}H_{15}F_3N_3$ found 281.9 $(M+H)^+$.

Step 6

Synthesis of (S)-5-(4-(6-(4-(trifluoromethyl)benzyl)-5,6-dihydroimidazo[1,5-a]pyrazin-7(8H)-yl)piperidin-1-yl)-4H-1,2,4-triazol-3-amine 2,2,2-trifluoroacetate (77)

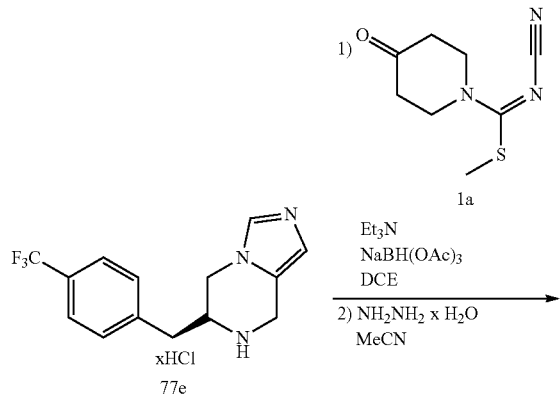

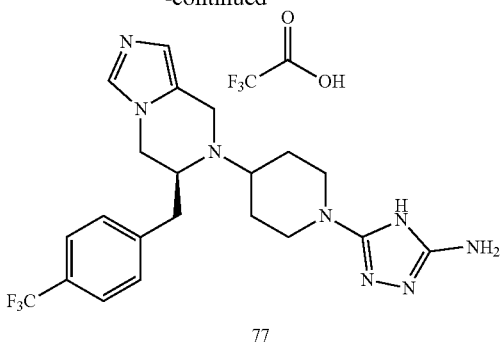

The title compound (77) was obtained as a TFA salt from 77e (244 mg; 0.77 mmol) according to the General Procedure Vb in 6% yield (24 mg; 0.043 mmol).

ESI-MS m/z for $C_{21}H_{26}F_3N_8$ found 447.1 (M+H); $^1$H NMR (700 MHz, DMSO-$d_6$) δ 8.99 (s, 1H), 7.71-7.67 (m, 2H), 7.53-7.50 (m, 2H), 7.48-7.44 (m, 1H), 4.18-4.08 (m, 2H), 4.04-4.00 (m, 1H), 4.00-3.94 (m, 1H), 3.78-3.65 (m, 3H), 3.10-3.03 (m, 1H), 2.99-2.90 (m, 3H), 2.83-2.73 (m, 1H), 1.87-1.78 (m, 2H), 1.57-1.47 (m, 2H).

Example 78

Synthesis of 5-(4-((3S,8aS)-7,7-difluoro-3-(4-(trifluoromethyl)benzyl)hexahydropyrrolo[1,2-a]pyrazin-2(1H)-yl)piperidin-1-yl)-4H-1,2,4-triazol-3-amine 2,2,2-trifluoroacetate (78)

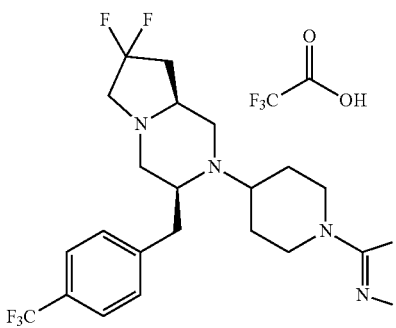

Step 1

Synthesis of methyl (2S,4R)-1-((R)-2-((tert-butoxycarbonyl)amino)-3-(4-(trifluoromethyl)-phenyl)propanoyl)-4-hydroxypyrrolidine-2-carboxylate (78a)

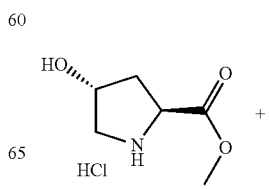

-continued

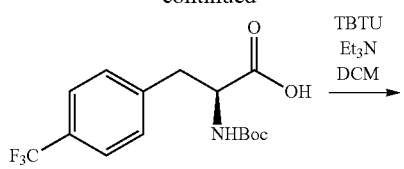

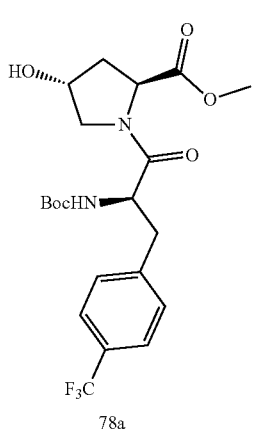

78a

The title compound (78a) was obtained from trans-4-hydroxy-L-proline methyl ester hydrochloride (3.12 g; 17.15 mmol) and Boc-4-trifluoromethyl-L-phenylalanine (5.72 g; 17.15 mmol) according to the General Procedure III in 61% yield (7.82 g; 10.49 mmol).

ESI-MS m/z for $C_{21}H_{28}F_3N_2O_6$ found 461.2 (M+H)$^+$.

Step 2

Synthesis of methyl (2S,4R)-1-((R)-2-amino-3-(4-(trifluoromethyl)phenyl)propanoyl)-4-hydroxypyrrolidine-2-carboxylate (78b)

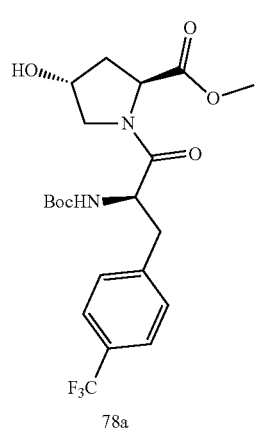

-continued

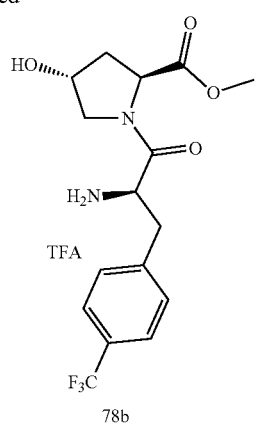

78b

The title compound (78b) was obtained as a TFA salt from 78a (7.82 g; 10.49 mmol) according to the General Procedure IVb in 99% yield (4.93 g; 10.39 mmol).

ESI-MS m/z for $C_{16}H_{20}F_3N_2O_4$ found 361.1 (M+H)$^+$.

Step 3

Synthesis of (3S,7R,8aS)-7-hydroxy-3-(4-(trifluoromethyl)benzyl)hexahydropyrrolo[1,2-a]pyrazine-1,4-dione (78c)

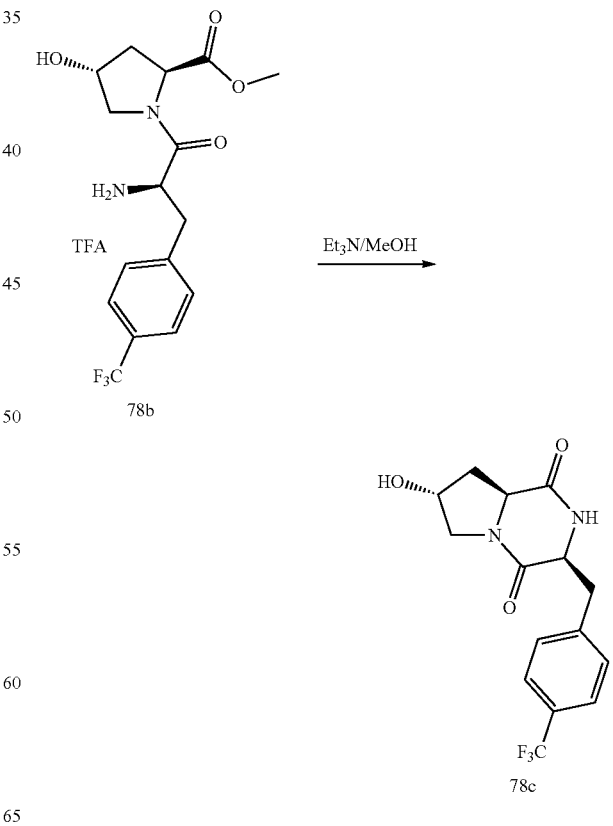

To a solution of crude 78b (6.05 g; 16.81 mmol) in MeOH (90 mL) Et$_3$N (16.7 mL; 120.05 mmol) was added and the mixture was heated to reflux for 80 minutes and then at room temperature overnight. LC-MS showed completion of the reaction. The mixture was concentrated and the yellow oily residue was partitioned between AcOEt (3×120 mL) and water (100 mL). The combined organic solutions were dried over anhydrous Na$_2$SO$_4$, filtered and concentrated in vacuo. The crude product was used in the next step without additional purification. Compound 78c was obtained as an yellow oil in 79% yield (4.37 g; 13.3 mmol).

ESI-MS m/z for C$_{15}$H$_{16}$F$_3$N$_2$O$_3$ found 329.1 (M+H)$^+$.

Step 4

Synthesis of (3S,7R,8aS)-3-(4-(trifluoromethyl)benzyl)octahydropyrrolo[1,2-a]pyrazin-7-ol (78d)

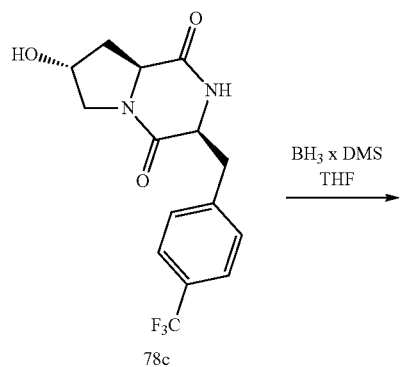

The title compound (78d) was obtained from 78c (4.37 g; 13.3 mmol) according to the General Procedure Ib in 99% yield (3.95 g; 13.17 mmol).

ESI-MS m/z for C$_{15}$H$_{20}$F$_3$N$_2$O found 301.1 (M+H)$^+$.

Step 5

Synthesis of tert-butyl (3S,7R,8aS)-7-hydroxy-3-(4-(trifluoromethyl)benzyl)hexahydropyrrolo-[1,2-a]pyrazine-2(1H)-carboxylate (78e)

To a solution of compound 78d (3.95 g; 13.17 mmol) in THF (120 mL), 4 N NaOH (35 mL) and Boc$_2$O (3.5 g; 16 mmol) were added in one portion and reaction was stirred overnight after which time TLC and LC-MS control indicated completion of the reaction. Reaction mixture was concentrated to remove THF. Water residue was saturated with NaCl and extracted with EtOAc (3×). Organic layer was washed with brine, dried over anhydrous MgSO$_4$ and concentrated. The crude product was purified by flash column chromatography (hexane/EtOAc 1:1 to 0:100 v/v). Compound 78e was obtained in 59% yield (3.10 g; 7.74 mmol).

ESI-MS m/z' for C$_{20}$H$_{28}$F$_3$N$_2$O$_3$ found 401.2 (M+H)$^+$.

Step 6

Synthesis of tert-butyl (3S,8aS)-7-oxo-3-(4-(trifluoromethyl)benzyl)hexahydropyrrolo[1,2-a]pyrazine-2(1H)-carboxylate (78f)

-continued

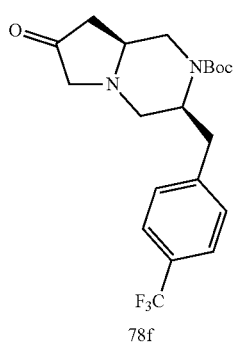

78f

To the solution of 78e (3 g; 7.49 mmol) and Et₃N (3.2 mL; 22.5 mmol) in DCM/DMSO (10 mL/10 mL) the solution of pyridine×SO₃ (3.58 g; 22.5 mmol) in DCM/DMSO (20 mL/20 mL) was added dropwise at 0° C. over 15 minutes and then this reaction mixture was stirred at this temperature for 2 hours. The reaction progress was monitored by TLC and LC-MS. When analyses indicated completion of the reaction, the reaction mixture was diluted with saturated solution of NaCl (300 mL) and 1 µM K₂CO₃ (100 mL) and extracted with CHCl₃ (3×100 mL), then with AcOEt (2×100 mL). Combined organic extracts were dried over Na₂SO₄, filtered and concentrated in vacuo and the crude product was purified by flash column chromatography (hexane/EtOAc 1:1 to 0:100 v/v) to give 78f as a two rotamers (in ratio 0.7:1) in 84% yield (2.5 g; 6.27 mmol).

ESI-MS m/z for $C_{20}H_{26}F_3N_2O_3$ found 399.2 $(M+H)^+$; $^1H$ NMR (400 MHz, CDCl₃) δ 7.52-7.42 (m, 2H), 7.32-7.16 (m, 2H), 4.48-3.98 (m, 2H), 3.36-3.22 (m, 1H), 3.12-2.74 (m, 4H), 2.49-2.39 (m, 1H), 2.36-2.26 (m, 2H), 2.17-2.04 (m, 1H), 1.73-1.64 (m, 1H), 1.35-1.14 (m, 9H).

Step 7

Synthesis of (3S,8aS)-7,7-difluoro-3-(4-(trifluoromethyl)benzyl)octahydropyrrolo[1,2-a]pyrazine (78g)

To a cooled to −78° C. solution of 78f (2.5 g; 6.27 mmol) in anhydrous DCM 60 mL) DAST (2.5 mL; 18.82 mmol) was added dropwise and the reaction was allowed to room temperature and stirred overnight. The reaction progress was monitored by LC-MS. When analysis indicated completion of the reaction, the reaction mixture was poured into 5% NaHCO₃ and stirred for 15 minutes, then was extracted with DCM, washed with brine, dried over MgSO₄, concentrated in vacuo. The crude product was purified by flash column chromatography (hexane/EtOAc 8:2 to 0:100 v/v) to give 78g in two fractions: compound with Boc group in 57% yield (1.51 g; 3.59 mmol) and appropriate product (free base) in 17% yield (350 mg; 1.09 mmol).

For free base: ESI-MS m/z for $C_{15}H_{18}F_5N_2$ found 321.1 $(M+H)^+$; $^1H$ NMR (400 MHz, CDCl₃) δ 7.58-7.50 (m, 2H), 7.38-7.26 (m, 2H), 4.52-3.97 (m, 2H), 3.45-3.26 (m, 1H), 3.16-3.04 (m, 1H), 3.04-2.96 (m, 1H), 2.93-2.82 (m, 1H), 2.82-2.72 (m, 1H), 2.57-2.43 (m, 1H), 2.41-2.17 (m, 3H), 2.10-1.93 (m, 1H), 1.40-1.23 (m, 9H).

Step 8

Synthesis of tert-butyl 4-((3S,8aS)-7,7-difluoro-3-(4-(trifluoromethyl)benzyl)hexahydropyrrolo[1,2-a]pyrazin-2(1H)-yl)piperidine-1-carboxylate (78h)

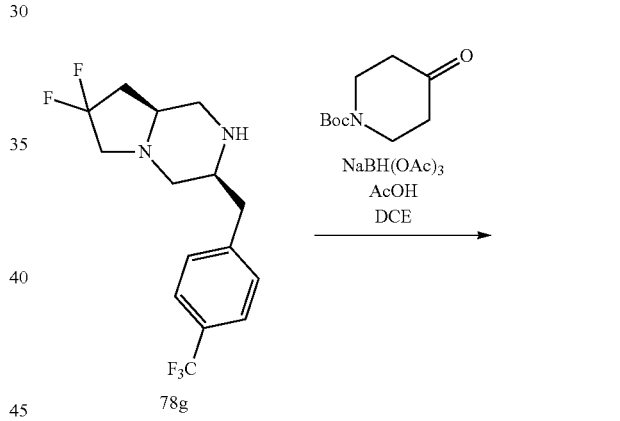

78g

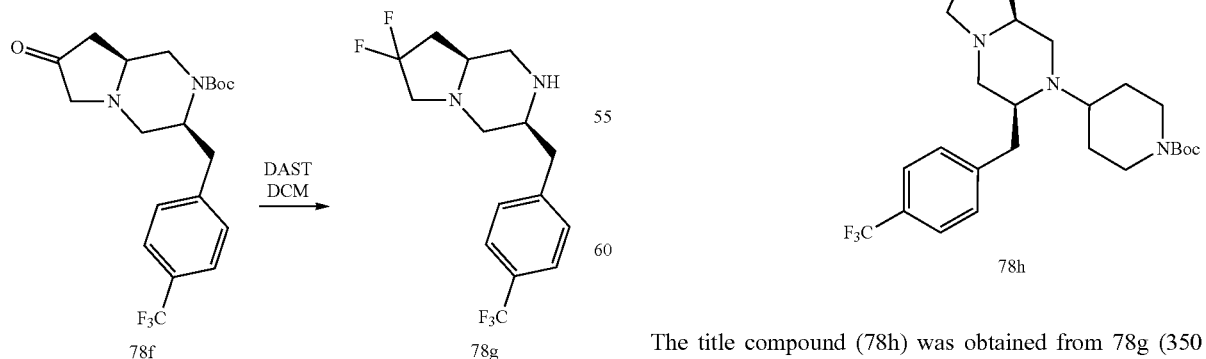

78f       78g

78h

The title compound (78h) was obtained from 78g (350 mg; 1.09 mmol) according to the General Procedure IX in 99% yield (544 mg; 1.08 mmol).

ESI-MS $C_{25}H_{35}F_5N_3O_2$ found 504.3 $(M+H)^+$.

Step 9

Synthesis of (3S,8aS)-7,7-difluoro-2-(piperidin-4-yl)-3-(4-(trifluoromethyl)benzyl)octahydropyrrolo[1,2-a]pyrazine 2,2,2-trifluoroacetate (78i)

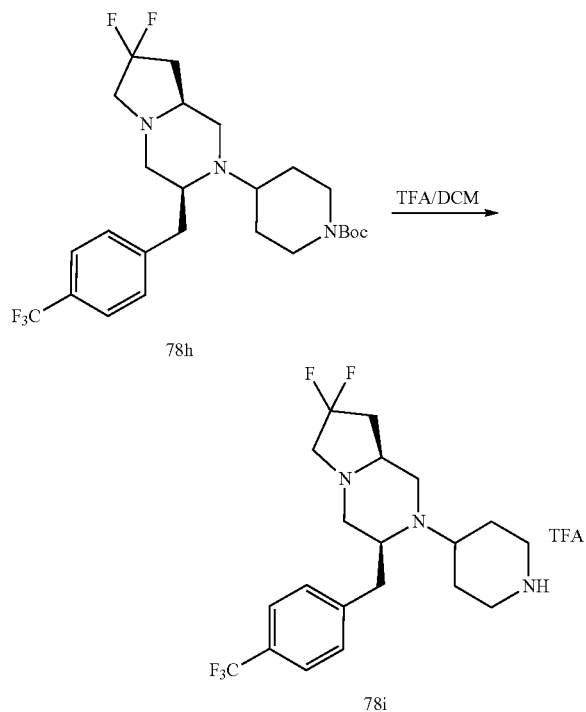

The title compound (78i) was obtained as a TFA salt from 78h (544 mg; 1.08 mmol) according to the General Procedure IVb in 99% yield (553 mg; 1.07 mmol).

ESI-MS m/z for $C_{20}H_{27}F_5N_3$ found 404.2 (M+H)$^+$; $^1$H NMR (400 MHz, Methanol-$d_4$) δ 7.74-7.65 (m, 2H), 7.58-7.43 (m, 2H), 4.08-3.93 (m, 1H), 3.86-3.72 (m, 2H), 3.67-3.57 (m, 2H), 3.56-3.46 (m, 1H), 3.46-3.36 (m, 1H), 3.29-3.18 (m, 2H), 3.18-3.07 (m, 2H), 3.01-2.91 (m, 1H), 2.88-2.81 (m, 1H), 2.77-2.64 (m, 1H), 2.64-2.44 (m, 4H), 2.35-2.17 (m, 1H), 2.11-1.94 (m, 2H).

Step 10

Synthesis of 5-(4-((3S,8aS)-7,7-difluoro-3-(4-(trifluoromethyl)benzyl)hexahydropyrrolo[1,2-a]pyrazin-2(1H)-yl)piperidin-1-yl)-4H-1,2,4-triazol-3-amine 2,2,2-trifluoroacetate (78)

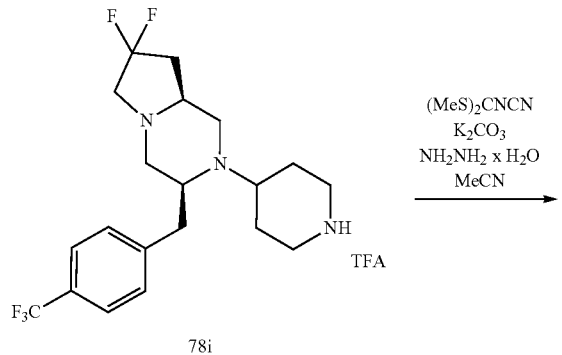

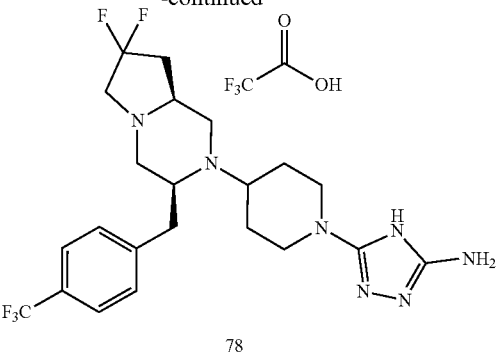

The title compound (78) was obtained as a TFA salt from 78i (553 mg; 1.07 mmol) according to the General Procedure Va in 54% yield (345 mg; 0.58 mmol).

ESI-MS m/z for $C_{22}H_{29}F_5N_7$ found 486.3 (M+H)$^+$; $^1$H NMR (400 MHz, Methanol-$d_4$) δ 7.73-7.66 (m, 2H), 7.56-7.51 (m, 2H), 4.13-3.97 (m, 3H), 3.93-3.83 (m, 1H), 3.82-3.72 (m, 1H), 3.63-3.50 (m, 1H), 3.44-3.35 (m, 1H), 3.29-3.22 (m, 1H), 3.13-3.01 (m, 2H), 2.90-2.76 (m, 2H), 2.72-2.43 (m, 4H), 2.43-2.32 (m, 2H), 2.32-2.13 (m, 1H), 1.93-1.72 (m, 2H).

INCORPORATION BY REFERENCE

All U.S. patents, U.S. published patent applications, and PCT published patent applications designating the U.S. mentioned herein are hereby incorporated by reference in their entirety as if each individual publication or patent was specifically and individually indicated to be incorporated by reference. In case of conflict, the present application, including any definitions herein, will control.

EQUIVALENTS

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

What is claimed is:

1. A compound represented by formula (I),

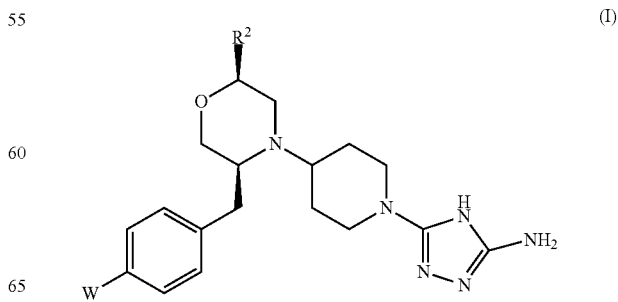

wherein:

W is Cl or Br; and $R^2$ is fluoro($C_1$-$C_6$)alkyl;

or a pharmaceutically acceptable salt thereof.

2. The compound of claim 1, wherein W is chloro.

3. The compound of claim 1, wherein $R^2$ is fluoro($C_1$-$C_2$)alkyl.

4. The compound of claim 1, wherein $R^2$ is fluoro($C_1$)alkyl.

5. The compound of claim 1, wherein $R^2$ is fluoro($C_2$)alkyl.

6. The compound of claim 1, wherein $R^2$ is —$CH_2F$.

7. The compound of claim 1, wherein $R^2$ is —$CHF_2$.

8. The compound of claim 1, wherein $R^2$ is —$CF_3$.

9. The compound of claim 1, wherein $R^2$ is —$CH_2CF_3$.

10. The compound of claim 1, wherein $R^2$ is —$CHFCH_3$.

11. The compound of claim 1, or a pharmaceutically acceptable salt thereof, represented by any one of the following structural formulae:

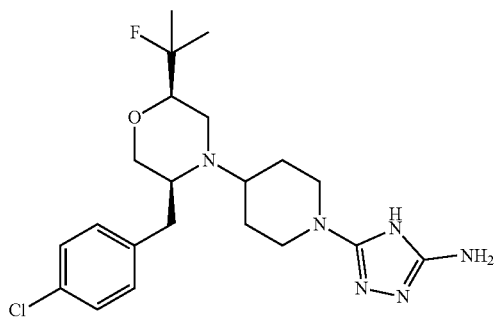

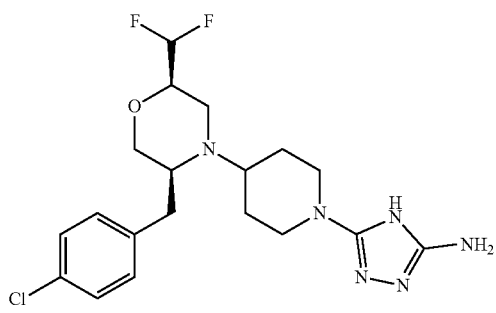 [SMILES: Nc1nnc(N2CCC(N3C[C@H](C(F)F)OC[C@@H]3Cc3ccc(Cl)cc3)CC2)[nH]1]

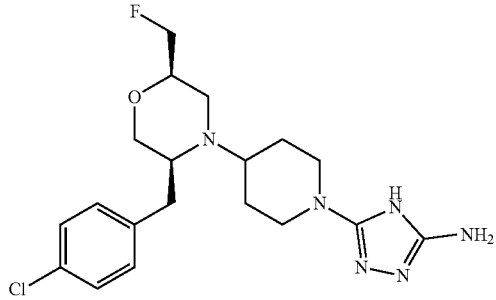 [SMILES: Nc1nnc(N2CCC(N3C[C@H](CF)OC[C@@H]3Cc3ccc(Cl)cc3)CC2)[nH]1]

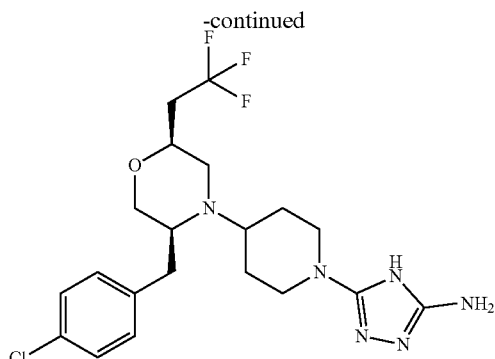

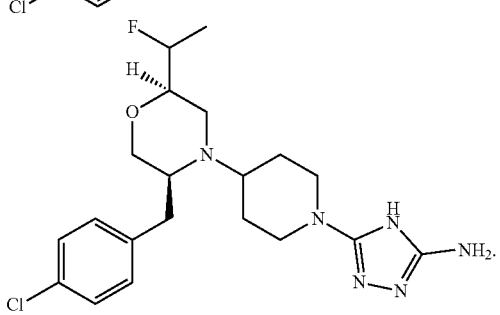

12. A pharmaceutical composition comprising a therapeutically effective amount of a compound of claim 1; and a pharmaceutically acceptable carrier.

13. The compound of claim 1, or a pharmaceutically acceptable salt thereof, represented by the following structure:

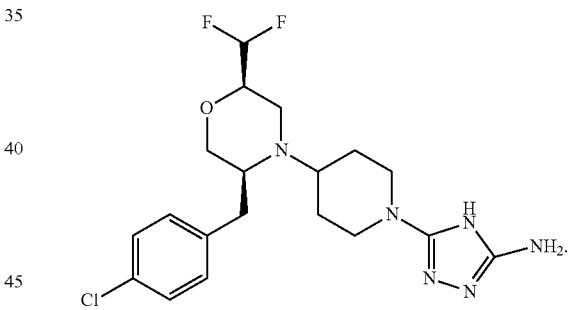

14. The compound of claim 1, or a pharmaceutically acceptable salt thereof, represented by the following structure:

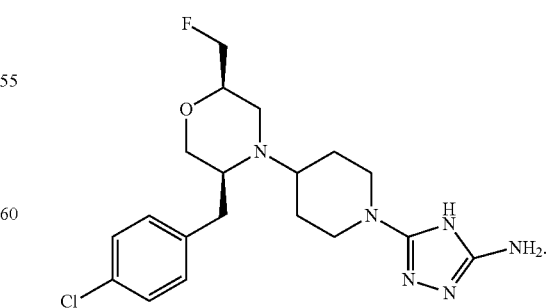

* * * * *